(12) United States Patent  
Thorpe

(10) Patent No.: US 7,976,868 B2
(45) Date of Patent: Jul. 12, 2011

(54) LIPOSOMES COMPRISING DURAMYCIN AND ANTI-VIRAL AGENTS

(75) Inventor: Philip E. Thorpe, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/717,295

(22) Filed: Mar. 4, 2010

(65) Prior Publication Data

US 2010/0310638 A1 Dec. 9, 2010

Related U.S. Application Data

(63) Continuation of application No. 10/642,064, filed on Aug. 15, 2003, now Pat. No. 7,678,386, which is a continuation-in-part of application No. 10/621,269, filed on Jul. 15, 2003, now Pat. No. 7,572,442.

(60) Provisional application No. 60/396,263, filed on Jul. 15, 2002.

(51) Int. Cl.
*A61K 9/127* (2006.01)

(52) U.S. Cl. ......................................... 424/450

(58) Field of Classification Search ........................ None
See application file for complete search history.

(56) References Cited

U.S. PATENT DOCUMENTS

| | | | |
|---|---|---|---|
| 4,939,098 A | 7/1990 | Suzuki et al. | 436/514 |
| 4,975,278 A | 12/1990 | Senter et al. | 424/94.3 |
| 5,627,036 A | 5/1997 | Reutelingersperger | 435/7.21 |
| 5,660,827 A | 8/1997 | Thorpe et al. | 424/152.1 |
| 5,677,171 A | 10/1997 | Hudziak et al. | 435/7.23 |
| 5,834,599 A | 11/1998 | Chang et al. | 530/388.35 |
| 5,849,706 A | 12/1998 | Molina y Vedia et al. | 514/12 |
| 5,863,538 A | 1/1999 | Thorpe et al. | 424/136.1 |
| 6,194,430 B1 | 2/2001 | Camden et al. | 514/303 |
| 6,300,308 B1 | 10/2001 | Schroit | 514/8 |
| 6,312,694 B1 | 11/2001 | Thorpe et al. | 424/178.1 |
| 6,333,348 B1 | 12/2001 | Vogel et al. | 514/8 |
| 6,406,693 B1 | 6/2002 | Thorpe et al. | 424/130.1 |
| 6,783,760 B1 | 8/2004 | Thorpe et al. | 424/178.1 |
| 6,806,354 B2 | 10/2004 | Schroit | 530/387.1 |
| 6,818,213 B1 | 11/2004 | Thorpe et al. | 424/130.1 |
| 7,034,113 B2 | 4/2006 | Olstein et al. | 530/350 |
| 7,067,109 B1 | 6/2006 | Thorpe et al. | 424/1.49 |
| 7,247,303 B2 | 7/2007 | Thorpe et al. | 424/141.1 |
| 7,378,386 B2 | 5/2008 | Thorpe et al. | 514/2 |
| 7,384,909 B2 | 6/2008 | Thorpe et al. | 514/2 |
| 7,422,738 B2 | 9/2008 | Thorpe et al. | 424/130.1 |
| 7,455,833 B2 | 11/2008 | Thorpe et al. | 424/130.1 |
| 7,511,124 B2 | 3/2009 | Thorpe et al. | 530/402 |
| 7,550,141 B2 | 6/2009 | Thorpe et al. | 424/130.1 |
| 7,611,704 B2 | 11/2009 | Thorpe et al. | 424/141.1 |
| 7,678,386 B2 | 3/2010 | Thorpe | 424/450 |
| 7,790,159 B2 | 9/2010 | Thorpe et al. | 424/130.1 |
| 7,879,801 B2 | 2/2011 | Thorpe et al. | 514/12 |
| 2002/0025319 A1 | 2/2002 | Brams | 424/178.1 |
| 2003/0004097 A1 | 1/2003 | Schroit | 514/7 |
| 2003/0175207 A1 | 9/2003 | Olstein et al. | 424/1.49 |
| 2003/0228625 A1 | 12/2003 | Toh et al. | 435/7.1 |
| 2004/0131610 A1 | 7/2004 | Thorpe et al. | 424/141.1 |
| 2004/0131621 A1 | 7/2004 | Thorpe et al. | 424/159.1 |
| 2004/0131622 A1 | 7/2004 | Thorpe et al. | 424/159.1 |
| 2004/0147440 A1 | 7/2004 | Thorpe et al. | 514/12 |
| 2004/0161429 A1 | 8/2004 | Thorpe et al. | 424/178.1 |
| 2004/0175378 A1 | 9/2004 | Thorpe et al. | 424/141.1 |
| 2004/0208868 A1 | 10/2004 | Thorpe et al. | 424/144.1 |
| 2004/0213779 A1 | 10/2004 | Thorpe et al. | 424/132.1 |
| 2004/0219155 A1 | 11/2004 | Thorpe et al. | 424/178.1 |
| 2005/0002941 A1 | 1/2005 | Thorpe et al. | 424/178.1 |
| 2005/0031620 A1 | 2/2005 | Thorpe et al. | 424/155.1 |
| 2005/0129696 A1 | 6/2005 | Thorpe et al. | 424/155.1 |
| 2005/0136059 A1 | 6/2005 | Thorpe et al. | 424/155.1 |
| 2008/0066741 A1 | 3/2008 | LeMahien et al. | 128/200.21 |

FOREIGN PATENT DOCUMENTS

| | | |
|---|---|---|
| JP | 08-092124 | 9/1994 |
| JP | 08092124 | * 9/1994 |
| WO | WO 00/02584 | 1/2000 |
| WO | WO 00/02587 | 1/2000 |
| WO | WO 00/33888 | 6/2000 |
| WO | WO 01/03735 | 1/2001 |
| WO | WO 01/68709 | 9/2001 |
| WO | WO 2004/006847 | 1/2004 |

OTHER PUBLICATIONS

Machine translation of JP 08092124, Date et al, Sep. 1994, 3 pages.*
Balasubramanian and Schroit, "Aminophospholipid Asymmetry: A Matter of Life and Death", *Annu. Rev. Physiol.*, 65:701-734, 2003.
Beck et al., "Combination of a Monoclonal Anti-Phosphatidylserine Antibody with Gemcitabine Strongly Inhibits the Growth and Metastasis of Orthotopic Pancreatic Tumors in Mice", *Int. J. Cancer*, 118:2639-2643, 2006.
Bowie et al., "Deciphering the Message in Protein Sequences: Tolerance to Amnio Acid Substitutions", *Science*, 147:1306-1310, 1990.
Güssow and Seemann, "Humanization of Monoclonal Antibodies", *Methods in Enzymology*, 203:99-121, 1991.
Herbert et al., Eds., Dictionary of Immunology, 4th ed. London:Academic Press, 1995.
Huang et al., "A Monoclonal Antibody that Binds Anionic Phospholipids on Tumor Blood Vessels Enhances the Antitumor Effect of Docetaxel on Human Breast Tumors in Mice", *Cancer Res.*, 65(10):4408-4416, 2005.
Janeway et al., "The Interaction of the Antibody Molecule with Specific Antigen", *Immunobiology*, 5th ed., 7 pages, 2001.

(Continued)

*Primary Examiner* — Laura B Goddard
(74) *Attorney, Agent, or Firm* — Shelley P. M. Fussey

(57) ABSTRACT

Disclosed are surprising discoveries concerning the role of anionic phospholipids and aminophospholipids in tumor vasculature and in viral entry and spread, and compositions and methods for utilizing these findings in the treatment of cancer and viral infections. Also disclosed are advantageous antibody, immunoconjugate and duramycin-based compositions and combinations that bind and inhibit anionic phospholipids and aminophospholipids, for use in the safe and effective treatment of cancer, viral infections and related diseases.

13 Claims, 53 Drawing Sheets

OTHER PUBLICATIONS

Lewis et al., "Differential Responses of Human Tumor Cell Lines to Anti-p185HER2 Monoclonal Antibodies", *Cancer Immunol. Immunother.*, 37:255-263, 1993.

Luster et al., "Plasma Protein Beta-2-glycoprotein 1 Mediates Interaction between the Anti-tumor Monoclonal Antibody 3G4 and Anionic Phospholipids on Endothelial Cells," *JBC Papers in Press*, www.jbc.org/cgi/doi/10.1074/jbc., M605252200:1-20, 2006.

Ran and Thorpe, "Phosphatidylserine is a Marker of Tumor Vasculature and a Potential Target for Cancer Imaging and Therapy", *Int. J. Radiation Oncology Biol. Phys.*, 54(5):1479-1484, 2002.

Ran et al., "Antitumor Effects of a Monoclonal Antibody that Binds Anionic Phospholipids on the Surface of Tumor Blood Vessels in Mice", *Clin. Cancer Res.*, 11:1551-1562, 2005.

Ran et al., "Increased Exposure of Anionic Phospholipids on the Surface of the Tumor Blood Vessels", *Cancer Res.*; 62:6132-6140, 2002.

Rudikoff, "Single Amino Acid Substitution Altering Antigen-Binding Specificity", *Proc. Natl. Acad. Sci. USA*, 79:1979-1983, 1982.

Schneider-Gadicke and Riethmüller, "Prevention of Manifest Metastasis with Monoclonal Antibodies: A Novel Approach to Immunotherapy of Solid Tumours", *Eur. J. Cancer*, 31A(7/8):1326-1330, 1995.

Stancovski et al., "Mechanistic Aspects of the Opposing Effects of Monoclonal Antibodies to the ERBB2 Receptor on Tumor Growth", *Proc. Natl. Acad. Sci. USA*, 88:8691-8695, 1991.

Strobel and Cannistra, "β1-Integrins Partly Mediate Binding of Ovarian Cancer Cells to Peritoneal Mesothelium in Vitro", *Gynecologic Oncology*, 73:362-367, 1999.

Thorpe et al., "Tumor Infarction: Immunoconjugates that Coagulate the Vasculature of Solid Tumors", *Proceeding of the American Association for Cancer Research*, 36:488, Abstract #2910, Mar. 1995.

Contractual European Search Report for counterpart PCT Application, PCT/US03/21925, mailed Mar. 31, 2004.

European Search Report for Counterpart European Application No. 03764600.7, dated Dec. 27, 2004.

International Search Report for counterpart PCT Application, PCT/US03/21925, mailed Feb. 24, 2005.

Casset et al., "A Peptide Mimetic of an Anti-CD4 Monoclonal Antibody by Rational Design", *Biochem. Biophys. Res. Commun.*, 307(1):198-205, 2003.

Hortobagyi, "Developments in Chemotherapy of Breast Cancer", *Cancer*, 88(S12):3073-3079, 2000.

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody", *J. Immunol.*, 169:3076-3084, 2002.

Paul, "Fv Structure and Diversity in Three Dimensions", *In Fundamental Immunology, Third Edition*, 1993, pp. 292-295.

Aggarwal and Ranjan, "Preventing and Treating Hepatitis B Infection", *BMJ*, 329:1080-1086, 2004.

Aoki et al., "A Novel Peptide Probe for Studying the Transbilayer Movement of Phosphatidylethanolamine", *J. Biochem.*, 116:291-297, 1994.

Borda et al., "Cell Tropism of Simian Immunodeficiency Virus in Culture Is Not Predictive of in Vivo Tropism or Pathogenesis", *Am. J. Pathol.*, 165(6):2111-2122, 2004.

Connor et al., "Differentiation-Dependent Expression of Phosphatidylserine in Mammalian Plasma Membranes: Quantitative Assessment of Outer-Leaflet Lipid by Prothrombinase Complex Formation", *Proc. Natl. Acad. Sci. USA*, 86:3184-3188, 1989.

De Palma, "Looking Inside the Black Box/Biological Pathways and Drug Discovery", *New York Academy of Sciences*, 1-3, 2006.

Emoto et al., "Exposure of Phosphatidylethanolamine on the Surface of Apoptotic Cells", *Exp. Cell Res.*, 232:430-434, 1997.

Ford et al., "The Intracellular Pharmacology of Antiretroviral Protease Inhibitors", *J. Antimibrobial Chemotherapy*, 54:982-990, 2004.

Gaertner and Offord, "Site-Specific Attachment of Functionalized Poly(ethylene glycol) to the Amino Terminus of Proteins", *Bioconjugate Chem.*, 7:38-44, 1996.

Gait and Karn, "Progress in Anti-HIV Structure-Based Drug Design", *TIBTech*, 13:430-438, 1995.

Hayashi et al., "The Structure of PA48009: The Revised Structure of Duramycin", *J. Antibiotics*, 43(11):1421-1430, 1990.

Iwamoto et al., "Curvature-dependent recognition of ethanolamine phospholipids by duramycin and cinnamycin", *Biophys. J.*, 93(5):1608-19, 2007.

Kenis and Reutelingsperger, "Targeting Phosphatidylserine in Anti-Cancer Therapy", *Current Pharmaceutical Design*, 15(23):2719-2723, 2009.

Koopman et al., "Annexin V for Flow Cytometric Detection of Phosphatidylserine Expression on B Cells Undergoing Apoptosis", *Blood*; 84(5):1415-1420, 1994.

Li et al., "Phosphatidylethanolamine at the Endothelial Surface of Aortic Flow Dividers", *J. Thromb. Haemost.*, 7:227-229, 2009.

Locarnini and Shaw, "Antiviral Drug Resistance in Hepatitis B and C", *J. Gastroenterol. Hepatol.*, 19:S322-S328, 2004.

Marconescu & Thorpe, "Coincident exposure of phosphatidylethanolamine and anionic phospholipids on the surface of irradiated cells", *Biochem. Biophys. Acta*, 1778(10):2217-2224, 2008.

Naruse et al., "Lanthiopeptin, A New Peptide Antibiotic Production, Isolation and Properties of Lanthiopeptin", *J. Antibiotics*, XLII(6):837-845, 1989.

On-Line Medical Dictionary, "Annexin".

On-Line Medical Dictionary, "kininogen".

Peter and Gambertoglio, "Intracellular Phosphorylation of Zidovudine (ZDV) and Other Nucleoside Reverse Transcriptase Inhibitors (RTI) Used for Human Immunodeficiency Virus (HIV) Infection", *Pharmaceutical Res.*, 15(6):819-825, 1998.

R&D Systems, "Kininogen"; http://www.rndsystems.com/molecule_detail.aspx?m=1749, 2005.

Rodriguez et al., "Intracellular Studies of the Nucleoside Reverse Transcriptase Inhibitor Active Metabolites: a Review", *Biochemistry*, 19(1):19-27, 2000.

Rote et al., "Immunologic Detection of Phosphatidylserine Externalization During Thrombin-Induced Platelet Activation", *Clin. Immunol. Immunopathol.*, 66:193-200, 1993.

Sidwell & Smee, "In Vitro and In Vivo Assay Systems for Study of Influenza Virus Inhibitors", *Antiviral Res.*, 48:1-16, 2000.

Steadman's Medical Dictionary, "peptide".

Willey et al., "Lantibiotics: Peptides of Diverse Structure and Function", *Annu. Rev. Microbiol.*, 61:477-501, 2007 (Abstract only).

Bhattacharya and Thomas, "Novel Distamycin Analogues: Facile Synthesis of Cholesterol Conjugates of Distamycin-Like Oligopeptides", *Tetrahedron Letters*, 42:3499-3502, 2001.

Zamai et al., "Antiangiogenic Naphthalene Sulfonic Distamycin-A Derivatives Tightly Interact With Human Basic Fibroblast Growth Factor", *Med. Chem. Res.*, 7:1:36-44, 1997.

* cited by examiner

FIG. 13A. DLB    Duramycin—NH.CO.(CH$_2$)$_5$.NH.CO—biotin
FIG. 13B. DIB    Duramycin—NH.C(CH$_2$)$_3$.S.CH$_2$.CO.NH.(CH$_2$)$_6$.NH.CO—biotin
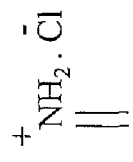
FIG. 13C. (DLB)$_4$NA
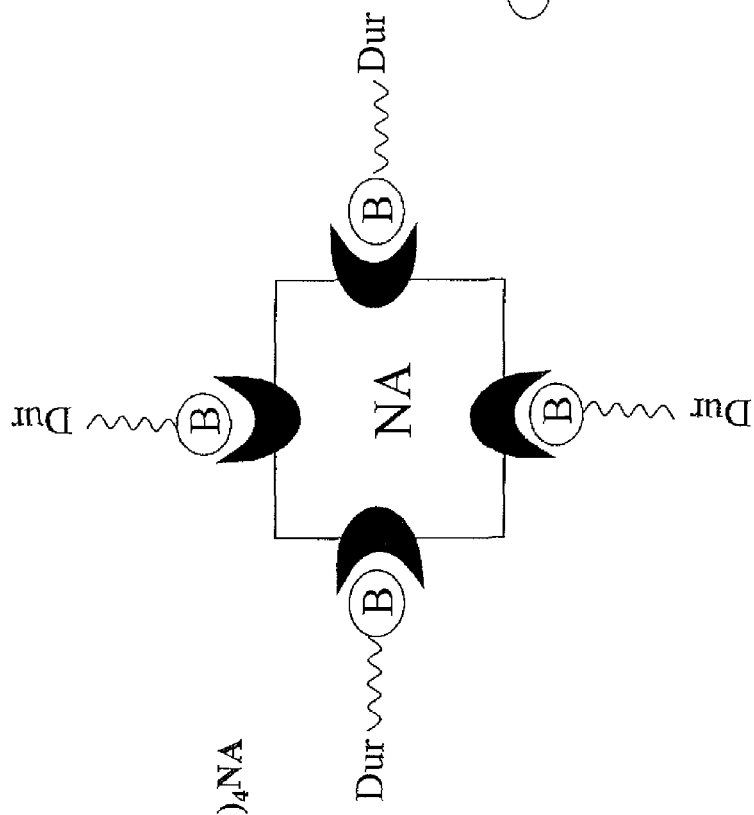

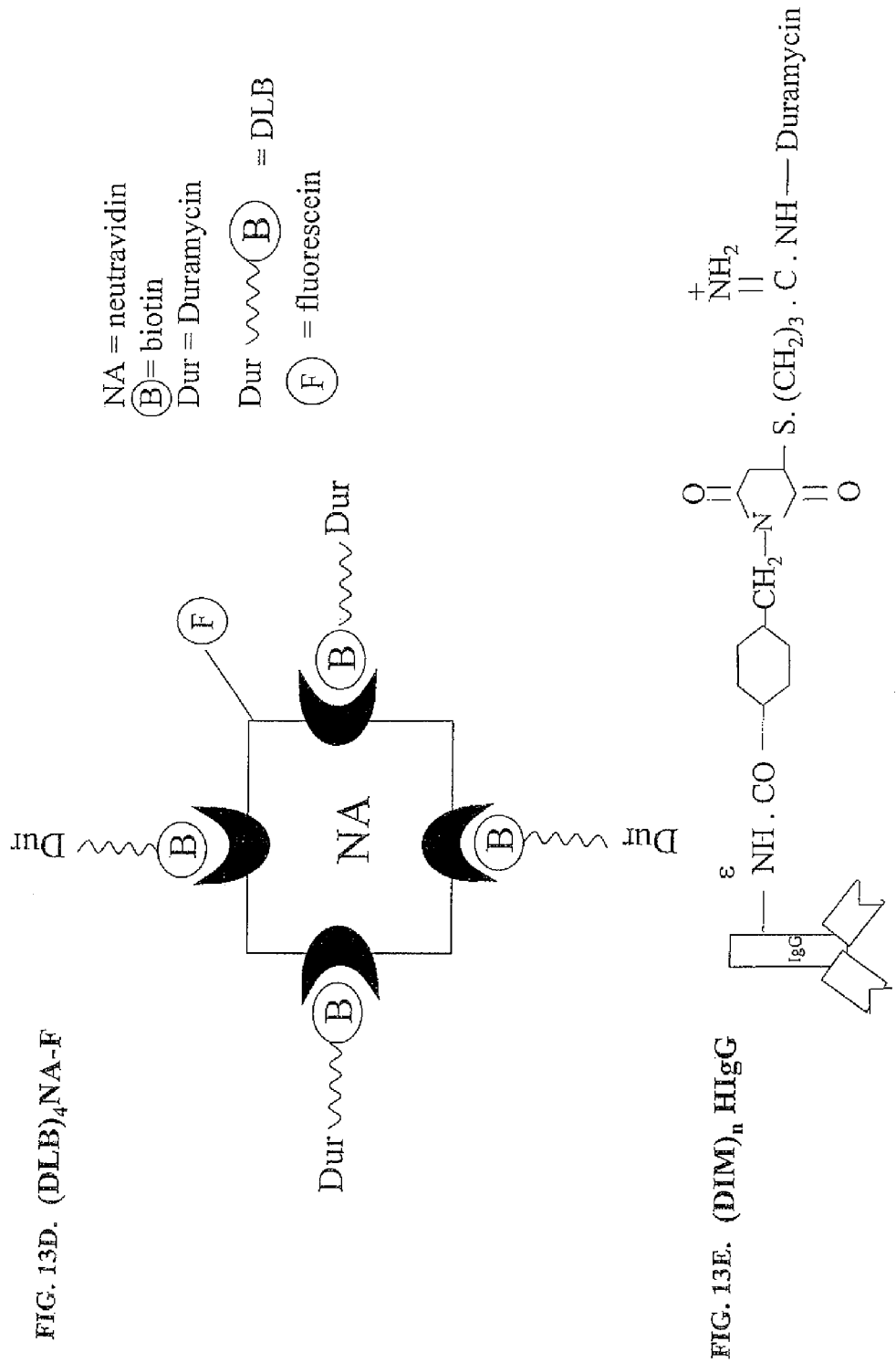
FIG. 13D. (DLB)₄NA-F
FIG. 13E. (DIM)ₙHIgG
n = 5 to 8 Duramycin residues per IgG Monomer (150,000 Da) is shown

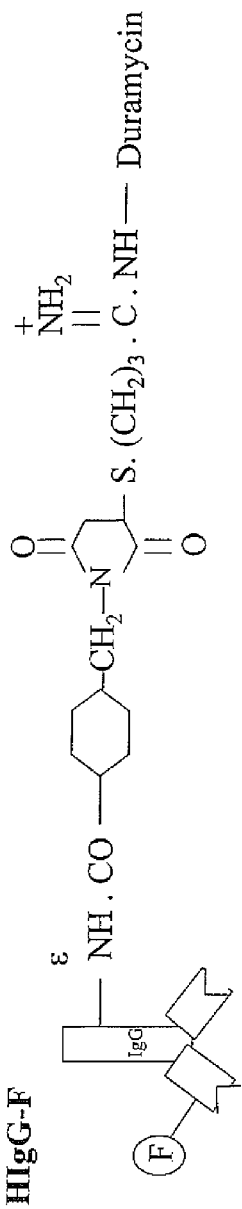
FIG. 13F. (DIM)$_n$ HIgG-F
n = 5 to 8 Duramycin residues per IgG
F = fluorescein
Monomer (150,000 Da) is shown
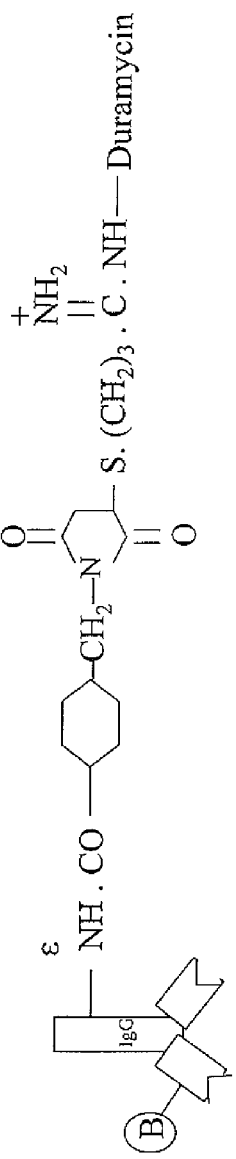
FIG. 13G. (DIM)$_n$ HIgG-B
n = 5 to 8 Duramycin residues per IgG
B = biotin
Monomer (150,000 Da) is shown

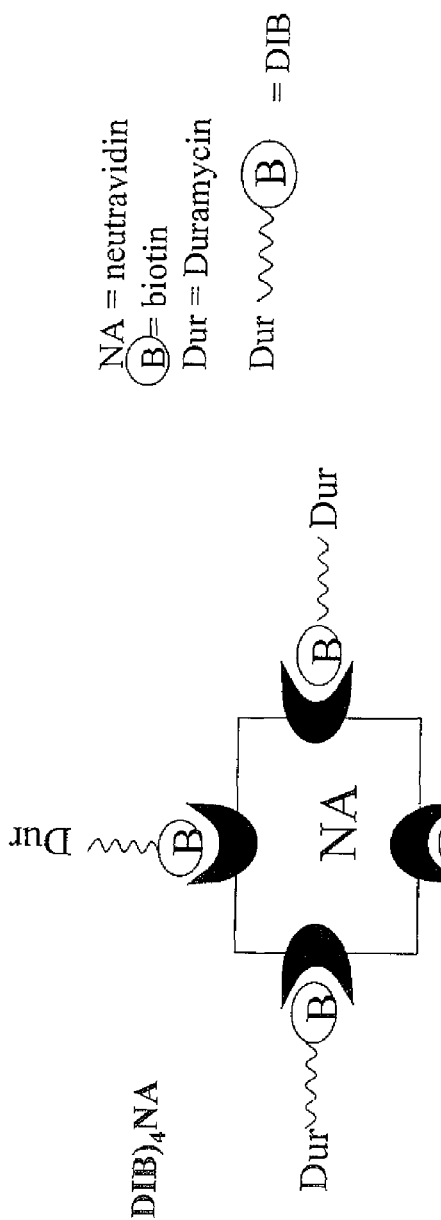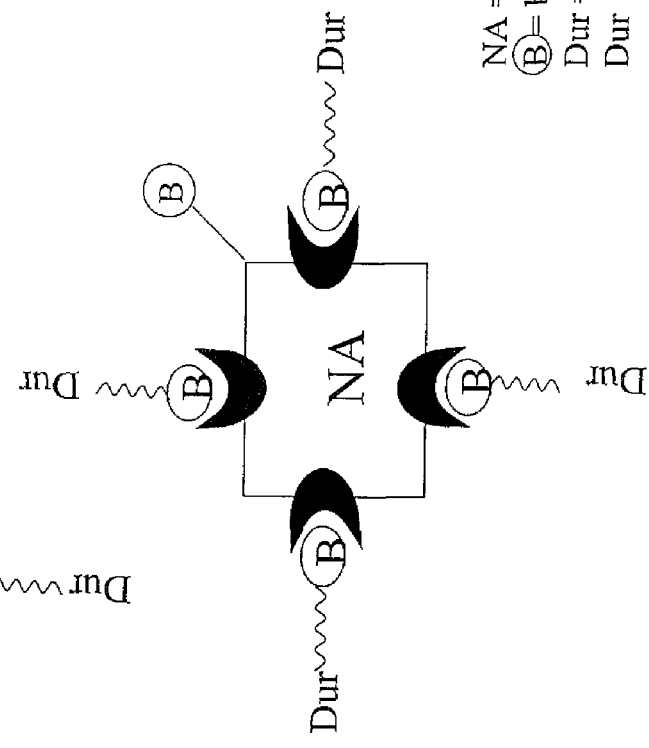
FIG. 13H. (DIB)₄NA
FIG. 13I. (DIB)₄NA-B

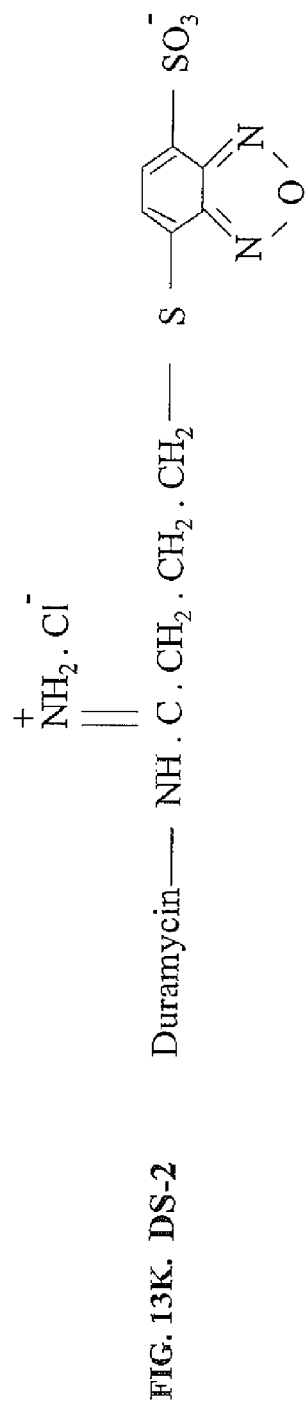
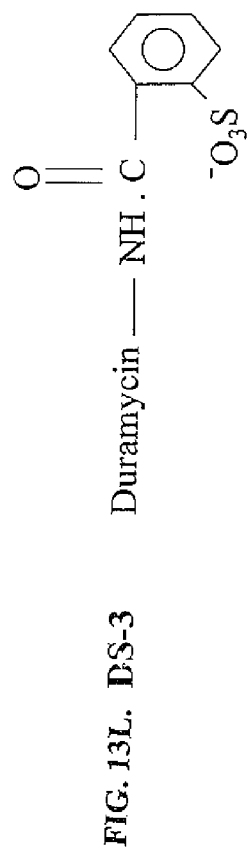
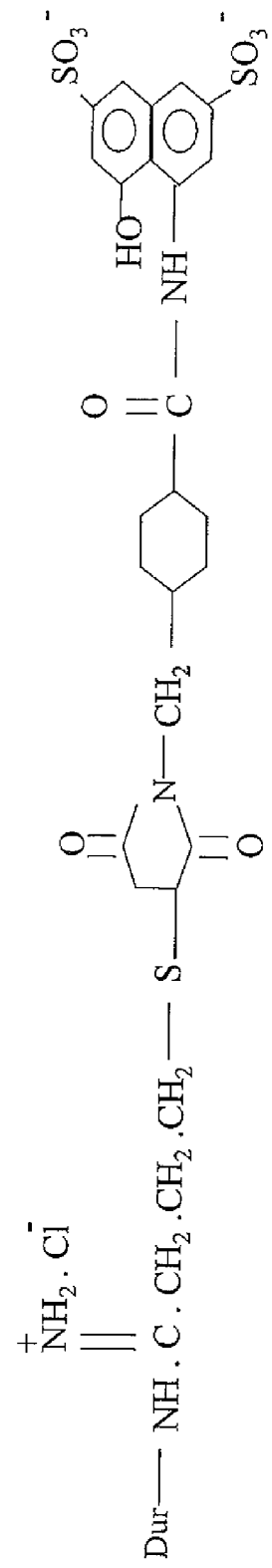
FIG. 13J. DS-1
FIG. 13K. DS-2
FIG. 13L. DS-3
FIG. 13M. DS-4

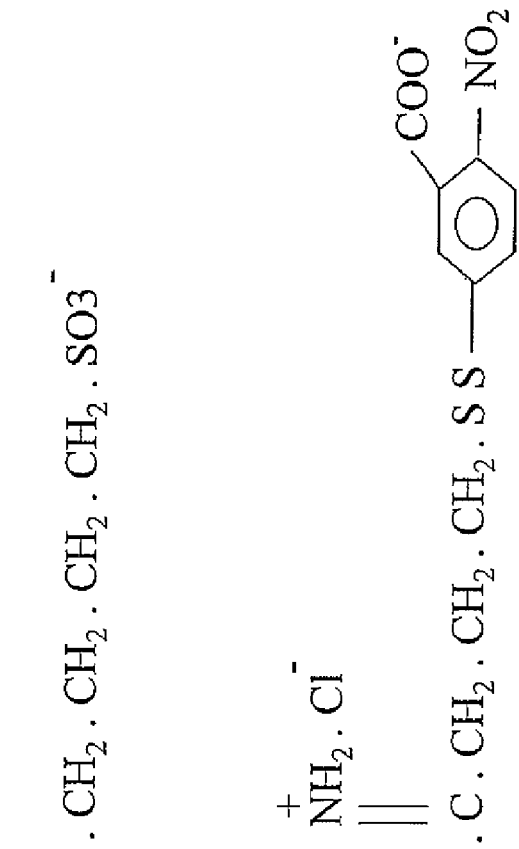
Duramycin—$NH_2.CH_2.CH_2.CH_2.CH_2.SO_3^-$
FIG. 13N. DS-5
Duramycin—$NH.C.CH_2.CH_2.CH_2.S\,S$—[phenyl with COO⁻ and NO_2]
with $\overset{+}{N}H_2.Cl^-$ on the C
FIG. 13O. DC-1

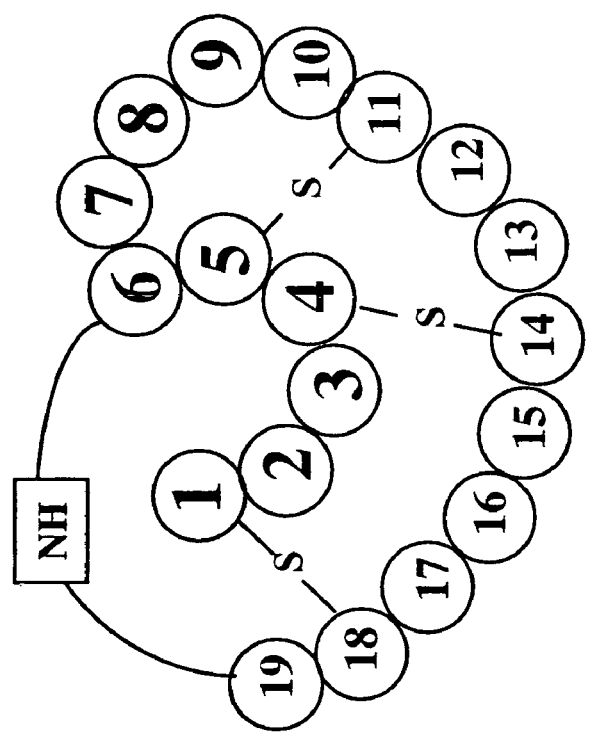
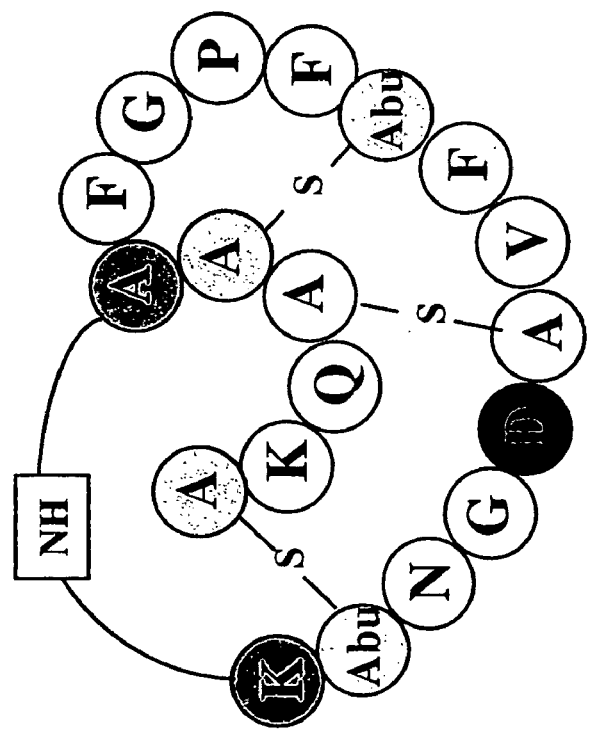
FIG. 13P

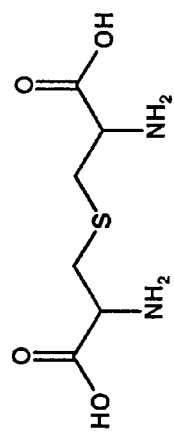 Lanthionine Ala-S-Ala
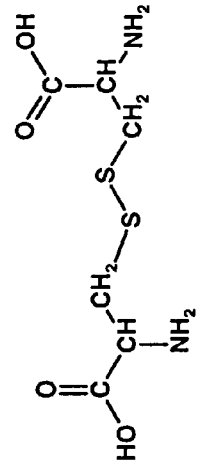 cystine
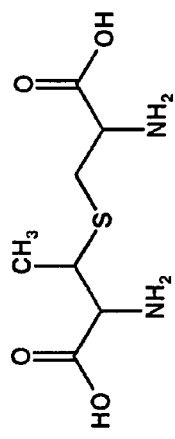 β-methyllanthionine Abu-S-Ala
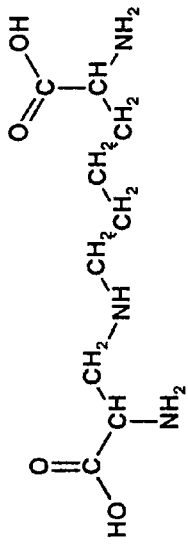 Lysinoalanine Ala-NH-Lys
FIG. 13Q R= OH, as in cidofovir, or labile hydrophobic group

FIG. 18A

3G4-2BVH original sequence:

```
                              M   G   W   T   W   I   F   I   L   I   L   S   V
121                          ATG GGA TGG ACC TGG ATC TTT ATT TTA ATC CTG TCA GTA
                             TAC CCT ACC TGG ACC TAG AAA TAA AAT TAG GAC AGT CAT
                                     PvuII
                                     ---------
         T   T   C   V   H   S   E   V   Q   L   Q   Q   S   G   P   E   L   E   K   P
181     ACT ACA GGT GTC CAC TCT GAG GTC CAG CTG CAG CAG TCT GGA CCT GAG CTG GAG AAG CCT
        TGA TGT CCA CAG GTG AGA CTC CAG GTC GAC GTC GTC AGA CCT GGA CTC GAC CTC TTC GGA
         G   A   S   V   K   L   S   C   K   A   S   G   Y   S   F   T   G   Y   N   M
241     GGC GCT TCA GTG AAG CTA TCC TGC AAG GCT TCT GGT TAC TCA TTC ACT GGC TAC AAC ATG
        CCG CGA AGT CAC TTC GAT AGG ACG TTC CGA AGA CCA ATG AGT AAG TGA CCG ATG TTG TAC
         N   W   V   K   Q   S   H   G   K   S   L   E   W   I   G   H   I   D   P   Y
301     AAC TGG GTG AAA CAG AGC CAT GGA AAG AGC CTT GAA TGG ATT GGA CAT ATT GAT CCT TAC
        TTG ACC CAC TTT GTC TCG GTA CCT TTC TCG GAA CTT ACC TAA CCT GTA TAA CTA GGA ATG
         Y   G   D   T   S   Y   N   Q   K   F   R   G   K   A   T   L   T   V   D   K
361     TAT GGT GAT ACT TCC TAC AAC CAG AAG TTC AGG GGC AAG GCC ACA TTG ACT GTA GAC AAA
        ATA CCA CTA TGA AGG ATG TTG GTC TTC AAG TCC CCG TTC CGG TGT AAC TGA CAT CTG TTT
         S   S   S   T   A   Y   M   Q   L   K   S   L   T   S   E   D   S   A   V   Y
421     TCC TCC AGC ACA GCC TAC ATG CAG CTC AAG AGC CTG ACA TCT GAG GAC TCT GCA GTC TAT
        AGG AGG TCG TGT CGG ATG TAC GTC GAG TTC TCG GAC TGT AGA CTC CTG AGA CGT CAG ATA
         Y   C   V   K   G   G   Y   Y   G   H   W   Y   F   D   V   W   G   A   G   T
481     TAC TGT GTA AAG GGG GGT TAC TAC GGG CAC TGG TAC TTC GAT GTC TGG GGC GCA GGG ACC
        ATG ACA CAT TTC CCC CCA ATG ATG CCC GTG ACC ATG AAG CTA CAG ACC CCG CGT CCC TGG
             BstEII
             ---------
         T   V   T   V   S   S   A   T   T   T   A   P   S   V   Y   P   L   V   P
541     ACG GTC ACC GTC TCC TCA GCT ACA ACA ACA GCC CCA TCT GTC TAT CCC TTG GTC CCG GGC
        TGC CAG TGG CAG AGG AGT CGA TGT TGT TGT CGG GGT AGA CAG ATA GGG AAC CAG GGC CCG
             BamHI                    EcoRI                                    XhoI
             ---------                ---------                                ---------
601     GGA TCC CCC GGG CTG CAG GAA TTC GAT ATC AAG CTT ATC GAT ACC GTC GAC CTC GAG GGG
        CCT AGG GGG CCC GAC GTC CTT AAG CTA TAG TTC GAA TAG CTA TGG CAG CTG GAG CTC CCC
```

The RACE product 3G4-2BVH is cloned and grafted onto the human γ1 constant region at the BstEII site. Thus, it contains the mouse leader sequence and its VH is joined with the human CH1 sequence in the following way: leader/3G4VH/VSS-AST...

```
          Mouse Leader        ↓mature protein
     1  MGWTWIFILI  LSVTTGVHSE  VQLQQSGPEL  EKPGASVKLS  CKASGYSFTG
    51  YNMNWVKQSH  GKSLEWIGHI  DPYYGDTSYN  QKFRGKATLT  VDKSSSTAYM
                                                 ↓BstEII graft site
   101  QLKSLTSEDS  AVYYCVKGGY  YGHWYFDVWG  AGTTVTVSS   ASTKGPSVFPL
   151  APSSKSTSG                                     ↑human γ1CH1
```

FIG. 18B

3G4-2BVL original sequence:

```
                                                                      M   D   M   R   A
 61                                                                  ATG GAC ATG AGG GCT
                                                                     TAC CTG TAC TCC CGA
       P   A   Q   I   L   G   F   L   L   L   F   P   G   T   R   C   D   I   Q
121   CCT GCA CAG ATT TTG GGC TTC TTG TTG CTC TTG TTT CCA GGT ACC AGA TGT GAC ATC CAG
      GGA CGT GTC TAA AAC CCG AAG AAC AAC GAG AAC AAA GGT CCA TGG TCT ACA CTG TAG GTC
       M   T   Q   S   P   S   S   L   S   A   S   L   G   E   R   V   S   L   T   C
181   ATG ACC CAG TCT CCA TCC TCC TTA TCT GCC TCT CTG GGA GAA AGA GTC AGT CTC ACT TGT
      TAC TGG GTC AGA GGT AGG AGG AAT AGA CGG AGA GAC CCT CTT TCT CAG TCA GAG TGA ACA
       R   A   S   Q   D   I   G   S   S   L   N   W   L   Q   Q   G   P   D   G   T
241   CGG GCA AGT CAG GAC ATT GGT AGT AGC TTA AAC TGG CTT CAG CAG GGA CCA GAT GGA ACT
      GCC CGT TCA GTC CTG TAA CCA TCA TCG AAT TTG ACC GAA GTC GTC CCT GGT CTA CCT TGA
       I   K   R   L   I   Y   A   T   S   S   L   D   S   G   V   P   K   R   F   S
301   ATT AAA CGC CTG ATC TAC GCC ACA TCC AGT TTA GAT TCT GGT GTC CCC AAA AGG TTC AGT
      TAA TTT GCG GAC TAG ATG CGG TGT AGG TCA AAT CTA AGA CCA CAG GGG TTT TCC AAG TCA
       G   S   R   S   G   S   D   Y   S   L   T   I   S   S   L   E   S   E   D   F
361   GGC AGT AGG TCT GGG TCA GAT TAT TCT CTC ACC ATC AGC AGC CTT GAG TCT GAA GAT TTT
      CCG TCA TCC AGA CCC AGT CTA ATA AGA GAG TGG TAG TCG TCG GAA CTC AGA CTT CTA AAA
       V   D   Y   Y   C   L   Q   Y   V   S   S   P   P   T   F   G   A   G   T   K
421   GTA GAC TAT TAC TGT CTA CAA TAT GTT AGT TCT CCT CCC ACG TTC GGT GCT GGG ACC AAG
      CAT CTG ATA ATG ACA GAT GTT ATA CAA TCA AGA GGA GGG TGC AAG CCA CGA CCC TGG TTC
                                                                BbsI              BamHI
                                                                ----              -----
       L   E   L   K   R   A   D   A   A   P   T   V   F   I   F   G   R   I   P
481   CTG GAG CTG AAA CGG GCT GAT GCT GCA CCA ACT GTC TTC ATC TTC GGG CGG ATC CCC CGG
      GAC CTC GAC TTT GCC CGA CTA CGA CGT GGT TGA CAG AAG TAG AAG CCC GCC TAG GGG GCC
```

The RACE product 3G4-2BVL is grafted to human κ constant region at the BbsI site. Thus, it contains the mouse leader sequence and its VL is joined withIN the human CL1 sequence in the following way: leader/3G4-VL/TVF-IFP...

```
          Mouse Leader         ↓mature protein
  1    MDMRAPAQIL  GFLLLLFPGT  RCDIQMTQSP  SSLSASLGER  VSLTCRASQD
 51    IGSSLNWLQQ  GPDGTIKRLI  YATSSLDSGV  PKRFSGSRSG  SDYSLTISSL
                                   FR4↓                 ↓BbsI graft site
101    ESEDFVDYYC  LQYVSSPPTF  GAGTKLELKR  ADAAPTVF    IFPPSDEQLKSGTAS
                                                      ↑ human kappa constant
```

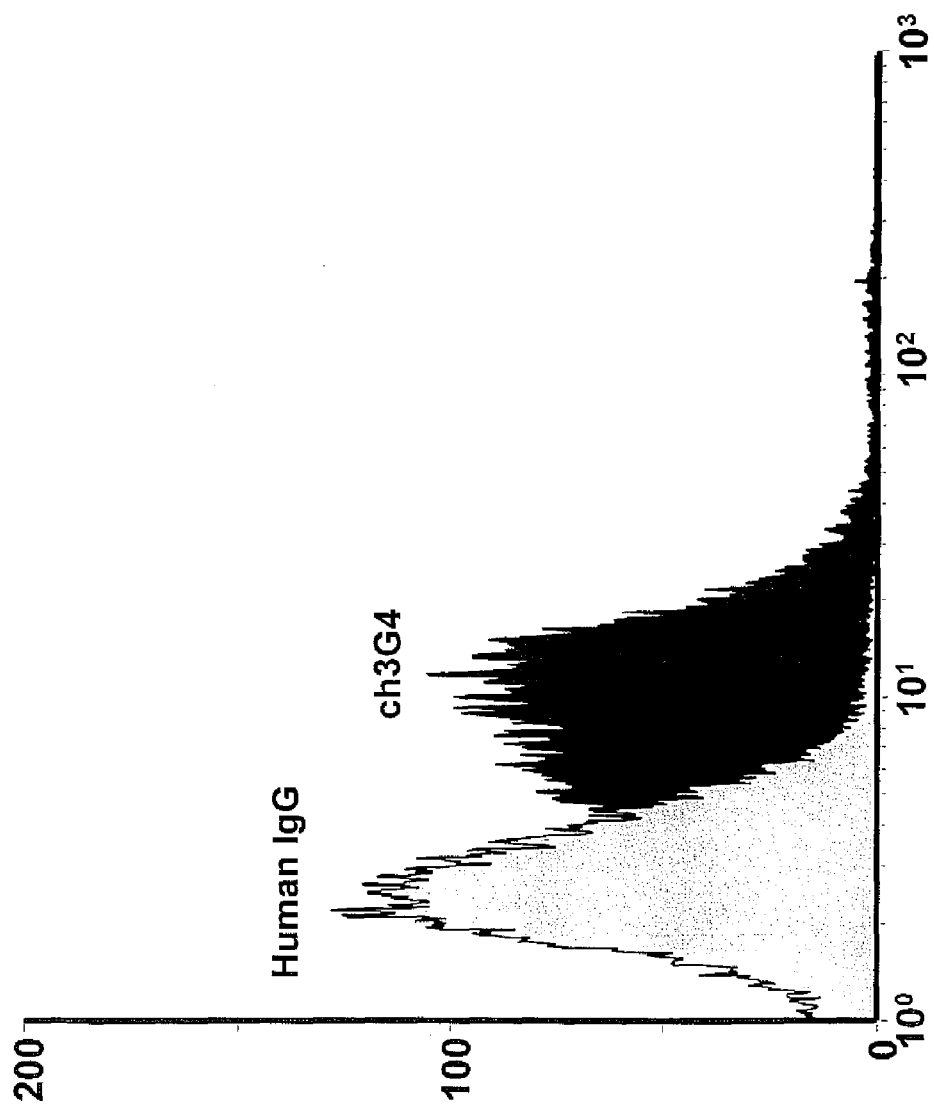

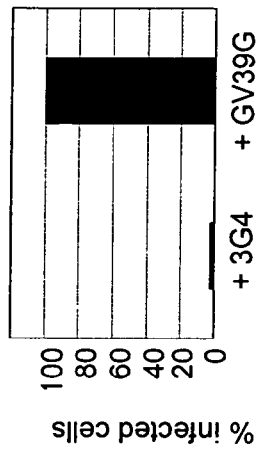
FIG. 30D
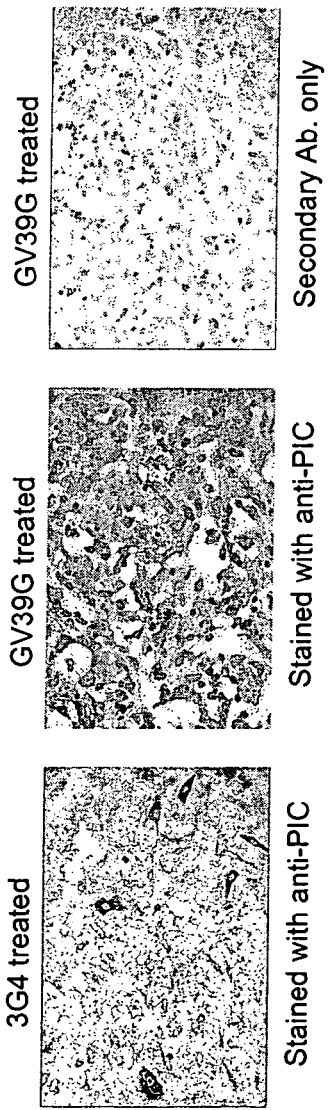
FIG. 30C
FIG. 30B
FIG. 30A

LIPOSOMES COMPRISING DURAMYCIN AND ANTI-VIRAL AGENTS

The present application is a continuation of U.S. application Ser. No. 10/642,064, filed Aug. 15, 2003, which as U.S. Pat. No. 7,678,386 on Mar. 16, 2010; which is a continuation-in-part of U.S. application Ser. No. 10/621,269, filed Jul. 15, 2003, which issued as U.S. Pat. No. 7,572,442 on Aug. 11, 2009; which claims priority to U.S. provisional application Ser. No. 60/396,263, filed Jul. 15, 2002, the disclosures of which applications, including the specification, claims, drawings and sequences, are specifically incorporated herein by reference without disclaimer.

BACKGROUND OF THE INVENTION

1. Field of the Invention

The present invention relates to the fields of aminophospholipid and anionic phospholipid biology, tumor blood vessels and viral infections. It provides surprising new compositions, methods and combinations for tumor vasculature targeting and cancer treatment, for inhibiting viral entry and spread and for treating viral infections. The invention further provides a number of preferred antibody, immunoconjugate and duramycin-based compositions that bind and inhibit aminophospholipids and anionic phospholipids for use in the treatment of cancer, viral infections and related diseases.

2. Description of the Related Art

Tumor cell resistance to chemotherapeutic agents represents a significant problem in clinical oncology. Another major problem to address in tumor treatment is the desire for a "total cell kill", i.e., killing all so-called "clonogenic" malignant cells that have the ability to grow uncontrolled and replace any tumor mass that might be removed by the therapy. Despite certain advances in the field, these are two of the main reasons why many prevalent forms of human cancer still resist effective chemotherapeutic intervention.

Due to the goal of developing treatments that approach a total cell kill, certain types of tumors have been more amenable to therapy than others. For example, the soft tissue tumors, e.g., lymphomas, and tumors of the blood and blood-forming organs, e.g., leukemias, have generally been more responsive to chemotherapeutic therapy than have solid tumors, such as carcinomas.

One reason for the susceptibility of soft and blood-based tumors to chemotherapy is the greater accessibility of lymphoma and leukemic cells to chemotherapeutic intervention. Simply put, it is much more difficult for most chemotherapeutic agents to reach all of the cells of a solid tumor mass than it is the soft tumors and blood-based tumors, and therefore much more difficult to achieve a total cell kill. Increasing the dose of chemotherapeutic agents most often results in toxic side effects, which generally limits the effectiveness of conventional anti-tumor agents.

Another tumor treatment strategy is the use of an "immunotoxin", in which an anti-tumor cell antibody is used to deliver a toxin to the tumor cells. However, in common with chemotherapeutic approaches, immunotoxin therapy also suffers from significant drawbacks when applied to solid tumors. For example, antigen-negative or antigen-deficient cells can survive and repopulate the tumor or lead to further metastases. A further reason for solid tumor resistance to antibody-based therapies is that the tumor mass is generally impermeable to macromolecular agents such as antibodies and immunotoxins. Both the physical diffusion distances and the interstitial pressure within the tumor are significant limitations to this type of therapy.

An improved treatment strategy is to target the vasculature of solid tumors. Targeting the blood vessels of the tumors, rather than the tumor cells themselves, has certain advantages in that it is not likely to lead to the development of resistant tumor cells, and that the targeted cells are readily accessible. Moreover, destruction of the blood vessels leads to an amplification of the anti-tumor effect, as many tumor cells rely on a single vessel for their oxygen and nutrients. Exemplary vascular targeting agents (VTAs) are described in U.S. Pat. Nos. 5,855,866, 5,965,132, 6,261,535, 6,051,230 and 6,451,312, which describe the targeted delivery of anti-cellular agents and toxins to markers of tumor vasculature.

Another effective version of the vascular targeting approach is to target a coagulation factor to a marker expressed or adsorbed within the tumor vasculature or stroma (Huang et al., 1997; U.S. Pat. Nos. 6,093,399, 6,004,555, 5,877,289, and 6,036,955). The delivery of coagulants, rather than toxins, to tumor vasculature has the further advantages of reduced immunogenicity and even lower risk of toxic side effects. As disclosed in U.S. Pat. No. 5,877,289, a preferred coagulation factor for use in such tumor-specific "coaguligands" is a truncated version of the human coagulation-inducing protein, Tissue Factor (TF), the major initiator of blood coagulation.

Recently, the aminophospholipids phosphatidylserine (PS) and phosphatidylethanolamine (PE) were identified as specific markers of tumor vasculature (Ran et al., 1998). This led to the development of new anti-PS and anti-PE immunoconjugates for delivering anti-cellular agents, toxins and coagulation factors to tumor blood vessels (U.S. Pat. No. 6,312,694). In addition, it was discovered that unconjugated antibodies to PS and PE exerted an anti-cancer effect without attachment to a therapeutic agent, which became known as the aminophospholipid "naked antibody" approach to tumor vascular targeting and treatment (U.S. Pat. No. 6,406,693).

Although the foregoing immunoconjugate and aminophospholipid vascular targeting methods represent significant advances in tumor treatment, certain peripheral tumor cells can survive the widespread tumor destruction caused by such therapies. Anti-angiogenic strategies, which inhibit the development of new vasculature from preexisting blood vessels and/or circulating endothelial stem cells, are therefore contemplated for use in combination with the VTA, coaguligand and aminophospholipid targeting methods of U.S. Pat. Nos. 5,855,866, 6,093,399, 6,312,694 and 6,406,693.

Angiogenesis plays an important role in physiological processes, such as embryogenesis, wound healing and menstruation, but is also involved in certain pathological events, such as in tumor growth, arthritis, psoriasis and diabetic retinopathy (Ferrara, 1995). As applied to tumor treatment, anti-angiogenic strategies are based upon inhibiting the proliferation of budding vessels, generally at the periphery of a solid tumor. These therapies are mostly applied to reduce the risk of micrometastasis or to inhibit further growth of a solid tumor after more conventional intervention (such as surgery or chemotherapy).

U.S. Pat. Nos. 6,342,219, 6,524,583, 6,342,221 and 6,416,758 describe antibodies and immunoconjugates that bind to vascular endothelial growth factor-A (VEGF, formerly known as vascular permeability factor, VPF), a primary stimulant of angiogenesis. These antibodies have the important advantage of inhibiting VEGF binding to only one of the two primary VEGF receptors. By blocking VEGF binding to VEGFR2, but not VEGFR1, these antibodies have an improved safety profile, maintaining beneficial effects mediated via VEGFR1, e.g. in macrophage, osteoclast and chondroclast functions.

Although the foregoing methods have advanced the art of tumor treatment, the development of additional or alternative vascular targeting therapies is still sought. The identification of new markers of tumor vasculature is needed to expand the number of therapeutic options. The development of new naked antibodies with anti-cancer properties would be a particularly important advance, as this permits the same targeting moiety to be used both as a single-agent therapeutic and as a vascular targeting agent for the delivery of other drugs. Therapeutic agents that have both anti-angiogenic and anti-vascular, i.e., tumor destructive, properties within the same molecule would be of great value. An even more important advance would be the identification of a class of therapeutic agents with anti-cancer properties and therapeutic effects in other systems. The development of agents capable of treating both cancer and viral infections, two of the most significant medical challenges of this era, would be a remarkable and important breakthrough.

SUMMARY OF THE INVENTION

The present invention addresses the foregoing and other needs of the prior art by providing new methods and compositions for safe and effective tumor vascular targeting, anti-angiogenesis and tumor destruction, which methods and compositions are also surprisingly effective in inhibiting viral entry, replication and spread and for treating viral infections and diseases. The invention is based, in part, on surprising discoveries concerning the expression and role of anionic phospholipids in tumor vasculature and the involvement of aminophospholipids and anionic phospholipids in viral entry, replication and spread. The present invention further provides particularly advantageous antibodies and immunoconjugates that bind to aminophospholipids and anionic phospholipids, and a new class of peptide-based derivatives that bind to phosphatidylethanolamine.

Overview: In a first overall embodiment, the invention provides new methods for tumor vascular targeting, tumor imaging and treatment based upon the unexpected finding that anionic phospholipids, such as phosphatidylinositol (PI), phosphatidic acid (PA) and phosphatidylglycerol (PG), (as well as phosphatidylserine, PS), are accessible and stably targetable markers of tumor vasculature. This embodiment arose from the unexpected discovery that antibodies against PA, PI, PG, and other anionic phospholipid components, specifically localize to the vasculature of solid tumors.

Further aspects within this embodiment were developed from the unexpected discovery that naked antibodies against anionic phospholipids, such as PA, PI and PG (as well as PS), specifically inhibit tumor blood vessel angiogenesis and induce tumor vasculature destruction and tumor necrosis in vivo in the absence of conjugation to effector molecules, such as toxins or coagulants. The invention thus provides safe and effective methods of vascular targeting, anti-angiogenesis and tumor treatment using single component antibody-based therapeutics that bind to anionic phospholipids.

An underlying surprising feature of the invention is that translocation of anionic phospholipids to the surface of tumor vascular endothelial cells occurs, at least in a significant part, independently of cell damage and apoptotic or other cell-death mechanisms. Anionic phospholipid expression in tumor vasculature is therefore not a consequence of, or a trigger for, cell death and destruction, but occurs on morphologically intact vascular endothelial cells. This means that anionic phospholipid expression on tumor vasculature is not transient, but rather is stable enough to provide a target for therapeutic intervention.

Given the finding that anionic phospholipids are stably induced in tumor vasculature, the invention further provides a range of new methods and compositions for tumor vasculature imaging and destruction using immunoconjugates of antibodies against anionic phospholipids. These immunoconjugates comprise antibodies against anionic phospholipids that are operatively attached to therapeutic agents, such as toxins and coagulants, and are useful in the specific delivery of diagnostics and therapeutics to the surface of tumor vascular endothelial cell membranes. The therapeutic agents are delivered in intimate contact with the tumor vascular endothelial cell membrane, allowing either rapid entry into the target cell or rapid association with effector cells, components of the coagulation cascade, and such like In a second overall embodiment, the invention provides a number of preferred antibodies that bind to aminophospholipids and anionic phospholipids (and related immunoconjugates and compositions), which antibodies have structures and properties that provide advantages over those known in the art. These so-called "second generation" or improved antibodies will preferably be used in the anti-angiogenic, anti-cancer and anti-viral and other treatment methods disclosed herein.

The new classes of antibodies that bind to aminophospholipids and anionic phospholipids provided by the present invention overcome various drawbacks in the prior art by providing therapeutic antibodies without the pathogenic properties usually associated with antibodies to aminophospholipids and anionic phospholipids in the art. The invention was developed, in part, using new immunization and screening techniques developed from the inventors' unique observations on phospholipid behaviour in tumor vascular endothelial cells, and distancing the antibodies generated from anti-phospholipid antibodies associated with disease. Such antibodies not only have unique properties and improved safety, but are equally or more effective than existing antibodies in comparative studies. The compositions and methods of these aspects of invention also extend to the use of immunoconjugates and combinations, using the specific category of antibodies provided.

Prior to the present invention, antibodies that bind to aminophospholipids and anionic phospholipids and have the properties of the new antibodies disclosed herein were not known. However, in light of the invention disclosed herein, the art is now provided with the methodology for generating new candidate antibodies and with the techniques to test such antibodies to identify further useful antibodies from the pool of candidates. In light of this invention, therefore, a range of antibodies with advantageous properties and aminophospholipid and anionic phospholipid binding profiles can be made that do not suffer from the notable drawbacks and side effects associated with the prior art antibodies. Such antibodies can thus be used in a variety of embodiments, including in the inhibition of angiogenesis and the treatment of cancer and viral infections.

In addition to the new immunization and screening techniques provided herein, antibodies that bind to aminophospholipids and anionic phospholipids and have a number of advantageous properties can now be identified by competition and/or functional assays using the monoclonal antibodies 1B9, 1B12, 3B10, 2G7, 7C5, 9D2 or 3G4. Currently, the 1B12, 3B10, 9D2 and 3G4 antibodies are preferred, as these antibodies do not require serum for phospholipid binding. The monoclonal antibodies 9D2 and 3G4 are more preferred, with monoclonal antibody 3G4 (ATCC 4545) currently being the most preferred. To identify additional antibodies that compete with any of the foregoing antibodies, preferably 3G4, the preferred assays are currently competition assays based upon an ELISA, a number of which are described herein, and working examples of which are disclosed.

In a third overall embodiment, the present invention provides a new class of cell-impermeant peptide-based derivatives that bind to the aminophospholipid, phosphatidylethanolamine (PE). These "PE-binding peptide derivatives" comprise at least a first PE-binding peptide, preferably duramycin, which has been modified to substantially prevent non-specific toxicity, preferably by modifying the PE-binding peptide, preferably duramycin, to form a substantially cell impermeant or substantially non-pore forming PE-binding construct.

The generation of a "substantially cell impermeant" or "substantially non-pore forming" PE-binding construct or duramycin is preferably achieved by attaching the PE-binding peptide or duramycin to at least a first cell impermeant group, preferably a group that prevents clustering of the PE-binding peptide or duramycin. The synthesis of a number of exemplary duramycin derivatives is described herein. The "cell impermeant group or groups" may be small molecules, inert carriers, or may themselves be targeting agents that impart a further targeting function to the resultant construct, such as targeting to tumor vasculature. Thus, the PE-binding peptide can be the sole targeting agent linked to an inert carrier, or can be one of two agents that each impart a targeting function to the construct. Additionally, PE-binding peptides, preferably duramycin, are operatively attached to effectors, such that the PE-binding peptide or duramycin provides the targeting function and the attached agent has a substantial therapeutic effect once delivered to the target cell. Preferred examples are PE-binding peptides or duramycin linked to anti-viral agents, such as nucleosides.

As PE is essentially absent from the surface of normal cells under normal conditions, the substantially cell impermeant PE-binding peptides of the present invention function to selectively bind to PE at the surface of aberrant cells or cells associated with disease, such as tumor vascular endothelial cells, proliferating and/or virally infected cells. Upon binding to such aberrant target cells, the PE-binding constructs or derivatives inhibit or interrupt PE functions in those cells, thus resulting in an overall therapeutic benefit, e.g., in the treatment of tumors and/or viral diseases. The successful use of substantially cell impermeant PE-binding peptides in inhibiting viral entry and spread is disclosed herein. In embodiments where the PE-binding peptides are attached to anti-viral agents, such as cidofovir, enhanced and safer anti-viral treatment is provided.

In a fourth overall embodiment, the invention further provides an important new class of compositions and methods for inhibiting viral replication, infection and spread for use in treating viral infections and diseases. These methods are based on the surprising insight that antibodies and peptides that bind to aminophospholipids and anionic phospholipids, such as PS, PE, PI, PA and PG, particularly PS and PE, would be safe and effective anti-viral agents. Not only has this insight proven to be correct, but the present invention provides data showing the unexpectedly effective use of antibodies and peptides that bind to aminophospholipids and anionic phospholipids in combating viral spread, meaning that these agents are broadly applicable in the treatment of a range of viral infections and associated diseases.

These discoveries further encompass new categories of immunoconjugates, compositions, kits and methods of use in which an antibody to an aminophospholipid or anionic phospholipid, particularly PS and PE, is operatively attached to an anti-viral agent. The substantially cell impermeant PE-binding peptide derivatives, such as the duramycin peptide derivatives, may also be linked to anti-viral agents. Each of these agents thus provide new anti-viral drugs uniquely targeted to virally infected cells.

The development of new safe, therapeutic agents effective in the treatment of aberrant angiogenesis, cancer and viral infections and diseases is thus a breakthrough in the art.

Although uniquely effective, the various methods and compositions of the present invention can also be used to advantage in combination with other therapies and agents to provide combined treatment methods, and related compositions, pharmaceuticals and kits of the invention. In a fifth overall embodiment, therefore, the invention further provides particular combined compositions, methods and kits, e.g. for cancer treatment, which have been selected and discovered to work surprisingly well together, as explained in more detail herein.

Second Generation Antibodies: Certain methods discovered to function well in the generation of antibodies with the sought properties are described herein in Example IV and embodied in the pending claims. These methods permitted the generation of the advantageous antibodies of the invention as exemplified by the monoclonal antibodies 1B9, 1B12, 3B10, 2G7, 7C5, 9D2 and 3G4, particularly 3G4 (ATCC 4545).

The present invention thus provides purified antibodies, antigen-binding fragments and immunoconjugates thereof, which bind to at least one aminophospholipid or anionic phospholipid, preferably PS, and that effectively compete with the monoclonal antibody 1B9, 1B12, 3B10, 2G7, 7C5, 9D2 or 3G4, preferably with 9D2 or 3G4 (ATCC 4545), and most preferably with 3G4, for binding to the aminophospholipid or anionic phospholipid, preferably PS.

As used throughout the entire application, the terms "a" and "an" are used in the sense that they mean "at least one", "at least a first", "one or more" or "a plurality" of the referenced components or steps, except in instances wherein an upper limit is thereafter specifically stated. Therefore, an "antibody", as used herein, means "at least a first antibody". The operable limits and parameters of combinations, as with the amounts of any single agent, will be known to those of ordinary skill in the art in light of the present disclosure.

In certain aspects, the antibodies will effectively compete with the monoclonal antibody 1B9, 1B12, 3B10, 2G7, 7C5, 9D2 or 3G4, preferably with 9D2 or 3G4, and most preferably with 3G4 (ATCC 4545), for binding to an aminophospholipid or anionic phospholipid, preferably PS, or will have the aminophospholipid or anionic phospholipid binding profile of the monoclonal antibody 1B9, 1B12, 3B10, 2G7, 7C5, 9D2 or 3G4, preferably of 9D2 or 3G4, and most preferably of 3G4, as set forth in Table 4; and will not be serum dependent, i.e., will not require serum to bind to the aminophospholipid or anionic phospholipid; not be derived from a patient with a disease, and will not significantly inhibit coagulation reactions in vitro, cause significant thrombosis in vivo or have lupus anticoagulant activities.

Preferably, such antibodies will also demonstrate an improvement in structural properties or in the range or degree of advantageous functional properties in controlled studies in comparison to an antibody in the literature, such as being IgG, having a higher affinity or demonstrating enhanced binding to activated endothelial cells, increased inhibition of endothelial cell proliferation or angiogenesis, improved tumor blood vessel localization, anti-cancer and/or anti-viral effects.

Particular aspects of the invention are therefore based on the inventors' original, surprising generation of antibodies having the foregoing, other disclosed and inherent advantageous properties. Now that a panel of preferred antibodies, and a number of particularly preferred antibodies, have been provided, the present invention further encompasses a class of antibodies of defined epitope-specificity, wherein such antibodies, or antigen-binding fragments thereof, effectively compete with the monoclonal antibody 1B9, 1B12, 3B10, 2G7, 7C5, 9D2 or 3G4, preferably with 9D2 or 3G4, and most preferably with 3G4 (ATCC 4545), for antigen binding, such that they bind to essentially the same epitope as the monoclonal antibody 1B9, 1B12, 3B10, 2G7, 7C5, 9D2 or 3G4, preferably with 9D2 or 3G4, and most preferably with 3G4 (ATCC 4545).

The invention as claimed is enabled in accordance with the present specification and readily available technological references, know-how and starting materials. Nonetheless, on behalf of the present Applicant, Board of Regents, The University of Texas System, samples of the hybridoma cell line producing the 3G4 monoclonal antibody were submitted for deposit with the American Type Culture Collection (ATCC), 10801 University Blvd., Manassas, Va. 20110-2209, U.S.A. The samples were submitted by Avid Biosciences, Inc., 14272 Franklin Avenue, Tustin, Calif. 92780, U.S.A., a subsidiary of the licensee, Peregrine Pharmaceuticals, Inc., during the week beginning Jul. 8, 2002, were received on July 10 and Jul. 12, 2002, shown to be viable, and given ATCC Accession number PTA 4545 on Jul. 30, 2002.

This deposit was made under the provisions of the Budapest Treaty on the International Recognition of the Deposit of Microorganisms for the Purposes of Patent Procedure and the regulations thereof (Budapest Treaty). The hybridoma will be made available by the ATCC under the terms of the Budapest Treaty upon issue of a U.S. patent with pertinent claims. Availability of the deposited hybridoma is not to be construed as a license to practice the invention in contravention of the rights granted under the authority of any government in accordance with its patent laws.

In light of the panel of antibodies, the preferred antibodies and the techniques disclosed herein and known in the art, those of ordinary skill in the art are now provided with a new class antibodies that bind to aminophospholipids or anionic phospholipids and have advantageous properties. These antibodies are "like" or "based on" the monoclonal antibodies 1B9, 1B12, 3B10, 2G7, 7C5, 9D2 or 3G4. Preferably, the antibodies of the invention are "9D2-based or 9D2-like antibodies", and most preferably, the antibodies of the invention are "3G4-based or 3G4-like antibodies". The following description of "like" antibodies is provided in terms of the 3G4 antibody (ATCC 4545) for simplicity, but is specifically incorporated herein by reference as applicable to each of the 1B9, 1B12, 3B10, 2G7, 7C5 and 9D2 antibodies.

A 3G4-like antibody is an antibody, or antigen-binding fragment thereof, that binds to substantially the same epitope as the monoclonal antibody 3G4 (ATCC 4545) or that binds to at least a first aminophospholipid or anionic phospholipid, preferably PS, at essentially the same epitope as the monoclonal antibody 3G4 (ATCC 4545). Preferably, the antibody, or antigen-binding fragment thereof, will bind to the same epitope as the monoclonal antibody 3G4 (ATCC 4545).

The terms "that bind to about, substantially or essentially the same, or the same, epitope as" the monoclonal antibody 3G4 (ATCC 4545) mean that an antibody "cross-reacts" with the monoclonal antibody 3G4 (ATCC 4545). "Cross-reactive antibodies" are those that recognize, bind to or have immunospecificity for substantially or essentially the same, or the same, epitope, epitopic site or common aminophospholipid or anionic phospholipid epitope as the monoclonal antibody 3G4 (ATCC 4545) such that are able to effectively compete with the monoclonal antibody 3G4 (ATCC 4545) for binding to at least one aminophospholipid or anionic phospholipid, more than one aminophospholipid or anionic phospholipid or to all aminophospholipid or anionic phospholipids to which the monoclonal antibody 3G4 (ATCC 4545) binds. "3G4-cross-reactive antibodies" are succinctly termed "3G4-like antibodies" and "3G4-based antibodies", and such terms are used interchangeably herein and apply to compositions, uses and methods.

The identification of one or more antibodies that bind(s) to about, substantially, essentially or at the same epitope as the monoclonal antibody 3G4 (ATCC 4545) is a straightforward technical matter now that 3G4, with its advantageous properties, has been provided. As the identification of cross-reactive antibodies is determined in comparison to a reference antibody, it will be understood that actually determining the epitope to which the reference antibody (3G4) and the test antibody bind is not in any way required in order to identify an antibody that binds to the same or substantially the same epitope as the monoclonal antibody 3G4. However, considerable information on the epitope bound by 3G4 is included herein and epitope mapping can be further performed.

The identification of cross-reactive antibodies can be readily determined using any one of variety of immunological screening assays in which antibody competition can be assessed. All such assays are routine in the art and are further described herein in detail. Each of U.S. Pat. Nos. 6,342,219, 6,342,221, 6,524,583, and 6,416,758 are specifically incorporated herein by reference for purposes including even further supplementing the present teaching concerning how to make antibodies that bind to the same or substantially or essentially the same epitope as a given antibody, such as 3G4, or that effectively compete with a given antibody for binding to an antigen.

For example, where the test antibodies to be examined are obtained from different source animals, or are even of a different isotype, a simple competition assay may be employed in which the control (3G4) and test antibodies are admixed (or pre-adsorbed) and applied to an aminophospholipid or anionic phospholipid antigen composition, preferably PS. By "aminophospholipid or anionic phospholipid antigen composition" is meant any composition that contains a 3G4-binding antigen as described herein, such as described in Table 4. Thus, protocols based upon ELISAs and Western blotting are suitable for use in such simple competition studies.

In certain embodiments, one would or pre-mix the control antibodies (3G4) with varying amounts of the test antibodies (e.g., 1:10 or 1:100) for a period of time prior to applying to an antigen composition. In other embodiments, the control and varying amounts of test antibodies can simply be admixed during exposure to the antigen composition. In any event, by using species or isotype secondary antibodies one will be able to detect only the bound control antibodies, the binding of which will be reduced by the presence of a test antibody that recognizes substantially the same epitope.

In conducting an antibody competition study between a control antibody and any test antibody (irrespective of species or isotype), one may first label the control (3G4) with a detectable label, such as, e.g., biotin or an enzymatic (or even radioactive) label to enable subsequent identification. In these cases, one would pre-mix or incubate the labeled control antibodies with the test antibodies to be examined at various ratios (e.g., 1:10, 1:100 or 1:1000) and (optionally after a suitable period of time) then assay the reactivity of the labeled control antibodies and compare this with a control value in which no potentially competing test antibody was included in the incubation.

The assay may again be any one of a range of immunological assays based upon antibody hybridization, and the control antibodies would be detected by means of detecting their label, e.g., using streptavidin in the case of biotinylated antibodies or by using a chromogenic substrate in connection with an enzymatic label (such as 3,3',5,5'-tetramethylbenzidine (TMB) substrate with peroxidase enzyme) or by simply detecting a radioactive label. An antibody that binds to the same epitope as the control antibodies will be able to effectively compete for binding and thus will significantly reduce control antibody binding, as evidenced by a reduction in bound label.

The reactivity of the (labeled) control antibodies in the absence of a completely irrelevant antibody would be the control high value. The control low value would be obtained by incubating the labeled (3G4) antibodies with unlabelled antibodies of exactly the same type (3G4), when competition would occur and reduce binding of the labeled antibodies. In a test assay, a significant reduction in labeled antibody reactivity in the presence of a test antibody is indicative of a test antibody that recognizes the same epitope, i.e., one that "cross-reacts" with the labeled (3G4) antibody.

A significant reduction is a "reproducible", i.e., consistently observed, reduction in binding. A "significant reduction" in terms of the present application is defined as a reproducible reduction (in 3G4 binding to one or more aminophospholipid or anionic phospholipids, preferably PS, in an ELISA) of at least about 70%, about 75% or about 80% at any ratio between about 1:10 and about 1:1000. Antibodies with even more stringent cross-blocking activities will exhibit a reproducible reduction (in 3G4 binding to one or more aminophospholipid or anionic phospholipids, preferably PS, in an ELISA or other suitable assay) of at least about 82%, about 85%, about 88%, about 90%, about 92% or about 95% or so at any ratio between about 1:10 and about 1:1000. Complete or near-complete cross-blocking, such as exhibiting a reproducible reduction in 3G4 binding to one or more aminophospholipid or anionic phospholipids of about 97% or about 96% or so, although by no means required to practice the invention, is certainly not excluded.

As to the second generation antibodies overall, the competition may be measured in reference to an antibody that at least binds to phosphatidylserine, wherein the second generation antibody effectively competes for binding to phosphatidylserine; in reference to an antibody that at least binds to phosphatidic acid, wherein the second generation antibody effectively competes for binding to phosphatidic acid; in reference to an antibody that at least binds to phosphatidylinositol, wherein the second generation antibody effectively competes for binding to phosphatidylinositol; in reference to an antibody that at least binds to phosphatidylglycerol, wherein the second generation antibody effectively competes for binding to phosphatidylglycerol; in reference to an antibody that at least binds to cardiolipin, wherein the second generation antibody effectively competes for binding to cardiolipin; and optionally in reference to an antibody that at least binds to phosphatidylethanolamine, wherein the second generation antibody effectively competes for binding to phosphatidylethanolamine.

In certain embodiments, the second generation antibodies may be measured in reference to an antibody that binds to at least a first and second aminophospholipid or anionic phospholipid, and wherein the second generation antibody effectively competes for binding to the first and second aminophospholipid or anionic phospholipid; in reference to an antibody that binds to at least a first, second and third aminophospholipid or anionic phospholipid, and wherein the second generation antibody effectively competes for binding to the first, second and third aminophospholipid or anionic phospholipid; in reference to an antibody that binds to at least a first, second, third and fourth aminophospholipid or anionic phospholipid, and wherein the second generation antibody effectively competes for binding to the first, second, third and fourth aminophospholipid or anionic phospholipid; or in reference to an antibody that binds to at least a first, second, third, fourth and fifth aminophospholipid or anionic phospholipid, and wherein the second generation antibody effectively competes for binding to the first, second, third, fourth and fifth aminophospholipid or anionic phospholipid.

In further embodiments, a second generation antibody may be characterized as an antibody that exhibits significant binding to at least one aminophospholipid or anionic phospholipid, no detectable binding to a choline-containing neutral phospholipid and that effectively competes with a monoclonal antibody of the invention, preferably 3G4 (ATCC 4545).

In particular embodiments, the antibody exhibits significant binding to the anionic phospholipids PS, PA, PI, PG and CL; has a phospholipid binding profile of PS=PA=PI=PG>CL>>PE, wherein > indicates at least 2-fold difference in binding and >> indicates at least 10-fold difference in binding to such phospholipids; exhibits no detectable binding to phosphatidylcholine or sphingomyelin; and effectively competes with the monoclonal antibody 3G4 (ATCC 4545) for binding to each of the anionic phospholipids PS, PA, PI PG and CL.

Preferably, the second generation antibodies will have the foregoing characteristics and also exhibits significant binding to at least one anionic phospholipid present at the cell surface of activated, dividing, injured, apoptotic or virally infected cells. More preferably, the antibody also significantly inhibits the proliferation of dividing endothelial cells without significantly altering quiescent cells, and more preferably, has no significant lupus anticoagulant activities.

Functionally, the second generation antibodies will preferably suppresses angiogenesis, have an anti-tumor effect and an anti-viral effect, preferably in vivo, and more preferably, will do so without causing significant thrombotic complications in animals or patients. Thus, the preferred antibodies possess the combined properties of an anti-angiogenic, anti-tumor vascular, anti-tumor and anti-viral agent.

The invention is exemplified by monoclonal antibody 3G4, produced by hybridoma ATCC 4545, or an antigen-binding fragment of such a monoclonal antibody. A hybridoma that produces a monoclonal antibody that binds to substantially the same epitope as the monoclonal antibody 3G4 (ATCC 4545) is another aspect of the invention.

The invention further provides antibodies that bind to substantially the same epitope as the monoclonal antibody 3G4 (ATCC 4545), prepared by a process comprising immunizing an animal with a composition comprising at least a first immunogenic aminophospholipid or anionic phospholipid, including a composition comprising activated endothelial cells, and selecting from the immunized animal an antibody that substantially cross-reacts with the monoclonal antibody 3G4 (ATCC 4545); and antibodies that bind to substantially the same epitope as the monoclonal antibody 3G4 (ATCC 4545), prepared by a process comprising immunizing an animal with a composition comprising at least a first immunogenic aminophospholipid or anionic phospholipid, including a composition comprising activated endothelial cells, and selecting a competing antibody from the immunized animal by identifying an antibody that substantially reduces the binding of the 3G4 (ATCC 4545) antibody to at least a first aminophospholipid or anionic phospholipid, preferably PS.

In the following descriptions of the compositions, immunoconjugates, pharmaceuticals, combinations, cocktails, kits, first and second medical uses and all methods in accordance with this invention, the terms "antibody" and "immunoconjugate", or an antigen-binding region thereof, unless otherwise specifically stated or made clear from the scientific terminology, refer to a range of anti-aminophospholipid or anti-anionic phospholipid antibodies as well as to specific 3G4-cross-reactive antibodies.

The terms "antibody" and "immunoglobulin", as used herein, refer broadly to any immunological binding agent, including polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. The heavy-chain constant domains that correspond to the difference classes of immunoglobulins are termed α, δ, ε, γ and μ, respectively. The subunit structures and three-dimensional configurations of different classes of immunoglobulins are well known.

Generally, where antibodies rather than antigen binding regions are used in the invention, IgG and/or IgM are preferred because they are the most common antibodies in the physiological situation and because they are most easily made in a laboratory setting. The "light chains" of mammalian antibodies are assigned to one of two clearly distinct types: kappa (κ) and lambda (λ), based on the amino acid sequences of their constant domains. There is essentially no preference to the use of κ or λ light chains in the antibodies of the present invention.

The use of monoclonal antibodies (MAbs) or derivatives thereof is much preferred. MAbs are recognized to have certain advantages, e.g., reproducibility and large-scale production, which makes them suitable for clinical treatment. The invention thus provides monoclonal antibodies of the murine, human, monkey, rat, hamster, rabbit and even frog or chicken origin. Murine, human or humanized monoclonal antibodies will generally be preferred.

As will be understood by those in the art, the immunological binding reagents encompassed by the term "antibody" extend to all antibodies from all species, and antigen binding fragments thereof, including dimeric, trimeric and multimeric antibodies; bispecific antibodies; chimeric antibodies; human and humanized antibodies; recombinant, engineered and camelized (camelised) antibodies, and fragments thereof.

The term "antibody" is thus used to refer to any antibody-like molecule that has an antigen binding region, and this term includes antibody fragments such as Fab', Fab, F(ab')$_2$, single domain antibodies (DABs), Fv, scFv (single chain Fv), linear antibodies, diabodies, camelized antibodies and the like. The techniques for preparing and using various antibody-based constructs and fragments are well known in the art (see Kabat et al., 1991, specifically incorporated herein by reference). Diabodies, in particular, are further described in EP 404,097 and WO 93/11161, each specifically incorporated herein by reference; whereas linear antibodies are further described in Zapata et al. (1995), specifically incorporated herein by reference.

The antibodies of the invention include those that bind to phosphatidylserine and comprises at least one CDR of an antibody provided herein, preferably the 9D2 or 3G4 (ATCC 4545) antibody. For example, the invention provides antibodies that bind to phosphatidylserine and comprise at least one CDR from the monoclonal antibody 3G4 produced by the hybridoma deposited as ATCC PTA 4545; or at least one CDR that has the amino acid sequence of SEQ ID NO:2 or SEQ ID NO:4, or a variant or mutagenized form of the amino acid sequence of SEQ ID NO:2 or SEQ ID NO:4, wherein such a variant or mutagenized form maintains binding to phosphatidylserine.

Certain antibodies thus comprise at least one CDR from the variable regions of each of the heavy and light chains of monoclonal antibody 3G4 (ATCC 4545), at least one CDR1-3 of the monoclonal antibody 3G4 (ATCC 4545), or CDR1-3 of the variable regions of each of the heavy and light chains of monoclonal antibody 3G4 (ATCC PTA 4545). Other antibodies comprise at least a first variable region that includes an amino acid sequence region having the amino acid sequence of SEQ ID NO:2 or SEQ ID NO:4, as exemplified by variable regions that include an amino acid sequence region encoded by the nucleic acid sequences of SEQ ID NO:1 or SEQ ID NO:3. Such sequences are the sequences of Vh and Vκ of the 3G4 ScFv encompassing CDR1-3 (complementarity determining regions) of the variable regions of the heavy and light chains.

In certain embodiments, second generation antibodies are provided that have enhanced or superior properties in comparison to an original anti-aminophospholipid or anti-anionic phospholipid antibody, such as 3G4 (ATCC 4545). These are exemplified by antibodies that comprise at least one CDR that has a variant or mutagenized form of the amino acid sequence of SEQ ID NO:2 or SEQ ID NO:4, wherein such a variant or mutagenized form maintains binding to phosphatidylserine.

The anti-aminophospholipid or anti-anionic phospholipid antibodies thus include those that comprises at least a first variable region that includes an amino acid sequence region of at least about 75%, more preferably, at least about 80%, more preferably, at least about 85%, more preferably, at least about 90% and most preferably, at least about 95% or so amino acid sequence identity to the amino acid sequence of SEQ ID NO:2 or SEQ ID NO:4; wherein said anti-aminophospholipid or anti-anionic phospholipid antibody at least substantially maintains the biological properties of the anti-aminophospholipid or anti-anionic phospholipid antibodies of the present invention, as exemplified by the 3G4 antibody.

Identity or homology with respect to these and other anti-aminophospholipid or anti-anionic phospholipid antibody sequences of the present invention is defined herein as the percentage of amino acid residues in a candidate sequence that are identical to the sequences of SEQ ID NO:2 or SEQ ID NO:4, or to the sequence of another anti-aminophospholipid or anti-anionic phospholipid antibody of the invention, after aligning the sequences and introducing gaps, if necessary, to achieve the maximum percent sequence identity. The maintenance of substantially the same, or even more effective biological properties of the anti-aminophospholipid or anti-anionic phospholipid antibody used for the sequence comparison is particularly important. Such comparisons are easily conducted, e.g., using one or more of the various assays described in detail herein.

In further embodiments, the antibodies employed will be "humanized", part-human or human antibodies. "Humanized" antibodies are generally chimeric monoclonal antibodies from mouse, rat, or other non-human species, bearing human constant and/or variable region domains ("part-human chimeric antibodies"). Various humanized monoclonal antibodies for use in the present invention will be chimeric antibodies wherein at least a first antigen binding region, or complementarity determining region (CDR), of a mouse, rat or other non-human monoclonal antibody is operatively attached to, or "grafted" onto, a human antibody constant region or "framework".

"Humanized" monoclonal antibodies for use herein may also be monoclonal antibodies from non-human species wherein one or more selected amino acids have been exchanged for amino acids more commonly observed in human antibodies. This can be readily achieved through the use of routine recombinant technology, particularly site-specific mutagenesis.

Entirely human, rather than "humanized", antibodies may also be prepared and used in the present invention. Such human antibodies may be obtained from healthy subjects by simply obtaining a population of mixed peripheral blood lymphocytes from a human subject, including antigen-presenting and antibody-producing cells, and stimulating the cell population in vitro by admixing with an immunogenically effective amount of an aminophospholipid or anionic phospholipid sample. The human anti-aminophospholipid or anti-anionic phospholipid antibody-producing cells, once obtained, are used in hybridoma and/or recombinant antibody production.

Further techniques for human monoclonal antibody production include immunizing a transgenic animal, preferably a transgenic mouse, which comprises a human antibody library with an immunogenically effective amount of an aminophospholipid or anionic phospholipid sample. This also generates human anti-aminophospholipid or anti-anionic phospholipid antibody-producing cells for further manipulation in hybridoma and/or recombinant antibody production, with the advantage that spleen cells, rather than peripheral blood cells, can be readily obtained from the transgenic animal or mouse.

Antibodies in accordance with the invention may be readily prepared by selecting an antibody that substantially cross-reacts or competes with the monoclonal antibody 9D2 or 3G4 (ATCC PTA 4545). Suitable preparative processes and methods comprise:
 (a) preparing candidate antibody-producing cells; and
 (b) selecting from the candidate antibody-producing cells an antibody that substantially cross-reacts or competes with the monoclonal antibody 9D2 or 3G4 (ATCC PTA 4545).

One process of preparing suitable antibody-producing cells and obtaining antibodies therefrom may be conduced in situ in a given patient. That is, simply providing an immunogenically effective amount of an immunogenic aminophospholipid or anionic phospholipid sample to a patient will result in appropriate antibody generation. Thus, the antibody is still "obtained" from the antibody-producing cell, but it does not have to be isolated away from a host and subsequently provided to a patient, being able to spontaneously localize to the tumor vasculature and exert its biological antitumor effects. However, such embodiments are not currently preferred.

Suitable antibody-producing cells may also be obtained, and antibodies subsequently isolated and/or purified, by stimulating peripheral blood lymphocytes with aminophospholipid or anionic phospholipid in vitro.

Other methods comprise administering to an animal an immunizing composition comprising at least a first immunogenic aminophospholipid or anionic phospholipid component and selecting from the immunized animal an antibody that substantially cross-reacts or competes with the monoclonal antibody 9D2 or 3G4 (ATCC PTA 4545). These methods generally comprise:
 (a) immunizing an animal by administering to the animal at least one dose, and optionally more than one dose, of a composition comprising an immunogenically effective amount of an immunogenic aminophospholipid or anionic phospholipid; and
 (b) obtaining a suitable antibody-producing cell from the immunized animal, such as an antibody-producing cell that produces an antibody that substantially cross-reacts or competes with the monoclonal antibody 9D2 or 3G4 (ATCC PTA 4545).

A preferred "composition comprising an immunogenically effective amount of an immunogenic aminophospholipid or anionic phospholipid", as used herein, is a composition comprising activated endothelial cells. "Activated endothelial cells" are preferably prepared by placing endothelial cells under at least a first condition, or in contact with at least a first factor, which activates the endothelial cells, and/or mimics a tumor environment, for a time effective to substantially maintain cell viability and stimulate expression of at least one anionic phospholipid at the surface of the endothelial cells.

Examples "conditions" effective to prepare activated endothelial cells are hypoxic and/or acidic environments. Examples of "factors" effective to prepare activated endothelial cells are effective concentrations of $H_2O_2$, thrombin, inflammatory cytokine(s), such as IL-1α, IL-1β, interferon or TNFα, and generally, combinations of conditions and/or factors that mimic a tumor environment.

Irrespective of the nature of the immunization process, or the type of immunized animal, suitable antibody-producing cells are obtained from the immunized animal and, preferably, further manipulated by the hand of man. "An immunized animal", as used herein, is a non-human animal, unless otherwise expressly stated. Although any antibody-producing cell may be used, most preferably, spleen cells are obtained as the source of the antibody-producing cells. The antibody-producing cells may be used in a preparative process that comprises:
 (a) fusing a suitable anti-aminophospholipid or anti-anionic phospholipid antibody-producing cell with an immortal cell to prepare a hybridoma that produces a monoclonal antibody in accordance with the present invention; and
 (b) obtaining a suitable anti-aminophospholipid or anti-anionic phospholipid antibody in accordance with the invention from the hybridoma.

"Suitable" anti-aminophospholipid or anti-anionic phospholipid antibody-producing cells, hybridomas and antibodies are those that produce, or exist as, anti-aminophospholipid or anti-anionic phospholipid antibodies, preferably antibodies that substantially cross-react or compete with the monoclonal antibody 9D2 or 3G4 (ATCC PTA 4545).

Hybridoma-based monoclonal antibody preparative methods thus include those that comprise:
 (a) immunizing an animal by administering to the animal at least one dose, and optionally more than one dose, of a composition comprising an immunogenically effective amount of an immunogenic aminophospholipid or anionic phospholipid, preferably a composition comprising activated endothelial cells;
 (b) preparing a collection of monoclonal antibody-producing hybridomas from the immunized animal;
 (c) selecting from the collection at least a first hybridoma that produces at least a first anti-aminophospholipid or anti-anionic phospholipid monoclonal antibody in accordance with the invention, optionally an anti-aminophospholipid or anti-anionic phospholipid antibody that substantially cross-reacts or competes with the monoclonal antibody 9D2 or 3G4 (ATCC PTA 4545); and (d) culturing the at least a first antibody-producing hybridoma to provide the at least a first anti-aminophospholipid or anti-anionic phospholipid monoclonal antibody; and preferably (e) obtaining the at least a first anti-aminophospholipid or anti-anionic phospholipid monoclonal antibody from the cultured at least a first hybridoma.

In identifying an anti-aminophospholipid or anti-anionic phospholipid antibody that substantially cross-reacts with the monoclonal antibody 9D2 or 3G4 (ATCC PTA 4545), the selecting step may comprise:

(a) contacting an aminophospholipid or anionic phospholipid sample, preferably a PS sample, with effective amounts of the monoclonal antibody 9D2 or 3G4 (ATCC PTA 4545) and a candidate antibody; and (b) determining the ability of the candidate antibody to substantially reduce the binding of the 9D2 or 3G4 antibody to the aminophospholipid or anionic phospholipid, preferably PS, sample; wherein the ability of a candidate antibody to substantially reduce the binding of the 9D2 or 3G4 antibody to the aminophospholipid or anionic phospholipid, preferably PS sample is indicative of an anti-aminophospholipid or anti-anionic phospholipid antibody that binds to substantially the same epitope as the monoclonal antibody 9D2 or 3G4 (ATCC PTA 4545).

The selecting step may further comprise:

(a) contacting a first aminophospholipid or anionic phospholipid sample, preferably PS, with an effective binding amount of the monoclonal antibody 9D2 or 3G4 (ATCC PTA 4545) and determining the amount of 9D2 or 3G4 that binds to the aminophospholipid or anionic phospholipid, preferably PS;

(b) contacting a second aminophospholipid or anionic phospholipid sample, preferably PS, with an effective binding amount of the monoclonal antibody 9D2 or 3G4 (ATCC PTA 4545) in combination with an effective competing amount of a candidate antibody and determining the amount of 9D2 or 3G4 that binds to the aminophospholipid or anionic phospholipid, preferably PS, in the presence of the candidate antibody; and (c) identifying an anti-aminophospholipid or anti-anionic phospholipid antibody that binds to substantially the same epitope as the monoclonal antibody 9D2 or 3G4 (ATCC PTA 4545) by selecting a candidate antibody that reduces the amount of 9D2 or 3G4 that binds to the aminophospholipid or anionic phospholipid, preferably PS, preferably by at least about 80%.

All selection criteria, as used herein, are preferably conducted in the absence of serum, to avoid the drawbacks with generating antibodies that could mimic the pathological antibodies of patients, which bind to aminophospholipids or anionic phospholipids in conjunction with proteins.

As non-human animals are used for immunization, the monoclonal antibodies obtained from such a hybridoma will often have a non-human make up. Such antibodies may be optionally subjected to a humanization process, grafting or mutation, as known to those of skill in the art and further disclosed herein. Alternatively, transgenic animals, such as mice, may be used that comprise a human antibody gene library. Immunization of such animals will therefore directly result in the generation of suitable human antibodies.

After the production of a suitable antibody-producing cell, most preferably a hybridoma, whether producing human or non-human antibodies, the monoclonal antibody-encoding nucleic acids may be cloned to prepare a "recombinant" monoclonal antibody. Any recombinant cloning technique may be utilized, including the use of PCR™ to prime the synthesis of the antibody-encoding nucleic acid sequences. Therefore, yet further appropriate monoclonal antibody preparative methods include those that comprise using the antibody-producing cells as follows:

(a) obtaining at least a first suitable anti-aminophospholipid or anti-anionic phospholipid antibody-encoding nucleic acid molecule or segment from a suitable anti-aminophospholipid or anti-anionic phospholipid antibody-producing cell, preferably a hybridoma; and (b) expressing the nucleic acid molecule or segment in a recombinant host cell to obtain a recombinant anti-aminophospholipid or anti-anionic phospholipid monoclonal antibody in accordance with the present invention.

However, other powerful recombinant techniques are available that are ideally suited to the preparation of recombinant monoclonal antibodies. Such recombinant techniques include the phagemid library-based monoclonal antibody preparative methods comprising:

(a) immunizing an animal by administering to the animal at least one dose, and optionally more than one dose, of a composition comprising an immunogenically effective amount of an immunogenic aminophospholipid or anionic phospholipid, preferably a composition comprising activated endothelial cells;

(b) preparing a combinatorial immunoglobulin phagemid library expressing RNA isolated from the antibody-producing cells, preferably from the spleen, of the immunized animal;

(c) selecting from the phagemid library at least a first clone that expresses at least a first anti-aminophospholipid or anti-anionic phospholipid antibody, optionally one that substantially cross-reacts or competes with the monoclonal antibody 9D2 or 3G4 (ATCC PTA 4545);

(d) obtaining anti-aminophospholipid or anti-anionic phospholipid antibody-encoding nucleic acids from the at least a first selected clone and expressing the nucleic acids in a recombinant host cell to provide the at least a first anti-aminophospholipid or anti-anionic phospholipid antibody; and preferably (e) obtaining the at least a first anti-aminophospholipid or anti-anionic phospholipid antibody expressed by the nucleic acids obtained from the at least a first selected clone.

Again, in such phagemid library-based techniques, transgenic animals bearing human antibody gene libraries may be employed, thus yielding recombinant human monoclonal antibodies.

Irrespective of the manner of preparation of a first anti-aminophospholipid or anti-anionic phospholipid antibody nucleic acid segment, further suitable antibody nucleic acid segments may be readily prepared by standard molecular biological techniques. In order to confirm that any variant, mutant or second generation anti-aminophospholipid or anti-anionic phospholipid antibody nucleic acid segment is suitable for use in the present invention, the nucleic acid segment will be tested to confirm expression of an anti-aminophospholipid or anti-anionic phospholipid antibody in accordance with the present invention. Preferably, the variant, mutant or second generation nucleic acid segment will also be tested to confirm hybridization under standard, more preferably, standard stringent hybridization conditions. Exemplary suitable hybridization conditions include hybridization in about 7% sodium dodecyl sulfate (SDS), about 0.5 M $NaPO_4$, about 1 mM EDTA at about 50° C.; and washing with about 1% SDS at about 42° C.

As a variety of recombinant monoclonal antibodies, whether human or non-human in origin, may be readily prepared, any of the treatment methods of the invention may be executed by providing to the animal or patient at least a first nucleic acid segment that expresses a biologically effective amount of at least a first anti-aminophospholipid or anti-anionic phospholipid antibody in the patient. The "nucleic acid segment that expresses an anti-aminophospholipid or anti-anionic phospholipid, 3G4-like or 3G4-based antibody" will generally be in the form of at least an expression construct, and may be in the form of an expression construct comprised within a virus or within a recombinant host cell. Preferred gene therapy vectors of the present invention will generally be viral vectors, such as comprised within a recombinant retrovirus, herpes simplex virus (HSV), adenovirus, adeno-associated virus (AAV), cytomegalovirus (CMV), and the like.

Cell Impermeant Duramycin Derivatives: The invention further provides substantially cell impermeant phosphatidylethanolamine (PE)-binding peptide constructs and derivatives, which comprise at least a first PE-binding peptide that has been modified to form a substantially cell impermeant PE-binding construct.

Preferably, the invention provides pharmaceutical compositions comprising, in a pharmaceutically acceptable carrier, a biologically or therapeutically effective amount of at least a first substantially cell impermeant PE-binding construct, which comprises at least a first PE-binding peptide that has been modified to form a substantially cell impermeant PE-binding construct. Thus, the substantially cell impermeant PE-binding constructs are constructs for pharmaceutical, pharmacological and therapeutic, i.e., medical uses, preferably for use in treating viral infections. In certain embodiments, the invention provides a substantially cell impermeant PE-binding construct other than cinnamycin linked to biotin.

Most preferably, the substantially cell impermeant PE-binding peptide derivatives of the invention are substantially cell impermeant duramycin peptide derivatives and pharmaceutical compositions thereof. The duramycin peptide is typically modified to form a substantially cell impermeant duramycin derivative by operative attachment to at least a first substantially cell impermeant group. Operative attachment of a substantially cell impermeant group may be via the lysine residue at amino acid position 2 in SEQ ID NO:9.

The substantially cell impermeant group may have a positive or negative charge at physiological pH or may be polar at physiological pH. Exemplary groups include sulfate, sulfonate, phosphate, carboxyl, phenolic, quaternary ammonium ion and amine groups. A pharmaceutical composition comprising duramycin linked to biotin is a particular example within the invention.

Substantially cell impermeant duramycins may also be operatively attached to a sugar, oligo- or polysaccharide, amino acid, peptide, polypeptide, protein or a polyalcohol group. Certain cell impermeant duramycins are those operatively attached to a carrier protein or "an inert carrier protein", such as neutravidin, streptavidin, albumin or an immunoglobulin carrier protein (an inert immunoglobulin carrier protein), of which duramycin attached to human IgG (HIgG) is particularly preferred. Other examples of cell impermeant duramycins are those linked to targeting agents, preferably wherein the targeting agent is a protein, antibody, or antigen binding region thereof, that binds to a component of a tumor cell, tumor vasculature or tumor stroma or to a virally-infected cell. Examples of targeting agents that bind to a component of a tumor cell, tumor vasculature or tumor stroma are taught in U.S. Pat. Nos. 6,093,399, 6,004,555, 5,877,289, and 6,036,955, each specifically incorporated herein by reference.

Conjugates, Compositions and Kits: Unless otherwise specifically stated or made clear in scientific terms, the terms "antibody and fragment thereof", as used herein, therefore mean an "unconjugated or naked" antibody or fragment, which is not attached to another agent, particularly a therapeutic or diagnostic agent. These definitions do not exclude modifications of the antibody, such as, by way of example, modifications to improve the biological half life, affinity, avidity or other properties of the antibody, or combinations of the antibody with other effectors.

Similarly, the terms PE-binding peptide and duramycin "derivative", as used herein, mean PE-binding and duramycin peptides that are not specifically attached to a selected therapeutic agent, particularly an anti-viral agent. Naturally, as the preferred PE-binding peptide and duramycin "derivatives" of the invention are already attached to at least a first substantially cell impermeant group, this definition refers to the lack of an attached agent "selected" for a therapeutic effect, particularly an anti-viral effect.

The invention further provides a range of antibody (immunoconjugate) and peptide conjugates. The immunoconjugates of the invention comprise an anti-aminophospholipid or anti-anionic phospholipid antibody, preferably one that binds to substantially the same epitope as, or competes with, the monoclonal antibody 9D2 or 3G4 (ATCC PTA 4545), operatively attached to at least a first biological, diagnostic or therapeutic agent. Any of the range of antibodies described above may be used in such an immunoconjugate.

The "biological agent" need not directly be a therapeutic or diagnostic agent. For example, as the invention can be used in connection with prodrugs, including ADEPT embodiments, the biological agent may be an agent, preferably an enzyme, which cleaves a substantially inactive prodrug to release a substantially active drug. Such agents and enzymes are described below in relation to the prodrug and ADEPT method embodiments.

As to "diagnostic agents", preferred diagnostic agents for attachment are in vivo diagnostic agents. Such diagnostic immunoconjugates may be used in imaging pre-apoptotic and apoptotic cells in a range of diseases, in combined tumor imaging and treatment, and in methods of using the invention as a surrogate marker to monitor chemotherapy.

Suitable detectable labels include an X-ray detectable compound, such as bismuth (III), gold (III), lanthanum (III) or lead (II); a radioactive ion, such as copper$^{67}$, gallium$^{67}$, gallium$^{68}$, indium$^{111}$, indium$^{113}$, iodine$^{123}$, iodine$^{125}$, iodine$^{131}$, mercury$^{197}$, mercury$^{203}$, rhenium$^{186}$, rhenium$^{188}$, rubidium$^{97}$, rubidium$^{103}$, technetium$^{99m}$ or yttrium$^{90}$; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

Regarding "therapeutic agents", certain preferred therapeutic agents are cytotoxic, cytostatic or anti-cancer agents. The antibodies of the invention, preferably 9D2- or 3G4-like antibodies, may therefore be linked to at least a first radiotherapeutic, chemotherapeutic, anti-cellular, cytotoxic, anti-angiogenic or apoptosis-inducing agent or to an anti-tubulin drug or cytokine.

Currently preferred agents are the cytotoxic agent, gelonin; cytokines, such as TNFα, IL-12 and LEC (liver-expressed chemokine); anti-cancer agents with anti-angiogenic effects, as in Table E; anti-cancer agents that induce apoptosis, as in Table F; and anti-tubulin drugs from the combretastatin family.

For attachment to at least a first biological, diagnostic, cytotoxic, cytostatic or anti-cancer agent, antibodies that bind to substantially the same epitope as, i.e., compete with, the monoclonal antibody 9D2 or 3G4 (ATCC PTA 4545) are particularly preferred. Given the surprising connection between the antibodies and peptides of the invention and viral infections, the present invention further provides a range of new therapeutic conjugates for use in treating viral infections. Other preferred therapeutic agents for attachment to antibodies are therefore anti-viral agents or drugs. The anti-viral immunoconjugates of the invention comprise an antibody that binds to at least a first aminophospholipid or anionic phospholipid, preferably to an aminophospholipid, and most preferably to PS or PE, operatively attached to at least a first anti-viral agent or drug.

The peptide conjugates of the invention comprise a substantially cell impermeant PE-binding peptide, preferably a duramycin peptide, operatively attached to at least a first anti-viral agent or drug. Such peptide conjugates are herein termed "PE-binding peptide anti-viral conjugates" or succinctly, "anti-viral peptide conjugates". Any of the range of PE-binding peptides described above may be used in such a conjugate, with duramycin being particularly preferred.

Virtually any one or more "anti-viral agents or drugs" may be attached to an antibody that binds to at least a first aminophospholipid or anionic phospholipid, preferably to an aminophospholipid, and most preferably to PS or PE; or to a PE-binding peptide, preferably a duramycin peptide. Anti-retroviral drugs may be used, for example, nucleoside reverse transcriptase (RT) inhibitors (NTRIs), non-nucleoside RT inhibitors and protease inhibitors. Other suitable anti-viral agents for attachment to the antibodies and peptides of the invention include those set forth in Table G, particularly AZT or cidofovir.

For antibody- and peptide-based conjugates, the term "conjugate" is generally used to define the operative association of the antibody or peptide with another effective agent and is not intended to refer solely to any type of operative association, and is particularly not limited to chemical "conjugation". Recombinant fusion proteins are particularly contemplated. So long as the antibody or peptide is able to bind to the target aminophospholipid or anionic phospholipid and the attached agent functions sufficiently as intended, particularly when delivered to the target site, any mode of attachment will be suitable.

The invention further provides compositions comprising at least a first purified anti-aminophospholipid or anti-anionic phospholipid antibody, or antigen-binding fragment or immunoconjugate thereof, optionally one that binds to essentially the same epitope as the monoclonal antibody 9D2 or 3G4 (ATCC PTA 4545), or a substantially cell impermeant PE-binding peptide derivative, preferably a substantially cell impermeant duramycin derivative, or an anti-viral conjugate thereof. The compositions preferably comprise a biologically effective amount of any such agent, such as an amount effective to bind a target antigen, inhibit proliferation, viral replication or such like.

The compositions of the invention are preferably pharmaceutically acceptable compositions, particularly those for the substantially cell impermeant PE-binding peptide derivatives, preferably substantially cell impermeant duramycin derivatives. The pharmaceutical compositions include those formulated for parenteral administration, such as for intravenous administration, or for administration as a liposome or as an aerosol. The aerosol formulations are particularly suitable for treating viral infections. Pharmaceutical compositions preferably comprise a biologically or therapeutically effective amount of any such agent, such as an amount effective for treating a disease or disorder, particularly angiogenesis, cancer or a viral infection.

Aspects of the invention further include compositions, pharmaceutical compositions, combinations, mixtures, medicaments and/or medicinal cocktails of agents, comprising at least a first purified anti-aminophospholipid or anti-anionic phospholipid antibody, or antigen-binding fragment or immunoconjugate thereof, optionally one that binds to essentially the same epitope as the monoclonal antibody 9D2 or 3G4 (ATCC PTA 4545), or a substantially cell impermeant PE-binding peptide derivative, preferably a substantially cell impermeant duramycin derivative, or an anti-viral conjugate thereof, in combination with a biologically or therapeutically effective amount of at least a second biological agent. All such combinations preferably comprise combined biologically or therapeutically effective amounts, such as combined amounts effective to inhibit proliferation or viral replication, or to treat a disease such as an angiogenic disease, cancer or a viral infection.

In the compositions, the "at least a second biological agent" will often be a diagnostic or therapeutic agent, but it need not be. For example, the second biological agent may be a component of a pharmaceutical composition such as a dispersion agent or an absorption delaying agent. Other biological agents, such as agents for making antibodies and prodrugs for use in prodrug and ADEPT methods, and diagnostic agents, are preferably maintained in combination, but separately, from the first composition of the invention and are therefore discussed below in reference to the kits of the invention. "In combination, but separately" means in close confinement together, but not part of the same composition, such as not part of the same solution or pharmaceutical composition.

As to the "at least a second therapeutic agent", the term "second" is in reference to the anti-aminophospholipid or anti-anionic phospholipid antibody, fragment or immunoconjugate, or substantially cell impermeant PE-binding peptide, duramycin derivative or anti-viral conjugate thereof, being the "first" therapeutic agent.

Where the invention is intended for use in cancer treatment, the at least a second therapeutic agent will preferably be "at least a second, distinct anti-cancer agent". The second, anti-cancer agents for combined use may be radiotherapeutic, chemotherapeutic, anti-angiogenic or apoptosis-inducing agents, cytokines or antibodies or an antibody-therapeutic agent constructs that bind to a tumor cell, an intracellular antigen released from a necrotic tumor cell or to a component of tumor vasculature (i.e., anti-cancer immunotoxins or coaguligands). The term "chemotherapeutic agent", as used herein, includes genes, vectors, antisense constructs and ribozymes.

Certain preferred second, anti-cancer agents for combined use are those that complement or enhance the therapeutic effect of the anti-aminophospholipid or anti-anionic phospholipid antibody or substantially cell impermeant PE-binding peptide derivative and/or those selected for a particular tumor type or patient. "Therapeutic agents that complement or enhance the therapeutic effect" include radiotherapeutic agents, vascular permeability enhancing agents, anti-angiogenic agents, apoptosis-inducing agents, certain cytokines, anti-tumor cell immunotoxins, as well as selected chemotherapeutic agents. Currently preferred "selected chemotherapeutic agents" are chemotherapeutic agents with antiangiogenic effects, as in Table E; chemotherapeutic agents that induce apoptosis, as in Table F; calcium flux inducing agents, inflammatory cytokines, $H_2O_2$, thrombin, and anti-tubulin drugs from the combretastatin family. Doxorubicin, etoposide and actinomycin-D are further preferred, with docetaxel being most preferred.

The invention further provides a liposome, lipid carrier, complex, mixture, supramolecular structure multimolecular aggregate or lipid-based drug delivery system comprising at least a first purified anti-aminophospholipid or anti-anionic phospholipid antibody, or antigen-binding fragment or immunoconjugate thereof, preferably one that binds to essentially the same epitope as the monoclonal antibody 9D2 or 3G4 (ATCC PTA 4545), or a substantially cell impermeant PE-binding peptide derivative, preferably a substantially cell impermeant duramycin derivative, or an anti-viral conjugate thereof. The liposome or liposome-like composition may be in the form of a monolayer, bilayer, multimolecular aggregate, vesicle, helix, disc, tube, fiber, torus, hexagonal phase, gel phase, liquid-crystalline phase, liquid-crystalline multimolecular aggregate, micelle, reverse micelle, microemulsion, emulsion, microreservoir, oil globule, fat globule, wax globule and/or colloidal particle.

Liposomes or liposome-like compositions generally comprise an "outer membrane" or bulk aqueous phase and "central core" or inner aqueous phase. In preferred embodiments, the liposome or liposome-like composition is a stealthed liposome, lipid carrier, complex, mixture, supramolecular structure multimolecular aggregate or lipid-based drug delivery system. "Stealthed" liposomes and liposome-like compositions comprise a biologically effective amount of at least a first stealthing agent in operative association with the outer membrane. A "stealthing agent" is a component that increases the biological half life of a liposome or liposome-like composition when operatively associated with the outer membrane of the liposome or liposome-like composition. In "operative association", the outer membrane of the liposome or liposome-like composition is preferably "coated" with the one or more stealthing agents.

Effective stealthing agents include a range of biocompatible hydrophilic polymers, such as polyamines, polylactic acid, polyglycolic acid, polylactic-polyglycolic acid (PLGA), polypeptides and related materials. A preferred stealthing agent is polyethylene glycol (PEG) component, wherein the resulting stealthed liposomes are termed "PEGylated liposomes".

Preferred liposomes of the invention are stealthed or PEGylated liposomes wherein an antibody to an aminophospholipid or anionic phospholipid, or antigen-binding fragment thereof, preferably one that competes with the monoclonal antibody 9D2 or 3G4 (ATCC PTA 4545), is operatively associated with the outer membrane of the liposome, preferably where the liposome is "coated" with the antibody or fragment thereof.

Particularly preferred liposomes are such "antibody-coated" stealthed or PEGylated liposomes wherein at least a first therapeutic agent, such as an anti-viral agent or preferably an anti-cancer agent, is operatively associated with the liposome or dispersed within the liposomal formulation. Preferably, the therapeutic, anti-viral or anti-cancer agent is operatively associated with or maintained within the central core of the liposome. Exemplary anti-cancer agents are radionuclide(s) and chemotherapeutic agents, such as anti-tubulin drugs, docetaxel and paclitaxel, with docetaxel being preferred.

For combinations with biological, diagnostic, anti-angiogenic, anti-cancer agents and stealthed liposomes, antibodies that bind to substantially the same epitope as, i.e., compete with, the monoclonal antibody 9D2 or 3G4 (ATCC PTA 4545) are particularly preferred. Where the invention is intended for use in treating a viral infection or disease, the at least a second therapeutic agent will preferably be "at least a second, anti-viral agent or drug". The invention thus also provides a range of combined anti-viral compositions and formulations, not limited to the 3G4 and like antibodies.

These aspects of the invention can be conveniently described as a composition, pharmaceutical composition, combination, mixture, medicament and/or medicinal cocktail comprising at least a first anti-viral agent or drug in combination with a biologically or therapeutically effective amount of at least one purified anti-aminophospholipid or anti-anionic phospholipid antibody, or antigen-binding fragment or immunoconjugate thereof, optionally one that binds to essentially the same epitope as the monoclonal antibody 9D2 or 3G4 (ATCC PTA 4545), or a substantially cell impermeant PE-binding peptide derivative, preferably a substantially cell impermeant duramycin derivative, or an anti-viral conjugate thereof.

In the foregoing description, the anti-viral agent or drug is recited as the "at least a first anti-viral agent or drug" and the antibody, fragment, immunoconjugate, substantially cell impermeant PE-binding peptide, duramycin derivative or an anti-viral conjugate thereof is recited as the second component of the combination. This is a matter of grammatical convenience.

The one or more anti-viral agents or drugs for use in the present combined compositions may be selected from any anti-viral agent or drug available at the time of practicing the invention, including the range of anti-viral agents and drugs described herein for attachment to antibodies and peptides of the invention. By way of example, anti-retroviral drugs such as NTRIs, non-nucleoside RT inhibitors and protease inhibitors, anti-viral agents as set forth in Table G, and preferably, AZT or cidofovir.

Further embodiments of the invention concern kits comprising, in at least a first composition or container, at least a first purified anti-aminophospholipid or anti-anionic phospholipid antibody, or antigen-binding fragment or immunoconjugate thereof, optionally one that binds to essentially the same epitope as the monoclonal antibody 9D2 or 3G4 (ATCC PTA 4545), or a substantially cell impermeant PE-binding peptide derivative, preferably a substantially cell impermeant duramycin derivative, or an anti-viral conjugate thereof, in combination with a biologically or therapeutically effective amount of at least a second biological agent, component or system.

The "second biological agents, components or systems" are not limited to therapeutic or diagnostic agents. For example, second biological agents, components or systems may comprise components for modification of the antibody and/or for attaching other agents to the antibody. Certain preferred second biological agents, components or systems are prodrugs or components for making and using prodrugs, including components for making the prodrug itself and components for adapting the antibodies of the invention to function in such prodrug or ADEPT embodiments.

The at least a "second diagnostic agent, component or system" may be a diagnostic agent, component or system directly or indirectly detectable by an in vitro diagnostic test. "Directly detectable in vitro reporter agents" include radiolabels, reporter agents detectable by immunofluorescence and luciferase. "Indirectly detectable in vitro reporter agents" function in conjunction with further exogenous agent(s), such as detectable enzymes that yield a colored product on contact with a chromogenic substrate. These include "secondary antibodies", which are attached to a direct or indirect detectable agent, such a radiolabel or enzyme, and "secondary and tertiary antibody detection systems" in which the tertiary antibody is attached to the detectable agent.

Preferred diagnostic kits of the invention are those comprising a diagnostic agent, component or system detectable by in vivo diagnosis or imaging. An advantage of the imaging embodiments of the invention is that the same antibody can be used for imaging and treatment. The invention therefore provides kits and medicaments that comprise:

(a) a first pharmaceutical composition comprising a diagnostically effective amount of an anti-aminophospholipid or anti-anionic phospholipid antibody, or antigen-binding fragment thereof, preferably one that binds to essentially the same epitope as the monoclonal antibody 9D2 or 3G4 (ATCC PTA 4545), operatively attached to a detectable label or diagnostic agent; and (b) a second pharmaceutical composition comprising a therapeutically effective amount of anti-aminophospholipid or anti-anionic phospholipid antibody, or antigen-binding fragment or immunoconjugate thereof, preferably one that binds to essentially the same epitope as the monoclonal antibody 9D2 or 3G4 (ATCC PTA 4545).

For use in therapeutic embodiments, the kits will comprise "at least a second therapeutic agent". Preferably, such kits comprise a combined biologically or therapeutically effective amount of at least the two specified agents, such as combined amounts effective to inhibit proliferation or viral replication, or to treat a disease such as an angiogenic disease, cancer or a viral infection.

In terms of cancer treatment, the kits of the invention include antibodies for use in combination with prodrugs and ADEPT. In such compositions, the antibody or fragment thereof is "modified to provide a converting or enzymatic capacity". This can be achieved by making a catalytic antibody. Preferably, the antibody is operatively associated with, preferably covalently linked or conjugated to, at least a first converting agent or enzyme capable of converting at least one prodrug to the active form of the drug.

The enzymatic or enzyme-conjugated antibody or fragment will combined with an initially separate formulation of the "prodrug". The prodrug will be an inactive or weakly active form of a drug that is that is converted to the active form of the drug on contact with the enzymatic capacity, converting function or enzyme associated with the anti-aminophospholipid or anti-anionic phospholipid antibody of the invention, preferably one that competes with the monoclonal antibody 9D2 or 3G4 (ATCC PTA 4545).

Accordingly, kits are provided that comprise, preferably in separate compositions and/or containers:

(a) a biologically effective amount of at least a first anti-aminophospholipid or anti-anionic phospholipid antibody, or antigen-binding fragment thereof, preferably one that competes with the monoclonal antibody 9D2 or 3G4 (ATCC PTA 4545), which has an enzymatic function, preferably where the antibody or fragment is operatively associated with, covalently linked or conjugated to, at least a first enzyme; and (b) a biologically effective amount of at least a first substantially inactive prodrug that is converted to a substantially active drug by the enzymatic function of, or by the enzyme associated with, linked to or conjugated to the anti-aminophospholipid or anti-anionic phospholipid antibody or fragment thereof.

Suitable enzymes that cleave a substantially inactive prodrug to release a substantially active drug include arylsulfatase, serratia protease, thermolysin, subtilisin, a carboxypeptidase, a cathepsin, D-alanylcarboxypeptidase, β-galactosidase, neuraminidase, β-lactamase, penicillin amidase and cytosine deaminase.

Other than prodrugs, the at least a second, anti-cancer agent may be any of the second, anti-cancer agents described above in relation to the combined anti-cancer compositions of the invention. For treating viral infections, the at least a second, anti-viral agent may also be any of the second, anti-viral agents described above in relation to the combined anti-viral compositions of the invention. However, the "kits" may comprise the at least two recited the agents "in combination, but separately", thus providing even more flexibility in the selection of agents.

The kits of the invention may therefore comprise combined biologically or therapeutically effective amounts of at least the two specified agents within a single container or container means, or within distinct containers or container means. The kits may also comprise instructions for using the biological and therapeutic agents included therein. Imaging components may also be included in combination, but separately with the therapeutic kits.

Anti-Angiogenic and Tumor Treatment: The present invention provides a number of methods and uses of the anti-aminophospholipid or anti-anionic phospholipid antibodies, including the 9D2- and 3G4-like antibodies, and the substantially cell impermeant PE-binding peptide and duramycin derivatives. Concerning all methods, the terms "a" and "an" are used to mean "at least one", "at least a first", "one or more" or "a plurality" of steps in the recited methods, except where specifically stated. This is particularly relevant to the administration steps in the treatment methods. Thus, not only may different doses be employed with the present invention, but different numbers of doses, e.g., injections or inhalations, may be used, up to and including multiple injections or inhalations.

Various useful in vitro methods and uses are provided that have important biological implications. First provided are methods of, and uses in, binding aminophospholipids or anionic phospholipids, preferably PS or PE, which generally comprise effectively contacting a composition comprising an aminophospholipid or anionic phospholipid, preferably PS or PE, with at least a first anti-aminophospholipid or anti-anionic phospholipid antibody, or antigen-binding fragment thereof, preferably an antibody that binds to substantially the same epitope as the monoclonal antibody 9D2 or 3G4 (ATCC PTA 4545), or with a substantially cell impermeant duramycin derivative. The "contacting" is under conditions effective to allow the formation of bound complexes, and any complexes so formed are detected. The detection methods and uses may be used in connection with biological samples, e.g., in diagnostics for apoptosis, tumors and virally infected cells, and diagnostic kits based thereon are also provided.

Proliferation inhibition methods and uses are provided, which preferably use the antibodies, antigen binding fragments and immunoconjugates of the invention. Methods to inhibit endothelial cell proliferation and/or migration generally comprise contacting a population of cells or tissues that includes a population of endothelial cells with a composition comprising a biologically effective amount of at least a first anti-aminophospholipid or anti-anionic phospholipid antibody, optionally one that binds to substantially the same epitope as the monoclonal antibody 9D2 or 3G4 (ATCC PTA 4545), or an antigen-binding fragment thereof, under conditions effective to inhibit endothelial cell proliferation and/or migration.

The foregoing methods and uses can be performed in vitro and in vivo, in the latter case, wherein the tissues or cells are located within an animal and the anti-aminophospholipid or anti-anionic phospholipid antibody is administered to the animal. In both cases, the methods and uses become methods and uses for inhibiting angiogenesis, comprising contacting a population of potentially angiogenic blood vessels, or a tissue comprising a population of potentially angiogenic blood vessels, with an anti-angiogenic composition comprising a biologically effective amount of at least a first anti-aminophospholipid or anti-anionic phospholipid antibody, optionally one that binds to substantially the same epitope as the monoclonal antibody 9D2 or 3G4 (ATCC PTA 4545), or an antigen-binding fragment thereof, under conditions effective to inhibit angiogenesis.

Where populations of potentially angiogenic blood vessels are maintained ex vivo, the present invention has utility in drug discovery programs. In vitro screening assays, with reliable positive and negative controls, are useful as a first step in the development of drugs to inhibit or promote angiogenesis, as well as in the delineation of further information on the angiogenic process. Where the population of potentially angiogenic blood vessels is located within an animal or patient, the anti-angiogenic composition is administered to the animal as a form of therapy.

Anti-angiogenic and anti-vascular therapies are provided in terms of animals and patients that have, or are at risk for developing, any disease or disorder characterized by undesired, inappropriate, aberrant, excessive and/or pathological vascularization. It is well known to those of ordinary skill in the art that as aberrant angiogenesis occurs in a wide range of diseases and disorders, a given anti-angiogenic therapy, once shown to be effective in any acceptable model system, can be used to treat the entire range of diseases and disorders connected with angiogenesis.

The methods and uses of the present invention are particularly intended for use in animals and patients that have, or are at risk for developing, any form of vascularized tumor; macular degeneration, including age-related macular degeneration; arthritis, including rheumatoid arthritis; atherosclerosis and atherosclerotic plaques; diabetic retinopathy and other retinopathies; thyroid hyperplasias, including Grave's disease; hemangioma; neovascular glaucoma; and psoriasis.

As disclosed in U.S. Pat. Nos. 5,712,291 and 6,524,583, specifically incorporated herein by reference, each of the foregoing treatment groups are by no means exhaustive of the types of conditions that are to be treated by the present invention. U.S. Pat. Nos. 5,712,291 and 6,524,583 are incorporated herein by reference for certain specific purposes, including the purpose of identifying a number of other conditions that may be effectively treated by an anti-angiogenic therapeutic; the purpose of showing that the treatment of all angiogenic diseases represents a unified concept, once a defined category of angiogenesis-inhibiting compounds have been disclosed and claimed (in the present case, anti-aminophospholipid or anti-anionic phospholipid antibodies, optionally those that bind to substantially the same epitope as the monoclonal antibody 9D2 or 3G4 (ATCC PTA 4545)); and the purpose of showing that the treatment of all angiogenic diseases is enabled by data from only a single model system.

In addition to the treatment of angiogenic and vascular diseases, important and unified aspects of the present invention are compositions and methods for treating cancer. Such methods comprise administering to an animal or patient that has, or is at risk for developing, cancer, a biologically or therapeutically effective amount of at least a first composition comprising at least a first purified anti-aminophospholipid or anti-anionic phospholipid antibody, or antigen-binding fragment or immunoconjugate thereof, preferably one that binds to essentially the same epitope as, or competes with, the monoclonal antibody 9D2 or 3G4 (ATCC PTA 4545), or a substantially cell impermeant PE-binding peptide derivative, preferably a substantially cell impermeant duramycin derivative.

The cancer treatment methods of the invention, even those using the antibodies, do not rely solely on exerting anti-vascular and/or anti-angiogenic effects. The cancer treatment methods and uses of the invention are suitable for treating all forms of cancer, including animals and patients that have, or are at risk for developing, a vascularized solid tumor, a metastatic tumor or metastases from a primary tumor. The methods of the invention preferably exert an anti-cancer effect without causing significant thrombotic complications.

Both unconjugated or naked antibodies, and fragments thereof, and immunoconjugates may be used in the cancer treatment aspects of the invention. As to the use of immunoconjugates, the invention provides methods for delivering selected therapeutic or diagnostic agents to tumors. Such embodiments comprise administering to an animal or patient having a tumor a biologically effective amount of a composition comprising at least a first immunoconjugate in which a diagnostic or therapeutic agent is operatively attached to an anti-aminophospholipid or anti-anionic phospholipid antibody, or antigen-binding fragment thereof, preferably one that binds to substantially the same epitope as, or competes with, the monoclonal antibody 9D2 or 3G4 (ATCC PTA 4545).

The invention therefore provides tumor diagnostic, prognostic, imaging and related methods using an anti-aminophospholipid or anti-anionic phospholipid antibody, or antigen-binding fragment thereof, preferably one that binds to substantially the same epitope as, or competes with, the monoclonal antibody 9D2 or 3G4 (ATCC PTA 4545), to detect pre-apoptotic and apoptotic cells. Such methods can be used as a surrogate marker to monitor the progress of other treatment, particularly chemotherapy, or to form an image of a tumor prior to treatment.

The use of the invention as a surrogate marker to monitor the progress of cancer treatment, particularly chemotherapy, comprises:

(a) subjecting an animal or patient with a tumor to at least a first treatment designed to exert an anti-tumor effect; and (b) subsequently administering to the same animal or patient a diagnostically effective amount of at least a first anti-aminophospholipid or anti-anionic phospholipid antibody, or antigen-binding fragment thereof, preferably one that binds to substantially the same epitope as, or competes with, the monoclonal antibody 9D2 or 3G4 (ATCC PTA 4545), operatively attached to a detectable label or diagnostic agent, thereby forming a detectable image of the tumor, preferably an image of pre-apoptotic or apoptotic tumor cells or tumor vascular endothelial cells within the tumor; and preferably (c) analyzing the detectable image of the tumor, preferably the image of the pre-apoptotic or apoptotic tumor cells or tumor vascular endothelial cells within the tumor, thereby assessing the progress or effectiveness of the at least a first treatment designed to exert an anti-tumor effect.

The combined imaging and cancer treatment methods comprise:

(a) forming an image of a tumor by administering to an animal or patient having a tumor a diagnostically minimal or effective amount of at least a first anti-aminophospholipid or anti-anionic phospholipid antibody, or antigen-binding fragment thereof, preferably one that binds to substantially the same epitope as, or competes with, the monoclonal antibody 9D2 or 3G4 (ATCC PTA 4545), operatively attached to a detectable label or diagnostic agent, thereby forming a detectable image of the tumor; and (b) subsequently administering to the same animal or patient a therapeutically optimized or effective amount of at least a first anti-aminophospholipid or anti-anionic phospholipid antibody, or antigen-binding fragment or immunoconjugate thereof, preferably one that binds to essentially the same epitope as, or competes with, the monoclonal antibody 9D2 or 3G4 (ATCC PTA 4545), thereby causing an anti-tumor effect.

For use in the cancer treatment methods of the invention, the currently preferred antibodies are those that bind to substantially the same epitope as, or compete with, the monoclonal antibody 9D2 and 3G4 (ATCC PTA 4545). In terms of immunoconjugates, anti-aminophospholipid or anti-anionic phospholipid antibodies, preferably those that compete with the monoclonal antibody 9D2 and 3G4 (ATCC PTA 4545), linked to an anti-cancer agent from Table E or Table F, a combretastatin, gelonin, TNFα, IL-12 and LEC are currently preferred. The currently preferred substantially cell impermeant PE-binding peptide derivatives use in cancer treatment are duramycin derivatives, most preferably duramycin linked to biotin or duramycin linked to HIgG.

Within the antibody-based cancer treatment methods of the invention, the invention further provides prodrug treatment methods, which generally comprise:

(a) administering to an animal or patient with a tumor a first pharmaceutical composition comprising a first anti-aminophospholipid or anti-anionic phospholipid antibody, or antigen-binding fragment thereof, preferably one that competes with the monoclonal antibody 9D2 or 3G4 (ATCC PTA 4545), which antibody or fragment thereof has an enzymatic function, preferably where the antibody or fragment is operatively associated with, covalently linked or conjugated to, at least a first enzyme; wherein the antibody or fragment localizes to the tumor after administration and (b) subsequently administering to the animal or patient, after an effective time period, at least a second pharmaceutical composition comprising a biologically effective amount of at least one substantially inactive prodrug; wherein the prodrug is converted to a substantially active drug by the enzymatic function of, or by the enzyme associated with, linked to or conjugated to the anti-aminophospholipid or anti-anionic phospholipid antibody, or fragment thereof, localized within the tumor.

The present invention further provides a range of combination cancer treatment methods, comprising administering to an animal or patient with cancer a therapeutically effective combined amount of at least a first purified anti-aminophospholipid or anti-anionic phospholipid antibody, or antigen-binding fragment or immunoconjugate thereof, optionally one that binds to essentially the same epitope as the monoclonal antibody 9D2 or 3G4 (ATCC PTA 4545), or a substantially cell impermeant PE-binding peptide derivative, preferably a substantially cell impermeant duramycin derivative, and at least a second, distinct therapeutic or anti-cancer agent.

Generally speaking, the at least a second anti-cancer agent may be administered to the animal or patient before, during or after administration of the anti-aminophospholipid or anti-anionic phospholipid antibody, 9D2- or 3G4-based therapeutic or substantially cell impermeant duramycin derivative. The at least a second anti-cancer agent may be administered to the animal or patient "substantially simultaneously" with the anti-aminophospholipid or anti-anionic phospholipid antibody, 9D2- or 3G4-based therapeutic or substantially cell impermeant duramycin derivative; such as from a single pharmaceutical composition or from two pharmaceutical compositions administered closely together.

Alternatively, the at least a second anti-cancer agent may be administered to the animal or patient at a time sequential to the administration of the anti-aminophospholipid or anti-anionic phospholipid antibody, 9D2- or 3G4-based therapeutic or substantially cell impermeant duramycin derivative. "At a time sequential", as used herein, means "staggered", such that the at least a second anti-cancer agent is administered to the animal or patient at a time distinct to the administration of the anti-aminophospholipid or anti-anionic phospholipid antibody, 3G4-based therapeutic or substantially cell impermeant duramycin derivative.

In sequential administration, the two agents are administered at times effectively spaced apart to allow the two agents to exert their respective therapeutic effects, i.e., they are administered at "biologically effective time intervals". The at least a second anti-cancer agent may be administered to the animal or patient at a biologically effective time prior to the anti-aminophospholipid or anti-anionic phospholipid antibody, 9D2- or 3G4-based therapeutic or substantially cell impermeant duramycin derivative, or at a biologically effective time subsequent to that therapeutic.

Any therapeutic or anti-cancer agent may be used as the second, therapeutic or anti-cancer agent in the combined cancer treatment methods of the invention, including any of the therapeutic or anti-cancer agents described above in relation to the anti-cancer compositions and kits of the invention. Preferred agents are those that complement or enhance the therapeutic effects of the antibodies, fragments, immunotoxins or peptide derivatives, such as vascular permeability enhancing agents, anti-angiogenic agents, apoptosis-inducing agents, calcium flux inducing agents, inflammatory cytokines, antibodies and immunotoxins to tumor cells and necrotic tumor cells, chemotherapeutic agents from Table E or Table F, a combretastatin, doxorubicin, etoposide and actinomycin-D.

Docetaxel is a particularly preferred agent for use in combination therapy. Docetaxel may be administered separately to the anti-aminophospholipid or anti-anionic phospholipid antibody, substantially cell impermeant PE-binding peptide or duramycin derivative, either before or afterwards. As to simultaneous administration, docetaxel may be given in separate or the same formulations, optionally within a liposome or stealthed liposome, and preferably within the core of a stealthed liposome coated with an antibody that binds to an aminophospholipid or anionic phospholipid, preferably an antibody that binds to essentially the same epitope as, or competes with, the monoclonal antibody 9D2 or 3G4 (ATCC PTA 4545).

Treating Viral Infections: Particularly important and surprising developments of the invention concern antibodies, immunoconjugates, peptides, peptide conjugates, compositions, combinations, kits, methods, uses and medicaments for inhibiting viruses and for treating or preventing viral infections. In a first instance, the anti-viral methods of the invention concern contacting a composition comprising, or population of cells or tissue(s) that contains or is suspected to contain, a virally infected cell with at least a first composition comprising a biologically effective amount of at least a first purified antibody that binds to an aminophospholipid or anionic phospholipid, preferably to PS or PE, optionally one that binds to essentially the same epitope as, or competes with, the monoclonal antibody 9D2 or 3G4 (ATCC PTA 4545), or antigen-binding fragment, immunoconjugate or anti-viral conjugate thereof, or a substantially cell impermeant PE-binding peptide derivative, preferably a substantially cell impermeant duramycin derivative, or an anti-viral conjugate thereof. The virally infected cell is preferably a eukaryotic cell, such as an animal cell, and preferably a mammalian or human cell.

The anti-viral methods and uses can be performed in vitro and in vivo. In the in vitro embodiments, the methods have important utilities. For example, in drug discovery programs for the development of anti-viral drugs or combinations thereof, as well as in the delineation of further information on viral infection, replication and spread. The in vitro anti-viral methods may also be used in purging viruses from biological samples, such as cell populations and tissue cultures for laboratory use, from samples, tissues, seeds, plant parts and plants for agricultural use, and from blood and tissue samples for therapeutic use. In the in vivo methods, where the cells, populations or tissues are located within an animal, the anti-aminophospholipid or anti-anionic phospholipid antibody, fragment, immunoconjugate, substantially cell impermeant PE-binding peptide, duramycin derivative or anti-viral conjugate thereof, is administered to the animal as anti-viral therapy.

In both cases, the compositions, methods and uses inhibit one or more steps or stages necessary for a productive or ongoing viral infection, including inhibiting viral entry. Preferably, the compositions, methods and uses inhibit viral replication and/or spread, such as inhibiting one or more steps of viral transcription, translation, assembly, packaging and/or egress within or from an infected host cell, such as a mammalian or human cell. The invention therefore preferably limits or substantially confines viral infections to initially infected cells and cell populations, thus substantially inhibiting or preventing the subsequent or ongoing infection of additional host cells or tissues.

The anti-viral treatment methods of the invention preferably concern administering to an animal or patient having, suspected of having or at risk for developing a viral infection or associated disease at least a first composition comprising a biologically effective amount of at least a first purified antibody that binds to an aminophospholipid or anionic phospholipid, preferably to PS or PE, optionally one that binds to essentially the same epitope as, or competes with, the monoclonal antibody 9D2 or 3G4 (ATCC PTA 4545), or antigen-binding fragment, immunoconjugate or anti-viral conjugate thereof, or a substantially cell impermeant PE-binding peptide derivative, preferably a substantially cell impermeant duramycin derivative, or an anti-viral conjugate thereof.

Currently preferred therapeutic agents for use in anti-viral treatment are antibodies that bind to an aminophospholipid, preferably to PS or PE, and immunoconjugates of such antibodies operatively attached to at least a second, distinct anti-viral agent; duramycin peptides and derivatives linked to biotin or linked to HIgG, and conjugates of PE-binding peptides, preferably duramycins, operatively linked to at least a second, distinct anti-viral agent. Suitable anti-viral agents for attachment to the antibodies and peptides include those set forth in Table G, such as AZT or cidofovir.

As the invention inhibits one or more steps or stages necessary for productive or ongoing infection common to all viruses, the anti-viral methods and uses of the invention are suitable for treating all viruses, both enveloped and non-enveloped viruses, including those that infect plants, animals, vertebrates, mammals and human patients. The invention is suitable for treating all viruses that infect vertebrates, as listed herein in Table H, particularly humans, and particularly viruses that are pathogenic in animals and humans. The viral infections and associated and resultant diseases that can be treated by the invention include those viruses and diseases set forth in Table J, as exemplified by treating CMV, RSV, arenavirus and HIV infections, and the diseases hepatitis, influenza, pneumonia, Lassa fever and AIDS.

The anti-viral treatment methods of the invention may also be used in combination with other therapeutics and diagnostics. The combined treatment methods comprise administering to an animal or patient with a viral infection a therapeutically effective combined amount of at least a first composition comprising at least a first purified antibody that binds to an aminophospholipid or anionic phospholipid, preferably to PS or PE, optionally one that binds to essentially the same epitope as, or competes with, the monoclonal antibody 9D2 or 3G4 (ATCC PTA 4545), or antigen-binding fragment, immunoconjugate or anti-viral conjugate thereof, or a substantially cell impermeant PE-binding peptide derivative, preferably a substantially cell impermeant duramycin derivative, or an anti-viral conjugate thereof, and at least a second, distinct therapeutic or anti-viral agent.

The at least a "second, distinct" anti-viral agent is in reference to the anti-aminophospholipid or anti-anionic phospholipid antibody, fragment or immunoconjugate, or substantially cell impermeant PE-binding peptide, duramycin derivative or anti-viral conjugate thereof, being the "first" anti-viral agent. The at least a second anti-viral agent may be administered to the animal or patient during administration of, or substantially simultaneously with, the first anti-viral agent of the invention; or before or after, i.e., sequential to the administration of the first anti-viral agent of the invention.

Any therapeutic or anti-viral agent may be used as the second therapeutic or anti-viral agent in the combined anti-viral treatment methods of the invention, including any of the anti-viral agents described above in relation to the anti-viral conjugates, compositions and kits of the invention.

The foregoing cancer and anti-viral treatment methods and uses will often involve the administration of the pharmaceutically effective composition to the animal or patient systemically, such as by transdermal, intramuscular, intravenous injection and the like. For treating viral infections, particularly respiratory viral infections, delivery to the lung is another preferred embodiment, as may be achieved using an aerosol. However, any route of administration that allows the therapeutic agent to localize to the site of the tumor or viral infection will be acceptable. Therefore, other suitable routes of delivery include oral, rectal, nasal, topical, and vaginal. For uses and methods for the treatment of arthritis, e.g., intrasynovial administration may be employed, as described for other immunological agents in U.S. Pat. No. 5,753,230, specifically incorporated herein by reference. For conditions associated with the eye, ophthalmic formulations and administration are contemplated.

"Administration", as used herein, means provision or delivery of anti-aminophospholipid or anti-anionic phospholipid antibody or 9D2- or 3G4-based therapeutics, or substantially cell impermeant PE-binding peptide derivatives, preferably duramycin derivatives in an amount(s) and for a period of time(s) effective to exert a therapeutic effect. The passive administration of proteinaceous therapeutics is generally preferred, in part, for its simplicity and reproducibility.

However, the term "administration" is herein used to refer to any and all means by which the therapeutics are delivered. "Administration" therefore includes the provision of cells that produce the anti-aminophospholipid or anti-anionic phospholipid antibody, 3G4-based or duramycin derivative therapeutics in an effective manner. In such embodiments, it may be desirable to formulate or package the cells in a selectively permeable membrane, structure or implantable device, generally one that can be removed to cease therapy. Exogenous administration will still generally be preferred, as this represents a non-invasive method that allows the dose to be closely monitored and controlled.

The therapeutic methods and uses of the invention also extend to the provision of nucleic acids that encode anti-aminophospholipid or anti-anionic phospholipid antibody, 3G4-based or duramycin derivative therapeutics in a manner effective to result in their expression in vivo. Any gene therapy technique may be employed, such as naked DNA delivery, recombinant genes and vectors, cell-based delivery, including ex vivo manipulation of patients' cells, and the like. Liposomes and stealthed liposomes will be preferred for use in some embodiments.

The pharmaceutical compositions and treatment methods of the invention employ "therapeutically effective amounts" of an anti-aminophospholipid or anti-anionic phospholipid antibody, optionally one that binds to substantially the same epitope as the monoclonal antibody 9D2 or 3G4 (ATCC PTA 4545), or an antigen-binding fragment or immunoconjugate of such an antibody, or a substantially cell impermeant PE-binding peptide derivative, preferably a substantially cell impermeant duramycin derivative, or an anti-viral conjugate thereof. The "therapeutic effects" and consequent "therapeutically effective amounts" are measured by different parameters in cancer treatment vs. anti-viral treatment.

In cancer treatment, the amounts of the agents are effective to specifically kill at least a portion of tumor cells, tumor or intratumoral vascular endothelial cells; to specifically induce apoptosis in at least a portion of tumor cells, tumor or intratumoral vascular endothelial cells; to specifically promote coagulation in at least a portion of tumor or intratumoral blood vessels; to specifically occlude or destroy at least a portion of blood transporting vessels of the tumor; to specifically induce necrosis in at least a portion of a tumor; and/or to induce tumor regression or remission upon administration to an animal or patient.

In treating viral infections and related diseases, the amounts of the agents are effective to inhibit one or more requirements for ongoing viral infection, such as viral entry, and preferably, viral replication, egress and spread from the infected host cells. The amounts may also kill or remove at least a portion of the virally infected cells in a manner that counteracts viral replication, spread and ongoing infection. Overall, the amounts of the agents are effective to reduce, significantly reduce or eradicate the viral infection upon administration to an animal or patient.

The terms "preferentially" and "specifically", as used herein, mean that the anti-aminophospholipid or anti-anionic phospholipid antibody, 3G4-based therapeutics, or substantially cell impermeant PE-binding peptide derivatives, preferably duramycin derivatives, achieve anti-cancer or anti-viral effects that are substantially confined to the disease site, and do not substantially cause coagulation, destruction and/or tissue necrosis in normal, healthy tissues of the animal or subject. The structure and function of healthy cells and tissues is therefore maintained substantially unimpaired by the practice of the invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The U.S. file of this patent contains at least one drawing executed in color. Copies of this patent with color drawing(s) will be provided by the Patent and Trademark Office upon request and payment of the necessary fee.

Figure 7:
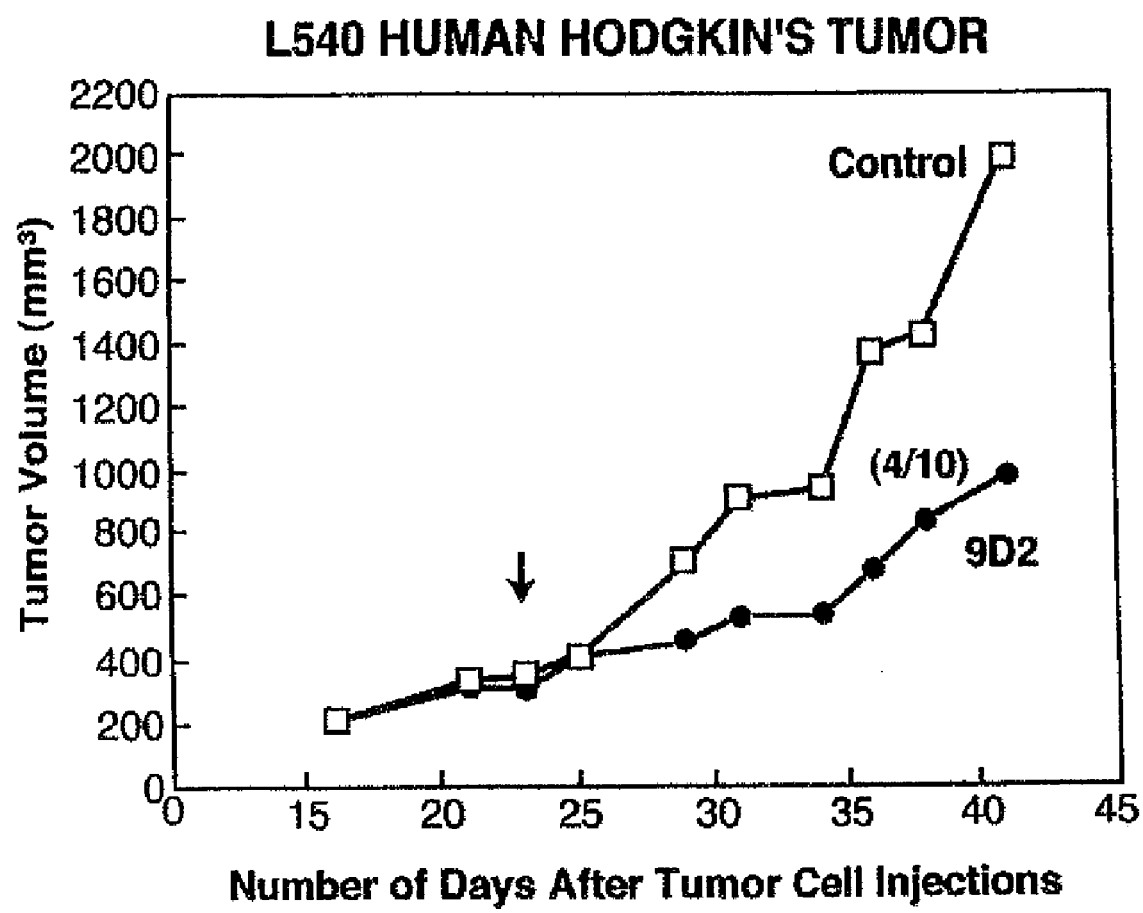

FIG. 7. Anti-tumor effects of 9D2 antibody in mice bearing L540 human Hodgkin's lymphoma. Groups of tumor-bearing mice were injected with 100 µg of 9D2 antibody (closed circles) intraperitoneally 3 times per week, as opposed to control (open squares). The tumor size was taken by calipers twice a week. The tumor volume is plotted against the number of days after tumor cell injections. The numbers in parentheses indicate number of mice with regressed tumors/total number of mice per group.

Figures 8A, 8B, 8C:
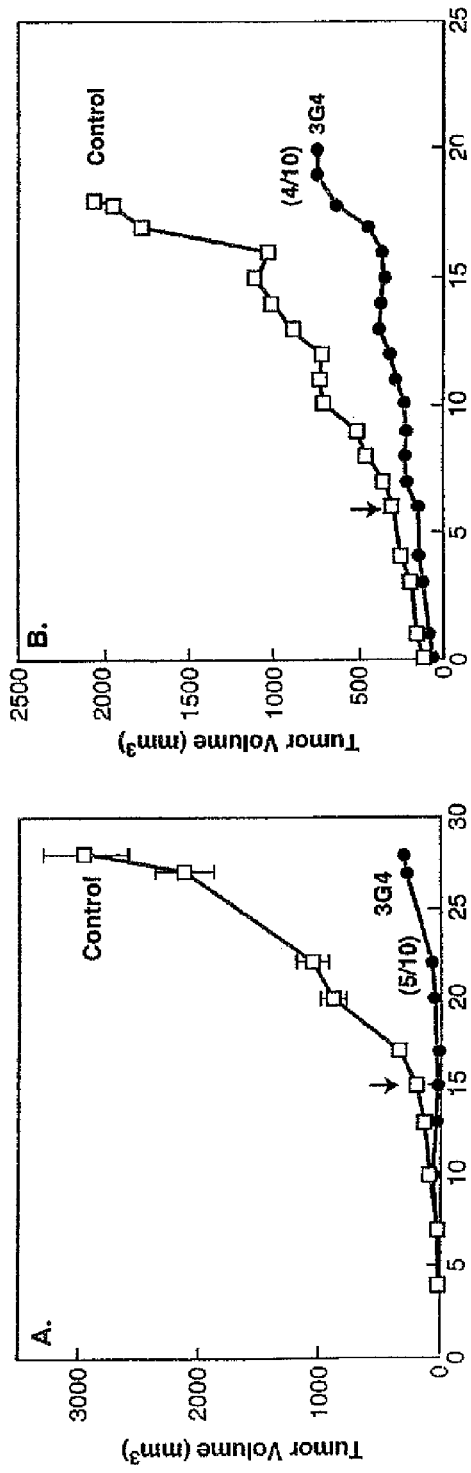
Figure 8F:
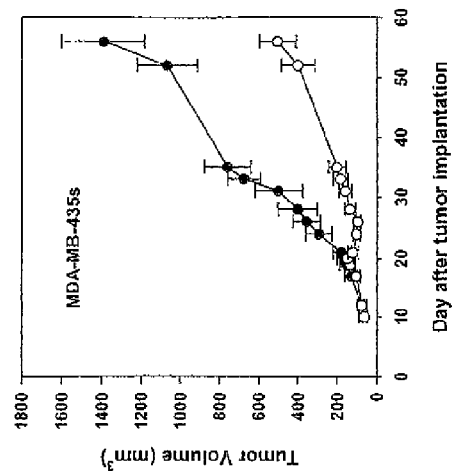
Figure 8E:
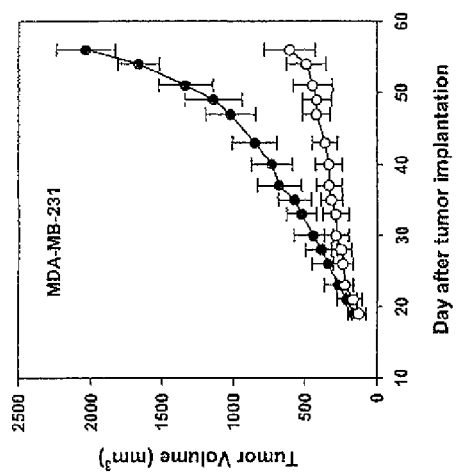
Figure 8D:
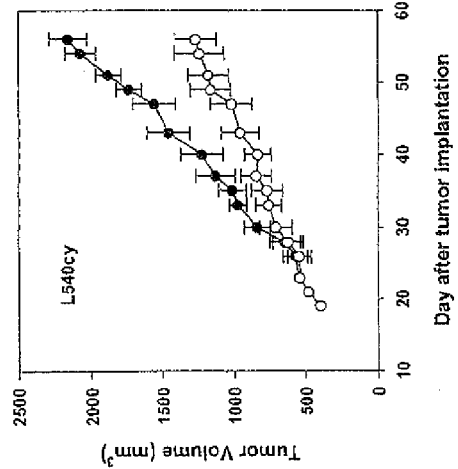
Figure 8G:
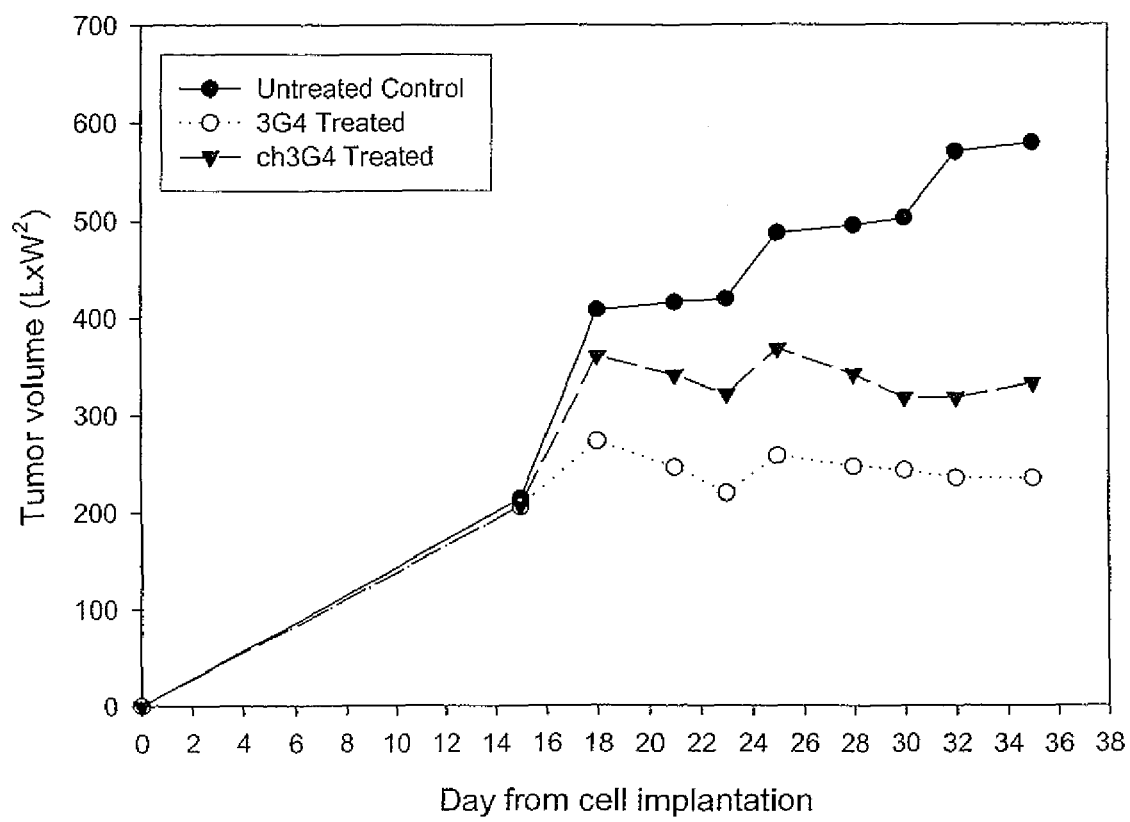

FIG. 8A, FIG. 8B, FIG. 8C, FIG. 8D, FIG. 8E, FIG. 8F and FIG. 8G. Anti-tumor effects of anti-PS antibody, 3G4, in animals with syngeneic and xenogeneic tumors. Cells of murine Meth A tumors (FIG. 8A), human MDA-MB-231 breast cancer (FIG. 8B and FIG. 8E), human Hodgkin's lymphoma L540 (FIG. 8C and FIG. 8D) and MDA-MB-231 cancer (FIG. 8F and FIG. 8G) were injected into mice. Tumors were allowed to grow to the sizes shown before treatment. The human Hodgkin's lymphoma cells were allowed to form large tumors. Each group of mice was injected intraperitoneally 3 times per week with 100 µg of 3G4 antibody as opposed to control (3G4 is stated on FIG. 8A, FIG. 8B, FIG. 8C; and shown by open circles on FIG. 8D, FIG. 8E, FIG. 8F). Animals were monitored twice a week for tumor measurements. The tumor volume is plotted against the number of days after tumor inoculation (FIG. 8A) or against the days of treatment (FIG. 8B and FIG. 8C) for 20-30 days (FIG. 8A, FIG. 8B and FIG. 8C; numbers in parentheses indicate number of mice with regressed tumors/total number of mice per group) or 60 days (FIG. 8D, FIG. 8E and FIG. 8F). The 3G4 antibody and chimeric 3G4 antibody (ch3G4) were used to treat MDA-MB-231 cancer cells, as opposed to control (FIG. 8G).

Figure 9A:
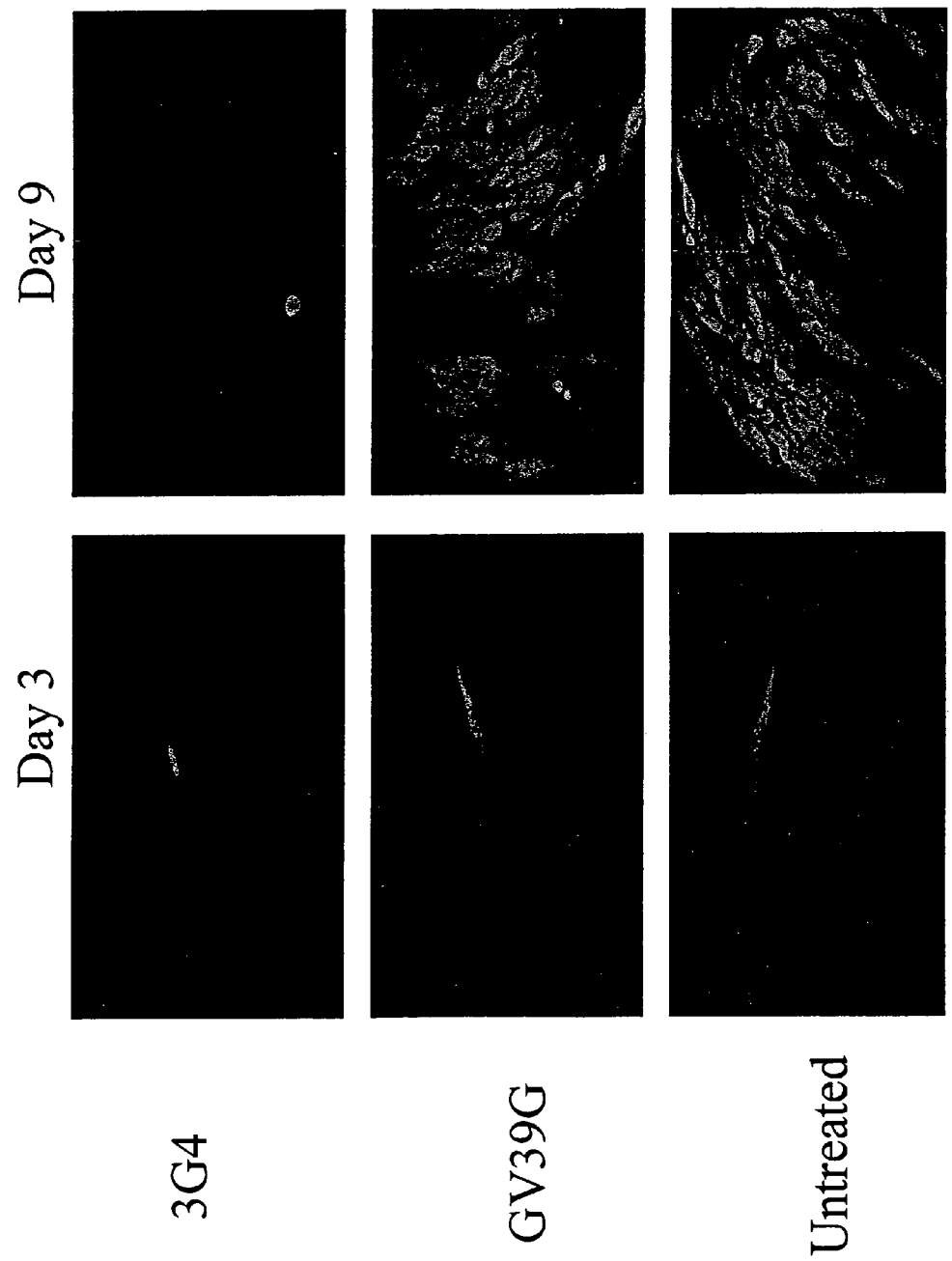
Figure 9B:
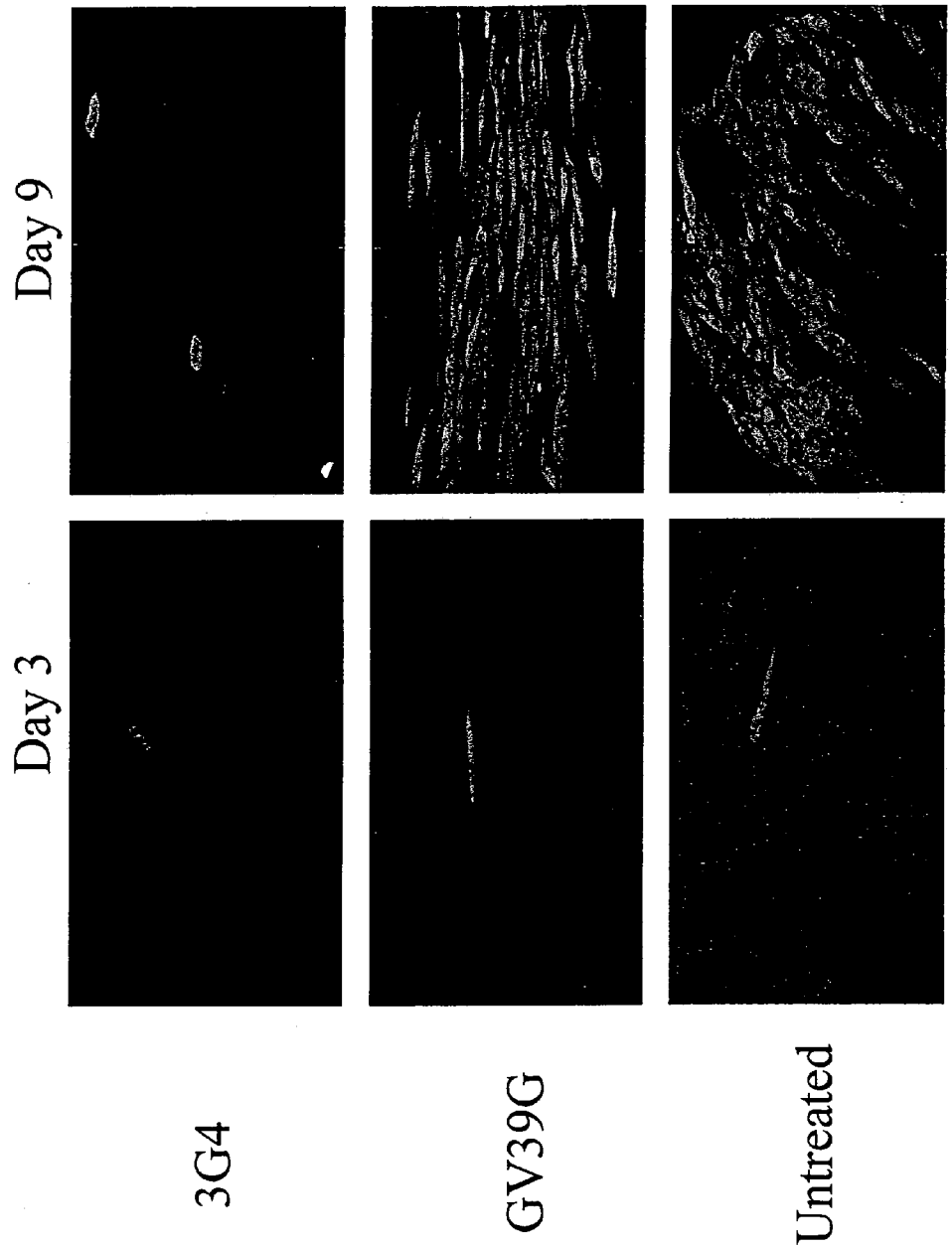

FIG. 9A and FIG. 9B. Inhibition of CMV replication in vitro by 3G4 antibody. CMV-infected HHF-R2 cells were treated with 3G4 (top two panels). The control wells were left untreated (bottom two panels) or were treated with the isotype matched control IgG₃ antibody GV39G (middle two panels). Cells were observed at different time points: day 3 (left column) and day 9 (right column). Infected cells appear green under the fluorescent microscope. Antibody treatment at 100 µg/ml (FIG. 9A) and 50 µg/ml (FIG. 9B).

Figure 10:
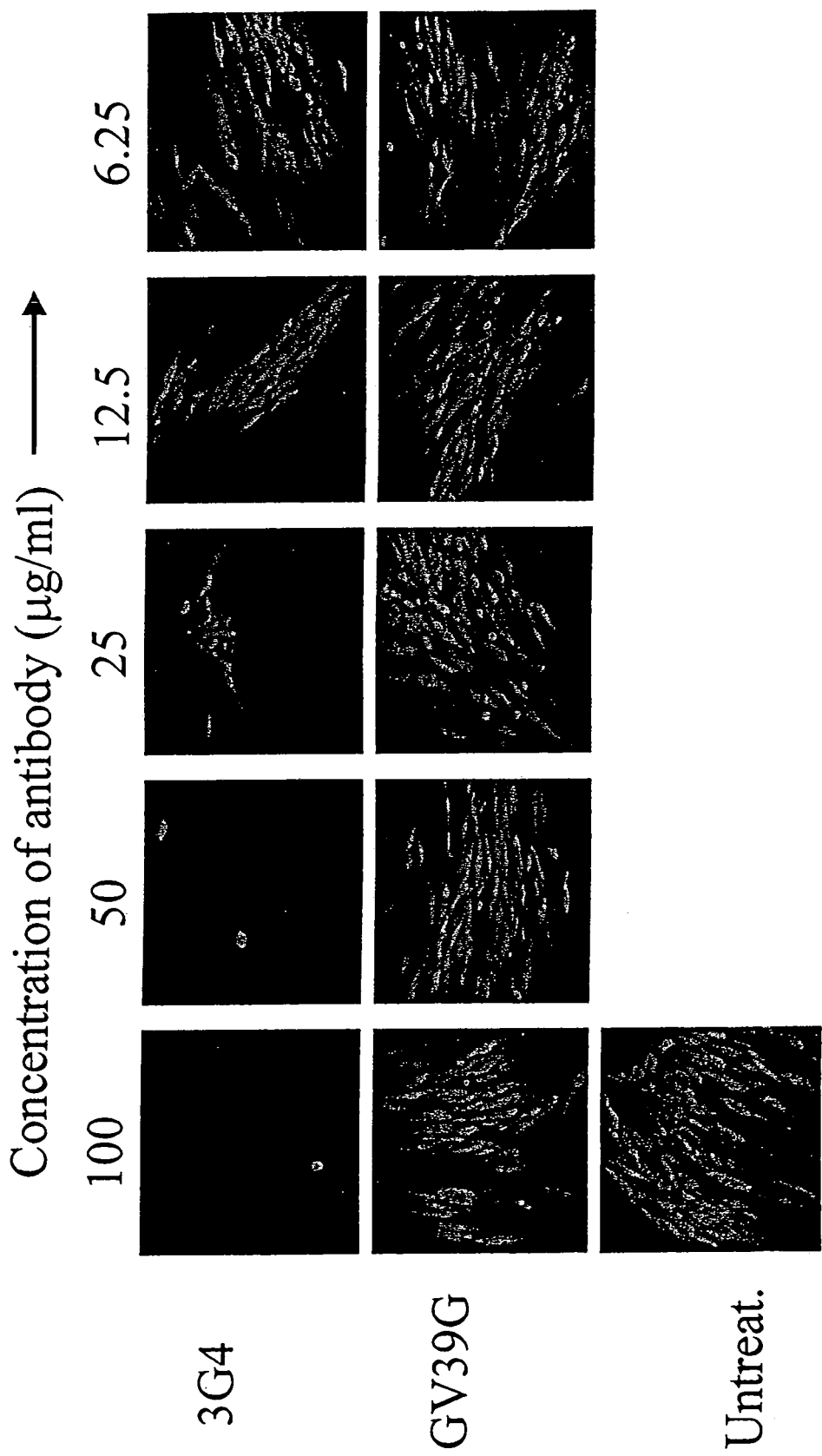

FIG. 10. Concentration dependent inhibition of CMV replication in vitro. CMV-infected HHF-R2 cells were treated with different concentrations of 3G4 (top panels). The control wells were left untreated (bottom panel) or were treated with the isotype matched control IgG₃ antibody GV39G (middle panels). Cells were observed on day 9. Infected cells appear green under the fluorescent microscope.

Figure 11A:
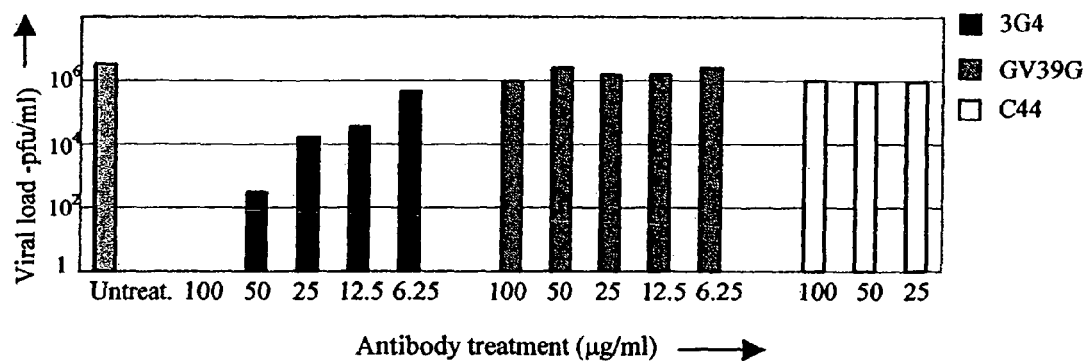
Figure 11B:
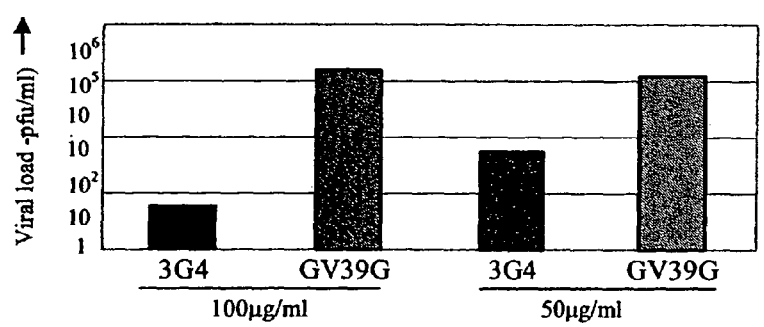
Figure 11C:
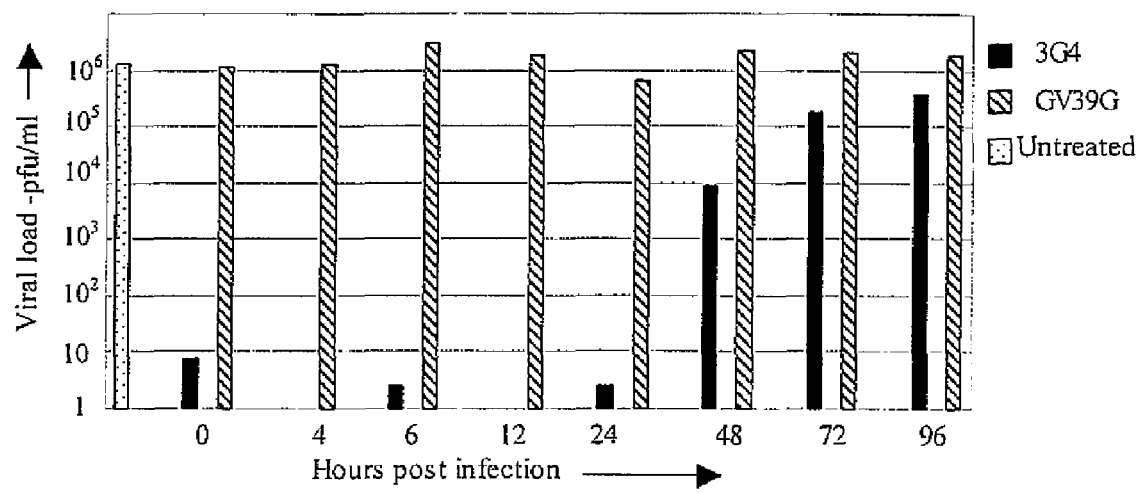

FIG. 11A, FIG. 11B and FIG. 11C. Quantification of CMV viral load in antibody-treated cells and inhibition of replication at a late stage of the viral replication cycle. Monolayers of human fibroblasts were infected with CMV at a low m.o.i. of 0.01 pfu/cell and treated with the indicated concentrations of the 3G4 antibody; the control antibody, GV39G; or the control anti-colchicine antibody, C44 (FIG. 11A; Untreat., untreated control). Monolayers of human fibroblasts were infected with CMV at a high m.o.i. of 3 pfu/cell and treated with 50 µg/ml or 100 µg/ml of the 3G4 antibody or the control antibody, GV39G (FIG. 11B). Monolayers of human fibroblasts were infected with CMV at a high m.o.i., the 3G4 antibody or the control antibody, GV39G were added at the indicated time points after infection (FIG. 11C). In each of FIG. 11A, FIG. 11B and FIG. 11C, the viral load in cells and supernatants was quantified using a standard plaque assay.

Figure 12:
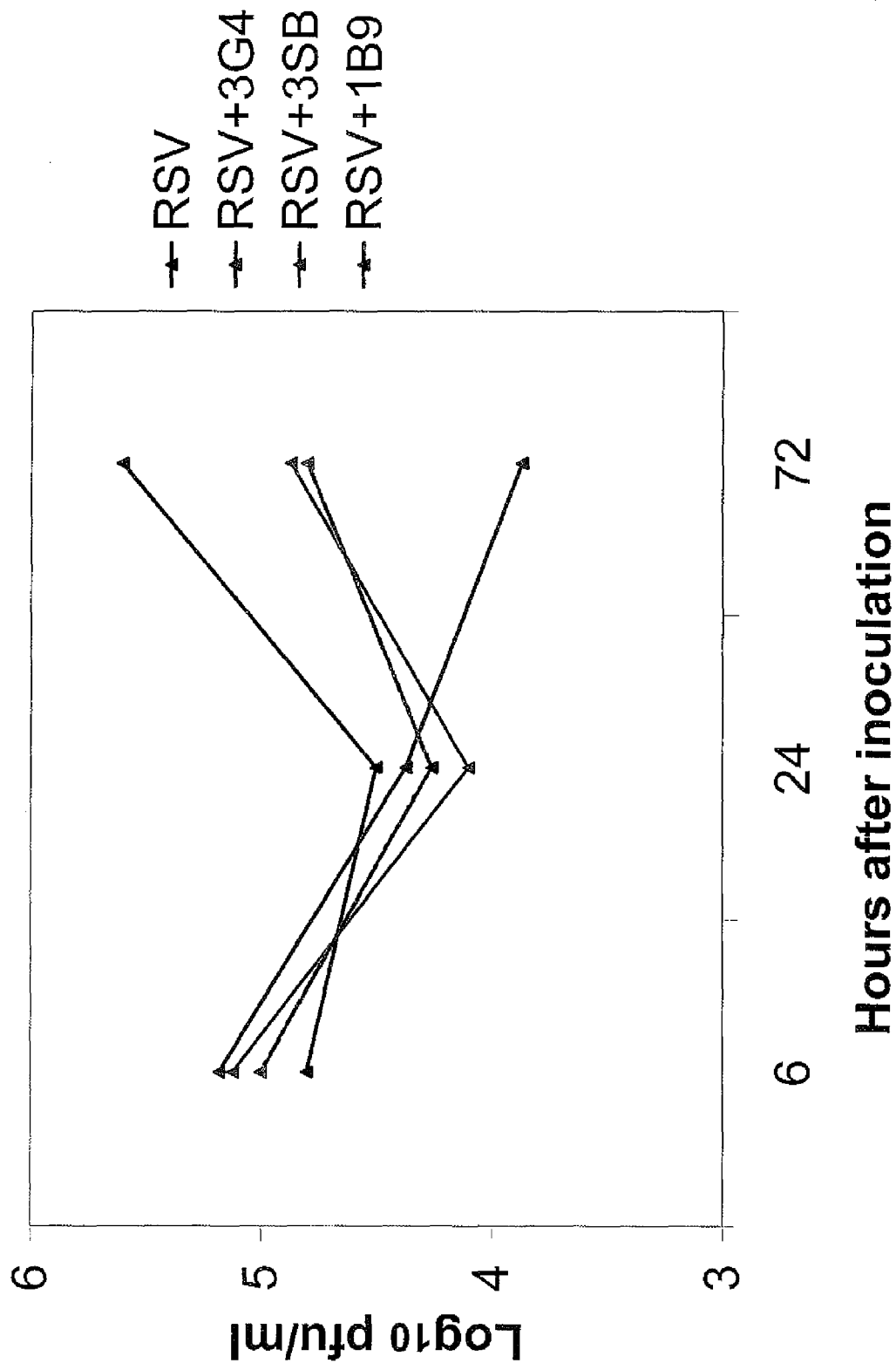

FIG. 12. Inhibition of RSV replication in vitro by 3G4, 1B9 and 3SB antibodies. RSV-infected A-549 cells were treated with 3G4, 1B9 or 3SB or left untreated as control. Treatment with 1B9 (green) and 3SB (red) resulted in a log decrease in viral replication (vs. control in blue). The even more pronounced anti-viral effect of 3G4 is shown in pink.

Figure 13R:
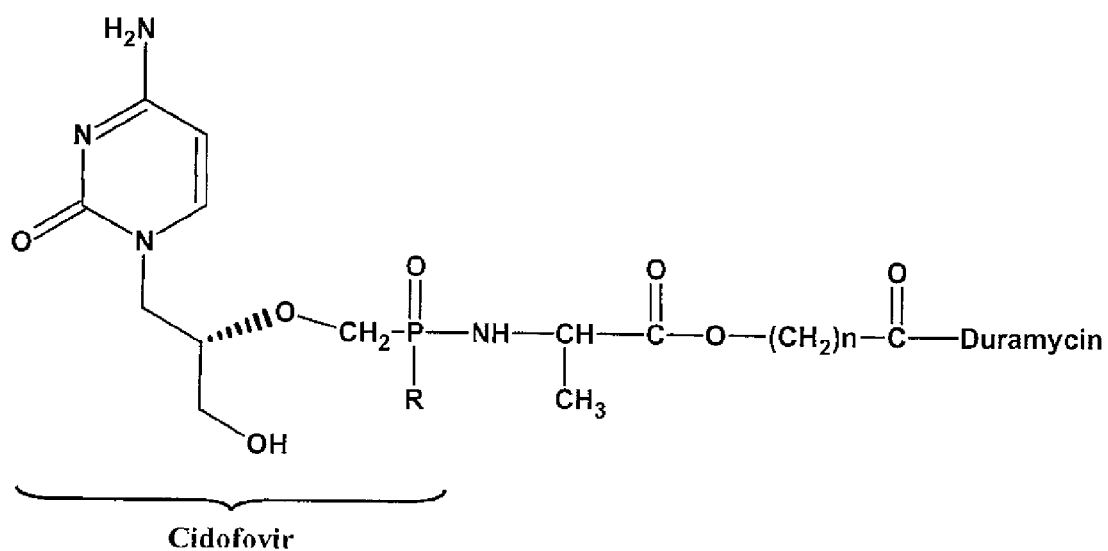

FIG. 13A, FIG. 13B, FIG. 13C, FIG. 13D, FIG. 13E, FIG. 13F, FIG. 13G, FIG. 13H, FIG. 13I, FIG. 13J, FIG. 13K, FIG. 13L, FIG. 13M, FIG. 13N, FIG. 13O, FIG. 13P, FIG. 13Q and FIG. 13R. Structures of duramycin derivatives. The chemical structures for exemplary duramycin derivatives from Example XV are depicted. In each of the compounds of FIG. 13A to FIG. 13O, the PE-binding peptide, duramycin, has been attached to a cell impermeant group to prevent the construct from exerting significant, non-specific toxic effects. The schematic structure of the parent duramycin cyclic peptide is shown in FIG. 13P. The linear sequence is represented by SEQ ID NO:9, and the structures of the modified amino acids in the sequence are depicted in FIG. 13Q. FIG. 13R depicts an exemplary duramycin anti-viral construct, in which duramycin is linked to cidofovir.

Figure 14A:
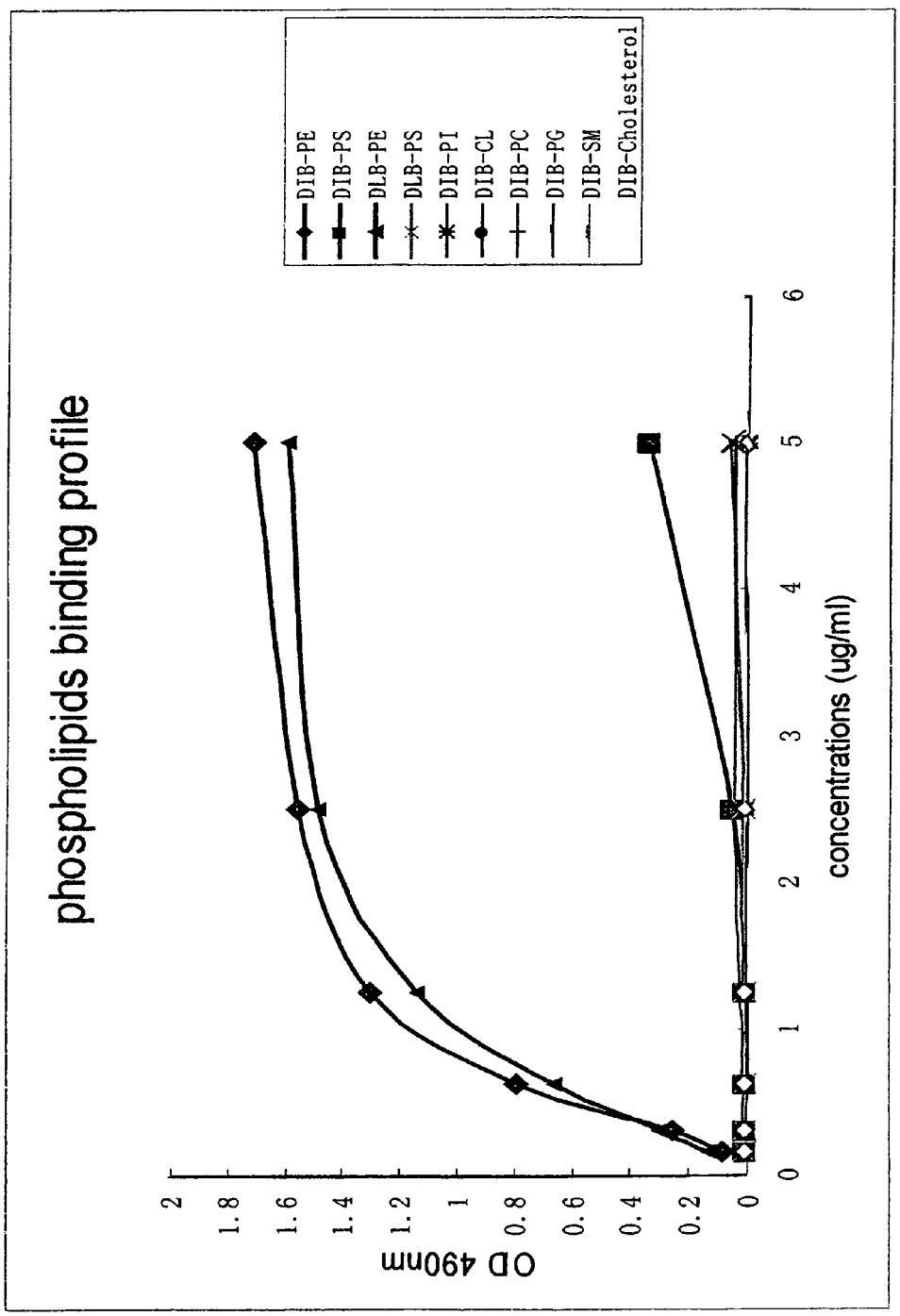
Figure 14B:
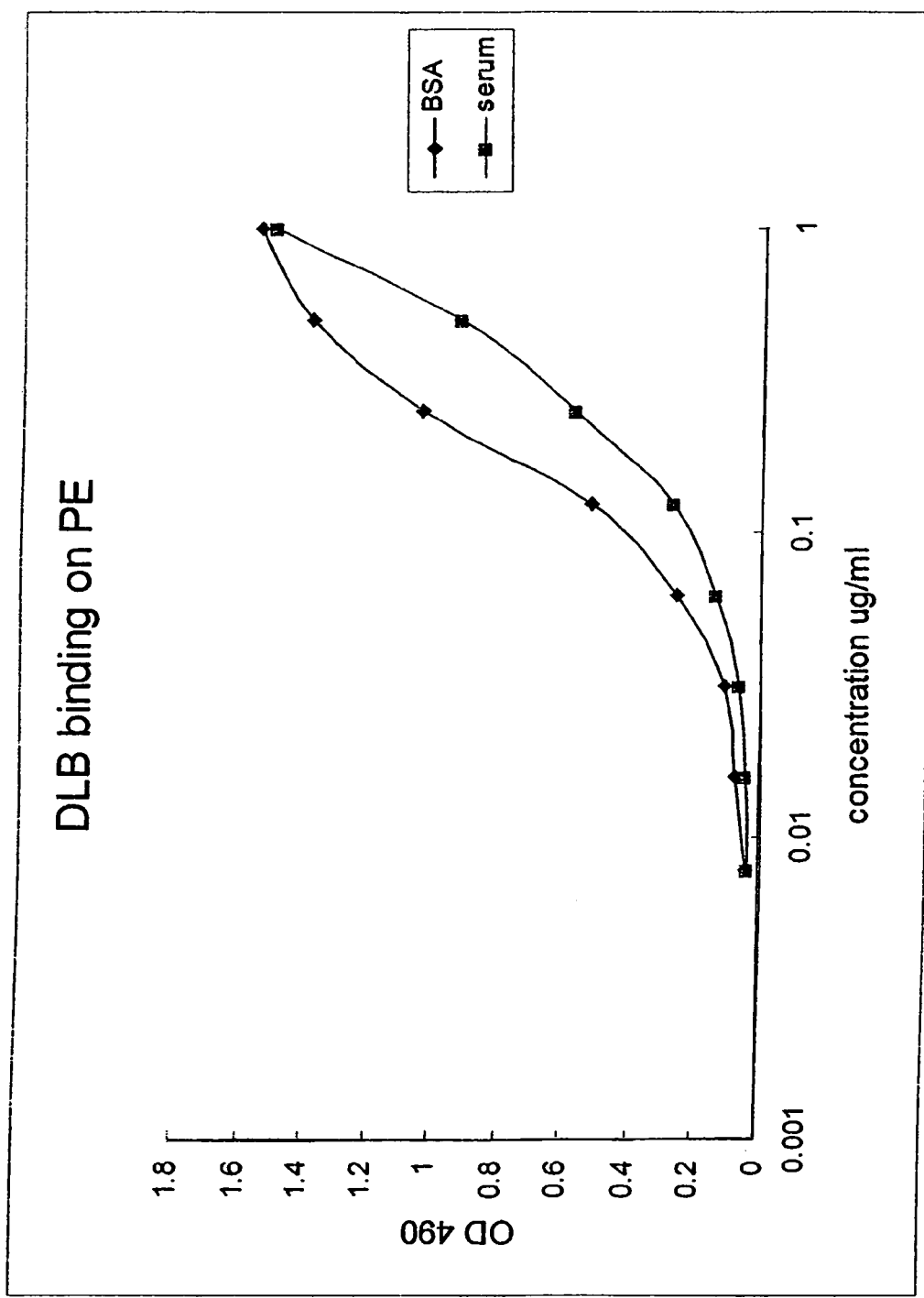
Figure 14D:
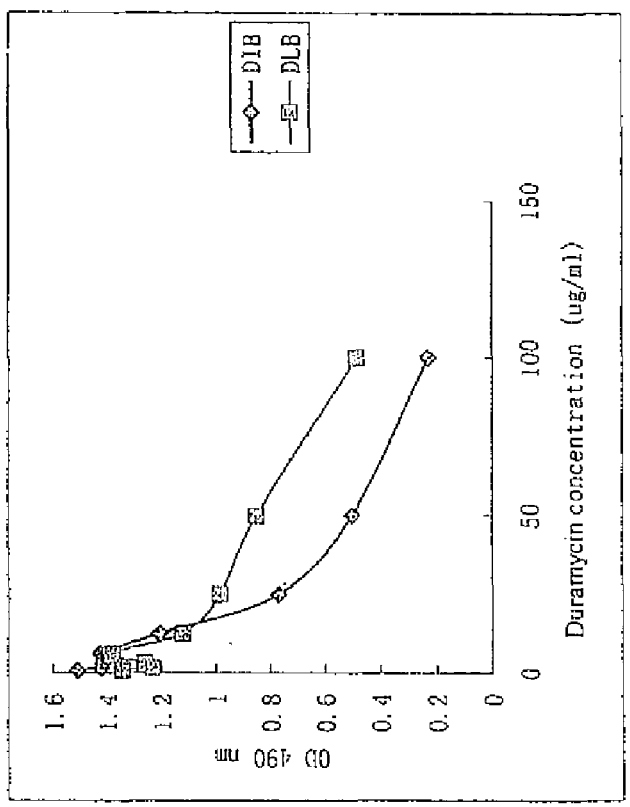
Figure 14C:
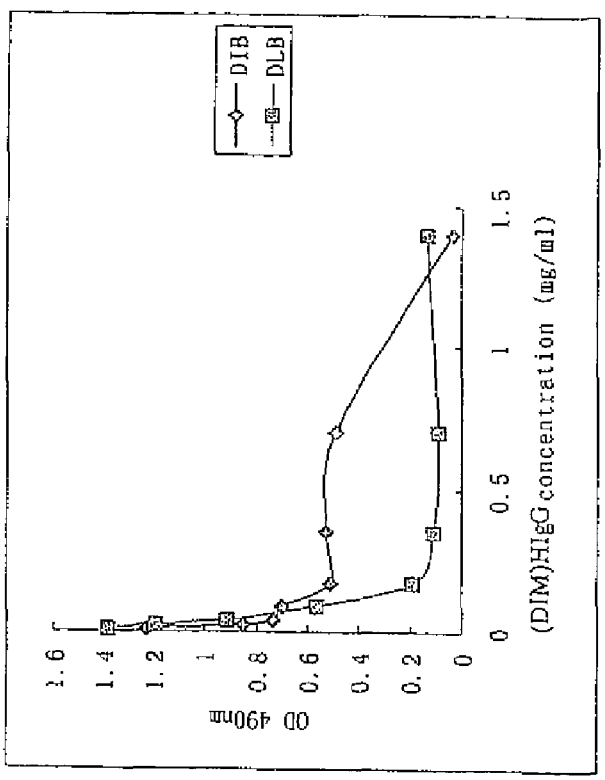

FIG. 14A, FIG. 14B, FIG. 14C and FIG. 14D. Binding specificities of duramycin derivatives. The duramycin derivatives were prepared as described in Example XV and their specificities determined using ELISAs and competition ELISAs, as described in Example XVI. FIG. 14A, phospholipid binding profile of duramycin derivatives against a panel of phospholipids, showing specificity for PE; FIG. 14B, serum has no significant effect on PE binding; FIG. 14C and FIG. 14D, results from competition ELISAs confirming specificity of duramycin derivatives for PE.

Figure 15:
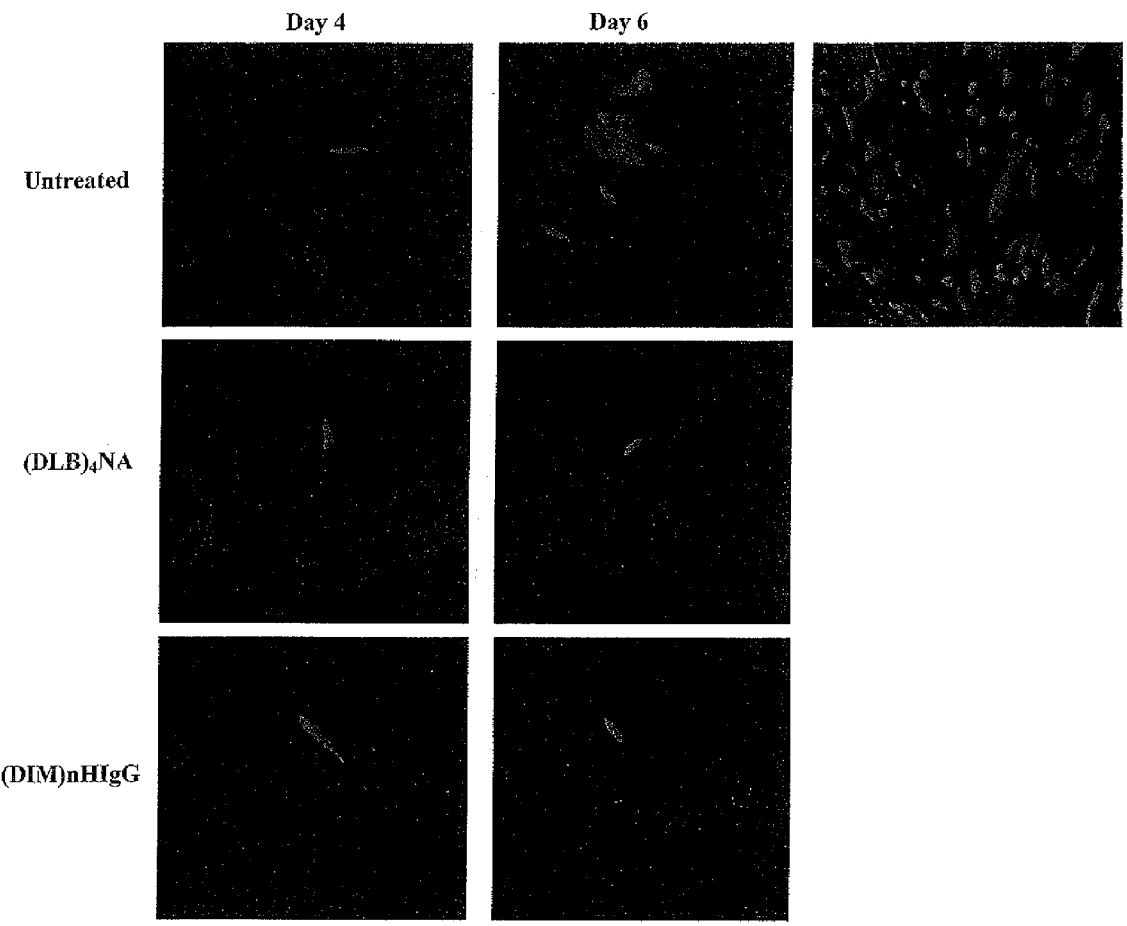

FIG. 15. Inhibition of CMV replication in vitro by duramycin derivatives. CMV infected HHF-R2 cells were treated with duramycin derivatives (DLB)₄NA and (DIM)ₙHIgG. The control wells were left untreated. Cells were observed at different time points: day 4 (left panels) and day 6 (right panels). Infected cells appear green under the fluorescent microscope. (DLB)₄NA and (DIM)ₙHIgG inhibit viral spread from singly-infected cells.

Figure 16:
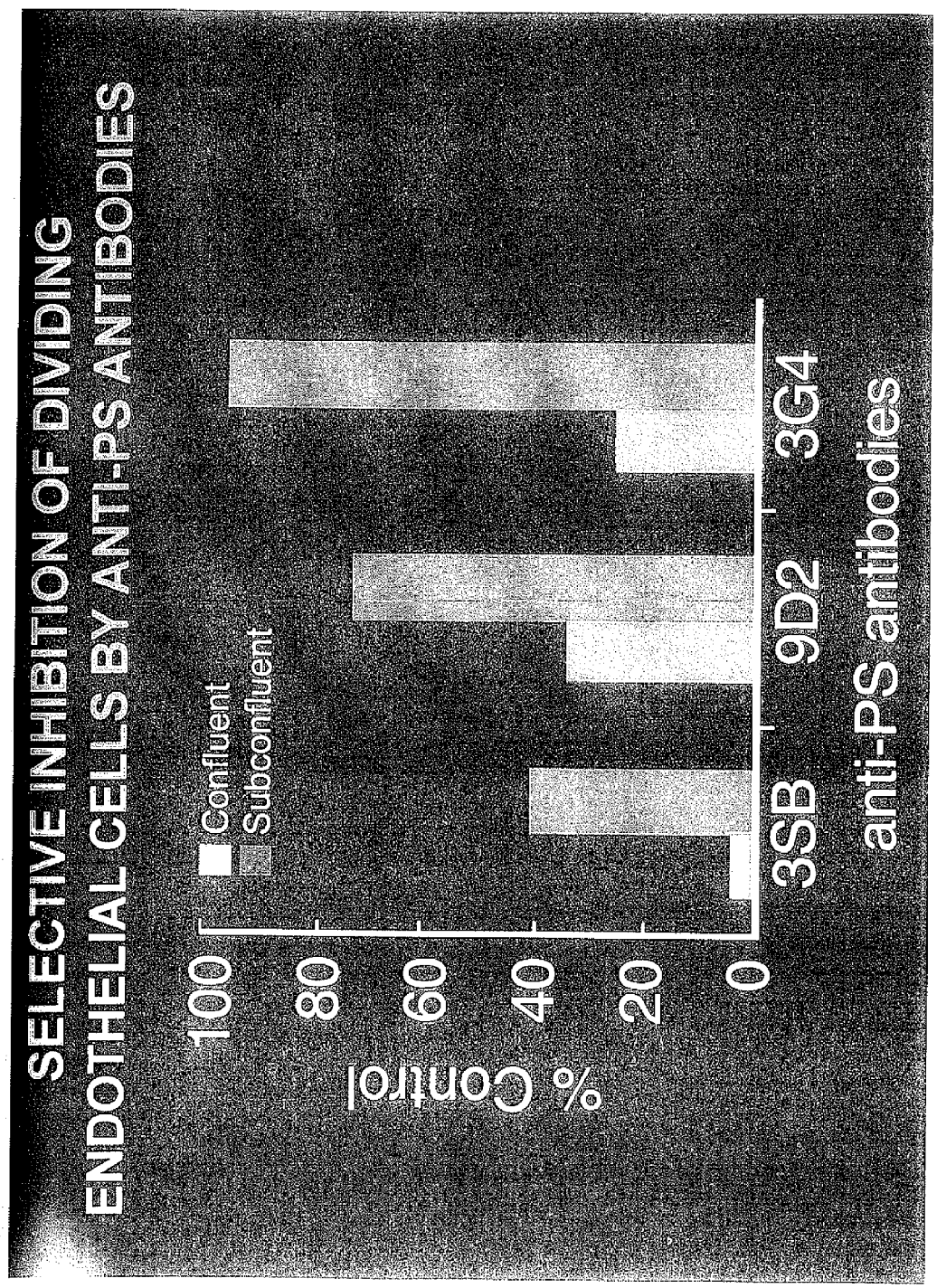

FIG. 16. Selective inhibition of dividing endothelial cells by anti-PS antibodies. The anti-PS antibodies 3SB, 9D2 and 3G4 were tested for inhibitory effects on endothelial cells in vitro as in Example XVIII. Each of the 3SB, 9D2 and 3G4 antibodies exhibit selective inhibition of dividing (subconfluent) endothelial cells as opposed to quiescent (confluent) cells. The 9D2 and 3G4 antibodies both have a greater inhibitory effect than 3SB.

Figure 17A:
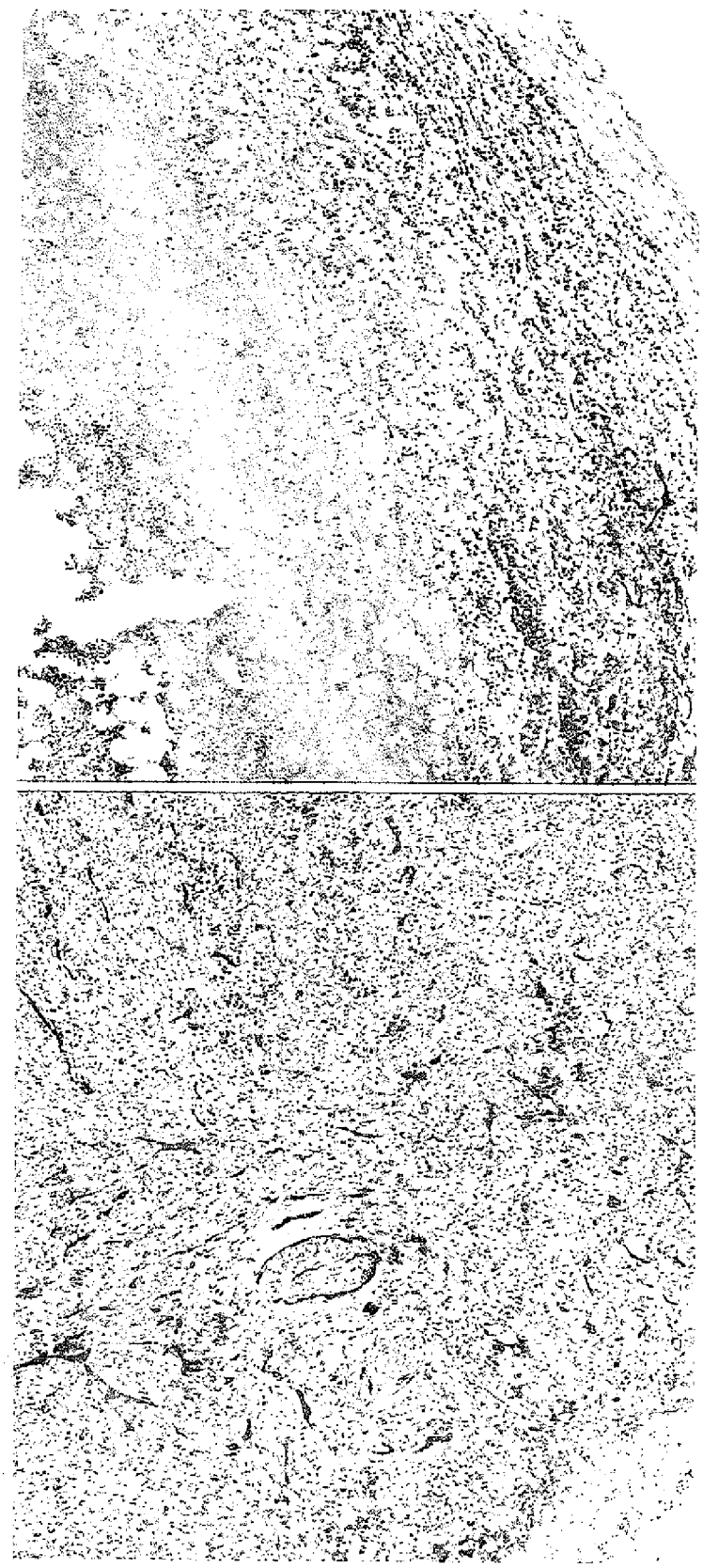
Figure 17B:
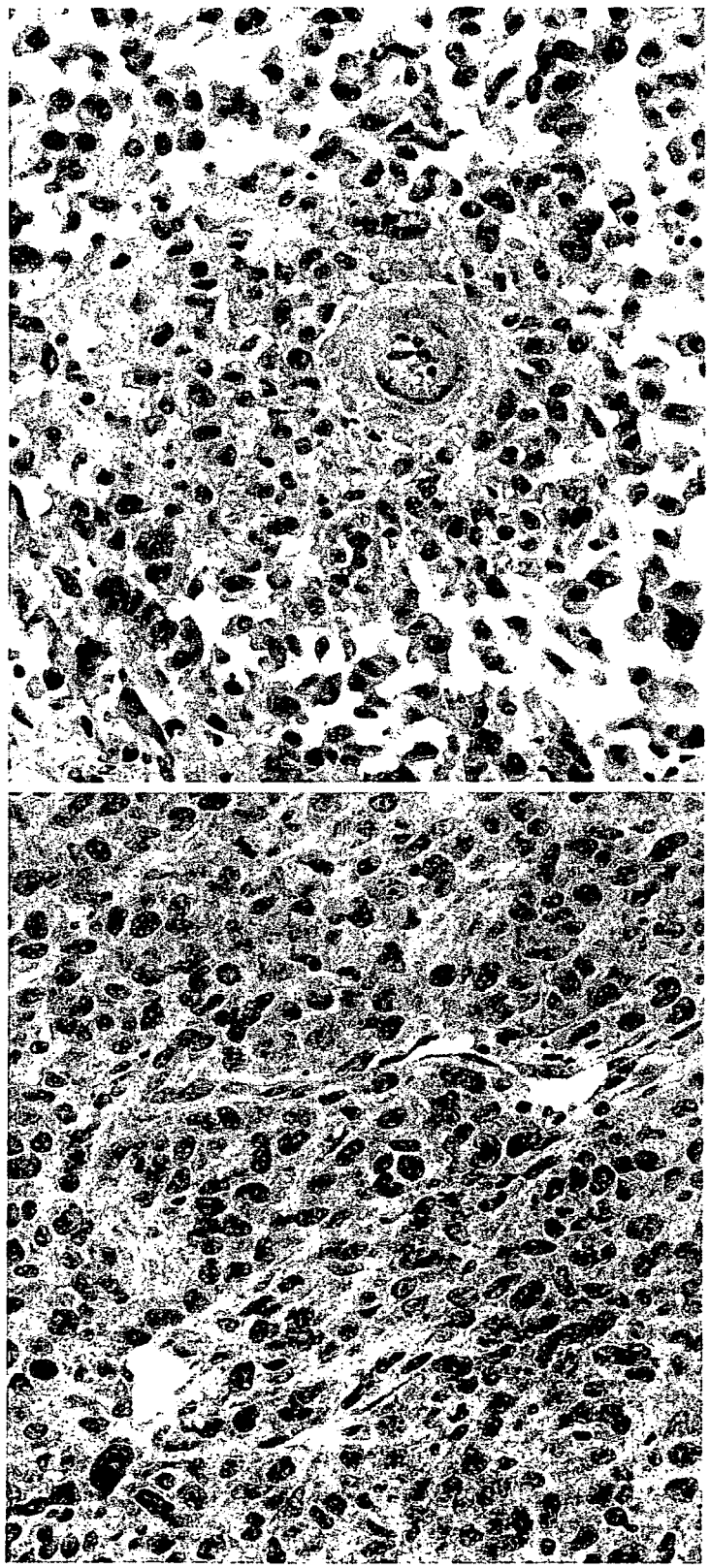

FIG. 17A and FIG. 17B. Anti-angiogenic and vascular targeting effects of the 3G4 antibody in tumor-bearing mice. Nude mice bearing MDA-MB-231 orthotopic tumors were treated 3 times a week with 100 µg/dose 3G4 antibody (treated, right panels) or with the same dose of an isotype-matched, control antibody (control, left panels). At the conclusion of treatment, animals were perfused and tumors were snap-frozen, cut and stained with an antibody to murine CD31 (rat, anti-mouse CD31), a pan-endothelial marker of murine vasculature (FIG. 17A), or embedded in paraffin and strained with H&E (FIG. 17B). Comparing the tumor sections from the control and treated animals shows that the administration of the 3G4 results in anti-angiogenic (FIG. 17A) and vascular targeting (FIG. 17B) effects.

FIG. 18A and FIG. 18B. DNA and amino acid sequences of the complementarity determining regions (CDRs) of the 3G4 antibody. DNA and amino acid sequences for the heavy (FIG. 18A; SEQ ID NO:1 and SEQ ID NO:2) and light (FIG. 18B; SEQ ID NO:3 and SEQ ID NO:4) chains are presented, and the restriction sites in the DNA sequences are shown. The leader sequence is distinguished from the mature protein, which begins as shown by the first arrow in each of FIG. 18A and FIG. 18B. Exemplary means of grafting each variable sequence with a human constant region are set forth, wherein the first part of the respective human constant region sequences (SEQ ID NO:7 and SEQ ID NO:8) is shown by the second arrow in each of FIG. 18A and FIG. 18B.

Figure 19A:
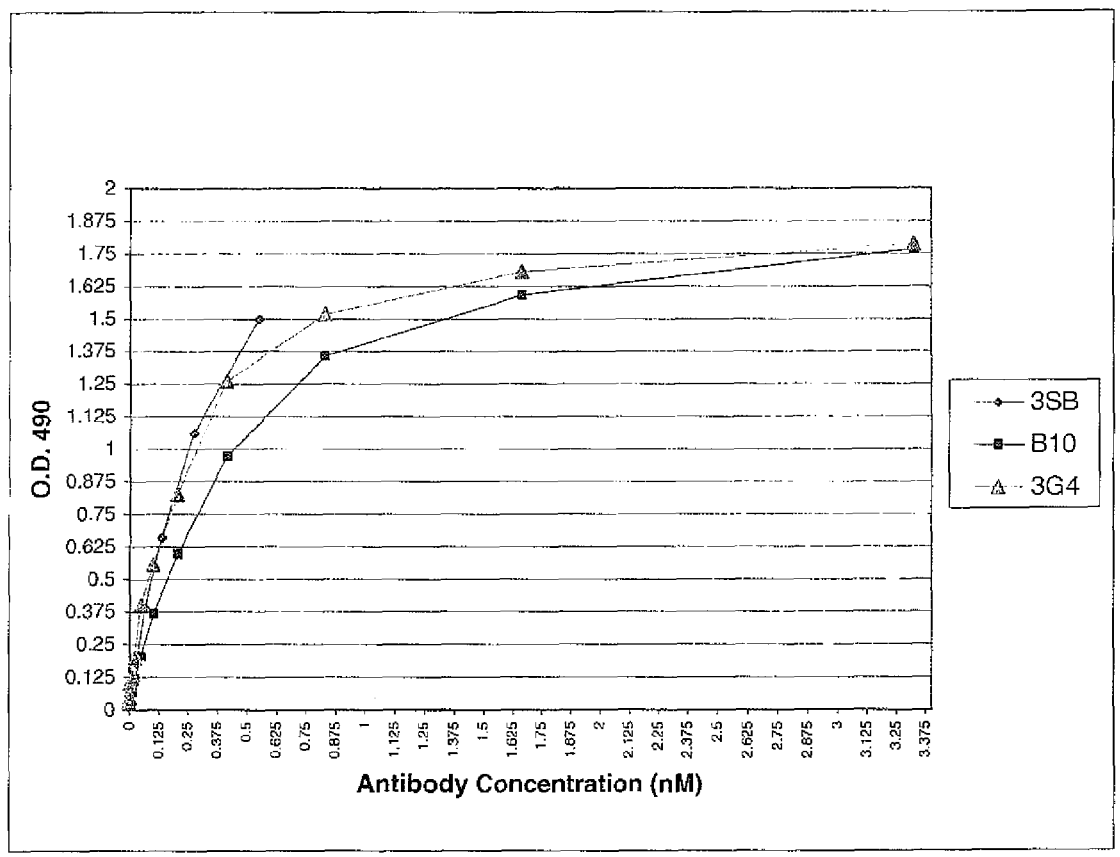
Figure 19B:
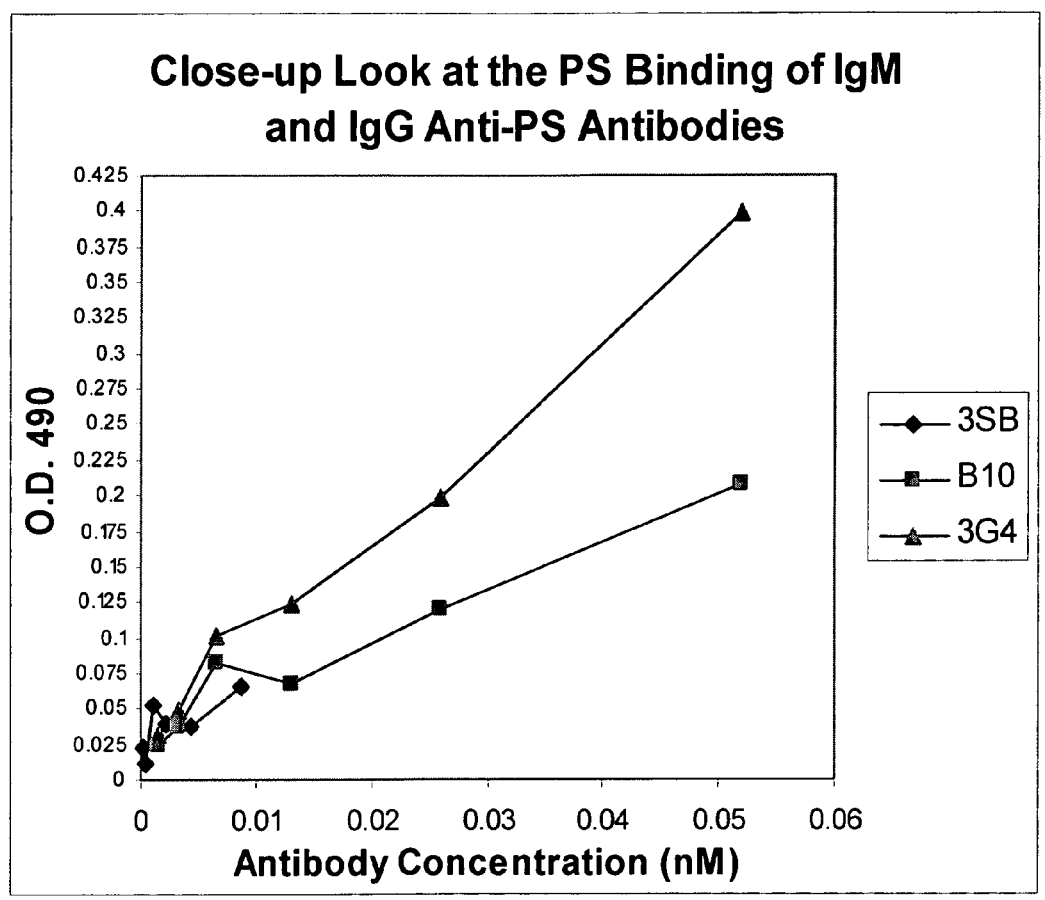

FIG. 19A and FIG. 19B. Comparison of the PS binding of the IgG anti-PS antibody, 3G4, with the IgM anti-PS antibody, 3SB. The PS binding of the IgM antibody, 3SB (♦) and two IgG antibodies, 3G4 (▲) and 3B10 (■), was determined by ELISA using antibody concentrations up to 3.375 nM (FIG. 19A). The PS binding of the 3SB (♦), 3G4 (▲) and 3B10 (■) antibodies at concentrations of up to 0.06 nM is shown separately (FIG. 19B).

Figure 20:
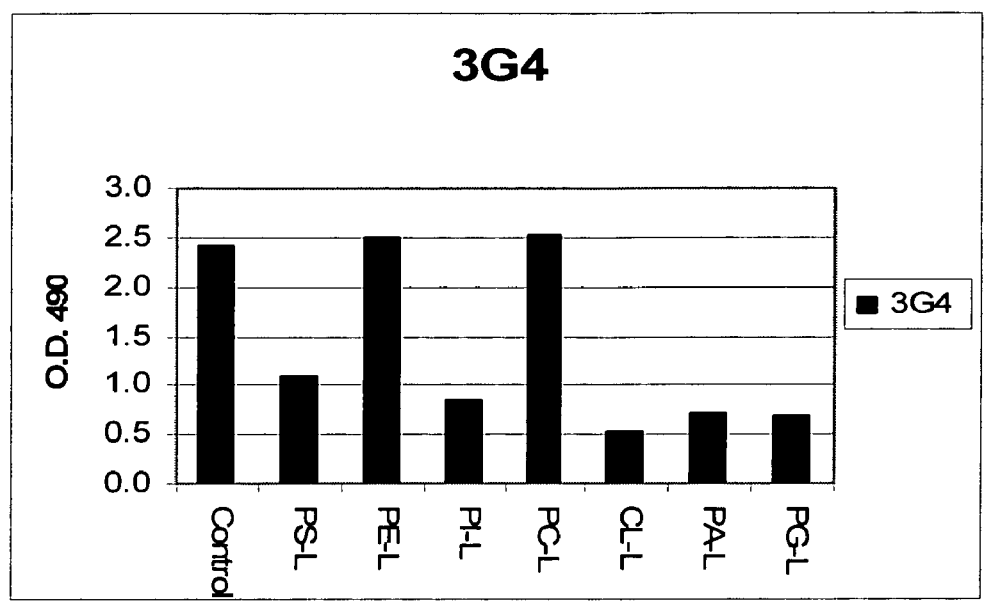

FIG. 20. Inhibition of binding of 3G4 antibody to immobilized PS using competing phospholipid liposomes. The 3G4 antibody (0.1 µg/ml) was pre-incubated for 30 minutes with various liposomes made from pure phospholipids (PS-L, PE-L, PI-L, PC-L, CL-L, PA-L and PG-L) or buffer alone (control). The mixtures were then added to PS-coated ELISA plates, washed and bound antibodies were detected using secondary antibodies and OPD. Binding in the presence of the listed liposomes is shown and compared to 3G4 antibody binding in the absence of any liposome.

Figure 21:
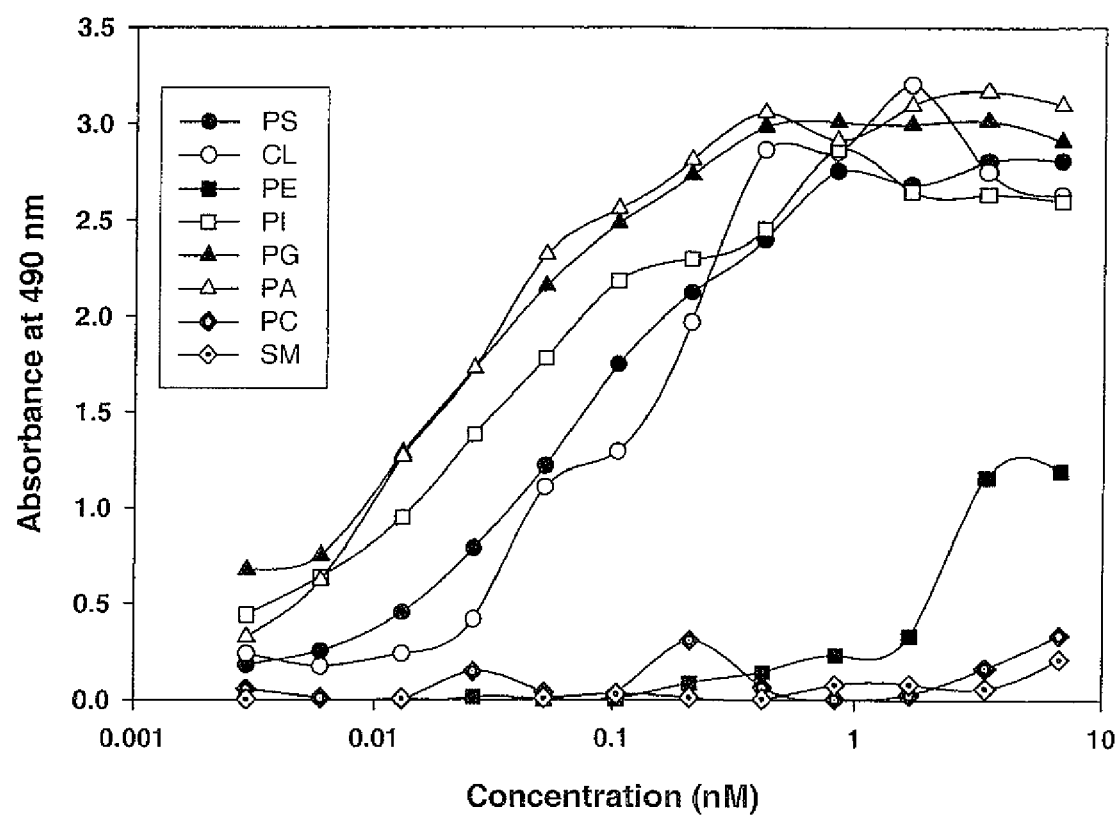

FIG. 21. Binding of chimeric 3G4 to phospholipids. The chimeric 3G4 antibody (ch3G4) was prepared as described in Example XIX. Phospholipids (PS, PI, PE, PC, SM, CL, PG and PA) were adsorbed to plastic of microtiter plates. After blocking, chimeric 3G4 antibody was added at the concentrations shown. The plates were washed and the bound chimeric 3G4 antibody was detected via secondary antibody binding and development.

Figure 22:
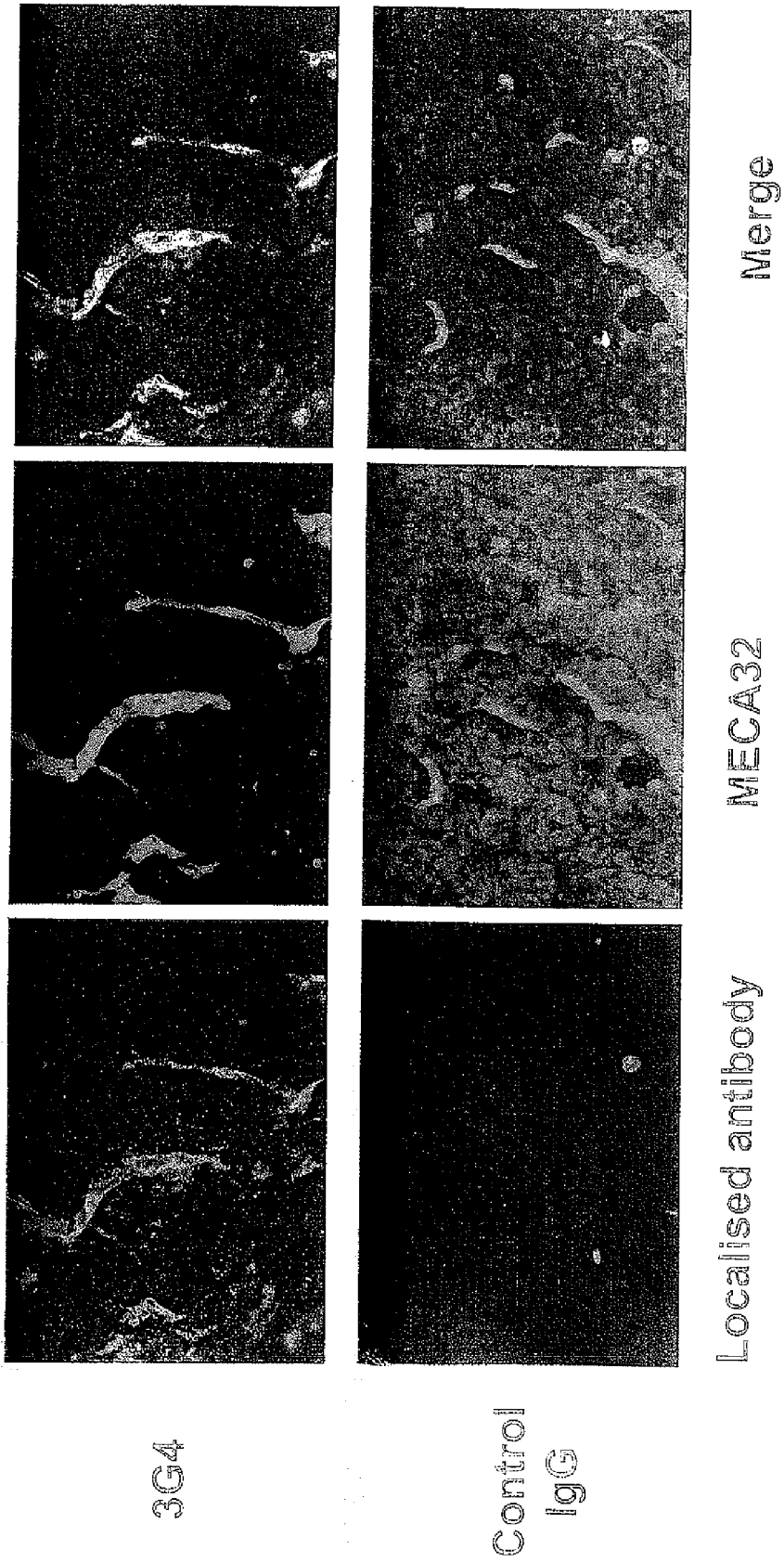

FIG. 22. Localization of chimeric 3G4 to tumor vascular endothelium in vivo. Biotinylated ch3G4 (top panels) and control IgG (bottom panels) were administered to mice bearing MD-MBA-435s tumors. Tumor sections were stained with Cy3-conjugated streptavidin to detect the biotinylated antibodies (left panels). Staining with the MECA 32 antibody followed by FITC-tagged anti-rat IgG secondary antibody was conducted to detect vascular endothelium (middle panels). The red and green images are merged (right panels), whereupon biotinylated proteins bound to the tumor vascular endothelium appear yellow. The coincident staining of the localized 3G4 antibody and the MECA 32 marker of the vascular endothelium is shown by the yellow color on the superimposed images (top right).

Figure 23:
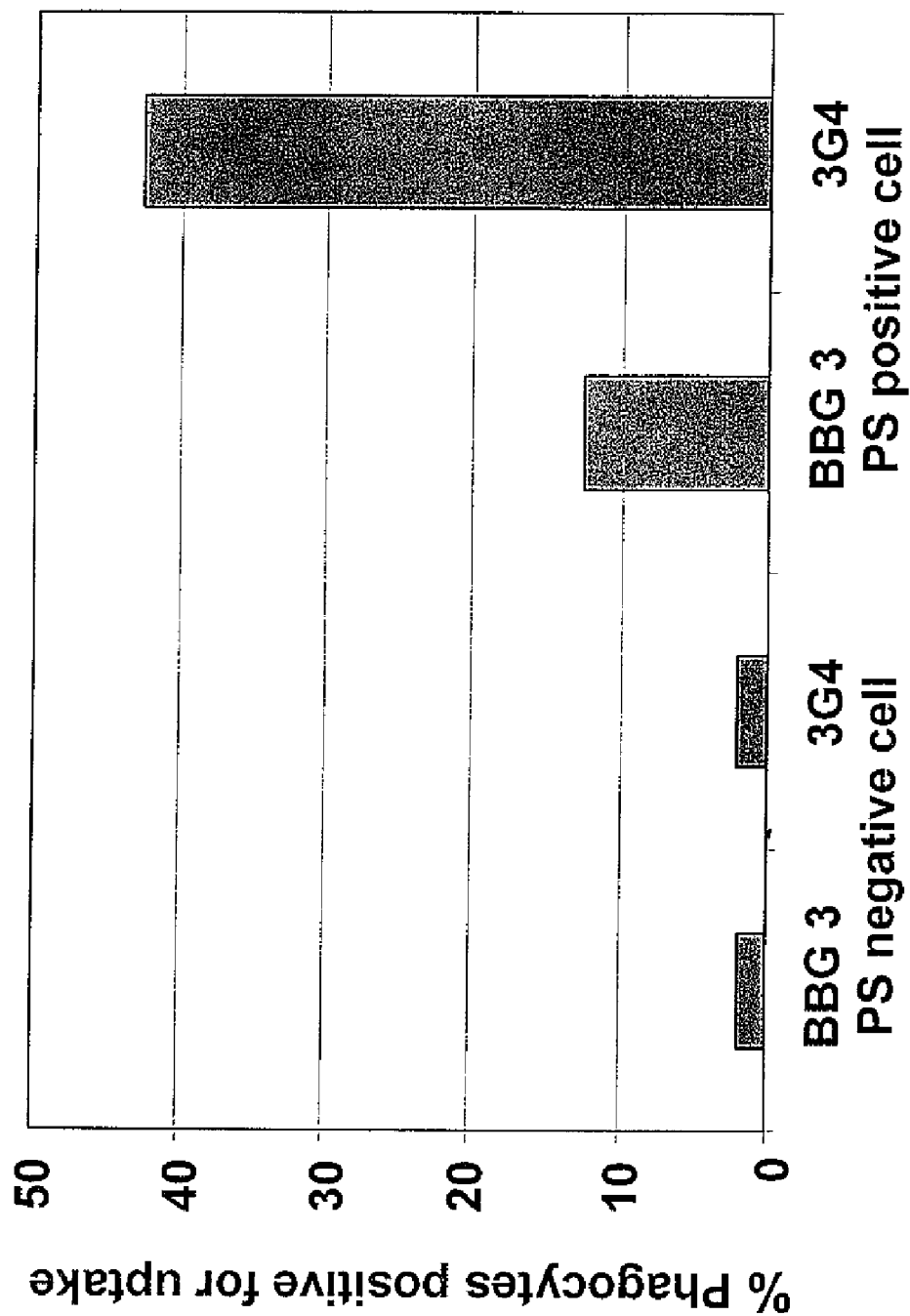

FIG. 23. Enhancement of macrophage phagocytosis of PS-positive cells by 3G4. HL-60 tumor cells were labeled with the green fluorescent dye CFDA, and PS exposure was induced by 200 µM $H_2O_2$. Treated cells were harvested and opsonized for 1 hr using 5 µg/ml 3G4 or an isotype-matched control antibody (BBG3). Target cells were then added to macrophages, which were isolated from mouse bone marrow and cultured in chamber slides for 5 days in media containing 5 ng/ml GM-CSF. After 2 hrs, the slides were fixed and phagocytosis was visually counted under the fluorescent microscope. Results are presented as the percentage of phagocytosing macrophages (macrophages that have phagocytosed at least one tumor cell).

Figure 24A:
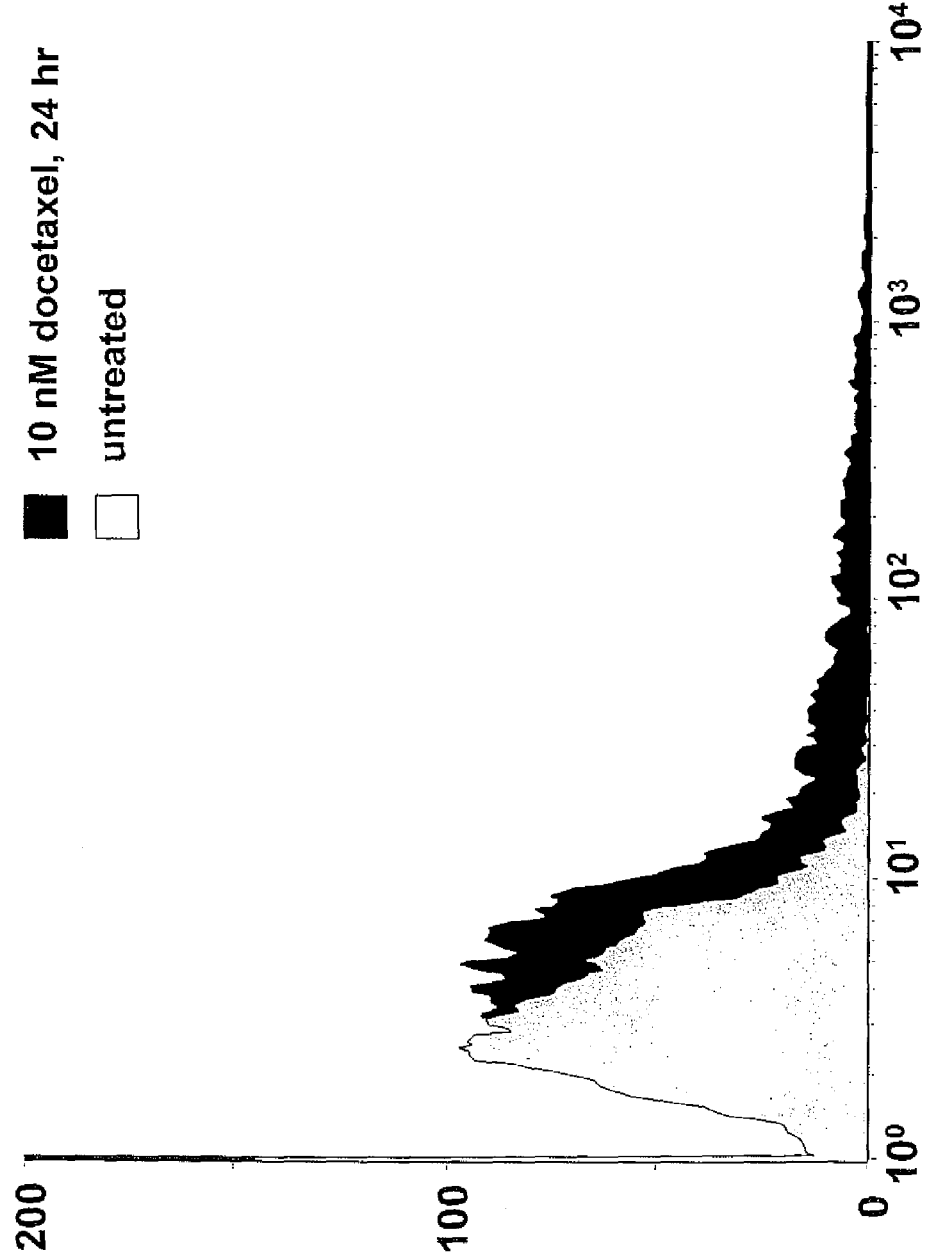
Figure 24B:
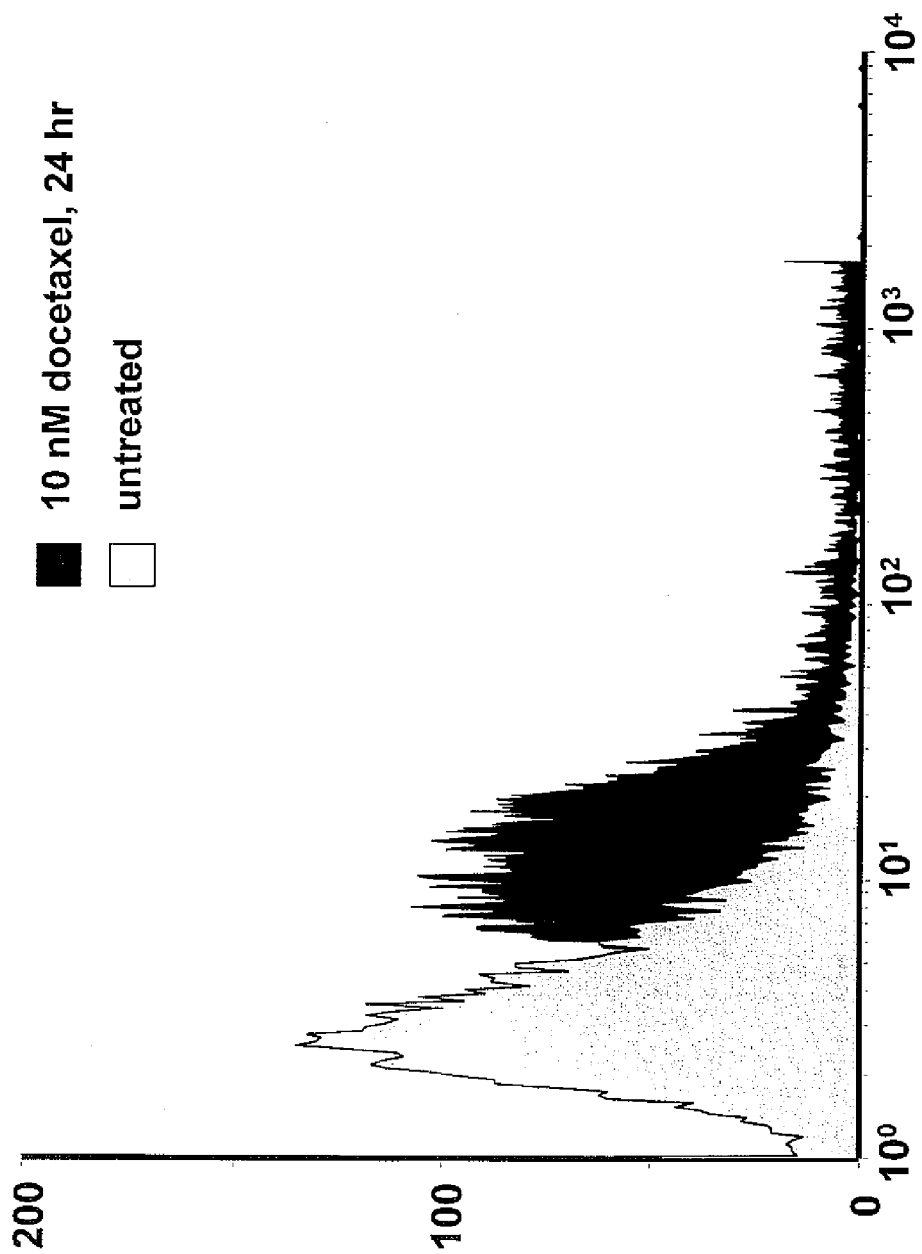

FIG. 24A and FIG. 24B. Induction of PS exposure on endothelial cells by docetaxel. Human umbilical vein endothelial cells (HUVEC) and human microvessel endothelial cells (HMVEC) were treated with 10 nM of docetaxel for 24 hrs. Cells were harvested, washed with PBS and incubated with 3G4 at 10 µg/ml for 30 mins. on ice. The cells were then washed twice, FITC labeled goat anti-mouse IgG was added and the cells incubated for a further 30 mins. on ice. The cells were then washed and analyzed by FACS using a FACSCalibur cytometer (Becton-Dickinson, San Jose, Calif.) with CellQuest acquisition software. Both treated HUVEC (FIG. 24A) and HMVEC (FIG. 24B) show significant increases in 3G4 binding as compared to untreated cells.

Figure 25A:
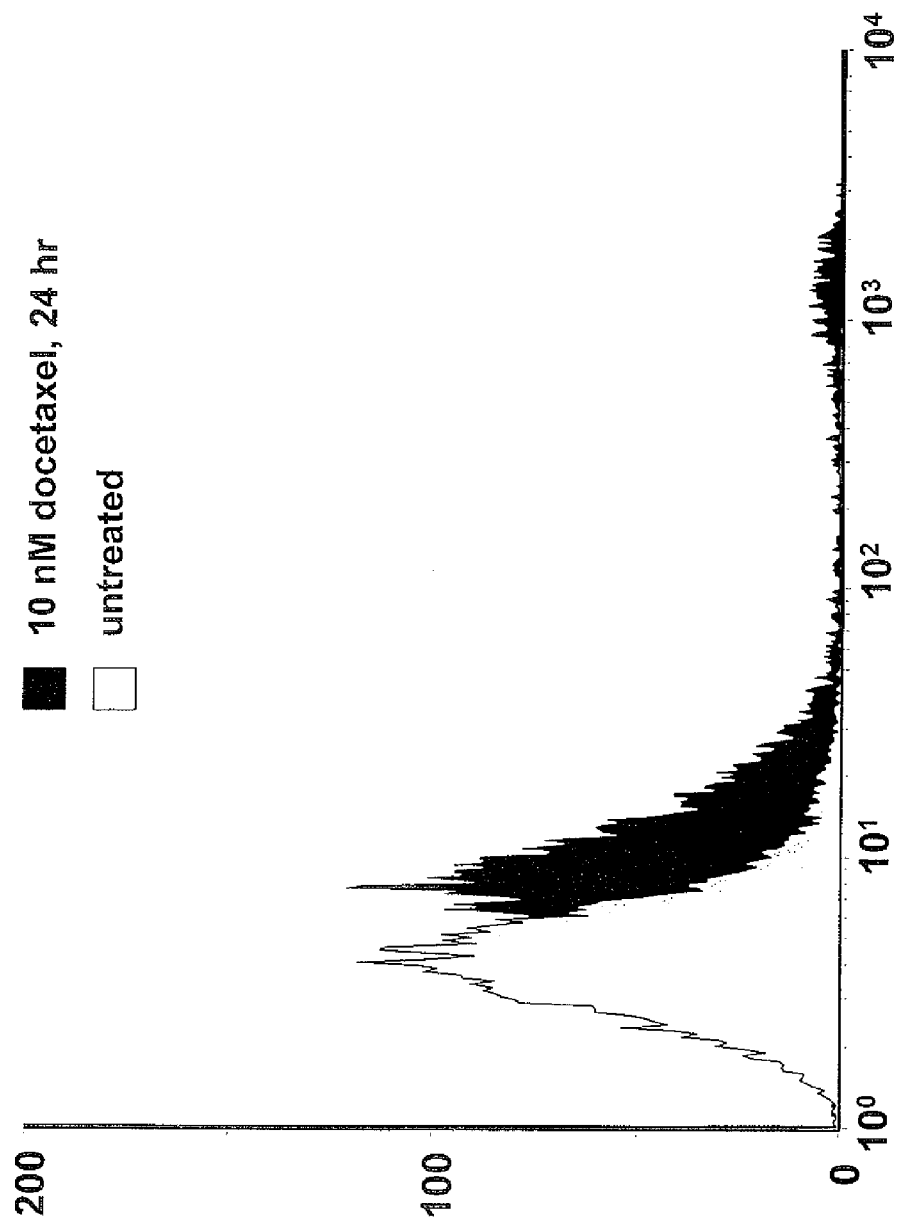
Figure 25B:
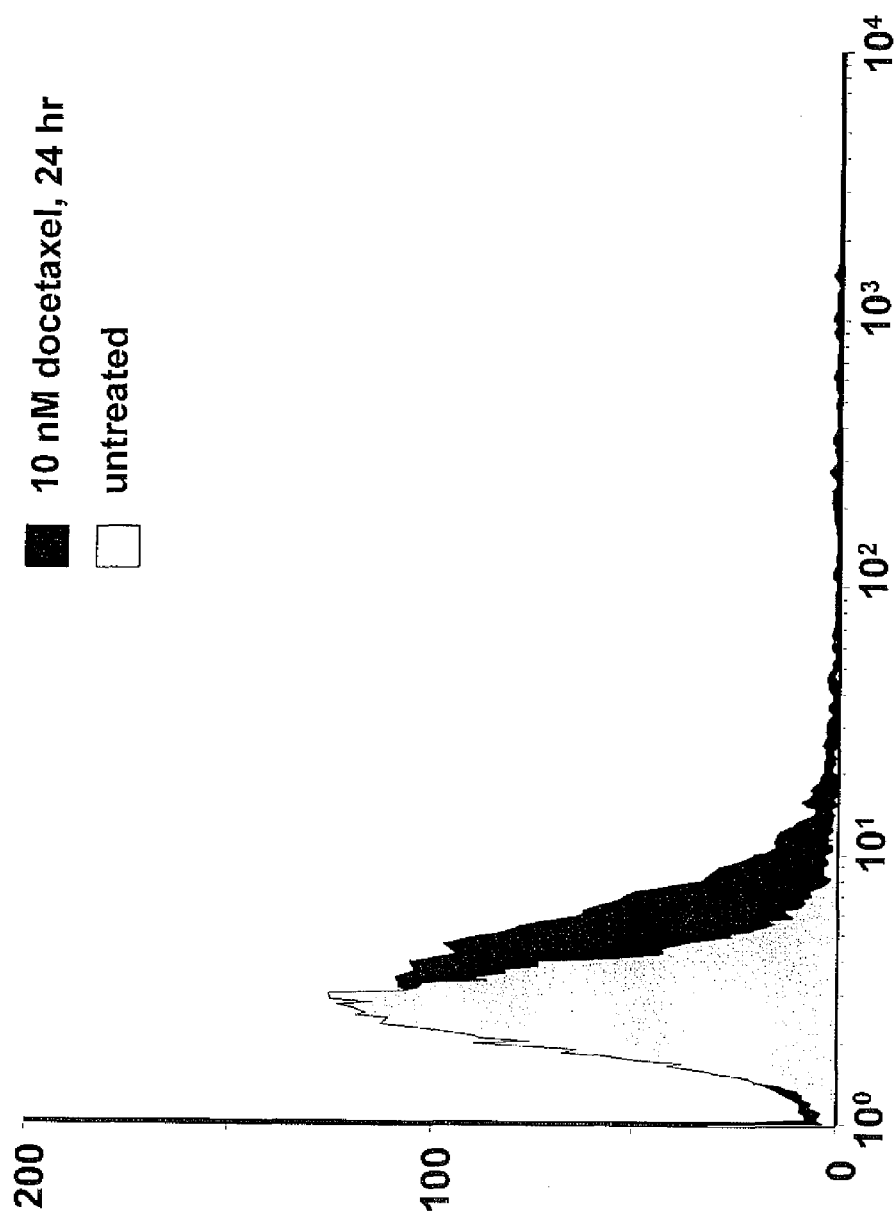
Figure 25C:
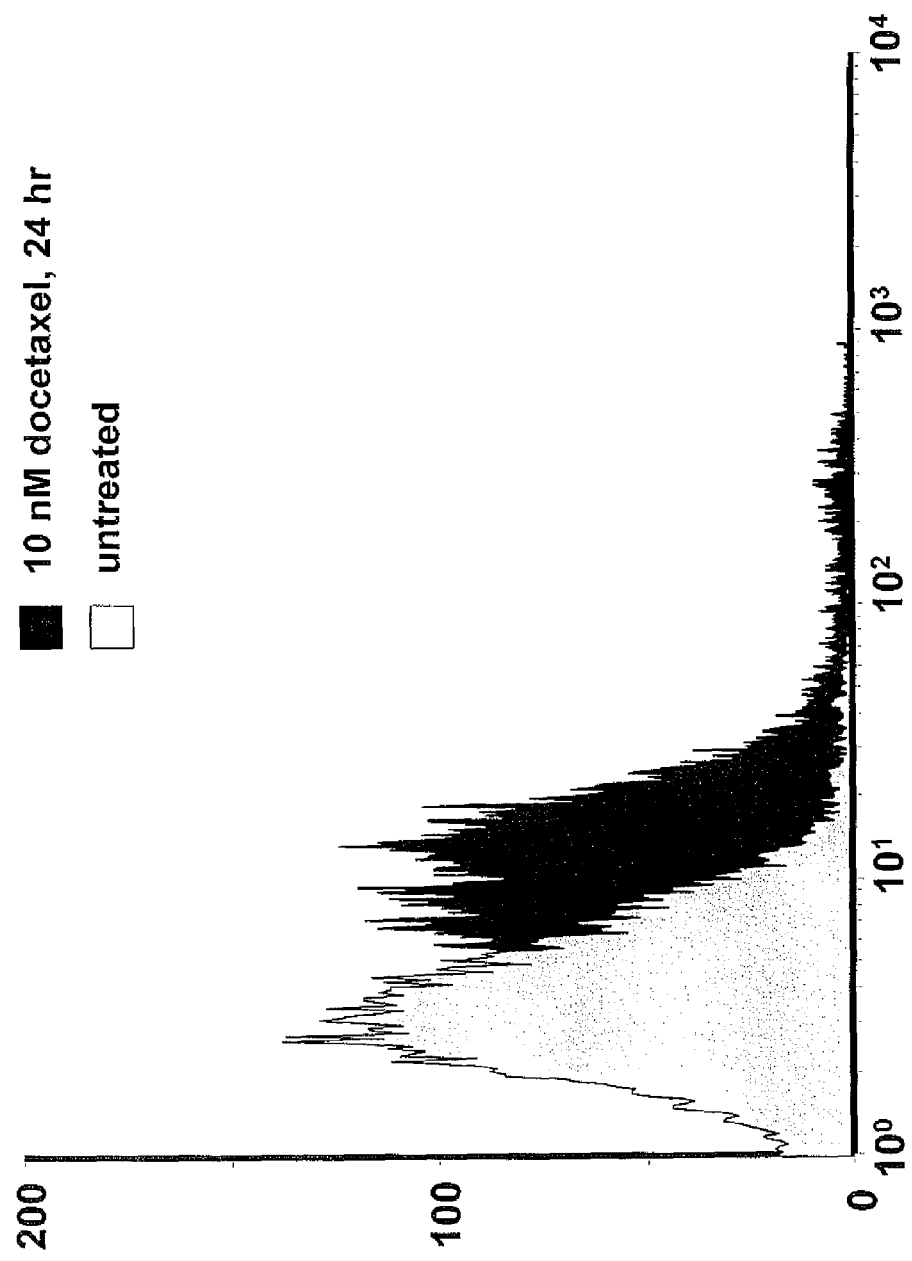

FIG. 25A, FIG. 25B and FIG. 25C. Induction of PS exposure on tumor cell lines by docetaxel. Mouse lewis lung carcinoma 3LL, mouse colon carcinoma Colo26 and human breast cancer MDA-MB-435 cells were treated with 10 nM of docetaxel for 24 hrs. Cells were harvested, washed with PBS and incubated with 3G4 at 10 µg/ml for 30 mins. on ice. The cells were then washed twice, FITC labeled goat anti-mouse IgG was added and the cells incubated for a further 30 mins. on ice. The cells were then washed and analyzed by FACS using a FACSCalibur cytometer (Becton-Dickinson, San Jose, Calif.) with CellQuest acquisition software. The treated 3LL (FIG. 25A), Colo26 (FIG. 25B) and MDA-MB-435 cells (FIG. 25C) show significant increases in 3G4 binding as compared to untreated cells.

FIG. 26. Induction of PS exposure on human breast cancer MDA-MB-231 cells by docetaxel. Human breast cancer MDA-MB-231 cells were treated with 10 nM of docetaxel for 24 hrs. Cells were harvested, washed with PBS and incubated with chimeric 3G4 (ch3G4) or control, human IgG for 30 mins. on ice. The cells were then washed twice, FITC labeled anti-IgG was added and the cells analyzed by FACS, as above. There is a significant increase in ch3G4 binding as compared to control, human IgG.

Figure 27:
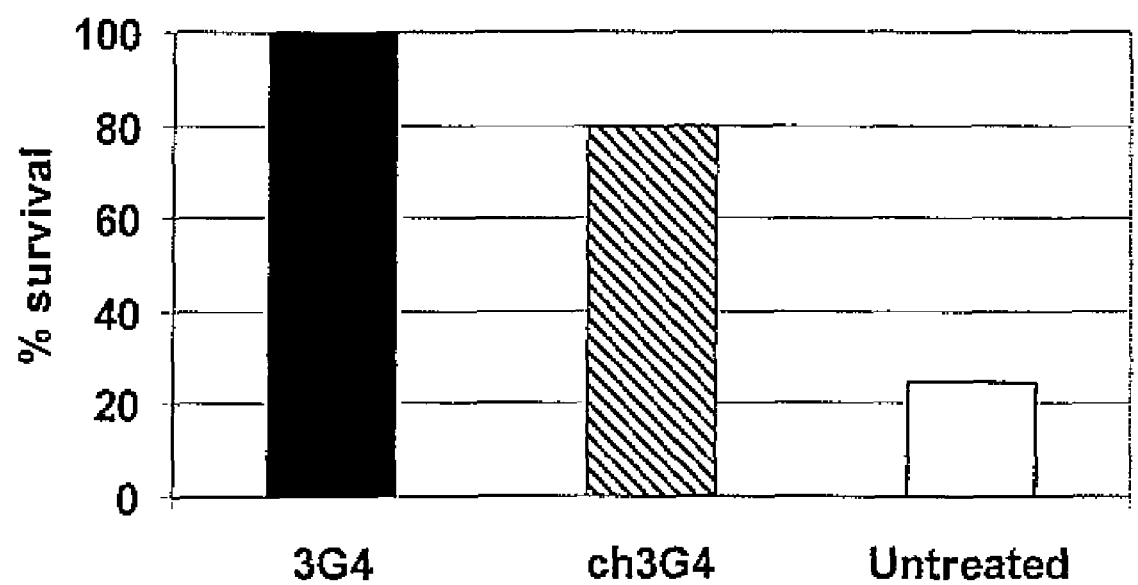

FIG. 27. Treatment with anti-PS antibodies increases survival of mCMV-infected mice. Balb/C mice were infected with mCMV and treated with 3G4 or ch3G4 as described in Example XXI. The mice were monitored for survival past 90 days after infection.

Figure 28:
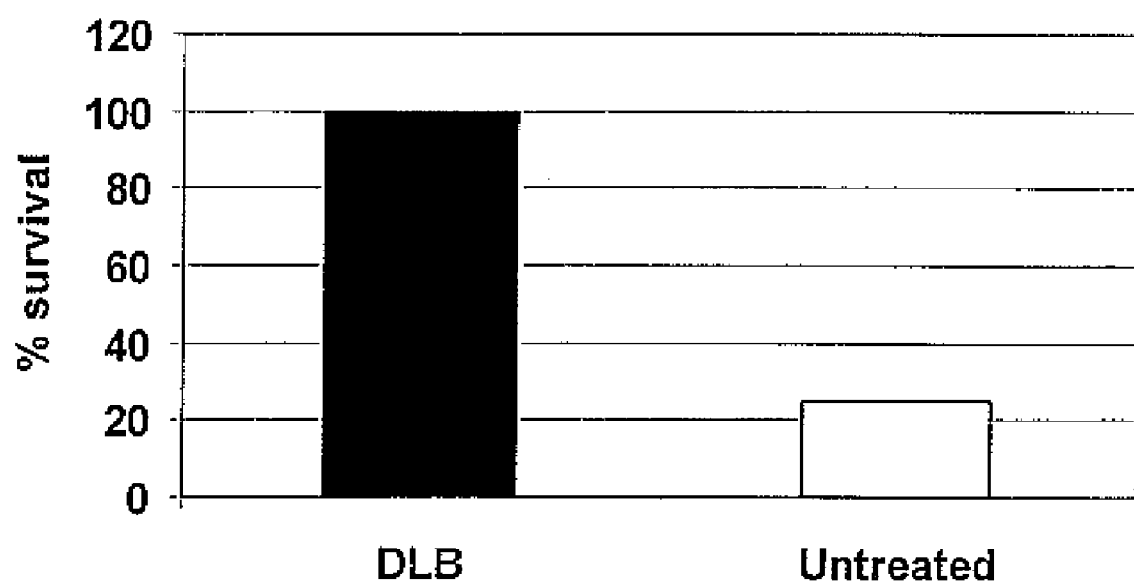

FIG. 28. Treatment with the duramycin-biotin derivative, DLB increases survival of mCMV-infected mice. Balb/C mice were infected with mCMV and treated with DLB as described in Example XXII. The mice were monitored for survival past 90 days after infection.

Figure 29A:
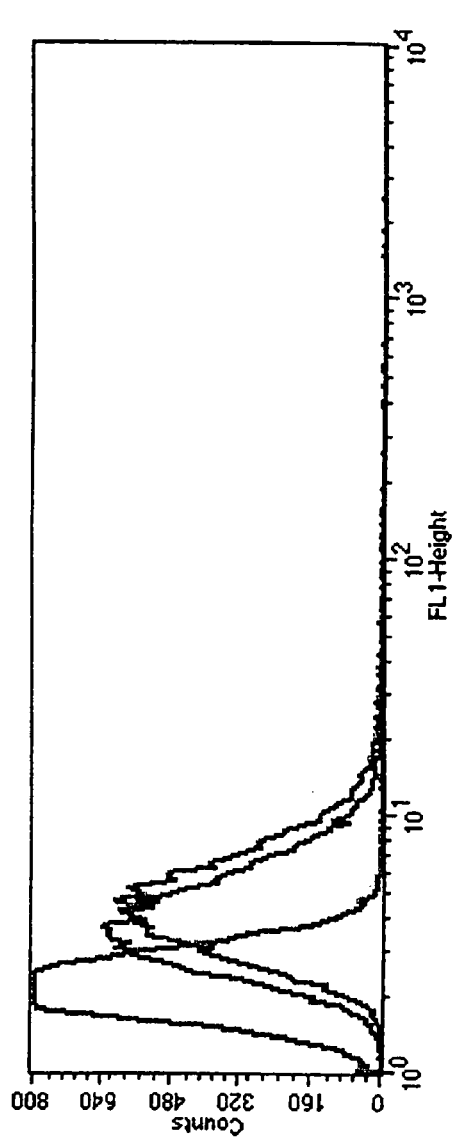
Figure 29B:
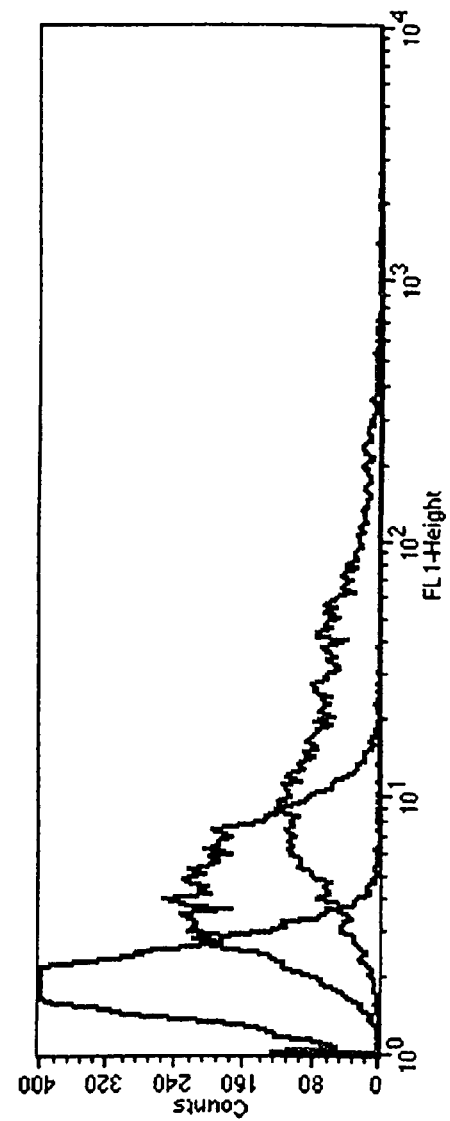

FIG. 29A and FIG. 29B. Binding of chimeric 3G4 to cells infected with Vaccinia virus. U937 cells were infected with Vaccinia virus and stained with the chimeric 3G4 antibody (ch3G4) or control human IgG (HIgG) on day 2 after infection. FIG. 29A, uninfected U-937 cells. FIG. 29B, Vaccinia virus-infected U937 cells. The peaks in FIG. 29A and FIG. 29B are: left (red) peak, secondary antibody alone control; middle (blue) peak, control HIgG; right (green) peak, ch3G4.

FIG. 30A, FIG. 30B, FIG. 30C and FIG. 30D. Inhibition of Pichinde virus replication in vitro by 3G4 antibody. Vero cells were infected with Pichinde virus at an m.o.i. of 0.01 pfu/cell. The infected cells were treated with 100 µg/ml of 3G4 (FIG. 30A) or isotype-matched control antibody, GV39G (FIG. 30B). On day 2 after infection, the cells were harvested with trypsin and allowed to adhere to slides. The cells were fixed with acetone, and stained with anti-PIC rabbit polyclonal serum followed by goat anti-rabbit biotin conjugated secondary antibody. Infected cells are stained red-brown. Secondary antibody alone produced no staining (FIG. 30C). The % infected cells in the 3G4 vs. control treated cells is also shown (FIG. 30D).

Figure 31:
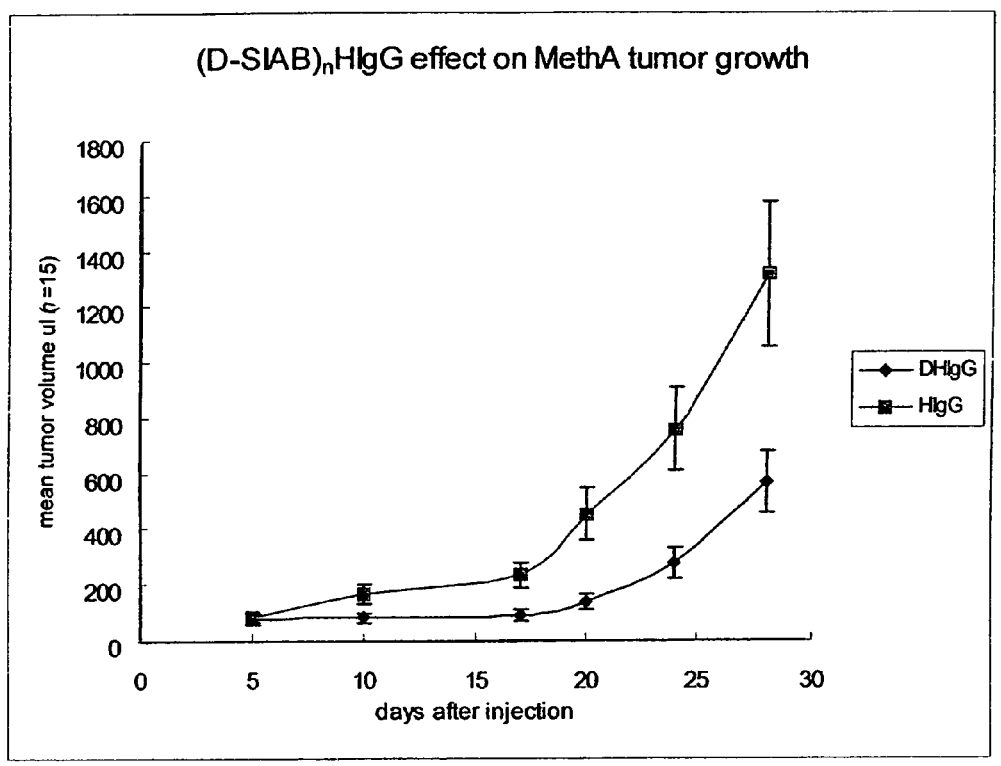

FIG. 31. Duramycin-Human IgG (HIgG) conjugate inhibits MethA tumor growth in vivo. BALB/c mice bearing MethA tumor cells were treated with the duramycin-HIgG conjugate (D-SIAB)$_n$HIgG, in which duramycin is conjugated to HIgG using the SIAB linker, or with control HIgG as described in Example XXV.

Figure 32:
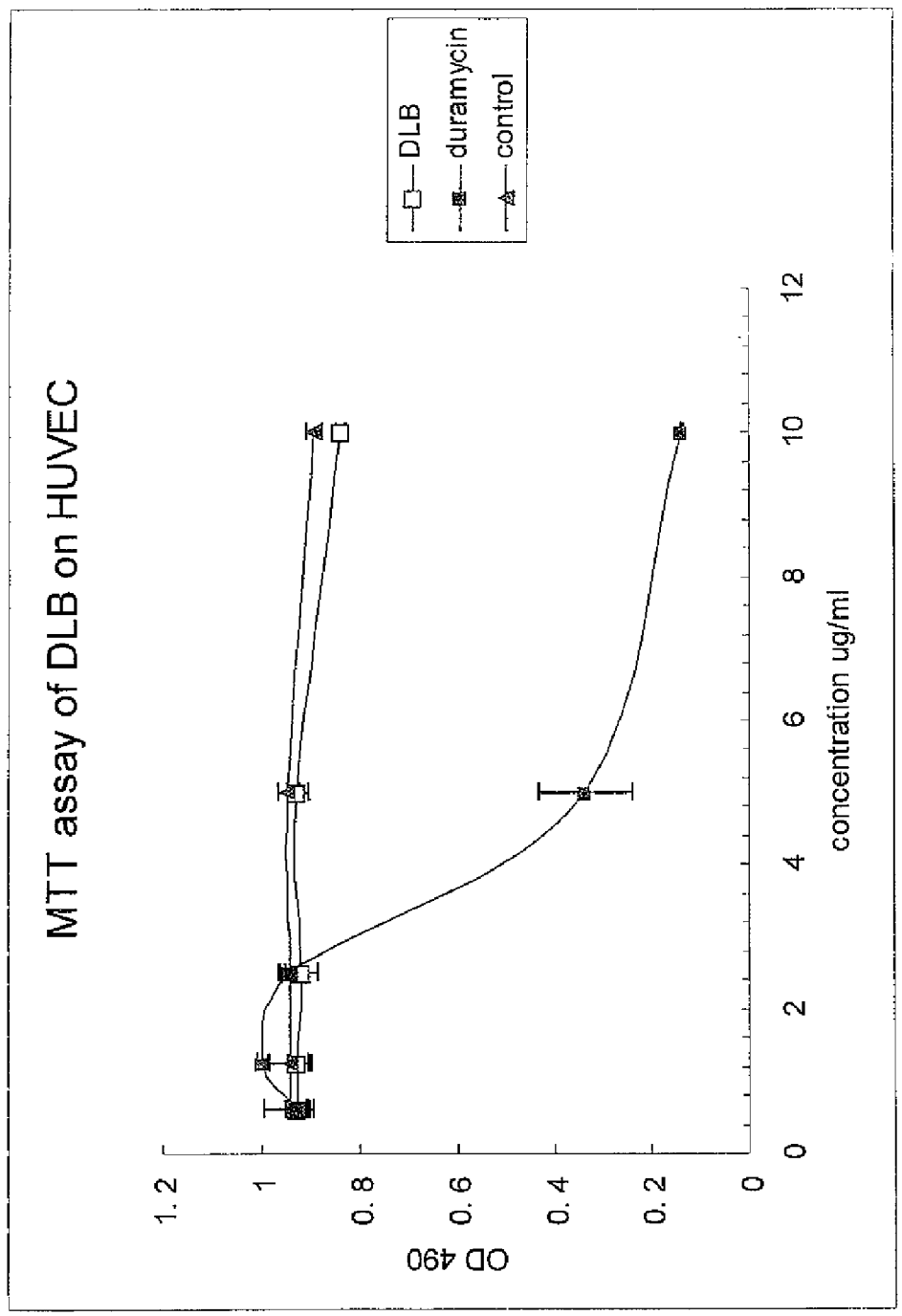

FIG. 32. Duramycin conjugate is not cytotoxic. The naturally occurring duramycin compound and the biotinylated duramycin construct, DLB were tested for cytotoxic effects on human umbilical vein endothelial cells (HUVEC) using an MTT assay.

Figure 33:
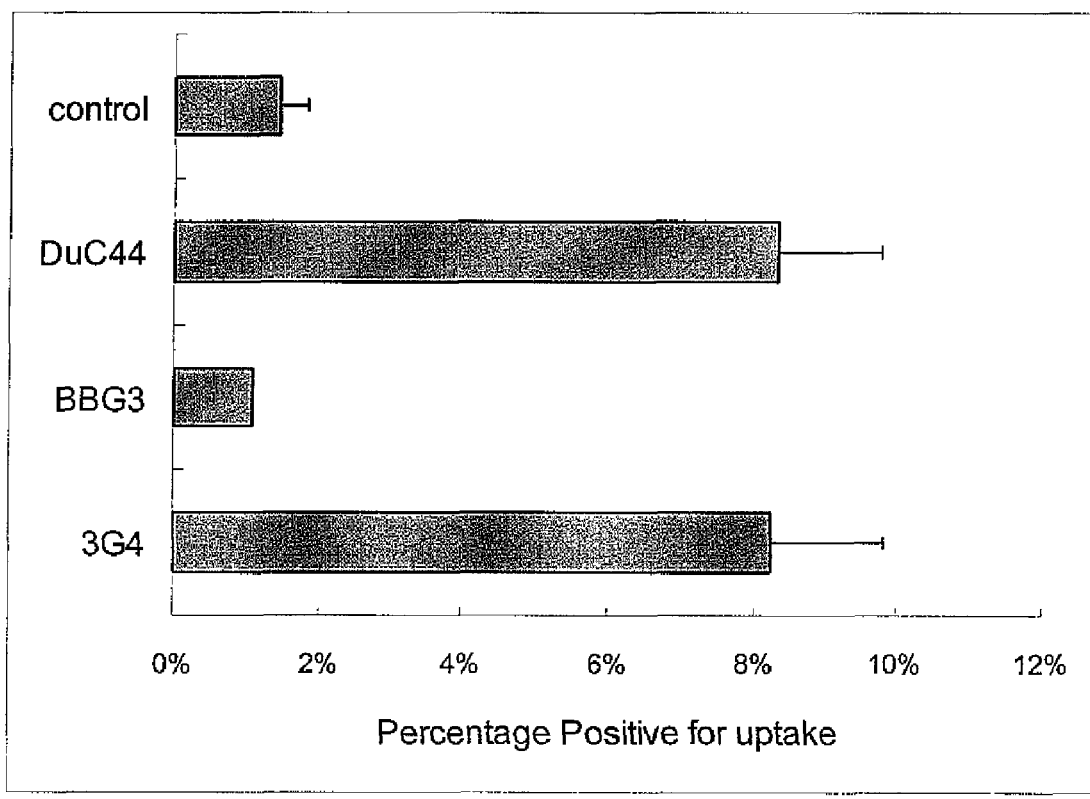

FIG. 33. Duramycin-antibody conjugate enhances macrophage phagocytosis of apoptotic cells. A duramycin-antibody conjugate was constructed by linking duramycin to C44, a mouse IgG$_{2a}$ antibody, to create duramycin-C44 (DuC44). Apoptotic HL-60 cells were incubated with mouse bone-marrow derived macrophages in the presence of DuC44, a control mouse antibody, BBG3 and the 3G4 antibody. Phagocytosis was evaluated as percent phagocytes positive for uptake. Data are mean values±S.E.

DESCRIPTION OF ILLUSTRATIVE EMBODIMENTS

Solid tumors and carcinomas account for more than 90% of all cancers in man. Although the use of monoclonal antibodies and immunotoxins has been investigated in the therapy of lymphomas and leukemias (Vitetta et al., 1991), these agents have been disappointingly ineffective in clinical trials against carcinomas and other solid tumors (Abrams and Oldham, 1985). A principal reason for the ineffectiveness of antibody-based treatments is that macromolecules are not readily transported into solid tumors. Even once within a tumor mass, these molecules fail to distribute evenly due to the presence of tight junctions between tumor cells, fibrous stroma, interstitial pressure gradients and binding site barriers (Denekamp, 1990; Dvorak et al., 1991).

In developing new strategies for treating solid tumors, the methods that involve targeting the vasculature of the tumor, rather than the tumor cells, offer distinct advantages. An effective destruction or blockade of the tumor vessels arrests blood flow through the tumor, resulting in an avalanche of tumor cell death. Antibody-toxin and antibody-coagulant constructs, examples of VTA which selectively destroy and/or occlude tumor blood vessels, have already been used to great effect in the specific targeting and destruction of tumor vasculature, resulting in tumor necrosis (Burrows et al., 1992; Burrows and Thorpe, 1993; WO 93/17715; WO 96/01653; Huang et al., 1997; each incorporated herein by reference).

VTAs exert their primary action on the pre-existing blood vessels of solid tumors, and differ from anti-angiogenic agents that prevent new blood vessel formation. There are numerous advantages of VTAs over other cancer therapies. First, a single vessel provides the nutrition for and facilitates removal of waste products of metabolism from hundreds or thousands of tumor cells, and only has to be damaged at one point to block blood flow upstream and downstream. VTAs are thus particularly effective on established tumors. Second, endothelial cell killing, although one useful mechanism, is not required. A change of shape or local initiation of blood coagulation can be sufficient. Third, the endothelial cell is adjacent to the blood stream, ensuring adequate drug delivery. Fourth, the target is a normal diploid cell that is unlikely to acquire genetic mutations that render it drug resistant. Fifth, a surrogate marker of biological activity, i.e., blood flow, is measurable.

Sixth, temporary effects on vascular function may be sufficient for significant anti-tumor effects. Studies indicate that over 99% of tumor cells in vivo can be killed during a 2 hour period of ischemia. Finally, unlike angiogenesis inhibitors, VTAs only require intermittent administration to synergize with conventional treatments, rather than chronic administration over months or years.

Cytotoxic VTAs are described in the following patents: U.S. Pat. Nos. 5,660,827, 5,776,427, 5,855,866, 5,863,538, 5,965,132, 6,004,554, 6,051,230, 6,261,535 and 6,451,312, each incorporated herein by reference. Where antibodies, growth factors or other binding ligands are used to specifically deliver a coagulant to the tumor vasculature, such agents are termed "coaguligands". Coaguligand VTAs are described in the following patents: U.S. Pat. Nos. 6,093,399, 6,004,555, 5,877,289 and 6,036,955, each incorporated herein by reference.

A currently preferred coagulant for use in coaguligands is truncated Tissue Factor (tTF) (Huang et al., 1997; WO 96/01653; U.S. Pat. No. 5,877,289). TF is the major initiator of blood coagulation (Ruf et al., 1991; Edgington et al., 1991). At sites of injury, Factor VII/VIIa in the blood comes into contact with, and binds to, TF on cells in the perivascular tissues. The TF:VIIa complex, in the presence of the phospholipid surface, activates factors IX and X. This, in turn, leads to the formation of thrombin and fibrin and, ultimately, a blood clot (Ruf and Edgington, 1994).

The recombinant, truncated form of tissue factor (tTF), lacking the cytosolic and transmembrane domains, is a soluble protein that has about five orders of magnitude lower coagulation inducing ability than native TF (Stone et al., 1995; Huang et al., 1997). This is because TF needs to be associated with phospholipids for the complex with VIIa to activate IXa or Xa efficiently. However, when tTF is delivered to tumor vascular endothelium by means of a targeting antibody or agent, it is brought back into proximity to a lipid surface and regains thrombogenic activity (Huang et al., 1997; U.S. Pat. Nos. 6,093,399, 6,004,555, 5,877,289 and 6,036,955). A coaguligand is thus created that selectively thromboses tumor vasculature.

Truncated TF has several advantages that commend its use in vascular targeted coaguligands: human tTF is readily available, and the human protein will have negligible or low immunogenicity in man; human tTF is fully functional in experimental animals, including mice; and targeted tTF is highly potent because it triggers the activation of a cascade of coagulation proteins, giving a greatly amplified effect (U.S. Pat. Nos. 6,093,399, 6,004,555, 5,877,289 and 6,036,955).

A range of suitable target molecules that are available on tumor endothelium, but largely absent from normal endothelium, have been described. For example, expressed targets may be utilized, such as endoglin, E-selectin, P-selectin, VCAM-1, ICAM-1, PSMA, a TIE, a ligand reactive with LAM-1, a VEGF/VPF receptor, an FGF receptor, $\alpha_v\beta_3$ integrin, pleiotropin or endosialin (U.S. Pat. Nos. 5,855,866 5,877,289; Burrows et al., 1992; Burrows and Thorpe, 1993; Huang et al., 1997; Liu et al., 1997; Ohizumi et al., 1997; each incorporated herein by reference).

Adsorbed targets are another suitable group, such as VEGF, FGF, TGFβ, HGF, PF4, PDGF, TIMP, a ligand that binds to a TIE or a tumor-associated fibronectin isoform (U.S. Pat. Nos. 5,877,289, 5,965,132, 6,051,230 and 6,004,555). Fibronectin isoforms are ligands that bind to the integrin family of receptors. Tumor-associated fibronectin isoforms are targetable components of both tumor vasculature and tumor stroma. The monoclonal antibody BC-1 (Carnemolla et al., 1989) specifically binds to tumor-associated fibronectin isoforms.

Other targets inducible by the natural tumor environment or following intervention by man are also targetable entities, as described in U.S. Pat. Nos. 5,776,427, 5,863,538 and 6,036,955. When used in conjunction with prior suppression in normal tissues and tumor vascular induction, MHC Class II antigens may also be employed as targets (U.S. Pat. Nos. 5,776,427, 5,863,538, 6,004,554 and 6,036,955).

One currently preferred target for clinical applications is vascular endothelial adhesion molecule-1 (VCAM-1) (U.S. Pat. Nos. 5,855,866, 5,877,289, 6,051,230, 6,004,555 and 6,093,399). VCAM-1 is a cell adhesion molecule that is induced by inflammatory cytokines IL-1α, IL-4 (Thornhill et al., 1990) and TNFα (Munro, 1993) and whose role in vivo is to recruit leukocytes to sites of acute inflammation (Bevilacqua, 1993).

VCAM-1 is present on vascular endothelial cells in a number of human malignant tumors including neuroblastoma (Patey et al., 1996), renal carcinoma (Droz et al., 1994), non-small lung carcinoma (Staal-van den Brekel et al., 1996), Hodgkin's disease (Patey et al., 1996), and angiosarcoma (Kuzu et al., 1993), as well as in benign tumors, such as angioma (Patey et al., 1996) and hemangioma (Kuzu et al., 1993). Constitutive expression of VCAM-1 in man is confined to a few vessels in the thyroid, thymus and kidney (Kuzu et al., 1993; Bruijn and Dinklo, 1993), and in the mouse to vessels in the heart and lung (Fries et al., 1993).

Certain of the data presented herein even further supplement those provided in U.S. Pat. Nos. 5,855,866, 5,877,289, 6,051,230, 6,004,555 and 6,093,399, and show the selective induction of thrombosis and tumor infarction resulting from administration of an anti-VCAM-1•tTF coaguligand. The results presented were generated using mice bearing L540 human Hodgkin lymphoma. When grown as a xenograft in SCID mice, this tumor shows close similarity to the human disease with respect to expression of inflammatory cytokines (Diehl et al., 1985) and the presence of VCAM-1 and other endothelial cell activation molecules on its vasculature.

Using a covalently-linked anti-VCAM-1•tTF coaguligand, in which tTF was directly linked to the anti-VCAM-1 antibody, it is shown herein that the coaguligand localizes selectively to tumor vessels, induces thrombosis of those vessels, causes necrosis to develop throughout the tumor and retards tumor growth in mice bearing solid L540 Hodgkin tumors. Tumors generally needed to be at least about 0.3 cm in diameter to respond to the coaguligand, because VCAM-1 was absent from smaller tumors. Presumably, in small tumors, the levels of cytokines secreted by tumor cells or host cells that infiltrate the tumor are too low for VCAM-1 induction. This is in accordance with the studies in U.S. Pat. Nos. 5,855,866, 5,877,289, 6,051,230, 6,004,555 and 6,093,399, where the inventions were shown to be most useful in larger solid tumors.

Although VCAM-1 staining was initially observed more in the periphery of the tumor, the coaguligand evidently bound to and occluded blood transporting vessels—as it was capable of curtailing blood flow in all tumor regions. Furthermore, one of the inventors contemplates that the thrombin generation caused by the initial administration of the coaguligand likely leads to further VCAM-1 induction on central vessels (Sluiter et al., 1993), resulting in an amplified signal and evident destruction of the intratumoral region. This type of coagulant-induced expression of further targetable markers, and hence signal amplification, is also disclosed in U.S. Pat. No. 6,036,955.

As shown herein, although localization to VCAM-1-expressing vessels in the heart and lungs of mice was observed upon administration of an anti-VCAM-1 coaguligand, this construct did not induce thrombosis in such non-tumor sites. Furthermore, the anti-VCAM-1 coaguligand was no more toxic to mice than was a control coaguligand of irrelevant specificity, again indicating that the constitutive expression of VCAM-1 on heart and lung vessels did not lead to toxicity. This data is important to the immediate clinical progress of coaguligand therapy, given that VCAM-1 is a naturally occurring marker of tumor vascular endothelium in humans. However, this phenomenon also provided the inventors with a unique insight, leading to a totally different approach to tumor vasculature destruction.

A. Tumor Treatment with Naked Antibodies to Aminophospholipids

The inventors sought to understand the mechanism behind the ability of the anti-VCAM-1 coaguligand to bind to the VCAM-1 constitutively expressed on blood vessels in the heart and lungs, and yet not to cause thrombosis in those vessels. There are numerous scientific possibilities for this empirical observation, generally connected with the prothrombotic nature of the tumor environment and any fibrinolytic predisposition in the heart and lungs.

Generally, there is a biological equilibrium between the coagulation system (fibrin deposition) and the fibrinolytic system (degradation of fibrin by enzymes). However, in malignant disease, particularly carcinomas, this equilibrium is disrupted, resulting in the abnormal activation of coagulation (hypercoagulability or the "prothrombotic state"). Despite extensive research, a clear molecular explanation for the prothrombotic nature of the tumor environment could not be discerned until recently.

After detailed analyses of many possible options, the inventors reasoned that the failure of the anti-VCAM-1 coaguligand to cause thrombosis in vessels of normal tissues was due to the absence of the aminophospholipid, phosphatidylserine (PS) from the luminal surface of such vessels. To complete the theory, therefore, not only would phosphatidylserine have to be shown to be absent from these normal vessels, but its presence on the luminal side of tumor-associated vessels would have to be demonstrated.

The inventors therefore used immunohistochemical staining to evaluate the distribution of a monoclonal anti-phosphatidylserine (anti-PS) antibody injected intravenously into tumor-bearing mice. These studies revealed that the VCAM-1 expressing vessels in the heart and lungs lacked PS, whereas the VCAM-1 expressing vessels in the tumor expressed PS. The need for surface PS expression in coaguligand action is further indicated by the inventors' finding that annexin V, which binds to PS, blocks anti-VCAM-1•tTF coaguligand action, both in vitro and in vivo.

The lack of thrombotic effect of the anti-VCAM-1 coaguligand on normal heart and lung vessels was thus explained, at least in part: the absence of the aminophospholipid, phosphatidylserine, means that the normal vessels lack a procoagulant surface upon which coagulation complexes can assemble. In the absence of surface PS, anti-VCAM-1•tTF binds to VCAM-1 expressing heart and lung vessels, but cannot induce thrombosis. In contrast, VCAM-1 expressing vessels in the tumor show coincident expression of surface PS. The coaguligand thus binds to tumor vessels and activates coagulation factors locally to form an occlusive thrombus.

In addition to delineating the tumor-specific thrombotic effects of anti-VCAM-1 coaguligands, the specific expression of the aminophospholipid, phosphatidylserine, on the luminal surface of tumor blood vessels also allowed the inventors to explain the prothrombotic phenotype observed, but not understood, in earlier studies. The PS expression plays a significant role in the prothrombotic state of tumor vasculature.

Following their discovery that the representative aminophospholipid, phosphatidylserine, was specifically expressed on the luminal surface of tumor blood vessels, but not in normal blood vessels, the inventors reasoned that other aminophospholipids had potential as targets for therapeutic intervention. The inventors therefore developed tumor vasculature targeting and treatment methods based on targeting the aminophospholipids phosphatidylserine and phosphatidylethanolamine (PE).

A particularly surprising aspect of the inventors' studies was that administration of an unconjugated anti-aminophospholipid antibody was effective in tumor treatment. This gave rise to important new avenues of tumor treatment using unconjugated or "naked" antibodies that bind to aminophospholipids. These tumor vasculature targeting and treatment methods are described in U.S. Pat. No. 6,406,693, incorporated herein by reference. Although anti-tumor effects in art-accepted animal models are demonstrated in U.S. Pat. No. 6,406,693, and extended herein, the ability of aminophospholipids to act as safe and effective targetable markers of tumor vasculature could not have been predicted from studies previous to U.S. Pat. No. 6,406,693.

Once the discovery of aminophospholipids as specific markers of tumor vasculature had been proven, the inventors began to develop a range of aminophospholipid-targeted immunotoxins and coaguligands for use in tumor treatment. As explained in U.S. Pat. No. 6,406,693, this led to the unexpected discovery of naked anti-aminophospholipid antibodies for use in tumor treatment. In investigating the potential of aminophospholipid targeting in the context of delivering a toxin or coagulant to the tumor vasculature, the inventors serendipitously found that naked anti-PS antibodies had a destructive effect on tumor vasculature in vivo in the absence of any additional effector moiety. The ability of anti-aminophospholipid antibodies to both specifically localize to tumor vasculature and to exert a concomitant destructive effect, leading to tumor necrosis, was most unexpected.

The present invention provides surprising and improved, "second generation" anti-PS antibodies for use, amongst other embodiments, as naked antibodies in tumor treatment. A panel of second generation anti-PS antibodies is disclosed herein, of which the monoclonal antibodies 9D2 and 3G4 (ATCC 4545) are currently preferred, along with particular immunization and screening techniques for the generation and selection of further antibodies with such advantageous properties. It is also shown herein that vascular damage to tumor vessels by anti-PS antibodies is mediated, at least in part, through host effectors. These and other insights of the present inventors allow for naked antibody treatment to be optimized, both when used alone, and in combination with other anti-cancer agents, as taught herein.

B. Tumor Treatment Using Antibodies to Anionic Phospholipids

U.S. Pat. No. 6,406,693 explains that the aminophospholipids phosphatidylserine and phosphatidylethanolamine are normally segregated to the inner surface of the plasma membrane bilayer in different cells (Gaffet et al., 1995; Julien et al., 1995) and that this lipid segregation creates an asymmetric transbilayer. Although the existence of membrane asymmetry has been discussed for some time, the reason for its existence and the mechanisms for its generation and control are poorly understood (Williamson and Schlegel, 1994), particularly in cells other than platelets.

The inventors earlier demonstrated that PS is translocated to the surface of tumor vascular endothelial cells and that this occurs, at least in significant part, independently of apoptotic or other cell-death mechanisms (U.S. Pat. No. 6,406,693). Thus, PS surface expression in the tumor environment is not a consequence of cell death, nor does it trigger immediate cell destruction. Despite PS exposure being detected consistently on intact vascular endothelial cells in various solid tumors, the tumor vascular endothelium is not frankly apoptotic, but is morphologically sound (although different to that in normal tissues) and metabolically active. This is important for therapeutic methods based on PS targeting, meaning that PS translocation to the outer membrane in tumor vascular endothelial cells is sufficiently stable for PS to serve as a targetable entity for successful therapy (using either naked antibodies or therapeutic conjugates).

Despite the important discoveries of U.S. Pat. No. 6,406, 693 (and 6,312,694, see below), the suggestions for phospholipid-based targeting of tumor vascular endothelial cells were confined to the targeting of aminophospholipids, such as PS and PE. Through the development of biological tools with exquisite specificity for different phospholipids and aminophospholipids, the present inventors have now identified a new category of phospholipids that are surprisingly upregulated on tumor vascular endothelial cells. These are the anionic phospholipids, which are shown herein to also be specific and stable markers of tumor vasculature, permitting therapeutic intervention using both naked antibodies and immunoconjugates that bind to anionic phospholipids.

Anionic phospholipids are largely absent from the surface of resting mammalian cells under normal conditions. Phosphatidylserine, which is the most abundant anionic phospholipid of the plasma membrane, is tightly segregated to the internal leaflet of the plasma membrane in most cell types under normal conditions (Williamson and Schlegel, 1994; Zwaal and Schroit, 1997). Phosphatidylinositol (PI), another major anionic phospholipid, is also predominantly situated in the internal leaflet of the plasma membrane (Calderon and DeVries, 1997). The minor anionic phospholipids, phosphatidic acid (PA) and phosphatidylglycerol (PG), have only been examined in a few cells types, but they also appear to be mainly situated in the internal leaflet of the plasma membrane (Hinkovska-Galcheva et al., 1989). Cardiolipin (CL), another anionic phospholipid, is present in the mitochondrial membrane and is absent from the plasma membrane (Daum, 1985).

The neutral phospholipids are also asymmetrically distributed in the plasma membrane. The neutral aminophospholipid, phosphatidylethanolamine (PE) is predominately on the internal leaflet. The choline-containing neutral phospholipids, phosphatidylcholine (PC) and sphingomyelin (SM), are predominantly on the external leaflet.

PS asymmetry, along with that of PE, is maintained by an ATP-dependent transporter, aminophospholipid translocase ($Mg^{2+}$ ATPase), which catalyzes the transport of aminophospholipids from the external leaflet to the internal leaflet of the plasma membrane (Seigneuret and Devaux, 1984). Loss or collapse of PS and PE asymmetry results from the outward movement of these phospholipids in the plasma membrane and is caused either by inhibition of the translocase (Bitbol et al., 1987; Comfurius et al., 1990), activation of PS transporters and/or activation of scramblase enzymes, $Ca^{2+}$ dependent enzymes that transport all lipids bidirectionally (Zhao et al., 1998).

Loss of PS asymmetry is observed under different pathological and physiological conditions, including cell injury, programmed cell death and apoptosis (Blankenberg et al., 1998; Bombeli et al., 1997), cell aging (Herrmann and Devaux, 1990), activation of platelets (Rote et al., 1993; Zwaal et al., 1989), injury (Boyle et al., 1996) and malignant transformation (Sugimura et al., 1994). Exposure of PS also plays a role in intercellular fusion of myoblasts (Sessions and Horwitz, 1981) and trophoblasts (Adler et al., 1995), cell migration (Vogt et al., 1996) and cell degranulation (Demo et al., 1999). Endothelial cells externalize PS in response to increased $Ca^{2+}$ fluxes induced by thrombin (Qu et al., 1996), calcium ionophore or phorbol esters (Julien et al., 1997), hyperlipidemia (Lupu et al., 1993), and non-lytic concentrations of complement proteins C5b-9 (Christiansen et al., 1997). Spontaneous PS exposure has been also observed in malignant cells in the absence of exogenous activators or cell injury (Utsugi et al., 1991).

Several major consequences follow membrane PS exposure. Phagocytic macrophages recognize, attach and eliminate PS-positive senescent and apoptotic cells (McEvoy et al., 1986; Tait and Smith, 1999). PS also mediates attachment of T lymphocytes to thrombin-activated endothelial cells (Qu et al., 1996). The complement system is activated by PS and contributes to the lysis of PS-positive cells (Test and Mitsuyoshi, 1997). Finally, PS exposure contributes to a procoagulant shift on the endothelium (Williamson and Schlegel, 1994; Bombeli et al., 1997) by providing a negatively charged lipid surface for assembly and activation of coagulation complexes (Bevers et al., 1985; Dachary-Prigent et al., 1996). The prothrombotic character of the tumor endothelium has long been recognized (Donati and Falanga, 2001).

Despite the focus on PS in the scientific literature, and the inventors' earlier work confined to aminophospholipids such as PS and PE (U.S. Pat. Nos. 6,406,693 and 6,312,694), the present inventors hypothesized that a wider category of phospholipids could become exposed on tumor vasculature. Due to the increased stress conditions of the tumor microenvironment, the inventors reasoned that a range of anionic phospholipids could be upregulated on tumor vasculature, providing potential new opportunities for therapeutic intervention.

The inventors realized that injury and activation of tumor endothelium are caused by: 1) tumor-derived cytokines, such as interleukin-1 and tumor necrosis factor, which activate the endothelium and induce expression of cell adhesion molecules (Shaughnessy et al., 1989; Orr et al., 2000); 2) reactive oxygen species (ROS) generated by leukocytes that adhere to the endothelium (Orr et al., 2000); and 3) ROS generated by tumor cells themselves as a byproduct of metabolism (Shaughnessy et al., 1989; Soares et al., 1994) or as a result of exposure to hypoxia followed by reoxygenation (Zulueta et al., 1995). These observations suggested that $Ca^{2+}$ fluxes might be generated by these stresses within the tumor endothelium that, in turn, cause exposure of PS and PE, through activation of scramblase or inhibition of aminophospholipid translocase.

However, the inventors extended these insights to the hypothesis that anionic phospholipids, not just the aminophospholipids PS and PE, would be upregulated on tumor vasculature. To detect cell surface anionic phospholipids, the inventors generated a new monoclonal antibody, 9D2, which reacts with anionic but not neutral phospholipids. 9D2 thus differentiates from general aminophospholipid binding agents, as it binds to the anionic aminophospholipid, PS, but not to the neutral aminophospholipid, PE. The 9D2 antibody is also more specific for anionic phospholipids than is the natural ligand, annexin V, which strongly binds to PE, in addition to anionic phospholipids (Blankenberg et al., 1998).

As detailed in the present application, the inventors found that 9D2 and annexin V localize specifically to tumor endothelium after intravenous injection to mice bearing various types of solid tumors. This finding validates the inventors' hypothesis that anionic phospholipids routinely become exposed on the surface of tumor vascular endothelium and can be used as target molecules for tumor therapy (and imaging). The present invention thus provides a range of new methods and antibody-based compositions for use in targeting anionic phospholipids and treating tumors, both in terms of naked antibodies and in the delivery of cytotoxic drugs, cytokines, coagulants and such like. In addition to targeting PS, as taught in U.S. Pat. Nos. 6,406,693 and 6,312,694, the currently preferred anionic phospholipids for targeting by the present invention are PI, a major anionic phospholipid, PA and PG, with targeting CL also being contemplated in certain embodiments.

One of the major findings to emerge from the present invention is that anionic phospholipids are exposed on the surface of tumor endothelium (Example VI). This phenomenon was demonstrated using two independent reagents that bind selectively to anionic phospholipids: a monoclonal antibody, 9D2, developed by the inventors particularly to validate this point, and annexin V. The 9D2 antibody and competing antibodies are further preferred components of the present invention.

9D2 antibody and annexin V bind with high affinity and specificity to anionic phospholipids adsorbed to plastic, as liposomes, or presented on the membrane surface of activated or apoptotic endothelial cells in vitro. 9D2 binds strongly to PS, PA and CL, but more weakly to PI and PG. Annexin V binds to PE in addition to PS, CL, PA, PI and PG, as found previously (Andree et al., 1990; Schlaepfer et al., 1987; Boustead et al., 1993; Blackwood and Ernst, 1990). Recognition of anionic phospholipids by 9D2 antibody was identical in the presence and absence of serum, indicating that binding does not require serum co-factors. Binding of 9D2 to anionic phospholipids, did not require $Ca^{2+}$ ions, whereas the binding of annexin V did require $Ca^{2+}$.

Cross-blocking studies on PS-coated plates showed that 9D2 and annexin V do not block each other's binding to PS. This indicates that the two reagents recognize different epitopes on the PS molecule, or, more likely, differently packed forms of PS. Annexin V is thought to bind to planar PS surfaces, whereas anti-PS antibodies are thought to bind to hexagonally packed PS (Rauch and Janoff, 1990). Both forms are probably present on PS-coated plates. These practical cross-blocking studies (Example VI) also serve to show that antibodies which effectively compete for binding to anionic phospholipids, i.e., bind to essentially the same epitope, can be readily identified once a reference antibody (e.g. 9D2) is provided.

The present application also shows that 9D2 antibody and annexin V specifically localize to tumor vessels, and to tumor cells in and around necrotic regions of all tumors examined in vivo (Example VI). Between 15 and 40% of blood vessels in the tumors had anionic phospholipid-positive endothelium. In contrast, none of the blood vessels in normal tissues had detectable externalized anionic phospholipids.

The specificity of staining of tumor vasculature by 9D2 was demonstrated by: 1) the lack of tumor vessel staining by control rat IgM; 2) the blocking of 9D2 or annexin V binding to $H_2O_2$-treated endothelial cells in vitro by liposomes prepared from anionic phospholipids, but not neutral phospholipids; 3) the finding that extraction of phospholipids from tumor sections with detergents or organic solvents abolished staining; and 4) the lack of localization of either 9D2 or annexin V to the quiescent endothelium in normal organs.

The main anionic phospholipid that is localized by 9D2 or annexin V on tumor vasculature is likely to be PS, as this is the most abundant anionic phospholipid and its exposure on the cell surface is regulated by environmental influences or injury. However, other anionic phospholipids (e.g., PI, PA, PG) are also likely to be exposed, despite being less abundant.

Although not detected by 9D2, the major neutral phospholipid, PE, is likely to contribute, together with PS, to the annexin localization observed on tumor vessels. PE is also known to be exposed on tumor endothelium, and the position of PE in the plasma membrane is regulated in a similar manner to PS (U.S. Pat. No. 6,406,693). PE is segregated to the internal leaflet of the plasma membrane in part by aminophospholipid translocase, although at a slower rate than PS (Devaux, 1992), and is transported to the external surface by scramblase (Zhou et al., 1997). PE, like PS, is also exposed during apoptosis and cell activation (Emoto et al., 1997; Umeda and Emoto, 1999).

To examine the mechanism of exposure of anionic phospholipids on tumor endothelial cells, a series of studies was performed in which endothelial cells in vitro were treated with various factors and conditions known to be present in the tumor microenvironment (Example VII). Hypoxia followed by re-oxygenation, acidity, and thrombin increased PS exposure on viable endothelial cells to between 10 and 22% of the level seen when all cells are apoptotic. Inflammatory cytokines (TNFα and IL-1) also caused a weak but definite induction of PS exposure.

These findings are consistent with the possibility that, in tumors, exposure of anionic phospholipids on the vascular endothelium is induced by hypoxia/reoxygenation in combination with inflammatory cytokines, thrombin and acidity. Although the precise mechanism does not need to be understood to practice the present invention, ROS may be generated by tumor cells as a by-product of metabolism or in response to hypoxia (Zulueta et al., 1995). Cytokines released by tumor cells may induce leukocytes adhesion molecules on the endothelium that mediate adherence of activated macrophages, polymorphonuclear cells and platelets to tumor endothelium and further secretion of ROS. The ROS may then induce PS translocation through oxidation of thiol-containing transport molecules or peroxidation of lipids (Herrmann and Devaux, 1990), possibly by causing an influx of $Ca^{2+}$ or release of $Ca^{2+}$ from intracellular stores (Wang and Joseph, 2000).

Exposure of PS and other anionic phospholipids in part explains the procoagulant status of tumor endothelium that has long been recognized (Donati and Falanga, 2001). The anionic phospholipids provide the surface upon which coagulation factors concentrate and assemble (Bevers et al., 1985; Dachary-Prigent et al., 1996). It also provides an attachment site for circulating macrophages (McEvoy et al., 1986), T lymphocytes (Qu et al., 1996) and polymorphonuclear cells that assists in leukocyte infiltration into tumors.

Antibodies and other ligands that bind to anionic phospholipids can thus be used for the targeting, imaging and/or treatment of tumor blood vessels. Anionic phospholipids are attractive as tumor target vessels for several reasons: they are abundant (PS is present at $3 \times 10^6$ molecules per cell); they are on the luminal surface of tumor endothelium, which is directly accessible for binding by vascular targeting agents in the blood; they are present on a major percentage of tumor endothelial cells in diverse solid tumors; and they are essentially absent from endothelium in all normal tissues.

Vascular targeting agents employing drugs or coagulants have been shown to be highly effective, and sometimes curative, in mice with large solid tumors (Huang et al., 1997; Nilsson et al., 2001; U.S. Pat. Nos. 5,660,827, 5,776,427, 5,855,866, 5,863,538, 5,965,132, 6,004,554, 6,051,230, 6,261,535, 6,093,399, 6,004,555, 5,877,289 and 6,036,955). The present invention thus provides naked antibodies and vascular targeting agents directed against anionic phospholipids for use in targeting tumor vasculature in the diagnosis and treatment of cancer in man.

Although a precise molecular understanding of how naked antibodies directed against anionic phospholipids and aminophospholipids function in tumor treatment is not necessary in order to practice the treatment, the inventors have contemplated several mechanisms that may account for the observed endothelial cell killing. The favored mechanisms (particularly for the 3G4 antibody described herein) are Fc domain-mediated immune effector functions, such as antibody-dependent cellular cytotoxicity (ADCC), complement-dependent cytotoxicity (CDC) and antibody mediated phagocytosis. Cell-mediated cytotoxicity, complement-mediated lysis and/or apoptosis, antibody-induced cell signaling and/or disturbances to the cytoskeleton may also be involved.

Binding of intact antibodies against anionic phospholipids and aminophospholipids, particularly 3G4, to the vascular endothelial cell surface means that the Fc portions of the antibodies protrude into the vessel lumen. As antibody Fc fragments activate the complement pathway, the observed cellular destruction may be a result of complement-directed lysis. Antibody binding thus activates the complement-dependent coagulation cascade, causing multi-component complexes to assemble and, ultimately, to generate a lytic complex that permeabilizes the target cell. "Complement-activated ADCC" may also be operating in the destruction, in which complement binds to the antibody-coated target cell, and in which cells, such as neutrophils, having receptors for complement, lyse the target cell.

As the naked or unconjugated antibodies, including the antigen binding fragments thereof, bind to anionic phospholipids and aminophospholipids at the surface of the tumor vascular endothelial cells, they will form an antibody coating on the luminal surface. This may function to attract immune effector cells, such as cytotoxic T cells and/or natural killer (NK) cells, which will then exert a cell-mediated cytotoxic effect on the vascular endothelial cells.

Antibody binding to anionic phospholipids and aminophospholipids may also induce apoptosis in the tumor vascular endothelial cells. Although there are no known reports of antibody binding to PS actually inducing apoptosis (rather than PS being a marker resulting from apoptosis), the inventors consider this to be another possible mechanism for the observed anti-tumor effects.

It is also possible that antibody binding to anionic phospholipids and aminophospholipids at the surface of tumor vascular endothelial cells may cause disturbances in the cytoskeletal organization of the cell. As the cytoskeleton plays a role in the organization of surface membranes, and as antibody binding may disturb (or further disturb) the membrane, binding of antibodies to anionic phospholipids and aminophospholipids may transmit changes to cytoskeletal proteins that interact with the bilayer. It is already known that the spatial organization of cytoskeletal proteins controls membrane stability and cell shape, and it is possible that perturbation of some cytoskeletal equilibrium may have far-reaching consequences on cell integrity.

A further mechanism of operation of the invention may be that antibody binding to anionic phospholipids and aminophospholipids at the endothelial cell surface may initiate signal transduction by, as yet, undefined pathways. Antibody binding may also disturb known signal transduction pathways, e.g., by altering the conformation and/or interactions of membrane receptors, signal transduction proteins, membrane channels, and the like. Signals for cell destruction (apoptosis) may be initiated or mimicked, and/or preservation/homeostatic signals may be inhibited.

Although of scientific interest, determining the exact nature of the vascular destruction achieved by the naked antibodies to anionic phospholipids and aminophospholipids is not necessary to practice the treatment. Given that the administration of these categories of antibodies is shown to advantageously result in specific anti-tumor effects in vivo, the treatment can be utilized irrespective of the molecular mechanism that underlies this phenomenon. The use of naked antibodies that bind to anionic phospholipids and aminophospholipids, thus represents an important advance in tumor therapy, providing advantages in preparation and cost.

C. Antibodies to Anionic Phospholipids and Aminophospholipids

As the present invention identifies a new category of tumor vasculature markers, the anionic phospholipids, naked antibodies and immunoconjugates that bind to one or more anionic phospholipids, optionally in combination with aminophospholipids, can now be used in tumor diagnosis and treatment.

C1. Polyclonal Antibodies

Means for preparing and characterizing antibodies are well known in the art (see, e.g., Antibodies: A Laboratory Manual, Cold Spring Harbor Laboratory, 1988; incorporated herein by reference). To prepare polyclonal antisera an animal is immunized with a composition comprising an immunogenic anionic phospholipid and/or aminophospholipid, including cells treated with $H_2O_2$ and other agents, as taught herein, and antisera collected from that immunized animal. A wide range of animal species can be used for the production of antisera. Typically the animal used for production of anti-antisera is a rabbit, mouse, rat, hamster, guinea pig or goat. Because of the relatively large blood volume of rabbits, a rabbit is a preferred choice for production of polyclonal antibodies.

The amount of immunogen composition used in the production of polyclonal antibodies varies upon the nature of the immunogen as well as the animal used for immunization. A variety of routes can be used to administer the immunogen; subcutaneous, intramuscular, intradermal, intravenous, intraperitoneal and intrasplenic. The production of polyclonal antibodies may be monitored by sampling blood of the immunized animal at various points following immunization. A second, booster injection, may also be given. The process of boosting and titering is repeated until a suitable titer is achieved. When a desired titer level is obtained, the immunized animal can be bled and the serum isolated and stored. The animal can also be used to generate monoclonal antibodies.

As is well known in the art, the immunogenicity of a particular composition can be enhanced by the use of non-specific stimulators of the immune response, known as adjuvants. Exemplary adjuvants include complete Freund's adjuvant, a non-specific stimulator of the immune response containing killed *Mycobacterium tuberculosis*; incomplete Freund's adjuvant; and aluminum hydroxide adjuvant.

It may also be desired to boost the host immune system, as may be achieved by associating anionic phospholipids and aminophospholipids with, or coupling to, a carrier. Exemplary carriers are keyhole limpet hemocyanin (KLH) and bovine serum albumin (BSA). Other albumins such as ovalbumin, mouse serum albumin or rabbit serum albumin can also be used as carriers.

As is also known in the art, a given composition may vary in its immunogenicity. However, the generation of antibodies against anionic phospholipids and aminophospholipids is not particularly difficult. For example, highly specific anti-phosphatidylserine antibodies were raised in rabbits immunized by intramuscular injections of phosphatidylserine-containing polyacrylamide gels and with phosphatidylserine-cytochrome c vesicles (Maneta-Peyret et al., 1988; 1989; each incorporated herein by reference). The use of acrylamide implants enhanced the production of antibodies (Maneta-Peyret et al., 1988; 1989). The anti-phosphatidylserine antibodies raised in this manner are able to detect phosphatidylserine in situ on human platelets (Maneta-Peyret et al., 1988). The groups of Inoue, Rote and Rauch have also developed anti-PS and anti-PE antibodies (see below).

Although the generation of antibodies against anionic phospholipids and aminophospholipids can be achieved by various means, certain preferred methods are described herein in Example IV.

C2. Monoclonal Antibodies

Various methods for generating monoclonal antibodies (MAbs) are also now very well known in the art. The most standard monoclonal antibody generation techniques generally begin along the same lines as those for preparing polyclonal antibodies (Antibodies: A Laboratory Manual, Cold Spring Harbor Laboratory, 1988; incorporated herein by reference). A polyclonal antibody response is initiated by immunizing an animal with an immunogenic anionic phospholipid and/or aminophospholipid composition and, when a desired titer level is obtained, the immunized animal can be used to generate MAbs. Preferably, the particular screening and selection techniques disclosed herein are used to select antibodies with the sought after properties.

MAbs may be readily prepared through use of well-known techniques, such as those exemplified in U.S. Pat. No. 4,196,265, incorporated herein by reference. Typically, this technique involves immunizing a suitable animal with the selected immunogen composition. The immunizing composition is administered in a manner effective to stimulate antibody producing cells. Rodents such as mice and rats are preferred animals, however, the use of rabbit, sheep and frog cells is also possible. The use of rats may provide certain advantages (Goding, 1986, pp. 60-61; incorporated herein by reference), but mice are preferred, with the BALB/c mouse being most preferred as this is most routinely used and generally gives a higher percentage of stable fusions.

Following immunization, somatic cells with the potential for producing the desired antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984; each incorporated herein by reference). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F, 4B210 or one of the above listed mouse cell lines; and U-266, GM1500-GRG2, LICR-LON-HMy2 and UC729-6, are all useful in connection with human cell fusions.

Methods for generating hybrids of antibody-producing spleen or lymph node cells and myeloma cells usually comprise mixing somatic cells with myeloma cells in a 4:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976; each incorporated herein by reference), and those using polyethylene glycol (PEG), such as 37% (v/v) PEG, by Gefter et al. (1977; incorporated herein by reference). The use of electrically induced fusion methods is also appropriate (Goding pp. 71-74, 1986; incorporated herein by reference).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations.

MAbs produced by either means will generally be further purified, e.g., using filtration, centrifugation and various chromatographic methods, such as HPLC or affinity chromatography, all of which purification techniques are well known to those of skill in the art. These purification techniques each involve fractionation to separate the desired antibody from other components of a mixture. Analytical methods particularly suited to the preparation of antibodies include, for example, protein A-Sepharose and/or protein G-Sepharose chromatography.

D. Second Generation Antibodies to Anionic Phospholipids and Aminophospholipids

The present invention provides "second generation" antibodies that bind to aminophospholipids and anionic phospholipids, which antibodies have improved properties and/or do not suffer from the drawback associated with the antibodies in the prior art. A panel of such antibodies is disclosed herein, of which the monoclonal antibodies 9D2 and 3G4 are currently preferred, with the 3G4 (ATCC 4545) antibody being particularly preferred. The invention also provides particular immunization and screening techniques, which permit "like" or "competing" antibodies with advantageous properties and/or less drawbacks to be produced.

D1. Antibody Properties

The second generation antibodies of the invention bind to aminophospholipids and anionic phospholipids and yet do not have pathogenic properties usually associated with antibodies to such phospholipids. This was made possible, in part, by the new immunization and screening techniques developed by the inventors.

Anti-phospholipid syndrome(s) (APS) are associated with autoantibodies termed "anti-cardiolipin" antibodies and "lupus anticoagulant antibodies". These syndromes are associated with a predisposition towards venous and arterial thromboemboli, thrombocytopenia and a number of neurological syndromes. The anti-phospholipid antibodies in these patients are thus "pathogenic antibodies".

Although described for years as "anti-phospholipid antibodies" and "anti-PS antibodies", such pathogenic antibodies in fact recognize protein cofactors that bind to cardiolipin, PS or both, not the phospholipids themselves (Galli et al., 1990; 1993; McNeil et al., 1990; Rote, 1996). Anti-cardiolipin antibodies recognize a particular region (between residue 281 and residue 288) on β2-glycoprotein I, whereas lupus anticoagulant antibodies recognize prothrombin. Similarly, anti-PE antibodies that occur in disease states bind to PE in combination with proteins, such as low and high molecular weight kininogen (HK), prekallikrein and factor XI (Sugi and McIntyre, 1995; 1996a; 1996b). Based upon this type of protein recognition, the anti-phospholipid antibodies in patients displace the protein cofactors from the phospholipids, thus creating the symptoms of disease.

The antibodies of the present invention have been particularly selected on the basis of not binding to aminophospholipids and anionic phospholipids in combination with protein cofactors, but rather are "true" anti-phospholipid antibodies. As such, the antibodies of the invention do not bind or displace the protein cofactors from the phospholipids and are therefore safe for administration. Indeed, mice treated with the antibodies of the invention at high doses for prolonged periods showed no changes in coagulation capability, yet mice respond with APS when injected with anticardiolipin or lupus anticoagulant antibodies.

Irrespective of the underlying mechanisms, anti-phospholipid antibodies occurring in the human population are correlated with autoimmune diseases, e.g., systemic lupus erythematosus (Branch et al., 1987; Staub et al., 1989; Drouvalakis and Buchanan, 1998; Smirnov et al., 1995; Rauch et al., 1986; Rauch and Janoff, 1990) and recurrent pregnancy loss (Rote et al., 1995; Rote, 1996; Vogt et al., 1996; 1997; Katsuragawa et al., 1997). No such symptoms have been associated when the antibodies of the present invention are administered to mice or monkeys.

Also, the epitope recognized by the antibodies of the invention, such as the 9D2 and 3G4 (ATCC 4545) antibodies, is not the same as that recognized by annexin V. This is shown herein, as the agents do not crossblock each others' binding to phospholipids. The epitope recognized by the 3G4 and 9D2 antibodies is probably a hexagonally packed form of PS, which is the immunogenic form. Annexin V likely binds to planar PS in addition to the hexagonal form. The hexagonal form of PS concentrates into protuberances in the plasma membrane associated with cell activation and into "blebs" on apoptotic cells. The restricted distribution of the antibodies of the invention, such as the 9D2 and 3G4 (ATCC 4545) antibodies, thus further contributes to the lack of detectable toxicity and lack of effect on coagulation of the antibodies.

In order to generate antibodies to aminophospholipids and anionic phospholipids with advantageous properties and/or reduced or essentially no side effects, the present invention provides preferred immunization and screening methods. Other immunization techniques and antibodies have been reported in the literature (Umeda et al., 1989; Igarashi et al., 1991; Rote et al., 1993), including those with reported specificity for the type of fatty acid chains involved (Levy et al., 1990; Qamar et al., 1990). However, the present immunization techniques, and particularly the selection of antibodies that are not serum dependent, provide particular benefits.

Umeda et al. (1989) reported the production of monoclonal antibodies recognizing stereo-specific epitopes of phosphatidylserine. However, the Umeda system suffers from the drawback of using direct immunization of phosphatidylserine into mouse spleen using a *Salmonella*-coated aminophospholipid sample (Umeda et al., 1989). Many of the antibodies reported by Umeda et al. (1989) also exhibit anticoagulant activity, which is a drawback not associated with the antibodies of the present invention. The binding profile of the 3G4 antibody is different to that of the PSC8 antibody of Umeda et al. (1989).

The antibodies of the invention also have the advantage of recognizing all or most anionic phospholipids, which can provide more targets for binding. Therefore, the second generation antibodies of the invention can be defined as having substantially the same, or the same, phospholipid specificity as the 9D2 or 3G4 (ATCC 4545) antibodies, as disclosed herein in Table 4, and as not being serum dependent.

Igarashi et al. (1991) also reported the induction of anti-PS antibodies, but again used intrasplenic immunization and only a slight increase of the titer was observed when the antigen was again injected intravenously. Most of the MAbs from Igarashi et al. (1991) cross-reacted with DNA and many exhibited lupus anticoagulant activity, neither of which drawbacks exist in the antibodies developed by the present inventors. The binding profile of the preferred, 3G4 antibody of the invention is also different to those of the antibodies in Table 1 of Igarashi et al. (1991).

Others have reported the lupus anticoagulant activities of murine monoclonal antibodies that cross react with more than one anionic phospholipid (Alving et al., 1987; Rauch and Janoff, 1990), but the present inventors have experienced no difficulty in obtaining antibodies free from lupus anticoagulant activity. This represents a distinct advantage of the methods, antibodies and competing antibodies in accordance with the present invention.

In addition to avoiding the use of antibodies from patients, such as described in Rauch et al. (1986), Hasegawa et al. (1994), Ravirajan et al. (1995) and Menon et al. (1997), the present application also demonstrates the advantageous properties of the antibodies provided by this invention in side-by-side comparisons with existing antibodies from the literature, such as the 3SB antibody described by Rote et al. (1993). Although the 3SB antibody has properties suitable for use in various of the methods disclosed herein, the antibodies developed by the present inventors nonetheless out-perform the 3SB antibody in comparative studies, e.g., as shown herein by the increased anti-viral effects of the 3G4 antibodies as opposed to the 3SB antibody (Example XIII).

The antibodies of the present invention can also be characterized by their affinity. Prior to the invention, the antibodies in the literature had relatively weak affinity (where reported). In certain embodiments, the second generation antibodies of the invention are therefore defined as those that have an affinity for PS of at least equal to the affinity of the 9D2 or 3G4 (ATCC 4545) antibodies for PS, in particular, the affinity when measured in an ELISA as described herein, as disclosed in Table 3, and as not being serum dependent.

More preferably, the second generation antibodies of the invention are defined as those having an affinity for PS of at least equal to the affinity of the 9D2 or 3G4 (ATCC 4545) antibodies for PS, as disclosed in Table 3, and as having substantially the same, or the same, phospholipid specificity as the 9D2 or 3G4 (ATCC 4545) antibodies, as disclosed in Table 4, and as not being serum dependent. Most preferably, the second generation antibodies are those having an affinity for PS of at least equal to the affinity of the 3G4 (ATCC 4545) antibody for PS, as disclosed in Table 3, and as having the same phospholipid specificity as the 3G4 (ATCC 4545) antibody, as disclosed in Table 4, and as not being serum dependent.

D2. CDR Technologies

Antibodies are comprised of variable and constant regions. The term "variable", as used herein in reference to antibodies, means that certain portions of the variable domains differ extensively in sequence among antibodies, and are used in the binding and specificity of each particular antibody to its particular antigen. However, the variability is not evenly distributed throughout the variable domains of antibodies. It is concentrated in three segments termed "hypervariable regions", both in the light chain and the heavy chain variable domains (other than camelized antibodies discussed below).

The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases, forming part of, the β-sheet structure.

The hypervariable regions in each chain are held together in close proximity by the FRs and, with the hypervariable regions from the other chain, contribute to the formation of the antigen-binding site of antibodies (Kabat et al., 1991, specifically incorporated herein by reference). The constant domains are not involved directly in binding an antibody to an antigen, but exhibit various effector functions, such as participation of the antibody in antibody-dependent cellular toxicity.

The term "hypervariable region", as used herein, refers to the amino acid residues of an antibody that are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-56 (H2) and 95-102 (H3) in the heavy chain variable domain; Kabat et al., 1991, specifically incorporated herein by reference) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain). "Framework" or "FR" residues are those variable domain residues other than the hypervariable region residues as herein defined.

The DNA and deduced amino acid sequences of the Vh and Vκ chains of the 3G4 antibody (ATCC 4545) are provided herein as SEQ ID NO:1, 2, 3 and 4, respectively. These sequences encompass CDR1-3 of the variable regions of the heavy and light chains of the antibody. In light of the sequence and other information provided herein, and the knowledge in the art, a range of 3G4-like and improved antibodies and antigen binding regions can now be prepared and are thus encompassed by the present invention.

In certain embodiments, the invention provides at least one CDR of the antibody produced by the hybridoma deposited as ATCC 4545. In other embodiments, the invention provides a CDR, antibody, or antigen binding region thereof, which binds to at least a first aminophospholipid or anionic phospholipid, preferably PS, and which comprises at least one CDR of the antibody produced by the hybridoma deposited as ATCC 4545.

Further aspects of the invention concern at least one CDR that has the amino acid sequence of SEQ ID NO:2 or SEQ ID NO:4, or a variant or mutagenized form thereof. Other aspects of the invention concern a CDR, antibody, or antigen binding region thereof, which binds to at least a first aminophospholipid or anionic phospholipid, preferably PS, and which comprises at least one CDR with the amino acid sequence of SEQ ID NO:2 or SEQ ID NO:4, or a variant or mutagenized form thereof, wherein such a variant or mutagenized form maintains binding to the aminophospholipid or anionic phospholipid, preferably PS.

In one particular embodiment, the invention provides an antibody, or antigen binding region thereof, in which the framework regions of the 3G4 antibody (ATCC 4545) have been changed from mouse to a human IgG, such as human $IgG_1$ or other IgG subclass to reduce immunogenicity in humans. In other embodiments, the sequences of the 3G4 antibody (ATCC 4545) are examined for the presence of T-cell epitopes, as is known in the art. The underlying sequence can then be changed to remove T-cell epitopes, i.e., to "deimmunize" the antibody.

The availability of the DNA and amino acid sequences of the Vh and Vκ chains of the 3G4 antibody (SEQ ID NO:1, 2, 3 and 4) means that a range of antibodies can now be prepared using CDR technologies. In particular, random mutations are made in the CDRs and the products screened to identify antibodies with higher affinities and/or higher specificities. Such mutagenesis and selection is routinely practiced in the antibody arts. It is particularly suitable for use in the present invention, given the advantageous screening techniques disclosed herein.

These techniques are used to generate antibody variants with improved biological properties relative to the parent antibody from which they are prepared, such as the 9D2 and 3G4 (ATCC 4545) antibodies. Such variants, or second generation compounds, are typically substitutional variants involving one or more substituted hypervariable region residues of a parent antibody. A convenient way for generating such substitutional variants is affinity maturation using phage display.

In affinity maturation using phage display, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding.

CDR shuffling and implantation technologies can also be used with the antibodies of the present invention, preferably the 9D2 and 3G4 (ATCC 4545) antibodies. CDR shuffling inserts CDR sequences into a specific framework region (Jirholt et al., 1998, specifically incorporated herein by reference). CDR implantation techniques permit the random combination of CDR sequences into a single master framework (Soderlind et al., 1999, 2000, each specifically incorporated herein by reference). Using such techniques, the CDR sequences of the 3G4 (ATCC 4545) antibody, for example, are mutagenized to create a plurality of different sequences, which are incorporated into a scaffold sequence and the resultant antibody variants screened for desired characteristics, e.g., higher affinity.

In light of the information in the present disclosure, the antigen binding fragment of the antibodies, preferably the 9D2 and 3G4 (ATCC 4545) antibodies, can also be minimized, giving enhanced stability. This can be achieved by preparing single domain binding proteins based upon immunoglobulin $V_H$ and $V_H$-like domains (Nuttall et al., 2000, specifically incorporated herein by reference).

Alternatively, or in addition, the crystal structure of the antigen-antibody complex can be delineated and analyzed to identify contact points between the antibody and target aminophospholipid or anionic phospholipid, e.g., PS. Such contact residues and neighboring residues are candidates for substitution. Once such variants are generated, the panel of variants is subjected to screening, as described herein, and antibodies with analogous but different or even superior properties in one or more relevant assays are selected for further development.

D3. Camelized Antibodies

Further examples of antibodies of the invention are "camelized" antibodies. Antibodies from camels and llamas (Camelidae, camelids) include a unique kind of antibody, which is devoid of light chains and thus formed by heavy chains only. These have been termed "camelized antibodies". The antigen-binding site of such antibodies is one single domain, referred to as $V_{HH}$ (VHH).

As the DNA and amino acid sequences of the Vh and Vκ chains of the 3G4 (ATCC 4545) antibody are provided herein (SEQ ID NOs:1, 2, 3 and 4), camelized versions of the 3G4 antibody can also be prepared. Mutations and structural adaptations can be made to reshape a $V_H$ of a $V_H$-$V_L$ pair into a single-domain $V_{HH}$ with retention of a sufficient variability (Muyldermans et al., 2001, specifically incorporated herein by reference). Such $V_{HH}$ constructs are small, robust and efficient recognition units (Riechmann and Muyldermans, 1999) with potent antigen-binding capacity, which can provide the further advantage of interacting with novel epitopes that are inaccessible to conventional $V_H$-$V_L$ pairs. Thus, camelised antibodies are akin to Fv fragments, but can have additional benefits.

U.S. Pat. Nos. 5,800,988, 6,005,079, PCT application No. WO 94/04678, PCT application No. WO 94/25591, Riechmann and Muyldermans (1999) and Muyldermans et al. (2001) are each specifically incorporated herein by reference for the purpose of even further describing and enabling the production of camelized antibodies. Accordingly, the CDR from the 3G4 antibody can be grafted on the framework of the variable domain of the heavy chain immunoglobulin of the Camelidae antibody.

D4. CDR Sequences

Further aspects of the invention therefore concern isolated DNA segments and recombinant vectors encoding CDR regions of antibody heavy and light chains, such as 9D2 and 3G4, and preferably 3G4 (ATCC 4545), heavy and light chains, and the creation and use of recombinant host cells and phage through the application of DNA technology, which express such CDR regions.

The invention thus provides an isolated polynucleotide that contains a nucleotide sequence that encodes at least one CDR of the antibody produced by the hybridoma deposited as ATCC 4545. The invention further provides an isolated polynucleotide that contains a nucleotide sequence that encodes a CDR, antibody, or antigen binding region thereof, which binds to at least a first aminophospholipid or anionic phospholipid, preferably PS, and which comprises at least one CDR of the antibody produced by the hybridoma deposited as ATCC 4545.

Further aspects of the invention concern an isolated polynucleotide that contains a nucleotide sequence that encodes at least one CDR that has the amino acid sequence of SEQ ID NO:2 or SEQ ID NO:4, or a variant or mutagenized form thereof. Other aspects of the invention concern an isolated polynucleotide that contains a nucleotide sequence that encodes a CDR, antibody, or antigen binding region thereof, which binds to at least a first aminophospholipid or anionic phospholipid, preferably PS, and which comprises at least one CDR with the amino acid sequence of SEQ ID NO:2 or SEQ ID NO:4, or a variant or mutagenized form thereof, wherein such a variant or mutagenized form maintains binding to the aminophospholipid or anionic phospholipid, preferably PS.

In other aspects of the invention, the isolated polynucleotide contains the nucleotide sequence of SEQ ID NO:1 or SEQ ID NO:3, or a variant or mutagenized form thereof. In particular, the isolated polynucleotide contains the nucleotide sequence of SEQ ID NO:1 or SEQ ID NO:3, or a variant or mutagenized form thereof, which nucleotide sequence encodes a CDR, antibody, or antigen binding region thereof that binds to at least a first aminophospholipid or anionic phospholipid, preferably PS, wherein any such variant or mutagenized form maintains binding to the aminophospholipid or anionic phospholipid, preferably PS.

The present invention thus concerns polynucleotide and DNA segments, isolatable from any mammal, preferably, human or murine, that are free from total genomic DNA and are capable of expressing CDR regions of anti-anionic phospholipid or anti-aminophospholipid antibody heavy and light chains, such as 9D2 and 3G4, and preferably 3G4 (ATCC 4545), heavy and light chains. As used herein, the terms "polynucleotide segment" and "DNA segment" refer to polynucleotides and DNA molecules that have been isolated free of total genomic DNA of a particular species. Included within the term "polynucleotide segment" and "DNA segment", are DNA segments and smaller fragments of such segments, and also recombinant vectors, including, for example, plasmids, cosmids, phage, viruses, and the like.

Similarly, a DNA segment comprising a coding segment or isolated gene portion encoding purified CDR regions of anti-anionic phospholipid or anti-aminophospholipid antibody heavy and light chains, such as 9D2 and 3G4, and preferably 3G4, heavy and light chains, refers to a DNA segment including such coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes the native antibody-encoding sequences and smaller engineered segments that express, or may be adapted to express, suitable antigen binding proteins, polypeptides or peptides.

"Isolated substantially away from other coding sequences" means that the coding segment or isolated gene portion of interest forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated coding segments or isolated gene portions and recombinant vectors incorporating DNA sequences that encode CDR regions of anti-anionic phospholipid or anti-aminophospholipid antibody heavy and light chains, such as 9D2 and 3G4, and preferably 3G4, heavy and light chains, that comprise at least a first sequence region that includes an amino acid sequence region of at least about 75%, more preferably, at least about 80%, more preferably, at least about 85%, more preferably, at least about 90%, 91%, 92%, 93%, 94%, and most preferably, at least about 95%, 96%, 97%, 98% or 99% or so amino acid sequence identity to the amino acid sequence of SEQ ID NO:2 or SEQ ID NO:4; wherein said CDR regions at least substantially maintain the biological properties of the CDR regions of amino acid sequences SEQ ID NO:2 or SEQ ID NO:4.

As disclosed herein, the sequences may comprise certain biologically functional equivalent amino acids or "conservative substitutions". Other sequences may comprise functionally non-equivalent amino acids or "non-conservative substitutions" deliberately engineered to improve the properties of the CDR or antibody containing the CDR, as is known those of ordinary skill in the art and further described herein.

It will also be understood that amino acid and nucleic acid sequences may include additional residues, such as additional N- or C-terminal amino acids or 5' or 3' sequences, and yet still correspond to a sequence of the invention, so long as the sequence meets the criteria set forth above, preferably including the maintenance or improvement of biological protein activity where protein expression is concerned. The addition of terminal sequences includes various non-coding sequences flanking either of the 5' or 3' portions of the coding region, and also control regions.

The nucleic acid segments of the present invention may thus be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Recombinant vectors therefore form further aspects of the present invention. Particularly useful vectors are contemplated to be those vectors in which the coding portion of the DNA segment is positioned under the control of a promoter. Generally, although not exclusively, a recombinant or heterologous promoter will be employed, i.e., a promoter not normally associated with coding sequences in their natural environment. Such promoters may include bacterial, viral, eukaryotic and mammalian promoters, so long as the promoter effectively directs the expression of the DNA segment in the cell type, organism, or even animal, chosen for expression.

The use of promoter and cell type combinations for protein expression is known to those of skill in the art of molecular biology. The promoters employed may be constitutive, or inducible, and can be used under the appropriate conditions to direct high level expression of the introduced DNA segment, such as is advantageous in the large-scale production of recombinant proteins or peptides.

The expression of the nucleic acid sequences of the invention may be conveniently achieved by any one or more standard techniques known those of ordinary skill in the art and further described herein. For example, the later description of the recombinant expression of fusion proteins applies equally well to antibodies and antibody fragments that are not operatively associated with another coding sequence at the nucleic acid level.

E. Further Antibody Preparation Techniques

E1. Antibodies from Phagemid Libraries

Recombinant technology now allows the preparation of antibodies having the desired specificity from recombinant genes encoding a range of antibodies (Van Dijk et al., 1989; incorporated herein by reference). Certain recombinant techniques involve the isolation of the antibody genes by immunological screening of combinatorial immunoglobulin phage expression libraries prepared from RNA isolated from the spleen of an immunized animal (Morrison et al., 1986; Winter and Milstein, 1991; Barbas et al., 1992; each incorporated herein by reference).

For such methods, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination, which further increases the percentage of appropriate antibodies generated.

One method for the generation of a large repertoire of diverse antibody molecules in bacteria utilizes the bacteriophage lambda as the vector (Huse et al., 1989; incorporated herein by reference). Production of antibodies using the lambda vector involves the cloning of heavy and light chain populations of DNA sequences into separate starting vectors. The vectors are subsequently combined randomly to form a single vector that directs the co-expression of heavy and light chains to form antibody fragments. The heavy and light chain DNA sequences are obtained by amplification, preferably by PCR™ or a related amplification technique, of mRNA isolated from spleen cells (or hybridomas thereof) from an animal that has been immunized with a selected antigen. The heavy and light chain sequences are typically amplified using primers that incorporate restriction sites into the ends of the amplified DNA segment to facilitate cloning of the heavy and light chain segments into the starting vectors.

Another method for the generation and screening of large libraries of wholly or partially synthetic antibody combining sites, or paratopes, utilizes display vectors derived from filamentous phage such as M13, fl or fd. These filamentous phage display vectors, referred to as "phagemids", yield large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries (Kang et al., 1991; Barbas et al., 1991; each incorporated herein by reference).

This general technique for filamentous phage display is described in U.S. Pat. No. 5,658,727, incorporated herein by reference. In a most general sense, the method provides a system for the simultaneous cloning and screening of pre-selected ligand-binding specificities from antibody gene repertoires using a single vector system. Screening of isolated members of the library for a pre-selected ligand-binding capacity allows the correlation of the binding capacity of an expressed antibody molecule with a convenient means to isolate the gene that encodes the member from the library.

Linkage of expression and screening is accomplished by the combination of targeting of a fusion polypeptide into the periplasm of a bacterial cell to allow assembly of a functional antibody, and the targeting of a fusion polypeptide onto the coat of a filamentous phage particle during phage assembly to allow for convenient screening of the library member of interest. Periplasmic targeting is provided by the presence of a secretion signal domain in a fusion polypeptide. Targeting to a phage particle is provided by the presence of a filamentous phage coat protein membrane anchor domain (i.e., a cpIII- or cpVIII-derived membrane anchor domain) in a fusion polypeptide.

The diversity of a filamentous phage-based combinatorial antibody library can be increased by shuffling of the heavy and light chain genes, by altering one or more of the complementarity determining regions of the cloned heavy chain genes of the library, or by introducing random mutations into the library by error-prone polymerase chain reactions. Additional methods for screening phagemid libraries are described in U.S. Pat. Nos. 5,580,717; 5,427,908; 5,403,484; and 5,223,409, each incorporated herein by reference.

Another method for the screening of large combinatorial antibody libraries has been developed, utilizing expression of populations of diverse heavy and light chain sequences on the surface of a filamentous bacteriophage, such as M13, fl or fd (U.S. Pat. No. 5,698,426; incorporated herein by reference). Two populations of diverse heavy (Hc) and light (Lc) chain sequences are synthesized by polymerase chain reaction (PCR™). These populations are cloned into separate M13-based vector containing elements necessary for expression. The heavy chain vector contains a gene VIII (gVIII) coat protein sequence so that translation of the heavy chain sequences produces gVIII-Hc fusion proteins. The populations of two vectors are randomly combined such that only the vector portions containing the Hc and Lc sequences are joined into a single circular vector.

The combined vector directs the co-expression of both Hc and Lc sequences for assembly of the two polypeptides and surface expression on M13 (U.S. Pat. No. 5,698,426; incorporated herein by reference). The combining step randomly brings together different Hc and Lc encoding sequences within two diverse populations into a single vector. The vector sequences donated from each independent vector are necessary for production of viable phage. Also, since the pseudo gVIII sequences are contained in only one of the two starting vectors, co-expression of functional antibody fragments as Lc associated gVIII-Hc fusion proteins cannot be accomplished on the phage surface until the vector sequences are linked in the single vector.

Surface expression of the antibody library is performed in an amber suppressor strain. An amber stop codon between the Hc sequence and the gVIII sequence unlinks the two components in a non-suppressor strain. Isolating the phage produced from the non-suppressor strain and infecting a suppressor strain will link the Hc sequences to the gVIII sequence during expression. Culturing the suppressor strain after infection allows the coexpression on the surface of M13 of all antibody species within the library as gVIII fusion proteins (gVIII-Fab fusion proteins). Alternatively, the DNA can be isolated from the non-suppressor strain and then introduced into a suppressor strain to accomplish the same effect.

The surface expression library is screened for specific Fab fragments that bind preselected molecules by standard affinity isolation procedures. Such methods include, for example, panning (Parmley and Smith, 1988; incorporated herein by reference), affinity chromatography and solid phase blotting procedures. Panning is preferred, because high titers of phage can be screened easily, quickly and in small volumes. Furthermore, this procedure can select minor Fab fragments species within the population, which otherwise would have been undetectable, and amplified to substantially homogenous populations. The selected Fab fragments can be characterized by sequencing the nucleic acids encoding the polypeptides after amplification of the phage population.

Another method for producing diverse libraries of antibodies and screening for desirable binding specificities is described in U.S. Pat. No. 5,667,988 and 5,759,817, each incorporated herein by reference. The method involves the preparation of libraries of heterodimeric immunoglobulin molecules in the form of phagemid libraries using degenerate oligonucleotides and primer extension reactions to incorporate the degeneracies into the CDR regions of the immunoglobulin variable heavy and light chain variable domains, and display of the mutagenized polypeptides on the surface of the phagemid. Thereafter, the display protein is screened for the ability to bind to a preselected antigen.

The method for producing a heterodimeric immunoglobulin molecule generally involves (1) introducing a heavy or light chain V region-coding gene of interest into the phagemid display vector; (2) introducing a randomized binding site into the phagemid display protein vector by primer extension with an oligonucleotide containing regions of homology to a CDR of the antibody V region gene and containing regions of degeneracy for producing randomized coding sequences to form a large population of display vectors each capable of expressing different putative binding sites displayed on a phagemid surface display protein; (3) expressing the display protein and binding site on the surface of a filamentous phage particle; and (4) isolating (screening) the surface-expressed phage particle using affinity techniques such as panning of phage particles against a preselected antigen, thereby isolating one or more species of phagemid containing a display protein containing a binding site that binds a preselected antigen.

A further variation of this method for producing diverse libraries of antibodies and screening for desirable binding specificities is described in U.S. Pat. No. 5,702,892, incorporated herein by reference. In this method, only heavy chain sequences are employed, the heavy chain sequences are randomized at all nucleotide positions which encode either the CDRI or CDRIII hypervariable region, and the genetic variability in the CDRs is generated independent of any biological process.

In the method, two libraries are engineered to genetically shuffle oligonucleotide motifs within the framework of the heavy chain gene structure. Through random mutation of either CDRI or CDRIII, the hypervariable regions of the heavy chain gene were reconstructed to result in a collection of highly diverse sequences. The heavy chain proteins encoded by the collection of mutated gene sequences possessed the potential to have all of the binding characteristics of an immunoglobulin while requiring only one of the two immunoglobulin chains.

Specifically, the method is practiced in the absence of the immunoglobulin light chain protein. A library of phage displaying modified heavy chain proteins is incubated with an immobilized ligand to select clones encoding recombinant proteins that specifically bind the immobilized ligand. The bound phage are then dissociated from the immobilized ligand and amplified by growth in bacterial host cells. Individual viral plaques, each expressing a different recombinant protein, are expanded, and individual clones can then be assayed for binding activity.

E2. Antibodies from Human Lymphocytes

Antibodies against phospholipids occur in the human population. However, these antibodies are typically associated with disease and their use in the present invention should preferably be avoided. However, human lymphocytes from healthy subjects can be used as appropriate as starting materials for generating an antibody for use in the invention.

In vitro immunization, or antigen stimulation, may also be used to generate a human antibody for use in the present invention. Such techniques can be used to stimulate peripheral blood lymphocytes from normal, healthy subjects simply by stimulating antibody-producing cells with anionic phospholipids and aminophospholipids in vitro.

Such "in vitro immunization" involves antigen-specific activation of non-immunized B lymphocytes, generally within a mixed population of lymphocytes (mixed lymphocyte cultures, MLC). In vitro immunizations may also be supported by B cell growth and differentiation factors and lymphokines. The antibodies produced by these methods are often IgM antibodies (Borrebaeck and Moller, 1986; incorporated herein by reference).

Another method has been described (U.S. Pat. No. 5,681, 729, incorporated herein by reference) wherein human lymphocytes that mainly produce IgG (or IgA) antibodies can be obtained. The method involves, in a general sense, transplanting human lymphocytes to an immunodeficient animal so that the human lymphocytes "take" in the animal body; immunizing the animal with a desired antigen, so as to generate human lymphocytes producing an antibody specific to the antigen; and recovering the human lymphocytes producing the antibody from the animal. The human lymphocytes thus produced can be used to produce a monoclonal antibody by immortalizing the human lymphocytes producing the antibody, cloning the obtained immortalized human-originated lymphocytes producing the antibody, and recovering a monoclonal antibody specific to the desired antigen from the cloned immortalized human-originated lymphocytes.

The immunodeficient animals that may be employed in this technique are those that do not exhibit rejection when human lymphocytes are transplanted to the animals. Such animals may be artificially prepared by physical, chemical or biological treatments. Any immunodeficient animal may be employed. The human lymphocytes may be obtained from human peripheral blood, spleen, lymph nodes, tonsils or the like.

The "taking" of the transplanted human lymphocytes in the animals can be attained by merely administering the human lymphocytes to the animals. The administration route is not restricted and may be, for example, subcutaneous, intravenous or intraperitoneal. The dose of the human lymphocytes is not restricted, and can usually be $10^6$ to $10^8$ lymphocytes per animal. The immunodeficient animal is then immunized with the desired antigen.

After the immunization, human lymphocytes are recovered from the blood, spleen, lymph nodes or other lymphatic tissues by any conventional method. For example, mononuclear cells can be separated by the Ficoll-Hypaque (specific gravity: 1.077) centrifugation method, and the monocytes removed by the plastic dish adsorption method. The contaminating cells originating from the immunodeficient animal may be removed by using an antiserum specific to the animal cells. The antiserum may be obtained by, for example, immunizing a second, distinct animal with the spleen cells of the immunodeficient animal, and recovering serum from the distinct immunized animal. The treatment with the antiserum may be carried out at any stage. The human lymphocytes may also be recovered by an immunological method employing a human immunoglobulin expressed on the cell surface as a marker.

By these methods, human lymphocytes mainly producing IgG and IgA antibodies specific to one or more selected anionic phospholipids and aminophospholipids can be obtained. Monoclonal antibodies are then obtained from the human lymphocytes by immortalization, selection, cell growth and antibody production.

E3. Transgenic Mice Containing Human Antibody Libraries

Recombinant technology is now available for the preparation of antibodies. In addition to the combinatorial immunoglobulin phage expression libraries disclosed above, another molecular cloning approach is to prepare antibodies from transgenic mice containing human antibody libraries. Such techniques are described in U.S. Pat. No. 5,545,807, incorporated herein by reference.

In a most general sense, these methods involve the production of a transgenic animal that has inserted into its germline genetic material that encodes for at least part of an immunoglobulin of human origin or that can rearrange to encode a repertoire of immunoglobulins. The inserted genetic material may be produced from a human source, or may be produced synthetically. The material may code for at least part of a known immunoglobulin or may be modified to code for at least part of an altered immunoglobulin.

The inserted genetic material is expressed in the transgenic animal, resulting in production of an immunoglobulin derived at least in part from the inserted human immunoglobulin genetic material. It is found the genetic material is rearranged in the transgenic animal, so that a repertoire of immunoglobulins with part or parts derived from inserted genetic material may be produced, even if the inserted genetic material is incorporated in the germline in the wrong position or with the wrong geometry.

The inserted genetic material may be in the form of DNA cloned into prokaryotic vectors such as plasmids and/or cosmids. Larger DNA fragments are inserted using yeast artificial chromosome vectors (Burke et al., 1987; incorporated herein by reference), or by introduction of chromosome fragments (Richer and Lo, 1989; incorporated herein by reference). The inserted genetic material may be introduced to the host in conventional manner, for example by injection or other procedures into fertilized eggs or embryonic stem cells.

In preferred aspects, a host animal that initially does not carry genetic material encoding immunoglobulin constant regions is utilized, so that the resulting transgenic animal will use only the inserted human genetic material when producing immunoglobulins. This can be achieved either by using a naturally occurring mutant host lacking the relevant genetic material, or by artificially making mutants e.g., in cell lines ultimately to create a host from which the relevant genetic material has been removed.

Where the host animal carries genetic material encoding immunoglobulin constant regions, the transgenic animal will carry the naturally occurring genetic material and the inserted genetic material and will produce immunoglobulins derived from the naturally occurring genetic material, the inserted genetic material, and mixtures of both types of genetic material. In this case the desired immunoglobulin can be obtained by screening hybridomas derived from the transgenic animal, e.g., by exploiting the phenomenon of allelic exclusion of antibody gene expression or differential chromosome loss.

Once a suitable transgenic animal has been prepared, the animal is simply immunized with the desired immunogen. Depending on the nature of the inserted material, the animal may produce a chimeric immunoglobulin, e.g. of mixed mouse/human origin, where the genetic material of foreign origin encodes only part of the immunoglobulin; or the animal may produce an entirely foreign immunoglobulin, e.g. of wholly human origin, where the genetic material of foreign origin encodes an entire immunoglobulin.

Polyclonal antisera may be produced from the transgenic animal following immunization. Immunoglobulin-producing cells may be removed from the animal to produce the immunoglobulin of interest. Preferably, monoclonal antibodies are produced from the transgenic animal, e.g., by fusing spleen cells from the animal with myeloma cells and screening the resulting hybridomas to select those producing the desired antibody. Suitable techniques for such processes are described herein.

In an alternative approach, the genetic material may be incorporated in the animal in such a way that the desired antibody is produced in body fluids such as serum or external secretions of the animal, such as milk, colostrum or saliva. For example, by inserting in vitro genetic material encoding for at least part of a human immunoglobulin into a gene of a mammal coding for a milk protein and then introducing the gene to a fertilized egg of the mammal, e.g., by injection, the egg may develop into an adult female mammal producing milk containing immunoglobulin derived at least in part from the inserted human immunoglobulin genetic material. The desired antibody can then be harvested from the milk. Suitable techniques for carrying out such processes are known to those skilled in the art.

The foregoing transgenic animals are usually employed to produce human antibodies of a single isotype, more specifically an isotype that is essential for B cell maturation, such as IgM and possibly IgD. Another preferred method for producing human antibodies is described in U.S. Pat. Nos. 5,545,806; 5,569,825; 5,625,126; 5,633,425; 5,661,016; and 5,770,429; each incorporated by reference, wherein transgenic animals are described that are capable of switching from an isotype needed for B cell development to other isotypes.

In the development of a B lymphocyte, the cell initially produces IgM with a binding specificity determined by the productively rearranged $V_H$ and $V_L$ regions. Subsequently, each B cell and its progeny cells synthesize antibodies with the same L and H chain V regions, but they may switch the isotype of the H chain. The use of mu or delta constant regions is largely determined by alternate splicing, permitting IgM and IgD to be coexpressed in a single cell. The other heavy chain isotypes (gamma, alpha, and epsilon) are only expressed natively after a gene rearrangement event deletes the C mu and C delta exons. This gene rearrangement process, termed isotype switching, typically occurs by recombination between so called switch segments located immediately upstream of each heavy chain gene (except delta). The individual switch segments are between 2 and 10 kb in length, and consist primarily of short repeated sequences.

For these reasons, it is preferable that transgenes incorporate transcriptional regulatory sequences within about 1-2 kb upstream of each switch region that is to be utilized for isotype switching. These transcriptional regulatory sequences preferably include a promoter and an enhancer element, and more preferably include the 5' flanking (i.e., upstream) region that is naturally associated (i.e., occurs in germline configuration) with a switch region. Although a 5' flanking sequence from one switch region can be operably linked to a different switch region for transgene construction, in some embodiments it is preferred that each switch region incorporated in the transgene construct have the 5' flanking region that occurs immediately upstream in the naturally occurring germline configuration. Sequence information relating to immunoglobulin switch region sequences is known (Mills et al., 1990; Sideras et al., 1989; each incorporated herein by reference).

In the method described in U.S. Pat. Nos. 5,545,806; 5,569,825; 5,625,126; 5,633,425; 5,661,016; and 5,770,429, the human immunoglobulin transgenes contained within the transgenic animal function correctly throughout the pathway of B-cell development, leading to isotype switching. Accordingly, in this method, these transgenes are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

An important requirement for transgene function is the generation of a primary antibody repertoire that is diverse enough to trigger a secondary immune response for a wide range of antigens. The rearranged heavy chain gene consists of a signal peptide exon, a variable region exon and a tandem array of multi-domain constant region regions, each of which is encoded by several exons. Each of the constant region genes encode the constant portion of a different class of immunoglobulins. During B-cell development, V region proximal constant regions are deleted leading to the expression of new heavy chain classes. For each heavy chain class, alternative patterns of RNA splicing give rise to both transmembrane and secreted immunoglobulins.

The human heavy chain locus consists of approximately 200 V gene segments spanning 2 Mb, approximately 30 D gene segments spanning about 40 kb, six J segments clustered within a 3 kb span, and nine constant region gene segments spread out over approximately 300 kb. The entire locus spans approximately 2.5 Mb of the distal portion of the long arm of chromosome 14. Heavy chain transgene fragments containing members of all six of the known $V_H$ families, the D and J gene segments, as well as the mu, delta, gamma 3, gamma 1 and alpha 1 constant regions are known (Berman et al., 1988; incorporated herein by reference). Genomic fragments containing all of the necessary gene segments and regulatory sequences from a human light chain locus is similarly constructed.

The expression of successfully rearranged immunoglobulin heavy and light transgenes usually has a dominant effect by suppressing the rearrangement of the endogenous immunoglobulin genes in the transgenic nonhuman animal. However, in certain embodiments, it is desirable to effect complete inactivation of the endogenous Ig loci so that hybrid immunoglobulin chains comprising a human variable region and a non-human (e.g., murine) constant region cannot be formed, for example by trans-switching between the transgene and endogenous Ig sequences. Using embryonic stem cell technology and homologous recombination, the endogenous immunoglobulin repertoire can be readily eliminated. In addition, suppression of endogenous Ig genes may be accomplished using a variety of techniques, such as antisense technology.

In other aspects of the invention, it may be desirable to produce a trans-switched immunoglobulin. Antibodies comprising such chimeric trans-switched immunoglobulins can be used for a variety of applications where it is desirable to have a non-human (e.g., murine) constant region, e.g., for retention of effector functions in the host. The presence of a murine constant region can afford advantages over a human constant region, for example, to provide murine effector functions (e.g., ADCC, murine complement fixation) so that such a chimeric antibody may be tested in a mouse disease model. Subsequent to the animal testing, the human variable region encoding sequence may be isolated, e.g., by PCR amplification or cDNA cloning from the source (hybridoma clone), and spliced to a sequence encoding a desired human constant region to encode a human sequence antibody more suitable for human therapeutic use.

E4. Humanized Antibodies

Human antibodies generally have at least three potential advantages for use in human therapy. First, because the effector portion is human, it may interact better with the other parts of the human immune system, e.g., to destroy target cells more efficiently by complement-dependent cytotoxicity (CDC) or antibody-dependent cellular cytotoxicity (ADCC). Second, the human immune system should not recognize the antibody as foreign. Third, the half-life in the human circulation will be similar to naturally occurring human antibodies, allowing smaller and less frequent doses to be given.

Various methods for preparing human antibodies are provided herein. In addition to human antibodies, "humanized" antibodies have many advantages. "Humanized" antibodies are generally chimeric or mutant monoclonal antibodies from mouse, rat, hamster, rabbit or other species, bearing human constant and/or variable region domains or specific changes. Techniques for generating a so-called "humanized" antibody are well known to those of skill in the art.

Humanized antibodies also share the foregoing advantages. First, the effector portion is still human. Second, the human immune system should not recognize the framework or constant region as foreign, and therefore the antibody response against such an injected antibody should be less than against a totally foreign mouse antibody. Third, injected humanized antibodies, as opposed to injected mouse antibodies, will presumably have a half-life more similar to naturally occurring human antibodies, also allowing smaller and less frequent doses.

A number of methods have been described to produce humanized antibodies. Controlled rearrangement of antibody domains joined through protein disulfide bonds to form new, artificial protein molecules or "chimeric" antibodies can be utilized (Konieczny et al., 1981; incorporated herein by reference). Recombinant DNA technology can also be used to construct gene fusions between DNA sequences encoding mouse antibody variable light and heavy chain domains and human antibody light and heavy chain constant domains (Morrison et al., 1984; incorporated herein by reference).

DNA sequences encoding the antigen binding portions or complementarity determining regions (CDR's) of murine monoclonal antibodies can be grafted by molecular means into the DNA sequences encoding the frameworks of human antibody heavy and light chains (Jones et al., 1986; Riechmann et al., 1988; each incorporated herein by reference). The expressed recombinant products are called "reshaped" or humanized antibodies, and comprise the framework of a human antibody light or heavy chain and the antigen recognition portions, CDR's, of a murine monoclonal antibody.

Another method for producing humanized antibodies is described in U.S. Pat. No. 5,639,641, incorporated herein by reference. The method provides, via resurfacing, humanized rodent antibodies that have improved therapeutic efficacy due to the presentation of a human surface in the variable region. In the method: (1) position alignments of a pool of antibody heavy and light chain variable regions is generated to give a set of heavy and light chain variable region framework surface exposed positions, wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of the complementarity determining regions of the rodent antibody; and (5) the humanized rodent antibody having binding specificity is produced.

A similar method for the production of humanized antibodies is described in U.S. Pat. Nos. 5,693,762; 5,693,761; 5,585,089; and 5,530,101, each incorporated herein by reference. These methods involve producing humanized immunoglobulins having one or more complementarity determining regions (CDR's) and possible additional amino acids from a donor immunoglobulin and a framework region from an accepting human immunoglobulin. Each humanized immunoglobulin chain usually comprises, in addition to the CDR's, amino acids from the donor immunoglobulin framework that are capable of interacting with the CDR's to effect binding affinity, such as one or more amino acids that are immediately adjacent to a CDR in the donor immunoglobulin or those within about 3 Å as predicted by molecular modeling. The heavy and light chains may each be designed by using any one, any combination, or all of the various position criteria described in U.S. Pat. Nos. 5,693,762; 5,693,761; 5,585,089; and 5,530,101, each incorporated herein by reference. When combined into an intact antibody, the humanized immunoglobulins are substantially non-immunogenic in humans and retain substantially the same affinity as the donor immunoglobulin to the original antigen.

An additional method for producing humanized antibodies is described in U.S. Pat. Nos. 5,565,332 and 5,733,743, each incorporated herein by reference. This method combines the concept of humanizing antibodies with the phagemid libraries also described in detail herein. In a general sense, the method utilizes sequences from the antigen binding site of an antibody or population of antibodies directed against an antigen of interest. Thus for a single rodent antibody, sequences comprising part of the antigen binding site of the antibody may be combined with diverse repertoires of sequences of human antibodies that can, in combination, create a complete antigen binding site.

The antigen binding sites created by this process differ from those created by CDR grafting, in that only the portion of sequence of the original rodent antibody is likely to make contacts with antigen in a similar manner. The selected human sequences are likely to differ in sequence and make alternative contacts with the antigen from those of the original binding site. However, the constraints imposed by binding of the portion of original sequence to antigen and the shapes of the antigen and its antigen binding sites, are likely to drive the new contacts of the human sequences to the same region or epitope of the antigen. This process has therefore been termed "epitope imprinted selection" (EIS).

Starting with an animal antibody, one process results in the selection of antibodies that are partly human antibodies. Such antibodies may be sufficiently similar in sequence to human antibodies to be used directly in therapy or after alteration of a few key residues. Sequence differences between the rodent component of the selected antibody with human sequences could be minimized by replacing those residues that differ with the residues of human sequences, for example, by site directed mutagenesis of individual residues, or by CDR grafting of entire loops. However, antibodies with entirely human sequences can also be created. EIS therefore offers a method for making partly human or entirely human antibodies that bind to the same epitope as animal or partly human antibodies respectively. In EIS, repertoires of antibody fragments can be displayed on the surface of filamentous phase and the genes encoding fragments with antigen binding activities selected by binding of the phage to antigen.

Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, each incorporated herein by reference.

E5. Mutagenesis by PCR™

Site-specific mutagenesis is a technique useful in the preparation of individual antibodies through specific mutagenesis of the underlying DNA. The technique further provides a ready ability to prepare and test sequence variants, incorporating one or more of the foregoing considerations, whether humanizing or not, by introducing one or more nucleotide sequence changes into the DNA.

Although many methods are suitable for use in mutagenesis, the use of the polymerase chain reaction (PCR™) is generally now preferred. This technology offers a quick and efficient method for introducing desired mutations into a given DNA sequence. The following text particularly describes the use of PCR™ to introduce point mutations into a sequence, as may be used to change the amino acid encoded by the given sequence. Adaptations of this method are also suitable for introducing restriction enzyme sites into a DNA molecule.

In this method, synthetic oligonucleotides are designed to incorporate a point mutation at one end of an amplified segment. Following PCR™, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR™. The 5' end of the oligonucleotides should then be phosphorylated.

The template DNA should be amplified by PCR™, using the oligonucleotide primers that contain the desired point mutations. The concentration of MgCl$_2$ in the amplification buffer will generally be about 15 mM. Generally about 20-25 cycles of PCR™ should be carried out as follows: denaturation, 35 sec. at 95° C.; hybridization, 2 min. at 50° C.; and extension, 2 min. at 72° C. The PCR™ will generally include a last cycle extension of about 10 min. at 72° C. After the final extension step, about 5 units of Klenow fragments should be added to the reaction mixture and incubated for a further 15 min. at about 30° C. The exonuclease activity of the Klenow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subclone the fragments and to check the point mutation, one would subclone the two amplified fragments into an appropriately digested vector by blunt-end ligation. This would be used to transform *E. coli*, from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR™ steps. In this procedure, the two fragments encompassing the mutation are annealed with each other and extended by mutually primed synthesis. This fragment is then amplified by a second PCR™ step, thereby avoiding the blunt-end ligation required in the above protocol. In this method, the preparation of the template DNA, the generation of the oligonucleotide primers and the first PCR™ amplification are performed as described above. In this process, however, the chosen oligonucleotides should be homologous to the template DNA for a stretch of between about 15 and about 20 bases and must also overlap with each other by about 10 bases or more.

In the second PCR™ amplification, one would use each amplified fragment and each flanking sequence primer and carry PCR™ for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art, and are further described in various publications, such as *Current Protocols in Molecular Biology*, 1995, incorporated herein by reference.

When performing site-specific mutagenesis, Table A can be employed as a reference.

TABLE A

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

E6. Antibody Fragments and Derivatives

Irrespective of the source of the original antibody against an anionic phospholipid or aminophospholipids, either the intact antibody, antibody multimers, or any one of a variety of functional, antigen-binding regions of the antibody may be used in the present invention. Exemplary functional regions include scFv, Fv, Fab', Fab and F(ab')$_2$ fragments of antibodies. Techniques for preparing such constructs are well known to those in the art and are further exemplified herein.

The choice of antibody construct may be influenced by various factors. For example, prolonged half-life can result from the active readsorption of intact antibodies within the kidney, a property of the Fc piece of immunoglobulin. IgG based antibodies, therefore, are expected to exhibit slower blood clearance than their Fab' counterparts. However, Fab' fragment-based compositions will generally exhibit better tissue penetrating capability.

Antibody fragments can be obtained by proteolysis of the whole immunoglobulin by the non-specific thiol protease, papain. Papain digestion yields two identical antigen-binding fragments, termed "Fab fragments", each with a single antigen-binding site, and a residual "Fc fragment".

Papain should first be activated by reducing the sulphydryl group in the active site with cysteine, 2-mercaptoethanol or dithiothreitol. Heavy metals in the stock enzyme should be removed by chelation with EDTA (2 mM) to ensure maximum enzyme activity. Enzyme and substrate are normally mixed together in the ratio of 1:100 by weight. After incubation, the reaction can be stopped by irreversible alkylation of the thiol group with iodoacetamide or simply by dialysis. The completeness of the digestion should be monitored by SDS-PAGE and the various fractions separated by protein A-Sepharose or ion exchange chromatography.

The usual procedure for preparation of F(ab')$_2$ fragments from IgG of rabbit and human origin is limited proteolysis by the enzyme pepsin. The conditions, 100× antibody excess w/w in acetate buffer at pH 4.5, 37° C., suggest that antibody is cleaved at the C-terminal side of the inter-heavy-chain disulfide bond. Rates of digestion of mouse IgG may vary with subclass and it may be difficult to obtain high yields of active F(ab')$_2$ fragments without some undigested or completely degraded IgG. In particular, IgG$_{2b}$ is highly susceptible to complete degradation. The other subclasses require different incubation conditions to produce optimal results, all of which is known in the art.

Pepsin treatment of intact antibodies yields an F(ab')$_2$ fragment that has two antigen-combining sites and is still capable of cross-linking antigen. Digestion of rat IgG by pepsin requires conditions including dialysis in 0.1 M acetate buffer, pH 4.5, and then incubation for four hours with 1% w/w pepsin; IgG$_1$ and IgG$_{2a}$ digestion is improved if first dialyzed against 0.1 M formate buffer, pH 2.8, at 4° C., for 16 hours followed by acetate buffer. IgG$_{2b}$ gives more consistent results with incubation in staphylococcal V8 protease (3% w/w) in 0.1 M sodium phosphate buffer, pH 7.8, for four hours at 37° C.

An Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. F(ab')$_2$ antibody fragments were originally produced as pairs of Fab' fragments that have hinge cysteines between them. Other chemical couplings of antibody fragments are also known.

An "Fv" fragment is the minimum antibody fragment that contains a complete antigen-recognition and binding site. This region consists of a dimer of one heavy chain and one light chain variable domain in tight, con-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "scFv" antibody fragments (now also known as "single chains") comprise the $V_H$ and $V_L$ domains of an antibody, wherein these domains are present in a single polypeptide chain. Generally, the Fv polypeptide further comprises a polypeptide linker between the $V_H$ and $V_L$ domains that enables the sFv to form the desired structure for antigen binding.

The following patents are specifically incorporated herein by reference for the purposes of even further supplementing the present teachings regarding the preparation and use of functional, antigen-binding regions of antibodies, including scFv, Fv, Fab', Fab and F(ab')$_2$ fragments of antibodies: U.S. Pat. Nos. 5,855,866; 5,877,289; 5,965,132; 6,093,399; 6,261,535 and 6,004,555. WO 98/45331 is also incorporated herein by reference for purposes including even further describing and teaching the preparation of variable, hypervariable and complementarity determining (CDR) regions of antibodies. Moreover, the successful production of scFv constructs within the scope of the present invention is detailed in Example XIV.

"Diabodies" are small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described in EP 404,097 and WO 93/11161, each specifically incorporated herein by reference. "Linear antibodies", which can be bispecific or monospecific, comprise a pair of tandem Fd segments ($V_H$-$C_H$1-$V_H$-$C_H$1) that form a pair of antigen binding regions, as described in Zapata et al. (1995), specifically incorporated herein by reference.

In using a Fab' or antigen binding fragment of an antibody, with the attendant benefits on tissue penetration, one may derive additional advantages from modifying the fragment to increase its half-life. A variety of techniques may be employed, such as manipulation or modification of the antibody molecule itself, and also conjugation to inert carriers. Any conjugation for the sole purpose of increasing half-life, rather than to deliver an agent to a target, should be approached carefully in that Fab' and other fragments are chosen to penetrate tissues. Nonetheless, conjugation to non-protein polymers, such PEG and the like, is contemplated.

Modifications other than conjugation are therefore based upon modifying the structure of the antibody fragment to render it more stable, and/or to reduce the rate of catabolism in the body. One mechanism for such modifications is the use of D-amino acids in place of L-amino acids. Those of ordinary skill in the art will understand that the introduction of such modifications needs to be followed by rigorous testing of the resultant molecule to ensure that it still retains the desired biological properties. Further stabilizing modifications include the use of the addition of stabilizing moieties to either the N-terminal or the C-terminal, or both, which is generally used to prolong the half-life of biological molecules. By way of example only, one may wish to modify the termini by acylation or amination.

Moderate conjugation-type modifications for use with the present invention include incorporating a salvage receptor binding epitope into the antibody fragment. Techniques for achieving this include mutation of the appropriate region of the antibody fragment or incorporating the epitope as a peptide tag that is attached to the antibody fragment. WO 96/32478 is specifically incorporated herein by reference for the purposes of further exemplifying such technology. Salvage receptor binding epitopes are typically regions of three or more amino acids from one or two lops of the Fc domain that are transferred to the analogous position on the antibody fragment. The salvage receptor binding epitopes of WO 98/45331 are incorporated herein by reference for use with the present invention.

F. Immunoconjugates Binding to Anionic Phospholipids and Aminophospholipids

The present inventors earlier developed a range of immunoconjugates that bind to aminophospholipids for use in targeting tumor vasculature (U.S. Pat. No. 6,312,694, specifically incorporated herein by reference). These agents use aminophospholipid-binding proteins, such as annexins and kininogens, and antibodies against aminophospholipids, such as PS and PE, to deliver attached therapeutic agents to tumor and intratumoral vasculature. The present invention now provides selected anti-PS antibodies with improved properties, such as 3G4 (ATCC 4545) and 9D2, and these and competing antibodies can now also be used as the antibody portions of immunoconjugates.

In addition to the use of vascular targeting agents that bind to aminophospholipids (U.S. Pat. No. 6,312,694), the present discovery that anionic phospholipids, as well as aminophospholipids, are stable and targetable entities within tumor vasculature provides for the use of a range of new tumor vascular targeting agents. The new compounds, not suggested in the earlier work directed to aminophospholipids, use antibodies directed against anionic phospholipids to deliver toxins, cytokines, coagulants and other therapeutic agents to anionic phospholipids upregulated on tumor and intratumoral vasculature. As detailed above in regard to the naked antibodies, the development of these aspects of the invention required the generation of biological tools, particularly antibodies, with exquisite specificity for different phospholipids, anionic phospholipids and aminophospholipids.

As the present invention shows that anionic phospholipids and aminophospholipids, such as PS, PE, PI, PA and PG, and most particularly PS and PE, are safe and effective targets for anti-viral therapy, antibodies and peptides that bind to these components, particularly PS and PE, may now be advantageously linked to a range of known anti-viral agents. These anti-viral conjugates include both peptide-based and antibody-based conjugates, the latter of which may be termed anti-viral immunoconjugates or "immunovirocides".

In these aspects of the invention, any antibody against an anionic phospholipid can be used to prepare an immunoconjugate, immunotoxin or coaguligand, with antibodies such as the second generation antibodies, particularly 9D2-like and 3G4-like antibodies, with their advantageous anionic phospholipid binding profiles, being preferred. Agents for use in such immunoconjugates preferably include anti-cellular or cytotoxic agents, coagulants (coagulation factors), cytokines, radiotherapeutic agents, anti-angiogenic agents, apoptosis-inducing agents, anti-tubulin drugs and anti-viral agents (and the PE-binding peptides, such as duramycin derivatives, as disclosed in detail herein). In the anti-viral immunoconjugates, there is no requirement to use a second generation antibody as disclosed herein, although these can certainly be employed. Any antibody to aminophospholipids or anionic phospholipids may be thus be linked to an anti-viral agent to form an anti-viral immunoconjugates or immunovirocide in accordance with the present invention.

F1. Anti-Cellular and Cytotoxic Agents

For certain applications, the therapeutic agents will be cytotoxic or pharmacological agents, particularly cytotoxic, cytostatic or otherwise anti-cellular agents having the ability to kill or suppress the growth or cell division of cells, particularly tumor endothelial cells or tumor cells. In general, these aspects of the invention contemplate the use of any pharmacological agent that can be conjugated to an antibody against an anionic phospholipid, preferably a 9D2-based or 3G4-based antibody, and delivered in active form to the targeted endothelium.

Exemplary anti-cellular agents include chemotherapeutic agents, as well as cytotoxins. Chemotherapeutic agents that may be used include: hormones, such as steroids; anti-metabolites, such as cytosine arabinoside, fluorouracil, methotrexate or aminopterin; anthracyclines; mitomycin C; vinca alkaloids; demecolcine; etoposide; mithramycin; anti-tumor alkylating agents, such as chlorambucil or melphalan. Other embodiments may include agents such as cytokines. Basically, any anti-cellular agent may be used, so long as it can be successfully conjugated to, or associated with, an antibody in a manner that will allow its targeting, internalization, release and/or presentation to blood components at the site of the targeted cells, such as endothelial cells.

There may be circumstances, such as when the target antigen does not internalize by a route consistent with efficient intoxication by the toxic compound, where one will desire to target chemotherapeutic agents, such as anti-tumor drugs, cytokines, antimetabolites, alkylating agents, hormones, and the like. A variety of chemotherapeutic and other pharmacological agents have now been successfully conjugated to antibodies and shown to function pharmacologically, including doxorubicin, daunomycin, methotrexate, vinblastine, neocarzinostatin, macromycin, trenimon and α-amanitin.

In other circumstances, any potential side-effects from cytotoxin-based therapy may be eliminated by the use of DNA synthesis inhibitors, such as daunorubicin, doxorubicin, adriamycin, and the like. These agents are therefore preferred examples of anti-cellular agents for use in certain aspects of the present invention. In terms of cytostatic agents, such compounds generally disturb the natural cell cycle of a target cell, preferably so that the cell is taken out of the cell cycle.

A wide variety of cytotoxic agents are known that may be conjugated to an antibody against an anionic phospholipid, preferably a 9D2-based or 3G4-based antibody. Examples include numerous useful plant-, fungus-or bacteria-derived toxins, which, by way of example, include various A chain toxins, particularly ricin A chain; ribosome inactivating proteins, such as saporin or gelonin; α-sarcin; aspergillin; restrictocin; ribonucleases, such as placental ribonuclease; diphtheria toxin; and *pseudomonas* exotoxin, to name just a few.

Of the toxins, the use of gelonin and ricin A chains are preferred. The use of gelonin as the effector or toxin portion of immunoconjugates that bind to markers expressed, accessible to binding, adsorbed or localized on intratumoral blood vessels of a vascularized tumor is described in U.S. Pat. No. 6,051,230, specifically incorporated herein by reference, and in U.S. Pat. No. 6,451,312, which particularly concerns gelonin linked to VEGF as a targeting agent.

As to ricin A chains, a further preferred toxin moiety is toxin A chain that has been treated to modify or remove carbohydrate residues, so-called deglycosylated A chain (dgA). Deglycosylated ricin A chain is preferred because of its extreme potency, longer half-life, and because it is economically feasible to manufacture it in a clinical grade and scale.

It may be desirable from a pharmacological standpoint to employ the smallest molecule possible that nevertheless provides an appropriate biological response. One may thus desire to employ smaller A chain peptides that will provide an adequate anti-cellular response. To this end, it has been discovered that ricin A chain may be "truncated" by the removal of 30 N-terminal amino acids by Nagarase (Sigma), and still retain an adequate toxin activity. It is proposed that where desired, this truncated A chain may be employed in conjugates in accordance with the invention.

Alternatively, one may find that the application of recombinant DNA technology to the toxin A chain moiety will provide additional benefits in accordance the invention. In that the cloning and expression of biologically active ricin A chain has been achieved, it is now possible to identify and prepare smaller, or otherwise variant peptides, which nevertheless exhibit an appropriate toxin activity. Moreover, the fact that ricin A chain has now been cloned allows the application of site-directed mutagenesis, through which one can readily prepare and screen for A chain-derived peptides and obtain additional useful moieties for use in connection with the present invention.

F2. Cytokines

Cytokines and chemokines are particular examples of agents for linking to the antibodies of the present invention. A range of cytokines may be used, including IL-3, IL-4, IL-5, IL-7, IL-8, IL-9, IL-11, IL-13, TGF-β, M-CSF, G-CSF, TNFβ, LAF, TCGF, BCGF, TRF, BAF, BDG, MP, LIF, OSM, TMF, IFN-α, IFN-β. More preferred cytokines include IL-1α, IL-1β, IL-2, IL-6, IL-10, GM-CSF, IFNγ, monocyte chemoattractant protein-1 (MCP-1), platelet-derived growth factor-BB (PDGF-BB) and C-reactive protein (CRP) and the like. Particularly preferred examples are TNFα, TNFα inducers and IL-12.

TNFα increases vascular permeability. This agent is contemplated for attachment to an antibody of the invention, particularly where the resultant immunoconjugate is used in combination therapy for the treatment of cancer. The antibody will deliver the attached TNFα to the tumor environment, and the enhanced vascular permeability cause in the tumor will facilitate the penetration of a second anti-cancer agent into the tumor, thus amplifying the overall anti-tumor effect. scFv constructs are particularly contemplated for use in such embodiments. This is partly because TNFα functions as a trimer and the scFv constructs will be able to trimerize readily.

IL-12, for example, may be attached to an antibody and used to redirect host defenses to attack the tumor vessels. In using IL-12, an scFv form of antigen binding region may be preferred. The chemokine LEC (liver-expressed chemokine, also known as NCC-4, HCC-4, or LMC) is another preferred component (Giovarelli et al., 2000). LEC is chemotactic for dendritic cells, monocytes, T cells, NK cells and neutrophils and can therefore improve host-mediated anti-tumor responses.

F3. Coagulation Factors

An antibody against an anionic phospholipid, or a second generation antibody based upon the preferred 9D2 and 3G4 (ATCC 4545) antibodies of the invention, may be linked to a component that is capable of directly or indirectly stimulating coagulation, to form a coaguligand. U.S. Pat. Nos. 6,093,399, 6,004,555, 5,877,289 and 6,036,955 are specifically incorporated herein by reference for purposes of further describing the operative association of coagulants with antibodies to form coaguligands.

The antibodies of the invention may be directly linked to the coagulant or coagulation factor, or may be linked to a second binding region that binds and then releases the coagulant or coagulation factor. As used herein, the terms "coagulant" and "coagulation factor" are each used to refer to a component that is capable of directly or indirectly stimulating coagulation under appropriate conditions, preferably when provided to a specific in vivo environment, such as the tumor vasculature.

Preferred coagulation factors are Tissue Factor compositions, such as truncated TF (tTF), dimeric, multimeric and mutant TF molecules. "Truncated TF" (tTF) refers to TF constructs that are rendered membrane-binding deficient by removal of sufficient amino acid sequences to effect this change in property. A "sufficient amount" in this context is an amount of transmembrane amino acid sequence originally sufficient to enter the TF molecule in the membrane, or otherwise mediate functional membrane binding of the TF protein. The removal of such a "sufficient amount of transmembrane spanning sequence" therefore creates a truncated Tissue Factor protein or polypeptide deficient in phospholipid membrane binding capacity, such that the protein is substantially a soluble protein that does not significantly bind to phospholipid membranes. Truncated TF thus substantially fails to convert Factor VII to Factor VIIa in a standard TF assay, and yet retains so-called catalytic activity including activating Factor X in the presence of Factor VIIa.

U.S. Pat. Nos. 5,504,067, 6,156,321, 6,132,729 and 6,132,730 are specifically incorporated herein by reference for the purposes of further describing such truncated Tissue Factor proteins. Preferably, the Tissue Factors for use in these aspects of the present invention will generally lack the transmembrane and cytosolic regions (amino acids 220-263) of the protein. However, there is no need for the truncated TF molecules to be limited to molecules of the exact length of 219 amino acids.

Tissue Factor compositions may also be useful as dimers. Any of the truncated, mutated or other Tissue Factor constructs may be prepared in a dimeric form for use in the present invention. As will be known to those of ordinary skill in the art, such TF dimers may be prepared by employing the standard techniques of molecular biology and recombinant expression, in which two coding regions are prepared in-frame and expressed from an expression vector. Equally, various chemical conjugation technologies may be employed in connection with the preparation of TF dimers. The individual TF monomers may be derivatized prior to conjugation. All such techniques would be readily known to those of skill in the art.

If desired, the Tissue Factor dimers or multimers may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metalloproteinase, such as collagenase, gelatinase or stromelysin.

In certain embodiments, the Tissue Factor dimers may further comprise a hindered hydrophobic membrane insertion moiety, to later encourage the functional association of the Tissue Factor with the phospholipid membrane, but only under certain defined conditions. As described in the context of the truncated Tissue Factors, hydrophobic membrane-association sequences are generally stretches of amino acids that promote association with the phospholipid environment due to their hydrophobic nature. Equally, fatty acids may be used to provide the potential membrane insertion moiety.

Such membrane insertion sequences may be located either at the N-terminus or the C-terminus of the TF molecule, or generally appended at any other point of the molecule so long as their attachment thereto does not hinder the functional properties of the TF construct. The intent of the hindered insertion moiety is that it remains non-functional until the TF construct localizes within the tumor environment, and allows the hydrophobic appendage to become accessible and even further promote physical association with the membrane. Again, it is contemplated that biologically-releasable bonds and selectively-cleavable sequences will be particularly useful in this regard, with the bond or sequence only being cleaved or otherwise modified upon localization within the tumor environment and exposure to particular enzymes or other bioactive molecules.

In other embodiments, the tTF constructs may be multimeric or polymeric. In this context a "polymeric construct" contains 3 or more Tissue Factor constructs. A "multimeric or polymeric TF construct" is a construct that comprises a first TF molecule or derivative operatively attached to at least a second and a third TF molecule or derivative. The multimers may comprise between about 3 and about 20 such TF molecules. The individual TF units within the multimers or polymers may also be linked by selectively-cleavable peptide linkers or other biological-releasable bonds as desired. Again, as with the TF dimers discussed above, the constructs may be readily made using either recombinant manipulation and expression or using standard synthetic chemistry.

Even further TF constructs useful in context of the present invention are those mutants deficient in the ability to activate Factor VII. Such "Factor VII activation mutants" are generally defined herein as TF mutants that bind functional Factor VII/VIIa, proteolytically activate Factor X, but are substantially free from the ability to proteolytically activate Factor VII. Accordingly, such constructs are TF mutants that lack Factor VII activation activity.

The ability of such Factor VII activation mutants to function in promoting tumor-specific coagulation is based upon their specific delivery to the tumor vasculature, and the presence of Factor VIIa at low levels in plasma. Upon administration of such a Factor VII activation mutant conjugate, the mutant will be localized within the vasculature of a vascularized tumor. Prior to localization, the TF mutant would be generally unable to promote coagulation in any other body sites, on the basis of its inability to convert Factor VII to Factor VIIa. However, upon localization and accumulation within the tumor region, the mutant will then encounter sufficient Factor VIIa from the plasma in order to initiate the extrinsic coagulation pathway, leading to tumor-specific thrombosis. Exogenous Factor VIIa could also be administered to the patient.

Any one or more of a variety of Factor VII activation mutants may be prepared and used in connection with the present invention. There is a significant amount of scientific knowledge concerning the recognition sites on the TF molecule for Factor VII/VIIa. It will thus be understood that the Factor VII activation region generally lies between about amino acid 157 and about amino acid 167 of the TF molecule. However, it is contemplated that residues outside this region may also prove to be relevant to the Factor VII activating activity, and one may therefore consider introducing mutations into any one or more of the residues generally located between about amino acid 106 and about amino acid 209 of the TF sequence (WO 94/07515; WO 94/28017; each incorporated herein by reference).

As detailed in U.S. Pat. Nos. 6,093,399, 6,004,555, 5,877,289 and 6,036,955, a variety of other coagulation factors may be used in connection with the present invention, as exemplified by the agents set forth below. Thrombin, Factor V/Va and derivatives, Factor VIII/VIIIa and derivatives, Factor IX/IXa and derivatives, Factor X/Xa and derivatives, Factor XI/XIa and derivatives, Factor XII/XIIa and derivatives, Factor XIII/XIIIa and derivatives, Factor X activator and Factor V activator may be used in the present invention.

Russell's viper venom Factor X activator is contemplated for use in this invention. Monoclonal antibodies specific for the Factor X activator present in Russell's viper venom have also been produced, and could be used to specifically deliver the agent as part of a bispecific binding ligand.

Thromboxane $A_2$ is formed from endoperoxides by the sequential actions of the enzymes cyclooxygenase and thromboxane synthetase in platelet microsomes. Thromboxane $A_2$ is readily generated by platelets and is a potent vasoconstrictor, by virtue of its capacity to produce platelet aggregation. Both thromboxane $A_2$ and active analogues thereof are contemplated for use in the present invention.

Thromboxane synthase, and other enzymes that synthesize platelet-activating prostaglandins, may also be used as "coagulants" in the present context. Monoclonal antibodies to, and immunoaffinity purification of, thromboxane synthase are known; as is the cDNA for human thromboxane synthase.

α2-antiplasmin, or α2-plasmin inhibitor, is a proteinase inhibitor naturally present in human plasma that functions to efficiently inhibit the lysis of fibrin clots induced by plasminogen activator. α2-antiplasmin is a particularly potent inhibitor, and is contemplated for use in the present invention.

As the cDNA sequence for α2-antiplasmin is available, recombinant expression and/or fusion proteins are preferred. Monoclonal antibodies against α2-antiplasmin are also available that may be used in the bispecific binding ligand embodiments of the invention. These antibodies could both be used to deliver exogenous α2-antiplasmin to the target site or to garner endogenous α2-antiplasmin and concentrate it within the targeted region.

F4. Anti-Tubulin Drugs

A range of drugs exert their effects via interfering with tubulin activity. As tubulin functions are essential to mitosis and cell viability, certain "anti-tubulin drugs" are powerful chemotherapeutic agents. "Anti-tubulin drug(s)", as used herein, means any agent, drug, prodrug or combination thereof that inhibits cell mitosis, preferably by directly or indirectly inhibiting tubulin activities necessary for cell mitosis, preferably tubulin polymerization or depolymerization.

Some of the more well known and currently preferred anti-tubulin drugs for use with the present invention are colchicine; taxanes, such as taxol; vinca alkaloids, such as vinblastine, vincristine and vindescine; and combretastatins. Other suitable anti-tubulin drugs are cytochalasins (including B, J, E), dolastatin, auristatin PE, paclitaxel, ustiloxin D, rhizoxin, 1069C85, colcemid, albendazole, azatoxin and nocodazole.

As described in U.S. Pat. Nos. 5,892,069, 5,504,074 and 5,661,143, each specifically incorporated herein by reference, combretastatins are estradiol derivatives that generally inhibit cell mitosis. Exemplary combretastatins that may be used in conjunction with the invention include those based upon combretastatin A, B and/or D and those described in U.S. Pat. Nos. 5,892,069, 5,504,074 and 5,661,143. Combretastatins A-1, A-2, A-3, A-4, A-5, A-6, B-1, B-2, B-3 and B-4 are exemplary of the foregoing types.

U.S. Pat. Nos. 5,569,786 and 5,409,953, are incorporated herein by reference for purposes of describing the isolation, structural characterization and synthesis of each of combretastatin A-1, A2, A-3, B-1, B-2, B-3 and B-4 and formulations and methods of using such combretastatins to treat neoplastic growth. Any one or more of such combretastatins may be used in conjunction with the present invention.

Combretastatin A-4, as described in U.S. Pat. Nos. 5,892,069, 5,504,074, 5,661,143 and 4,996,237, each specifically incorporated herein by reference, may also be used herewith. U.S. Pat. No. 5,561,122 is further incorporated herein by reference for describing suitable combretastatin A-4 prodrugs, which are contemplated for combined use with the present invention.

U.S. Pat. No. 4,940,726, specifically incorporated herein by reference, particularly describes macrocyclic lactones denominated combretastatin D-1 and 'Combretastatin D-2', each of which may be used in combination with the compositions and methods of the present invention. U.S. Pat. No.

5,430,062, specifically incorporated herein by reference, concerns stilbene derivatives and combretastatin analogues with anti-cancer activity that may be used in combination with the present invention.

F5. Anti-Angiogenic Agents

Anti-angiogenic agents are useful for attachment to the antibodies and peptides of the invention. Many anti-cancer agents have an anti-angiogenic effect as part of their mechanism of action. Any one or more of such agents described for use in combination therapies, including those in Table E, may also be conjugated to an antibody of the invention, as described herein. Certain other agents have been discovered, designed or selected to have an anti-angiogenic effect as a primary mechanism of action. Examples of such agents are described below, any of which may also be used to prepare an immunoconjugate or used separately in combination therapy with the invention.

Numerous tyrosine kinase inhibitors useful for the treatment of angiogenesis, as manifest in various diseases states, are now known. These include, for example, the 4-aminopyrrolo[2,3-d]pyrimidines of U.S. Pat. No. 5,639,757, specifically incorporated herein by reference, which may also be used in combination with the present invention. Further examples of organic molecules capable of modulating tyrosine kinase signal transduction via the VEGFR2 receptor are the quinazoline compounds and compositions of U.S. Pat. No. 5,792,771, which is specifically incorporated herein by reference for the purpose of describing further combinations for use with the present invention in the treatment of angiogenic diseases.

Compounds of other chemical classes have also been shown to inhibit angiogenesis and may be used in combination with the present invention. For example, steroids such as the angiostatic 4,9(11)-steroids and C21-oxygenated steroids, as described in U.S. Pat. No. 5,972,922, specifically incorporated herein by reference, may be employed in combined therapy. U.S. Pat. Nos. 5,712,291 and 5,593,990, each specifically incorporated herein by reference, describe thalidomide and related compounds, precursors, analogs, metabolites and hydrolysis products, which may also be used in combination with the present invention to inhibit angiogenesis. The compounds in U.S. Pat. Nos. 5,712,291 and 5,593,990 can be administered orally. Further exemplary anti-angiogenic agents that are useful in connection with combined therapy are listed in Table B. Each of the agents listed therein are exemplary and by no means limiting.

TABLE B

| Inhibitors and Negative Regulators of Angiogenesis | |
|---|---|
| Substances | References |
| Angiostatin | O'Reilly et al., 1994 |
| Endostatin | O'Reilly et al., 1997 |
| 16 kDa prolactin fragment | Ferrara et al., 1991; Clapp et al., 1993; D'Angelo et al., 1995; Lee et al., 1998 |
| Laminin peptides | Kleinman et al., 1993; Yamamura et al., 1993; Iwamoto et al., 1996; Tryggvason, 1993 |
| Fibronectin peptides | Grant et al., 1998; Sheu et al., 1997 |
| Tissue metalloproteinase inhibitors (TIMP 1, 2, 3, 4) | Sang, 1998 |
| Plasminogen activator inhibitors (PAI-1, -2) | Soff et al., 1995 |
| Tumor necrosis factor α (high dose, in vitro) | Frater-Schroder et al., 1987 |
| TGF-β1 | RayChadhury and D'Amore, 1991; Tada et al., 1994 |
| Interferons (IFN-α, -β, γ) | Moore et al., 1998; Lingen et al., 1998 |
| ELR-CXC Chemokines: IL-12; SDF-1; MIG; Platelet factor 4 (PF-4); IP-10 | Moore et al., 1998; Hiscox and Jiang, 1997; Coughlin et al., 1998; Tanaka et al., 1997 |
| Thrombospondin (TSP) | Good et al., 1990; Frazier, 1991; Bornstein, 1992; Tolsma et al., 1993; Sheibani and Frazier, 1995; Volpert et al., 1998 |
| SPARC | Hasselaar and Sage, 1992; Lane et al., 1992; Jendraschak and Sage, 1996 |
| 2-Methoxyoestradiol | Fotsis et al., 1994 |
| Proliferin-related protein | Jackson et al., 1994 |
| Suramin | Gagliardi et al., 1992; Takano et al., 1994; Waltenberger et al., 1996; Gagliardi et al., 1998; Manetti et al., 1998 |
| Thalidomide | D'Amato et al., 1994; Kenyon et al., 1997 Wells, 1998 |
| Cortisone | Thorpe et al., 1993 Folkman et al., 1983 Sakamoto et al., 1986 |
| Linomide | Vukanovic et al., 1993; Ziche et al., 1998; Nagler et al., 1998 |
| Fumagillin (AGM-1470; TNP-470) | Sipos et al., 1994; Yoshida et al., 1998 |
| Tamoxifen | Gagliardi and Collins, 1993; Linder and Borden, 1997; Haran et al., 1994 |
| Korean mistletoe extract (Viscum album coloratum) | Yoon et al., 1995 |
| Retinoids | Oikawa et al., 1989; Lingen et al., 1996; Majewski et al. 1996 |
| CM101 | Hellerqvist et al., 1993; Quinn et al., 1995; Wamil et al., 1997; DeVore et al., 1997 |
| Dexamethasone | Hori et al., 1996; Wolff et al., 1997 |
| Leukemia inhibitory factor (LIF) | Pepper et al., 1995 |

Certain preferred components for use in inhibiting angiogenesis are angiostatin, endostatin, vasculostatin, canstatin and maspin. The protein named "angiostatin" is disclosed in U.S. Pat. Nos. 5,776,704; 5,639,725 and 5,733,876, each incorporated herein by reference. Angiostatin is a protein having a molecular weight of between about 38 kD and about 45 kD, as determined by reducing polyacrylamide gel electrophoresis, which contains approximately Kringle regions 1 through 4 of a plasminogen molecule. Angiostatin generally has an amino acid sequence substantially similar to that of a fragment of murine plasminogen beginning at amino acid number 98 of an intact murine plasminogen molecule.

The amino acid sequence of angiostatin varies slightly between species. For example, in human angiostatin, the amino acid sequence is substantially similar to the sequence of the above described murine plasminogen fragment, although an active human angiostatin sequence may start at either amino acid number 97 or 99 of an intact human plasminogen amino acid sequence. Further, human plasminogen may be used, as it has similar anti-angiogenic activity, as shown in a mouse tumor model.

Certain anti-angiogenic therapies have already been shown to cause tumor regressions, and angiostatin is one such agent. Endostatin, a 20 kDa COOH-terminal fragment of collagen XVIII, the bacterial polysaccharide CM101, and the antibody LM609 also have angiostatic activity. However, in light of their other properties, they are referred to as anti-vascular therapies or tumor vessel toxins, as they not only inhibit angiogenesis but also initiate the destruction of tumor vessels through mostly undefined mechanisms.

Angiostatin and endostatin have become the focus of intense study, as they are the first angiogenesis inhibitors that have demonstrated the ability to not only inhibit tumor growth but also cause tumor regressions in mice. There are multiple proteases that have been shown to produce angiostatin from plasminogen including elastase, macrophage metalloelastase (MME), matrilysin (MMP-7), and 92 kDa gelatinase B/type IV collagenase (MMP-9).

MME can produce angiostatin from plasminogen in tumors and granulocyte-macrophage colony-stimulating factor (GMCSF) upregulates the expression of MME by macrophages inducing the production of angiostatin. The role of MME in angiostatin generation is supported by the finding that MME is in fact expressed in clinical samples of hepatocellular carcinomas from patients. Another protease thought to be capable of producing angiostatin is stromelysin-1 (MMP-3). MMP-3 has been shown to produce angiostatin-like fragments from plasminogen in vitro. The mechanism of action for angiostatin is currently unclear, it is hypothesized that it binds to an unidentified cell surface receptor on endothelial cells inducing endothelial cell to undergo programmed cell death or mitotic arrest.

Endostatin appears to be an even more powerful anti-angiogenesis and anti-tumor agent although its biology is less clear. Endostatin is effective at causing regressions in a number of tumor models in mice. Tumors do not develop resistance to endostatin and, after multiple cycles of treatment, tumors enter a dormant state during which they do not increase in volume. In this dormant state, the percentage of tumor cells undergoing apoptosis was increased, yielding a population that essentially stays the same size. Endostatin is thought to bind an unidentified endothelial cell surface receptor that mediates its effect.

U.S. Pat. No. 5,854,205, to Folkman and O'Reilly, specifically incorporated herein by reference, concerns endostatin and its use as an inhibitor of endothelial cell proliferation and angiogenesis. The endostatin protein corresponds to a C-terminal fragment of collagen type XVIII, and the protein can be isolated from a variety of sources. U.S. Pat. No. 5,854,205 also teaches that endostatin can have an amino acid sequence of a fragment of collagen type XVIII, a collasen type XV, or BOVMPE 1 pregastric esterase. Combinations of endostatin with other anti-angiogenic proteins, particularly angiostatin, are also described by U.S. Pat. No. 5,854,205, such that the combined compositions are capable of effectively regressing the mass of an angiogenesis-dependent tumor.

CM101 is a bacterial polysaccharide that has been well characterized in its ability to induce neovascular inflammation in tumors. CM101 binds to and cross-links receptors expressed on dedifferentiated endothelium that stimulates the activation of the complement system. It also initiates a cytokine-driven inflammatory response that selectively targets the tumor. It is a uniquely antipathoangiogenic agent that downregulates the expression VEGF and its receptors. CM101 is currently in clinical trials as an anti-cancer drug, and can be used in combination with this invention.

Thrombospondin (TSP-1) and platelet factor 4 (PF4) may also be used in the present invention. These are both angiogenesis inhibitors that associate with heparin and are found in platelet $\alpha$-granules. TSP-1 is a large 450 kDa multi-domain glycoprotein that is constituent of the extracellular matrix. TSP-1 binds to many of the proteoglycan molecules found in the extracellular matrix including, HSPGs, fibronectin, laminin, and different types of collagen. TSP-1 inhibits endothelial cell migration and proliferation in vitro and angiogenesis in vivo. TSP-1 can also suppress the malignant phenotype and tumorigenesis of transformed endothelial cells. The tumor suppressor gene p53 has been shown to directly regulate the expression of TSP-1 such that, loss of p53 activity causes a dramatic reduction in TSP-1 production and a concomitant increase in tumor initiated angiogenesis.

PF4 is a 70aa protein that is member of the CXC ELR-family of chemokines that is able to potently inhibit endothelial cell proliferation in vitro and angiogenesis in vivo. PF4 administered intratumorally or delivered by an adenoviral vector is able to cause an inhibition of tumor growth.

Interferons and metalloproteinase inhibitors are two other classes of naturally occurring angiogenic inhibitors that can be delivered according to the present invention. The anti-endothelial activity of the interferons has been known since the early 1980s, however, the mechanism of inhibition is still unclear. It is known that they can inhibit endothelial cell migration and that they do have some anti-angiogenic activity in vivo that is possibly mediated by an ability to inhibit the production of angiogenic promoters by tumor cells. Vascular tumors in particular are sensitive to interferon, for example, proliferating hemangiomas can be successfully treated with IFN$\alpha$.

Tissue inhibitors of metalloproteinases (TIMPs) are a family of naturally occurring inhibitors of matrix metalloproteases (MMPs) that can also inhibit angiogenesis and can be used in the treatment protocols of the present invention. MMPs play a key role in the angiogenic process as they degrade the matrix through which endothelial cells and fibroblasts migrate when extending or remodeling the vascular network. In fact, one member of the MMPs, MMP-2, has been shown to associate with activated endothelium through the integrin $\alpha v \beta 3$ presumably for this purpose. If this interaction is disrupted by a fragment of MMP-2, then angiogenesis is downregulated and in tumors growth is inhibited.

There are a number of pharmacological agents that inhibit angiogenesis, any one or more of which may be used as part of the present invention. These include AGM-1470/TNP-470, thalidomide, and carboxyamidotriazole (CAI). Fumagillin was found to be a potent inhibitor of angiogenesis in 1990, and since then the synthetic analogues of fumagillin, AGM-1470 and TNP-470 have been developed. Both of these drugs inhibit endothelial cell proliferation in vitro and angiogenesis in vivo. TNP-470 has been studied extensively in human clinical trials with data suggesting that long-term administration is optimal.

Thalidomide was originally used as a sedative but was found to be a potent teratogen and was discontinued. In 1994 it was found that thalidomide is an angiogenesis inhibitor. Thalidomide is currently in clinical trials as an anti-cancer agent as well as a treatment of vascular eye diseases.

CAI is a small molecular weight synthetic inhibitor of angiogenesis that acts as a calcium channel blocker that prevents actin reorganization, endothelial cell migration and spreading on collagen IV. CAI inhibits neovascularization at physiological attainable concentrations and is well tolerated orally by cancer patients. Clinical trials with CAI have yielded disease stabilization in 49% of cancer patients having progressive disease before treatment.

Cortisone in the presence of heparin or heparin fragments was shown to inhibit tumor growth in mice by blocking endothelial cell proliferation. The mechanism involved in the additive inhibitory effect of the steroid and heparin is unclear although it is thought that the heparin may increase the uptake of the steroid by endothelial cells. The mixture has been shown to increase the dissolution of the basement membrane underneath newly formed capillaries and this is also a possible explanation for the additive angiostatic effect. Heparin-cortisol conjugates also have potent angiostatic and anti-tumor effects activity in vivo.

Further specific angiogenesis inhibitors may be delivered to tumors using the tumor targeting methods of the present invention. These include, but are not limited to, Anti-Invasive Factor, retinoic acids and paclitaxel (U.S. Pat. No. 5,716,981; incorporated herein by reference); AGM-1470 (Ingber et al., 1990; incorporated herein by reference); shark cartilage extract (U.S. Pat. No. 5,618,925; incorporated herein by reference); anionic polyamide or polyurea oligomers (U.S. Pat. No. 5,593,664; incorporated herein by reference); oxindole derivatives (U.S. Pat. No. 5,576,330; incorporated herein by reference); estradiol derivatives (U.S. Pat. No. 5,504,074; incorporated herein by reference); and thiazolopyrimidine derivatives (U.S. Pat. No. 5,599,813; incorporated herein by reference) are also contemplated for use as anti-angiogenic compositions for the combined uses of the present invention.

Compositions comprising an antagonist of an $\alpha_v\beta_3$ integrin may also be used to inhibit angiogenesis as part of the present invention. As disclosed in U.S. Pat. No. 5,766,591 (incorporated herein by reference), RGD-containing polypeptides and salts thereof, including cyclic polypeptides, are suitable examples of $\alpha_v\beta_3$ integrin antagonists.

As angiopoietins are ligands for Tie2, other methods of therapeutic intervention based upon altering signaling through the Tie2 receptor can also be used in combination herewith. For example, a soluble Tie2 receptor capable of blocking Tie2 activation (Lin et al., 1998a) can be employed. Delivery of such a construct using recombinant adenoviral gene therapy has been shown to be effective in treating cancer and reducing metastases (Lin et al., 1998a).

The angiopoietins, in common with the members of the VEGF family, are growth factors specific for vascular endothelium (Davis and Yancopoulos, 1999; Holash et al., 1999; incorporated herein by reference). The angiopoietins first described were a naturally occurring receptor activator or agonist, angiopoietin-1 (Ang-1), and a naturally occurring receptor antagonist, angiopoietin-2 (Ang-2), both of which act by means of the endothelial cell tyrosine kinase receptor, Tie2.

Two new angiopoietins, angiopoietin-3 (mouse) and angiopoietin-4 (human) have also been identified (Valenzuela et al., 1999). Angiopoietin-3 appears to act as an antagonist (like Ang-2), whereas angiopoietin-4 appears to function as an agonist (like Ang-1) (Valenzuela et al., 1999). A protein termed angiopoietin-3 was also cloned from human heart and reported not to have mitogenic effects on endothelial cells (Kim et al., 1999).

Whereas VEGF is necessary for the early stages of vascular development, angiopoietin-1 is generally required for the later stages of vascularization. VEGF thus acts to promote endothelial cell differentiation, proliferation and primitive vessel formation. Angiopoietin-1 acts, via the Tie2 receptor, to promote maintenance and stabilization of mature vessels. Angiopoietin-1 is thus a maturation or stabilization factor, thought to convert immature vessels to immature vessels by promoting interactions between endothelial cells and surrounding support cells (Holash et al., 1999).

F6. Apoptosis-Inducing Agents

The present invention may also be used to deliver agents that induce apoptosis in any cells within the tumor, including tumor cells and tumor vascular endothelial cells. Many anti-cancer agents have, as part of their mechanism of action, an apoptosis-inducing effect. Any one or more of such agents described for use in combination therapies, including those in Table F, may also be conjugated to an antibody of the invention, as described herein. Certain other agents have been discovered, designed or selected to have an apoptosis-inducing effect as a primary mechanism. Examples of such agents are described below, any of which may also be used to prepare an immunoconjugate or used separately in combination therapy with the invention.

Many forms of cancer have reports of mutations in tumor suppressor genes, such as p53. Inactivation of p53 results in a failure to promote apoptosis. With this failure, cancer cells progress in tumorigenesis, rather than become destined for cell death. Thus, delivery of tumor suppressors is also contemplated for use in the present invention to stimulate cell death. Exemplary tumor suppressors include, but are not limited to, p53, Retinoblastoma gene (Rb), Wilm's tumor (WT1), bax alpha, interleukin-1b-converting enzyme and family, MEN-1 gene, neurofibromatosis, type 1 (NF1), cdk inhibitor p16, colorectal cancer gene (DCC), familial adenomatosis polyposis gene (FAP), multiple tumor suppressor gene (MTS-1), BRCA1 and BRCA2.

Preferred for use are the p53 (U.S. Pat. Nos. 5,747,469; 5,677,178; and 5,756,455; each incorporated herein by reference), Retinoblastoma, BRCA1 (U.S. Pat. Nos. 5,750,400; 5,654,155; 5,710,001; 5,756,294; 5,709,999; 5,693,473; 5,753,441; 5,622,829; and 5,747,282; each incorporated herein by reference), MEN-1 (GenBank accession number U93236) and adenovirus E1A (U.S. Pat. No. 5,776,743; incorporated herein by reference) genes.

Other oncogenes that inhibit apoptosis or programmed cell death include, but are not limited to, bcr-abl, bcl-2 (distinct from bcl-1, cyclin D1; GenBank accession numbers M14745, X06487; U.S. Pat. Nos. 5,650,491; and 5,539,094; each incorporated herein by reference) and family members including Bcl-xl, Mcl-1, Bak, A1, A20. Overexpression of bcl-2 was first discovered in T cell lymphomas. bcl-2 functions as an oncogene by binding and inactivating Bax, a protein in the apoptotic pathway. Inhibition of bcl-2 function prevents inactivation of Bax, and allows the apoptotic pathway to proceed. Thus, inhibition of this class of oncogenes, e.g., using antisense nucleotide sequences, is contemplated for use in the present invention in aspects wherein enhancement of apoptosis is desired (U.S. Pat. Nos. 5,650,491; 5,539,094; and 5,583,034; each incorporated herein by reference).

Other compositions that may be delivered by the antibodies of the present invention include genes encoding the tumor necrosis factor related apoptosis inducing ligand termed TRAIL, and the TRAIL polypeptide (U.S. Pat. No. 5,763,223; incorporated herein by reference); the 24 kD apoptosis-associated protease of U.S. Pat. No. 5,605,826 (incorporated herein by reference); Fas-associated factor 1, FAF1 (U.S. Pat. No. 5,750,653; incorporated herein by reference). Also contemplated for use in these aspects of the present invention is the provision of interleukin-1β-converting enzyme and family members, which are also reported to stimulate apoptosis.

Compounds such as carbostyril derivatives (U.S. Pat. Nos. 5,672,603; and 5,464,833; each incorporated herein by reference); branched apogenic peptides (U.S. Pat. No. 5,591,717; incorporated herein by reference); phosphotyrosine inhibitors and non-hydrolyzable phosphotyrosine analogs (U.S. Pat. Nos. 5,565,491; and 5,693,627; each incorporated herein by reference); agonists of RXR retinoid receptors (U.S. Pat. No. 5,399,586; incorporated herein by reference); and even antioxidants (U.S. Pat. No. 5,571,523; incorporated herein by reference) may also be used. Tyrosine kinase inhibitors, such as genistein, may also be linked to the antibodies of the present invention (as supported by U.S. Pat. No. 5,587,459; incorporated herein by reference).

F7. Anti-Viral Agents

As anionic phospholipids and aminophospholipids, particularly PS and PE, become exposed on virally infected cells, the antibodies of the invention, such as the 9D2 and 3G4 (ATCC 4545) antibodies, may also be linked to any one or more anti-viral agents. Additional reasons underlying these aspects of the invention, and the advantages thereof, are described in more detail below in regard to the PE-binding peptide, anti-viral conjugates.

Exemplary anti-viral agents are for linking to antibodies or peptides are also described in more detail in connection with the PE-binding peptide, anti-viral conjugates of the invention. Any one or more anti-viral agents, including those in Table G, may be conjugated to an antibody of the invention, as described herein. Such anti-viral agents may also be used separately in the combination anti-viral therapies of the invention.

G. Biologically Functional Equivalents

Equivalents, or even improvements, of antibodies and effectors can now be made, generally using the materials provided above as a starting point. Modifications and changes may be made in the structure of such an antibody and still obtain a molecule having like or otherwise desirable characteristics. For example, certain amino acids may substituted for other amino acids in a protein structure without appreciable loss of interactive binding capacity. These considerations also apply to toxins, anti-angiogenic agents, apoptosis-inducing agents, coagulants and the like.

Since it is the interactive capacity and nature of a protein that defines that protein's biological functional activity, certain amino acid sequence substitutions can be made in a protein sequence (or of course, the underlying DNA sequence) and nevertheless obtain a protein with like (agonistic) properties. It is thus contemplated that various changes may be made in the sequence of the antibodies or therapeutic agents (or underlying DNA sequences) without appreciable loss of their biological utility or activity. Biological functional equivalents made from mutating an underlying DNA sequence can be made using the codon information provided herein in Table A, and the supporting technical details on site-specific mutagenesis.

It also is well understood by the skilled artisan that, inherent in the definition of a "biologically functional equivalent" protein or peptide, is the concept that there is a limit to the number of changes that may be made within a defined portion of the molecule and still result in a molecule with an acceptable level of equivalent biological activity. Biologically functional equivalent proteins and peptides are thus defined herein as those proteins and peptides in which certain, not most or all, of the amino acids may be substituted. Of course, a plurality of distinct proteins/peptides with different substitutions may easily be made and used in accordance with the invention.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is thus understood that an amino acid can be substituted for another having a similar hydrophilicity value and still obtain a biologically equivalent protein. As detailed in U.S. Pat. No. 4,554,101 (incorporated herein by reference), the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon hydrophilicity values, the substitution of amino acids whose hydrophilicity values are within ±2 is preferred, those which are within ±1 are particularly preferred, and those within ±0.5 are even more particularly preferred.

H. Conjugation

Antibodies to aminophospholipids and anionic phospholipids, including selected anti-PS antibodies with improved properties, such as 9D2 and 3G4 (ATCC 4545), may be conjugated or attached to, or operatively associated with, anti-cellular and cytotoxic agents to prepare "immunotoxins"; to coagulants, either directly or indirectly, to prepare "coaguligands"; or to anti-viral agents, such as nucleosides, to prepare anti-viral immunoconjugates or "immunovirocides". PE-binding peptides such as duramycin may also be conjugated or attached to, or operatively associated with, inert carriers, targeting agents or anti-viral agents, to prepare a range of PE-binding peptide derivatives and anti-viral peptide conjugates.

Although covalent linkages are preferred, other means of operative attachment may also be used. For example, linked constructs may be generated using avidin:biotin bridges. In addition to the knowledge available to those of ordinary skill in the art, co-owned U.S. Pat. No. 6,093,399 is specifically incorporated herein by reference for purposes of even further describing and enabling the use of avidin:biotin in the operative attachment of antibodies and targeting agents to biological and therapeutic agents.

The two agents may also be joined by a second binding region, preferably an antibody or antigen binding region thereof. This is exemplified by coaguligands wherein the targeting agent is linked to the coagulant via a second binding region (U.S. Pat. Nos. 6,093,399, 6,004,555, 5,877,289, and 6,036,955, each specifically incorporated herein by reference), which have been made and used successfully in the treatment of cancer. Where the first targeting agent is an antibody or antigen binding region, the use of a second binding region that is also an antibody, or antigen binding region, results in a bispecific antibody construct. The preparation and use of bispecific antibodies in general is well known in the art, and is further disclosed herein.

Immunoconjugate technology is now generally known in the art. However, certain advantages may be achieved through the application of certain preferred technology, both in the preparation and purification for subsequent clinical administration. For example, while IgG based constructs will typically exhibit better binding capability and slower blood clearance than their Fab' counterparts, Fab' fragment-based constructs will generally exhibit better tissue penetrating capability.

Additionally, while numerous types of disulfide-bond containing linkers are known that can be successfully employed in antibody and peptide conjugation, certain linkers will generally be preferred over other linkers, based on differing pharmacological characteristics and capabilities. For example, linkers that contain a disulfide bond that is sterically "hindered" are to be preferred, due to their greater stability in vivo, thus preventing release of the coagulant prior to binding at the site of action.

Each type of cross-linker, as well as how the cross-linking is performed, will tend to vary the pharmacodynamics of the resultant conjugate. One may desire to have a conjugate that will remain intact under conditions found everywhere in the body except the intended site of action, at which point it is desirable that the conjugate have good "release" characteristics. Therefore, the particular cross-linking scheme, including in particular the particular cross-linking reagent used and the structures that are cross-linked, will be of some significance.

Depending on the specific agents to be conjugated, it may be necessary or desirable to provide a peptide spacer operatively attaching the antibody or PE-binding peptide and the second or therapeutic agent. Certain peptide spacers are capable of folding into a disulfide-bonded loop structure. Proteolytic cleavage within the loop would then yield a heterodimeric polypeptide wherein the antibody and the therapeutic agent are linked by only a single disulfide bond. An example of such a toxin is a Ricin A-chain toxin.

When certain other toxin compounds are utilized, a non-cleavable peptide spacer may be provided to operatively attach the antibody and the toxin compound of the fusion protein. Toxins which may be used in conjunction with non-cleavable peptide spacers are those which may, themselves, be converted by proteolytic cleavage, into a cytotoxic disulfide-bonded form. An example of such a toxin compound is a *Pseudonomas* exotoxin compound.

A variety of chemotherapeutic and other pharmacological agents have now been successfully conjugated to antibodies and shown to function pharmacologically. Exemplary antineoplastic agents that have been investigated include doxorubicin, daunomycin, methotrexate, vinblastine, and various others. Moreover, the attachment of other agents such as neocarzinostatin, macromycin, trenimon and α-amanitin has been described. These attachment methods can be adapted for use herewith.

Any covalent linkage to the antibody or PE-binding peptide should ideally be made at a site distinct from the functional site(s). The compositions are thus "linked" in any operative manner that allows each region to perform its intended function without significant impairment, in particular, so that the resultant construct still binds to the intended antigen or to PE and so that the attached agent substantially maintains biological activity and/or recovers biological activity when released from the construct.

Attachment of biological agents via the carbohydrate moieties on antibodies is also contemplated. Glycosylation, both O-linked and N-linked, naturally occurs in antibodies. Recombinant antibodies can be modified to recreate or create additional glycosylation sites if desired, which is simply achieved by engineering the appropriate amino acid sequences (such as Asn-X-Ser, Asn-X-Thr, Ser, or Thr) into the primary sequence of the antibody.

H1. Biochemical Cross-Linkers

In additional to the general information provided above, antibodies or PE-binding peptides may be conjugated to therapeutic or other agents using certain preferred biochemical cross-linkers. Cross-linking reagents are used to form molecular bridges that tie together functional groups of two different molecules. To link two different proteins in a step-wise manner, hetero-bifunctional cross-linkers can be used that eliminate unwanted homopolymer formation. Exemplary hetero-bifunctional cross-linkers are referenced in Table C.

TABLE C

HETERO-BIFUNCTIONAL CROSS-LINKERS

| Linker | Reactive Toward | Advantages and Applications | Spacer Arm Length after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

Hetero-bifunctional cross-linkers contain two reactive groups: one generally reacting with primary amine group (e.g., N-hydroxy succinimide) and the other generally reacting with a thiol group (e.g., pyridyl disulfide, maleimides, halogens, etc.). Through the primary amine reactive group, the cross-linker may react with the lysine residue(s) of one protein (e.g., the selected antibody, fragment or PE-binding peptide) and through the thiol reactive group, the cross-linker, already tied up to the first protein, reacts with the cysteine residue (free sulfhydryl group) of the other protein.

Compositions therefore generally have, or are derivatized to have, a functional group available for cross-linking purposes. This requirement is not considered to be limiting in that a wide variety of groups can be used in this manner. For example, primary or secondary amine groups, hydrazide or hydrazine groups, carboxyl alcohol, phosphate, carbamate, or alkylating groups may be used for binding or cross-linking.

The spacer arm between the two reactive groups of a cross-linkers may have various length and chemical compositions. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents). The use of peptide spacers, such as L-Leu-L-Ala-L-Leu-L-Ala, is also contemplated.

It is preferred that a cross-linker having reasonable stability in blood will be employed. Numerous types of disulfide-bond containing linkers are known that can be successfully employed in conjugation. Linkers that contain a disulfide bond that is sterically hindered may prove to give greater stability in vivo, preventing release of the agent prior to binding at the site of action. These linkers are thus one preferred group of linking agents.

One of the most preferred cross-linking reagents is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the tumor site. It is contemplated that the SMPT agent may also be used in connection with the conjugates of this invention.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxysuccinimidyl group reacts with primary amino groups and the phenylazide (upon photolysis) reacts non-selectively with any amino acid residue.

In addition to hindered cross-linkers, non-hindered linkers can also be employed in accordance herewith. Other useful cross-linkers, not considered to contain or generate a protected disulfide, include SATA, SPDP and 2-iminothiolane. The use of such cross-linkers is well understood in the art.

Once conjugated, the conjugate is separated from unconjugated antibodies or peptides and other agents and from other contaminants. A large a number of purification techniques are available for use in providing conjugates of a sufficient degree of purity to render them clinically useful. Purification methods based upon size separation, such as gel filtration, gel permeation or high performance liquid chromatography, will generally be of most use. Other chromatographic techniques, such as Blue-Sepharose separation, may also be used.

H2. Biologically Releasable Linkers

Although it is preferred that any linking moiety will have reasonable stability in blood, to prevent substantial release of the attached therapeutic agent before targeting to the disease, e.g., tumor site, in certain aspects, the use of biologically-releasable bonds and/or selectively cleavable spacers or linkers is contemplated. "Biologically-releasable bonds" and "selectively cleavable spacers or linkers" still have reasonable stability in the circulation.

The antibodies or PE-binding peptides in accordance with the invention may thus be linked to one or more therapeutic or second agents via a biologically-releasable bond. Any form of targeting agent or antibody may be employed, including intact antibodies, although ScFv fragments will be preferred in certain embodiments.

"Biologically-releasable bonds" or "selectively hydrolyzable bonds" include all linkages that are releasable, cleavable or hydrolyzable only or preferentially under certain conditions. This includes disulfide and trisulfide bonds and acid-labile bonds, as described in U.S. Pat. Nos. 5,474,765 and 5,762,918, each specifically incorporated herein by reference.

The use of an acid sensitive spacer for attachment of a therapeutic agent to an antibody or PE-binding peptide of the invention is particularly contemplated. In such embodiments, the therapeutic agents are released within the acidic compartments inside a cell. It is contemplated that acid-sensitive release may occur extracellularly, but still after specific targeting, preferably to the tumor site or virally infected cell. Certain currently preferred examples include antibodies linked to colchicine or doxorubicin via an acid sensitive spacer. Attachment via carbohydrate moieties of antibodies is also contemplated. In such embodiments, the therapeutic agent are released within the acidic compartments inside a cell.

The antibody or PE-binding peptide may also be derivatized to introduce functional groups permitting the attachment of the therapeutic agents through a biologically releasable bond. The antibody or PE-binding peptide may thus be derivatized to introduce side chains terminating in hydrazide, hydrazine, primary amine or secondary amine groups. Therapeutic agents may be conjugated through a Schiff's base linkage, a hydrazone or acyl hydrazone bond or a hydrazide linker (U.S. Pat. Nos. 5,474,765 and 5,762,918, each specifically incorporated herein by reference).

Also as described in U.S. Pat. Nos. 5,474,765 and 5,762,918, each specifically incorporated herein by reference, the antibody or PE-binding peptide may be operatively attached to the therapeutic agent through one or more biologically releasable bonds that are enzyme-sensitive bonds, including peptide bonds, esters, amides, phosphodiesters and glycosides.

Certain preferred aspects of the invention concern the use of peptide linkers that include at least a first cleavage site for a peptidase and/or proteinase that is preferentially located within a disease site, particularly within the tumor environment. The antibody- or peptide-mediated delivery of the attached therapeutic agent thus results in cleavage specifically within the disease site or tumor environment, resulting in the specific release of the active therapeutic agent. Certain peptide linkers will include a cleavage site that is recognized by one or more enzymes involved in remodeling.

Peptide linkers that include a cleavage site for urokinase, pro-urokinase, plasmin, plasminogen, TGFβ, staphylokinase, Thrombin, Factor IXa, Factor Xa or a metalloproteinase, such as an interstitial collagenase, a gelatinase or a stromelysin, are particularly preferred. U.S. Pat. Nos. 6,004,555, 5,877,289, and 6,093,399 are specifically incorporated herein by reference for the purpose of further describing and enabling how to make and use immunoconjugates comprising biologically-releasable bonds and selectively-cleavable linkers and peptides. U.S. Pat. No. 5,877,289 is particularly incorporated herein by reference for the purpose of further describing and enabling how to make and use immunoconjugates that comprise a selectively-cleavable peptide linker that is cleaved by urokinase, plasmin, Thrombin, Factor IXa, Factor Xa or a metalloproteinase, such as an interstitial collagenase, a gelatinase or a stromelysin, within a tumor environment.

Currently preferred selectively-cleavable peptide linkers are those that include a cleavage site for plasmin or a metalloproteinase (also known as "matrix metalloproteases" or "MMPs"), such as an interstitial collagenase, a gelatinase or a stromelysin. Additional peptide linkers that may be advantageously used in connection with the present invention include, for example, plasmin cleavable sequences, such as those cleavable by pro-urokinase, TGFβ, plasminogen and staphylokinase; Factor Xa cleavable sequences; MMP cleavable sequences, such as those cleavable by gelatinase A; collagenase cleavable sequences, such as those cleavable by calf skin collagen (α1(I) chain), calf skin collagen (α2(I) chain), bovine cartilage collagen (α1(II) chain), human liver collagen (α1(III) chain), human $α_2$M, human PZP, rat $α_1$M, rat $α_2$M, rat $α_1I_3$(2J), rat $α_1I_3$(27J), and the human fibroblast collagenase autolytic cleavage sites. In addition to the knowledge available to those of ordinary skill in the art, the text and sequences from Table B2 in co-owned U.S. Pat. Nos. 6,342,219, 6,524,583, 6,342,221 and 6,416,758, are specifically incorporated herein by reference for purposes of even further describing and enabling the use of such cleavable sequences.

H3. Bispecific Antibodies

Bispecific antibodies in general may be employed, so long as one arm binds to an aminophospholipid or anionic phospholipid and the bispecific antibody is attached, at a site distinct from the antigen binding site, to a therapeutic agent.

In general, the preparation of bispecific antibodies is also well known in the art. One method involves the separate preparation of antibodies having specificity for the aminophospholipid or anionic phospholipid, on the one hand, and a therapeutic agent on the other. Peptic F(ab'γ)$_2$ fragments are prepared from the two chosen antibodies, followed by reduction of each to provide separate Fab'γSH fragments. The SH groups on one of the two partners to be coupled are then alkylated with a cross-linking reagent such as O-phenylenedimaleimide to provide free maleimide groups on one partner. This partner may then be conjugated to the other by means of a thioether linkage, to give the desired F(ab'γ)$_2$ heteroconjugate. Other techniques are known wherein cross-linking with SPDP or protein A is carried out, or a trispecific construct is prepared.

Another method for producing bispecific antibodies is by the fusion of two hybridomas to form a quadroma. As used herein, the term "quadroma" is used to describe the productive fusion of two B cell hybridomas. Using now standard techniques, two antibody producing hybridomas are fused to give daughter cells, and those cells that have maintained the expression of both sets of clonotype immunoglobulin genes are then selected.

A preferred method of generating a quadroma involves the selection of an enzyme deficient mutant of at least one of the parental hybridomas. This first mutant hybridoma cell line is then fused to cells of a second hybridoma that had been lethally exposed, e.g., to iodoacetamide, precluding its continued survival. Cell fusion allows for the rescue of the first hybridoma by acquiring the gene for its enzyme deficiency from the lethally treated hybridoma, and the rescue of the second hybridoma through fusion to the first hybridoma. Preferred, but not required, is the fusion of immunoglobulins of the same isotype, but of a different subclass. A mixed subclass antibody permits the use if an alternative assay for the isolation of a preferred quadroma.

In more detail, one method of quadroma development and screening involves obtaining a hybridoma line that secretes the first chosen MAb and making this deficient for the essential metabolic enzyme, hypoxanthine-guanine phosphoribosyltransferase (HGPRT). To obtain deficient mutants of the hybridoma, cells are grown in the presence of increasing concentrations of 8-azaguanine ($1 \times 10^{-7}$M to $1 \times 10^{-5}$M). The mutants are subcloned by limiting dilution and tested for their hypoxanthine/aminopterin/thymidine (HAT) sensitivity. The culture medium may consist of, for example, DMEM supplemented with 10% FCS, 2 mM L-Glutamine and 1 mM penicillin-streptomycin.

A complementary hybridoma cell line that produces the second desired MAb is used to generate the quadromas by standard cell fusion techniques. Briefly, $4.5 \times 10^7$ HAT-sensitive first cells are mixed with $2.8 \times 10^7$ HAT-resistant second cells that have been pre-treated with a lethal dose of the irreversible biochemical inhibitor iodoacetamide (5 mM in phosphate buffered saline) for 30 minutes on ice before fusion. Cell fusion is induced using polyethylene glycol (PEG) and the cells are plated out in 96 well microculture plates. Quadromas are selected using HAT-containing medium. Bispecific antibody-containing cultures are identified using, for example, a solid phase isotype-specific ELISA and isotype-specific immunofluorescence staining.

In one identification embodiment to identify the bispecific antibody, the wells of microtiter plates (Falcon, Becton Dickinson Labware) are coated with a reagent that specifically interacts with one of the parent hybridoma antibodies and that lacks cross-reactivity with both antibodies. The plates are washed, blocked, and the supernatants (SNs) to be tested are added to each well. Plates are incubated at room temperature for 2 hours, the supernatants discarded, the plates washed, and diluted alkaline phosphatase-anti-antibody conjugate added for 2 hours at room temperature. The plates are washed and a phosphatase substrate, e.g., P-Nitrophenyl phosphate (Sigma, St. Louis) is added to each well. Plates are incubated, 3N NaOH is added to each well to stop the reaction, and the $OD_{410}$ values determined using an ELISA reader.

In another identification embodiment, microtiter plates pre-treated with poly-L-lysine are used to bind one of the target cells to each well, the cells are then fixed, e.g. using 1% glutaraldehyde, and the bispecific antibodies are tested for their ability to bind to the intact cell. In addition, FACS, immunofluorescence staining, idiotype specific antibodies, antigen binding competition assays, and other methods common in the art of antibody characterization may be used in conjunction with the present invention to identify preferred quadromas.

Following the isolation of the quadroma, the bispecific antibodies are purified away from other cell products. This may be accomplished by a variety of protein isolation procedures, known to those skilled in the art of immunoglobulin purification. Means for preparing and characterizing antibodies are well known in the art (See, e.g., Antibodies: A Laboratory Manual, 1988).

For example, supernatants from selected quadromas are passed over protein A or protein G sepharose columns to bind IgG (depending on the isotype). The bound antibodies are then eluted with, e.g. a pH 5.0 citrate buffer. The elute fractions containing the BsAbs, are dialyzed against an isotonic buffer. Alternatively, the eluate is also passed over an anti-immunoglobulin-sepharose column. The BsAb is then eluted with 3.5 M magnesium chloride. BsAbs purified in this way are then tested for binding activity by, e.g., an isotype-specific ELISA and immunofluorescence staining assay of the target cells, as described above.

Purified BsAbs and parental antibodies may also be characterized and isolated by SDS-PAGE electrophoresis, followed by staining with silver or Coomassie. This is possible when one of the parental antibodies has a higher molecular weight than the other, wherein the band of the BsAbs migrates midway between that of the two parental antibodies. Reduction of the samples verifies the presence of heavy chains with two different apparent molecular weights.

H4. Fusion Proteins and Recombinant Expression

Antibodies to aminophospholipids and anionic phospholipids, including the 9D2 and 3G4 (ATCC 4545) antibodies and other competing antibodies with improved properties, and PE-binding peptides, can also be used to create fusion proteins using molecular biological techniques. Any fusion protein may be designed and made using any of the antibodies, PE-binding peptides and second or therapeutic agents disclosed herein and those known in the art. The fusion protein technology is readily adaptable to prepare fusion proteins with other modifications, such as optimizations in CDR sequences, linkage via a selectively cleavable peptide sequence, and such like.

The use of recombinant DNA techniques to achieve such ends is now standard practice to those of skill in the art. These methods include, for example, in vitro recombinant DNA techniques, synthetic techniques and in vivo recombination/genetic recombination. DNA and RNA synthesis may, additionally, be performed using an automated synthesizers (see, for example, the techniques described in Sambrook et al., 1989).

The preparation of such a fusion protein generally entails the preparation of a first and second DNA coding region and the functional ligation or joining of such regions, in frame, to prepare a single coding region that encodes the desired fusion protein. In the present context, the antibody sequence will be joined in frame with a DNA sequence encoding a therapeutic agent. It is not generally believed to be particularly relevant which portion of the immunoconjugate is prepared as the N-terminal region or as the C-terminal region.

Once the desired coding region has been produced, an expression vector is created. Expression vectors contain one or more promoters upstream of the inserted DNA regions that act to promote transcription of the DNA and to thus promote expression of the encoded recombinant protein. This is the meaning of "recombinant expression".

To obtain a so-called "recombinant" version of the immunoconjugate, the vector is expressed in a recombinant cell. The engineering of DNA segment(s) for expression in a prokaryotic or eukaryotic system may be performed by techniques generally known to those of skill in recombinant expression. It is believed that virtually any expression system may be employed in expression.

The immunoconjugates of the invention may be successfully expressed in eukaryotic expression systems, e.g., CHO cells, however, it is envisioned that bacterial expression systems, such as E. coli pQE-60 will be particularly useful for the large-scale preparation and subsequent purification of the constructs. cDNAs may also be expressed in bacterial systems, with the encoded proteins being expressed as fusions with β-galactosidase, ubiquitin, *Schistosoma japonicum* glutathione S-transferase, and the like. It is believed that bacterial expression will have advantages over eukaryotic expression in terms of ease of use and quantity of materials obtained thereby.

In terms of microbial expression, U.S. Pat. Nos. 5,583,013; 5,221,619; 4,785,420; 4,704,362; and 4,366,246 are incorporated herein by reference for the purposes of even further supplementing the present disclosure in connection with the expression of genes in recombinant host cells.

Recombinantly produced immunoconjugates may be purified and formulated for human administration. Alternatively, nucleic acids encoding the immunoconjugates may be delivered via gene therapy. Although naked recombinant DNA or plasmids may be employed, the use of liposomes or vectors is preferred. The ability of certain viruses to enter cells via receptor-mediated endocytosis and to integrate into the host cell genome and express viral genes stably and efficiently have made them attractive candidates for the transfer of foreign genes into mammalian cells. Preferred gene therapy vectors for use in the present invention will generally be viral vectors.

Retroviruses have promise as gene delivery vectors due to their ability to integrate their genes into the host genome, transferring a large amount of foreign genetic material, infecting a broad spectrum of species and cell types and of being packaged in special cell-lines. Other viruses, such as adenovirus, herpes simplex viruses (HSV), cytomegalovirus (CMV), and adeno-associated virus (AAV), such as those described by U.S. Pat. No. 5,139,941 (incorporated herein by reference), may also be engineered to serve as vectors for gene transfer.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

In certain further embodiments, the gene therapy vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (e.g., temporal, strength) makes it possible to control expression to a greater extent than in other systems. It also is an advantage that the virus has relatively few spliced messages, further easing genetic manipulations. HSV also is relatively easy to manipulate and can be grown to high titers.

Of course, in using viral delivery systems, one will desire to purify the virion sufficiently to render it essentially free of undesirable contaminants, such as defective interfering viral particles or pyrogens such that it will not cause any untoward reactions in the cell, animal or individual receiving the vector construct. A preferred means of purifying the vector involves the use of buoyant density gradients, such as cesium chloride gradient centrifugation.

I. Binding, Functional and Screening Assays

Although the present invention has significant utility in animal and human treatment regimens, it also has many other specific and credible uses, including practical uses in many in vitro embodiments. Certain of these uses are related to the specific binding properties of the antibodies, peptides and immunoconjugates. In that each of the constructs of the invention include at least one antibody or peptide component that binds to an aminophospholipid and/or an anionic phospholipid, they may be used in a variety of binding embodiments, including useful binding assays.

The presence of an attached agent, where relevant, although providing advantageous properties, does not negate the utility of the first antibody or peptide regions in any binding assay. Suitably useful binding assays thus include those commonly employed in the art, such as in immunoblots, Western blots, dot blots, RIAs, ELISAs, immunohistochemistry, fluorescent activated cell sorting (FACS), immunoprecipitation, affinity chromatography, and the like, as further described herein.

Certain standard binding assays are those in which an antigen is immobilized onto a solid support matrix, e.g., nitrocellulose, nylon or a combination thereof, such as in immunoblots, Western blots, ELISAs and related assays. Other important assays are those using cells, wherein the components of the present invention can be used to assay for cells with aminophospholipids and/or anionic phospholipids at the cell surface. Such assays can be applied in pre-clinical testing, e.g., regarding the design of drugs, testing the mechanism of action and/or selecting therapeutic agents for combined use.

Further in vitro assays are useful in the diagnosis of diseases connected with aberrant cell activation and/or apoptosis, wherein testing for the presence of aminophospholipids and/or anionic phospholipids at the cell surface would be particularly useful. The constructs of the invention may thus be used in conjunction with both fresh-frozen and formalin-fixed, paraffin-embedded tissue blocks in immunohistochemistry; in fluorescent activated cell sorting, flow cytometry or flow microfluorometry.

They constructs of the invention have further practical uses in immunoprecipitation, antigen purification embodiments, such as affinity chromatography, even including, in cases of bispecific antibodies, the one-step rapid purification of one or more antigens at the same time; and in many other binding assays that will be known to those of skill in the art given the information presented herein.

Yet further practical uses of the present constructs are as controls in functional assays, including many in vitro and ex vivo assays and systems. As the binding and functional properties of the antibodies, peptides and conjugates of the invention are particularly specific, as disclosed herein, such "control" uses are actually extremely valuable. The assays that benefit from such a practical application of the present invention include, for example, assays concerning detection of aminophospholipids and/or anionic phospholipids at the cell surface.

These assays systems can also be developed into in vitro or ex vivo drug screening assays, wherein the present provision of biological materials with well defined properties is particularly important. For example, in using the constructs of the present invention as positive controls in the selection of small molecules that have similar, equivalent or improved binding properties, e.g., in drug screening and development.

The binding assays and systems of the invention can also be developed into in vitro or ex vivo drug screening assays, wherein the present provision of biological materials with well defined properties, as in the antibodies disclosed herein, is particularly important. For example, in using the constructs of the present invention as positive controls in the selection of small molecules that have similar, equivalent or improved binding properties, e.g., in drug screening and development.

In this regard, the invention further provides methods of screening for compounds that mimic the binding and activity of the antibodies disclosed herein, preferably the 9D2 or 3G4 antibodies, and most preferably the 3G4 (ATCC 4545) antibody. As the antibodies of the invention bind to aminophospholipids and anionic phospholipids, preferably PS and PE, preferred screening methods are those that test compounds for the ability to inhibit the binding of the antibodies to one or more aminophospholipids or anionic phospholipids, such as PS and PE. The methods are suitable for use in screening for low molecular weight compounds for use as drugs that mimic the anti-tumor, anti-vascular and/or anti-viral activities of the antibodies.

The "screening assays or methods" of the invention are conducted on the same principles as the techniques employed in testing competing or cross-reactive antibodies, as taught herein and further exemplified in the working examples. The starting materials, steps, qualitative and quantitative guidelines for use in the antibody competition assays may thus be readily adapted for use in the present screening assays, particularly in light of the following information.

In the screening methods, the agents to be tested may be termed "candidate substances". Candidate substances for screening in such assays include those isolated from natural sources, including bacteria, fungi, plant sources, including leaves and bark, soil and marine samples. Other candidate substances that may be screened in this manner are those derived from chemical compositions or man-made compounds, particularly those in large chemical libraries.

As with the methods for identifying competing antibodies, the screening assays test the ability of a candidate substance to inhibit binding of a "control positive antibody", such as the 3G4 antibody, to an aminophospholipid or anionic phospholipid, preferably PS. Antibody binding is first measured in the absence of the candidate substance, which is preferably repeated once in each assay, but can also be referred to from a known standard. The candidate substance(s) are then admixed with samples of the antibody and the ability of the antibody to bind to the target, preferably PS, is determined in the presence of the candidate substance. A substance that reduces binding, and preferably significantly reduces binding, in comparison to the level in the absence of the substance, is indicative of a candidate substance with competitive capability. Such substances are "positive candidate substances" and are continued for further development.

In preferred embodiments, the screening is conducted using PS-coated microtiter plates. A high throughput screening procedure is considered most useful, many suitable examples of which are known and may now be used, in light of the motivation in the present disclosure, and in conjunction with the reagents provided by the invention. One example of high throughput screening concerns testing compounds for the ability to inhibit the binding of luciferase-labeled antibodies, such as luciferase-labeled 3G4, to PS-coated microtiter plates. Luciferase-labeled 3G4 antibodies, and kits comprising such antibodies, are thus further components within the overall invention.

It is expected that suitable positive candidate substances will be identified using the screening methods of the invention (notwithstanding the fact that the screening assays are useful in themselves, even without identifying effective candidate substances). If desired, chemical or biological modifications can be made to the positive candidate substances first identified, and the modified versions or "analogs" re-screened to continue the process of selecting the most useful agents, e.g., to select more optimal inhibitory compounds from chemical derivatives. Inhibitory activity can also be confirmed by re-screening after modifications based upon mechanistic considerations. For example, as cross-linking PS or PE on the target cells may be required for optimal biological activity in vivo, positive candidate substances from the first screening assays may be linked to form dimers, trimers, oligomers or multimers and re-screened to confirm inhibitory activity, preferably followed by further tests to confirm cross-linking in vitro.

J. Pharmaceutical Compositions

The therapeutic agents of the present invention will generally be formulated as pharmaceutical compositions. The pharmaceutical compositions will comprise a biologically or therapeutically effective amount of at least a first therapeutic agent of the invention, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

J1. Injectable Formulations

The therapeutic agents of the invention will often be formulated for parenteral administration, particularly for tumor treatment, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains an antibody, immunoconjugate or peptide conjugate as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The therapeutic agents can be formulated into a sterile aqueous composition in a neutral or salt form. Solutions of therapeutic agents as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the therapeutic agents should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the therapeutic agent admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. For human administration, preparations should meet sterility, pyrogenicity, general safety and purity standards as required by FDA Office of Biological Standards. Upon formulation, the therapeutic agents will be administered in a manner compatible with the dosage formulation and in such amount as is therapeutically effective.

J2. Sustained Release Formulations

Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, topical formulations, liposomal forms and the like. The type of form for administration will be matched to the disease or disorder to be treated.

Pharmaceutical "slow release" capsules or "sustained release" compositions or preparations may also be used. Slow release formulations are generally designed to give a constant drug level over an extended period and may be used to deliver therapeutic agents in accordance with the present invention. The slow release formulations are typically implanted in the vicinity of the disease site, for example, at the site of a tumor or viral infection.

Suitable examples of sustained-release preparations include semipermeable matrices of solid hydrophobic polymers containing therapeutic agents, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers, such as the Lupron Depot™ (injectable microspheres composed of lactic acid-glycolic acid copolymer and leuprolide acetate); and poly-D-(−)-3-hydroxybutyric acid.

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thiodisulfide interchange, stabilization is achieved by modifying sulfhydryl residues, lyophilizing from acidic solutions, controlling moisture content, using appropriate additives, developing specific polymer matrix compositions, and the like.

J3. Liposomes and Nanocapsules

In certain embodiments, liposomes and/or nanoparticles may also be employed with the therapeutic agents. The formation and use of liposomes is generally known to those of skill in the art, as summarized below. The present invention provides particular combinations of antibodies, liposomes and chemotherapeutic agents, which are described below. In addition, a liposomal formulation may be used as a routine component of any of the therapeutic agents of the overall invention.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

J4. Ophthalmic Formulations

Many diseases of the eye, particularly those having an angiogenic component, can be treated by the present invention. For example ocular neovascular disease, age-related macular degeneration, diabetic retinopathy, retinopathy of prematurity, corneal graft rejection, neovascular glaucoma, retrolental fibroplasias and other diseases associated with corneal neovascularization or retinal/choroidal neovascularization, as described hereinbelow.

The therapeutic agents of the present invention may thus be advantageously employed in the preparation of pharmaceutical compositions suitable for use as ophthalmic solutions, including those for intravitreal and/or intracameral administration. For the treatment of any of the foregoing or other disorders the therapeutic agents are administered to the eye or eyes of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.).

The ophthalmic preparations will contain a therapeutic agent in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

J5. Topical Formulations

In the broadest sense, formulations for topical administration include those for delivery via the mouth (buccal) and through the skin. "Topical delivery systems" also include transdermal patches containing the ingredient to be administered. Delivery through the skin can further be achieved by iontophoresis or electrotransport, if desired.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin include ointments, creams, gels and pastes comprising the ingredient to be administered in a pharmaceutical acceptable carrier. The formulation of therapeutic agents for topical use, such as in creams, ointments and gels, includes the preparation of oleaginous or water-soluble ointment bases, will be well known to those in the art in light of the present disclosure. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Formulations for rectal administration may be presented as a suppository with a suitable base comprising, for example, cocoa butter or a salicylate. Formulations suitable for vaginal administration may be presented as pessaries, tampons, creams, gels, pastes, foams or spray formulations containing in addition to the active ingredient such carriers as are known in the art to be appropriate.

J6. Nasal Formulations

Local delivery via the nasal and respiratory routes is contemplated for treating various conditions, particularly for use in the anti-viral treatment methods of the present invention. These delivery routes are also suitable for delivering agents into the systemic circulation. Formulations of active ingredients in carriers suitable for nasal administration are therefore also included within the invention, for example, nasal solutions, sprays, aerosols and inhalants. Where the carrier is a solid, the formulations include a coarse powder having a particle size, for example, in the range of 20 to 500 microns, which is administered, e.g., by rapid inhalation through the nasal passage from a container of the powder held close up to the nose.

Suitable formulations wherein the carrier is a liquid are useful in nasal administration. Nasal solutions are usually aqueous solutions designed to be administered to the nasal passages in drops or sprays and are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Inhalations and inhalants are pharmaceutical preparations designed for delivering a drug or compound into the respiratory tree of a patient. A vapor or mist is administered and reaches the affected area. This route can also be employed to deliver agents into the systemic circulation. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, comprises finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient. Particle size is of major importance in the administration of this type of preparation. It has been reported that the optimum particle size for penetration into the pulmonary cavity is of the order of 0.5 to 7 µm. Fine mists are produced by pressurized aerosols and hence their use in considered advantageous.

K. Diagnostic and Therapeutic Kits

This invention also provides diagnostic and therapeutic kits comprising at least a first therapeutic agent of the present invention, i.e., an antibody, immunoconjugate or peptide conjugate that binds to an aminophospholipid or anionic phospholipid, for use in treatment methods, combined treatment methods and/or in imaging and treatment embodiments. Such kits will generally contain, in at least a first suitable container (or container means), a pharmaceutically acceptable formulation of at least one therapeutic agent, antibody, immunoconjugate or peptide conjugate that binds to an aminophospholipid or anionic phospholipid. The kits may include written or electronic instructions for use, e.g. in pre-clinical, clinical and/or veterinary embodiments.

The kits may also contain other compositions, pharmaceutically acceptable formulations and second biological and therapeutic agents, including those for combined therapy and/or for diagnostic and imaging. For example, such kits may contain any one or more of a range of chemotherapeutic, radiotherapeutic or anti-angiogenic agents, anti-tumor cell, anti-tumor vasculature or anti-tumor stroma antibodies, immunotoxins or coaguligands, anti-viral agents and/or diagnostic components or agents. Written or electronic instructions for use in combined therapy and/or for diagnosis and imaging may also be included.

The kits may have a single container that contains the first antibody, immunoconjugate or peptide conjugate that binds to an aminophospholipid or anionic phospholipid, with or without any additional components, or they may have distinct containers for each desired agent. Where combined therapeutics are provided, a single solution may be pre-mixed, either in a molar equivalent combination, or with one component in excess of the other. Alternatively, the primary therapeutic agent of the invention and the second biological or therapeutic agent, such as a second anti-cancer or anti-viral agent, kit may be maintained separately within distinct containers of the kit prior to administration to a patient.

Diagnostic components will most often be maintained in at least a second container, distinct from the other or first container that comprises the one or more therapeutic agents. The diagnostic kits may include labeled antibodies or peptides that bind to the same aminophospholipid or anionic phospholipid as the primary therapeutic agent, or any other agent suitable for diagnosing the disease to be treated. The kits may include diagnostic agents for use in vitro, for use in vivo, or both such agent. The kits may include written or electronic instructions for use, e.g. in pre-clinical, clinical and/or veterinary diagnostic embodiments.

For immunodetection in vitro, the antibodies may be bound to a solid support, such as a well of a microtitre plate, although antibody solutions or powders for reconstitution are preferred. The immunodetection kits preferably comprise at least a first immunodetection reagent. The immunodetection reagents of the kit may take any one of a variety of forms, including those detectable labels that are associated with or linked to the given antibody, such as used in vivo. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. A number of exemplary labels are known in the art and all such labels may be employed in connection with the present invention. These kits may contain antibody-label conjugates either in fully conjugated form, in the form of intermediates, or as separate moieties to be conjugated by the user of the kit. The imaging kits will preferably comprise a targeting agent or antibody that is already attached to an in vivo detectable label. However, the label and attachment means could be separately supplied.

Either form of diagnostic kit may further comprise control agents, such as suitably aliquoted biological compositions, whether labeled or unlabeled, as may be used to prepare a standard curve for a detection assay. The components of the kits may be packaged either in aqueous media or in lyophilized form.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. The solvent may also be provided in another container within the kit.

The containers of the therapeutic and diagnostic kits will generally include at least one vial, test tube, flask, bottle, syringe or other container or container means, into which the therapeutic and any other desired agent are placed and, preferably, suitably aliquoted. As at least two separate components are preferred, the kits will preferably include at least two such containers. The kits may also comprise a third or fourth container for containing a sterile, pharmaceutically acceptable buffer or other diluent.

The kits may also contain a means by which to administer the therapeutic agents to an animal or patient, e.g., one or more needles or syringes, or even an eye dropper, pipette, or other such like apparatus, from which the formulations may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

L. Immunodetection and Imaging

The present invention further provides in vitro and in vivo diagnostic and imaging methods. Such methods are applicable for use in generating diagnostic, prognostic and/or imaging information, e.g., related to angiogenic diseases and viral infections, and preferably related to tumor treatment and imaging methods. The methods of the invention include in vitro diagnostic tests, e.g., wherein the samples can be obtained non-invasively and preferably tested in high throughput assays and/or where the clinical diagnosis in ambiguous and confirmation is desired. In the field of in vivo diagnostics and imaging, the antibodies and peptides of the invention are linked to one or more detectable agents and used to form an image of an angiogenic site or tumor, optionally as a first step prior to treatment.

L1. Immunodetection Methods and Kits

The invention thus concerns immunodetection methods for binding, purifying, quantifying or otherwise generally detecting aminophospholipids and anionic phospholipids, e.g., for use in diagnosing activated and apoptotic cells and associated diseases. The antibodies of the present invention, such as 9D2 and 3G4 (ATCC 4545), may be employed to detect aminophospholipids and anionic phospholipids in vivo (see below), in isolated issue samples, biopsies or swabs and/or in homogenized tissue samples. Such immunodetection methods have evident diagnostic utility, but also have applications to non-clinical samples, such as in the titering of antigen samples, and the like.

The steps of various useful immunodetection methods have been described in the scientific literature, such as, e.g., Nakamura et al., 1987, specifically incorporated herein by reference. In general, the immunobinding methods include obtaining a sample suspected of containing aminophospholipids and/or anionic phospholipids, preferably cells suspected of having aminophospholipids and/or anionic phospholipids at the cell surface, and contacting the sample with an antibody of the invention, such as 9D2 or 3G4 (ATCC 4545), under conditions effective to allow the formation of immune complexes. Any immune complexes formed during the binding process are then detected and preferably quantified.

The sample analyzed may be a cell sample, such as cells exposed to certain test conditions in the laboratory. The sample may also be a biological sample from an animal or patient, e.g., one suspected of having a disease associated with activation or apoptosis of one or more cell types. Such a sample may be a tissue section or specimen, a biopsy, a swab or smear test sample, a homogenized tissue extract or separated or purified forms of such.

Contacting the chosen biological sample with the antibody under conditions effective and for a period of time sufficient to allow the formation of immune complexes (primary immune complexes) is generally a matter of simply adding the antibody to the sample and incubating the mixture for a period of time long enough for the antibodies to form immune complexes with, i.e., to bind to, any aminophospholipids and/or anionic phospholipids present. After this time, the sample-antibody composition, such as a tissue section or ELISA plate, will generally be washed to remove any non-specifically bound antibody species, allowing only those antibodies specifically bound within the primary immune complexes to be detected.

The detection of immunocomplex formation is well known in the art and may be achieved through the application of numerous approaches. These methods are generally based upon the detection of a label or marker, such as any radioactive, fluorescent, biological or enzymatic tags or labels known in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. The use of enzymes that generate a colored product upon contact with a chromogenic substrate are generally preferred. Secondary binding ligands, such as a second antibody or a biotin/avidin ligand binding arrangement, may also be used, as is known in the art.

The antibodies of the invention, such as 9D2 and 3G4 (ATCC 4545), employed in the detection may themselves be linked to a detectable label, wherein one would then simply detect this label, thereby allowing the amount of the primary immune complexes in the composition to be determined.

Preferably, the primary immune complexes are detected by means of a second binding ligand that has binding affinity for the antibodies of the invention. In such cases, the second binding ligand may be linked to a detectable label. The second binding ligand is itself often an antibody, and may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if desired.

Clinical diagnosis or monitoring may be applied to patients with a variety of diseases, particularly those associated with increased aminophospholipid and/or anionic phospholipid exposure at the cell surface. The detection of an aminophospholipid and/or anionic phospholipid, or an increase in the levels of an aminophospholipid and/or anionic phospholipid, in comparison to the levels in a corresponding biological sample from a normal subject, is indicative of a patient with such a disease.

However, as is known to those of skill in the art, such a clinical diagnosis would not likely be made on the basis of this method in isolation. Those of skill in the art are very familiar with differentiating between significant expression of a biomarker, which represents a positive identification, and low level or background expression of a biomarker. Indeed, background expression levels are often used to form a "cut-off" above which increased staining will be scored as significant or positive.

L2. In Vivo Imaging

The present invention provides a variety of in vivo diagnostic and imaging embodiments. Certain aspects of the invention concern new and surprisingly effective compositions for in vivo diagnosis and imaging. For example, any one or more of the panel of new anti-PS antibodies of the invention, preferably the 9D2 or 3G4 (ATCC 4545) antibodies or competing antibodies with like properties, are linked to an in vivo detectable agent to form an immunodiagnostic conjugate of the invention. Although the antibodies represent an important development in the field, the resultant immunodiagnostics may now be used in any previously described diagnostic or imaging embodiment connected with the detection of an aminophospholipid and/or anionic phospholipid.

In this regard, immunodiagnostics comprising an antibody of the invention, including the 9D2 or 3G4 (ATCC 4545) antibodies or competing antibodies with like properties, may be used in imaging vascular thromboses, particularly in or near the heart, such as in deep vein thrombosis, pulmonary embolism, myocardial infarction, atrial fibrillation, problems with prosthetic cardiovascular materials, stroke, and the like. Such compositions of the invention may also be used in imaging activated platelets, e.g., in conditions such as abscesses, restenosis, inflammation of joints and in hemostatic disorders, such as arterial, coronary, venous and cerebral thrombosis and the like. The immunodiagnostic compositions of the invention, preferably those comprising the 9D2 or 3G4 (ATCC 4545) antibodies or competing antibodies with like properties, may also be used in detecting apoptotic cells, as may be used in the diagnosis and imaging of a variety of diseases in which increased or inappropriate apoptosis occurs.

The invention further provides a range of new methods for in vivo diagnosis and imaging, which are not limited to the use of the panel of antibodies provided herein. For example, in light of the unexpected finding that anionic phospholipids such as PI, PA and PG are accessible and stably targetable markers of tumor vasculature, the invention provides methods for diagnosing and imaging tumors comprising administration of an immunodiagnostic that binds to PI, PA or PG, which will specifically localize to the vasculature of solid tumors. In addition, virally infected cells can now be detected, and viral infections diagnosed, using an immunodiagnostic conjugate that binds to an aminophospholipid and/ or an anionic phospholipid, such as PS, PE, PI, PA and PG, and preferably PS and PE.

The in vivo imaging compositions and methods of the invention can be used in imaging per se, or in pre-imaging a site in the body to form a reliable image prior to treatment. Preferably, the imaging is tumor imaging. These compositions and methods can also be applied to imaging and diagnosis of other diseases or conditions associated with aminophospholipids and anionic phospholipids, such those involving cell activation and/or apoptosis, including angiogenic diseases, atherosclerosis, viral infections, and other such conditions in which an internal image is desired for diagnostic or prognostic purposes or to design treatment.

In these embodiments, antibodies and peptides, preferably the antibodies of the invention, such as the 9D2, 3G4 (ATCC 4545) and like antibodies, are operatively attached, linked or conjugated to a detectable label. "Detectable labels" are compounds or elements that can be detected due to their specific functional properties, or chemical characteristics, the use of which allows the component to which they are attached to be detected, and further quantified if desired. In antibody and peptide conjugates for in vivo diagnostic protocols or "imaging methods", the labels can be detected using non-invasive methods.

Many appropriate imaging agents are known in the art, as are methods for their attachment to antibodies and binding ligands (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

An example of detectable labels are the paramagnetic ions. In this case, suitable ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III). Fluorescent labels include rhodamine, fluorescein and renographin. Rhodamine and fluorescein are often linked via an isothiocyanate intermediate.

In the case of radioactive isotopes for diagnostic applications, suitable examples include $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technetium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled antibodies and peptides for use in the present invention may be produced according to well-known methods in the art. For instance, intermediary functional groups that are often used to bind radioisotopic metallic ions to antibodies are diethylenetriaminepentaacetic acid (DTPA) and ethylene diaminetetraacetic acid (EDTA).

Monoclonal antibodies can also be iodinated by contact with sodium or potassium iodide and a chemical oxidizing agent such as sodium hypochlorite, or an enzymatic oxidizing agent, such as lactoperoxidase. Anti-tumor antibodies according to the invention may be labeled with technetium-$^{99}$ by a ligand exchange process, for example, by reducing pertechnate with stannous solution, chelating the reduced technetium onto a Sephadex column and applying the antibody to this column. Direct labeling techniques are also suitable, e.g., by incubating pertechnate, a reducing agent such as $SNCl_2$, a buffer solution such as sodium-potassium phthalate solution, and the antibody.

Any of the foregoing type of detectably labeled antibodies and binding ligands may be used in the imaging aspects of the invention, either for imaging alone or to form an image of a disease site or tumor prior to treatment. Either way, the methods generally comprise administering to an animal or patient a diagnostically effective amount of an antibody or binding ligand that is conjugated to a marker that is detectable by non-invasive methods. The antibody-or binding ligand-marker conjugate is allowed sufficient time to localize and bind to cells expressing aminophospholipids and/or anionic phospholipids in the disease site, such as the tumor or tumor vasculature. The patient is then exposed to a detection device to identify the detectable marker, thus forming an image of the disease site or tumor.

The nuclear magnetic spin-resonance isotopes, such as gadolinium, are detected using a nuclear magnetic imaging device; and radioactive substances, such as technicium$^{99m}$ or indium$^{111}$, are detected using a gamma scintillation camera or detector. U.S. Pat. No. 5,627,036 is also specifically incorporated herein by reference for purposes of providing even further guidance regarding the safe and effective introduction of detectably labeled constructs into the blood of an individual, and means for determining the distribution of the detectably labeled agent extracorporally, e.g., using a gamma scintillation camera or by magnetic resonance measurement.

Dosages for imaging embodiments are generally less than for therapy, but are also dependent upon the age and weight of a patient. A one time dose of between about 0.1, 0.5 or about 1 mg and about 9 or 10 mgs, and more preferably, of between about 1 mg and about 5-10 mgs of antibody-or binding ligand-conjugate per patient is contemplated to be useful.

L3. Surrogate Marker for Cancer Therapy

In regard to the in vivo diagnostic and imaging, the present invention further provides compositions and methods for use as a surrogate marker for cancer therapy. Such embodiments concern the use of an antibody that binds to an aminophospholipid and/or an anionic phospholipid, preferably PS, and most preferably to the use of the 9D2 or 3G4 (ATCC 4545) antibodies or competing antibodies, linked to an in vivo detectable agent.

Many anti-cancer therapies in current use induce apoptosis and necrosis. Aminophospholipids and anionic phospholipids, particularly PS, are markers of pre-apoptotic and apoptotic cells. Therefore, imaging with a suitable antibody, preferably 9D2, 3G4 (ATCC 4545) or competing antibodies, can be used to identify pre-apoptotic and apoptotic cells and thus provide information regarding the progress of the therapy. This is what is meant by a "surrogate marker for cancer therapy", as used herein.

The use of the antibodies of the invention, preferably those comprising the 9D2 or 3G4 (ATCC 4545) antibodies or competing antibodies with like properties, provides particular advantages as a surrogate marker for cancer therapy. For example, the ability to identify pre-apoptotic cells is a particular advantage. The specificity of the antibodies will also provide more meaningful imaging data for the physician. Also, the safety profile of these antibodies is impressive and provides advantages over annexin, for example, as annexin suffers from drawbacks associated with coagulation.

Accordingly, any of the in vivo diagnostic and imaging methods described above may be adapted for prognostic use as a surrogate marker for cancer therapy simply by use in a patient undergoing cancer therapy.

M. Tumor Treatment

Important aspects of the present invention concern the treatment of malignancies, tumors and vascularized tumors. This includes tumors in which angiogenesis is more or less important and tumors having prothrombotic blood vessels. The treatment of benign tumors is included in the invention, such as acoustic neuroma, neurofibroma, trachoma, pyogenic granulomas and BPH. The treatment of blood-born tumors, such as leukemias, and various acute or chronic neoplastic diseases of the bone marrow is also encompassed.

The present invention is broadly applicable to the treatment of any malignant tumor, whether having a vascular component or not. Tumors for treatment include solid tumors, particularly carcinomas, which require a vascular component for the provision of oxygen and nutrients. Exemplary solid tumors that may be treated using the invention include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, and the like.

The present invention is contemplated for use in the treatment of any patient that presents with a solid tumor. In general, the invention can be used to treat tumors of all sizes, including those about 0.3-0.5 cm and upwards, tumors of greater than 0.5 cm in size and patients presenting with tumors of between about 1.0 and about 2.0 cm in size, although tumors up to and including the largest tumors found in humans may also be treated.

Although the present invention is not generally intended as a preventative or prophylactic treatment, use of the invention is certainly not confined to the treatment of patients having tumors of only moderate or large sizes. There are many reasons underlying these aspects of the invention. For example, a patient presenting with a primary tumor of moderate size or above may also have various other metastatic tumors that are considered to be small-sized or even in the earlier stages of metastatic tumor seeding. Given that the anti-aminophospholipid or anti-anionic phospholipid antibodies or PE-binding peptide derivatives, or combinations, of the invention are generally administered into the systemic circulation of a patient, they will naturally have effects on the secondary, smaller and metastatic tumors, although this may not be the primary intent of the treatment. Furthermore, even in situations where the tumor mass as a whole is a single small tumor, certain beneficial anti-tumor effects will result from the use of the present treatments.

The guidance provided herein regarding the suitable patients for use in connection with the present invention is intended as teaching that certain patient's profiles may assist with the selection of patients for treatment by the present invention. The pre-selection of certain patients, or categories of patients, does not in any way negate the basic usefulness of the present invention in connection with the treatment of all patients having cancer. A further consideration is the fact that the assault on the tumor provided by the antibody therapy of the invention may predispose the tumor to further therapeutic treatment, such that the subsequent treatment results in an overall synergistic effect or even leads to total remission or cure.

It is not believed that any particular type of tumor should be excluded from treatment using the present invention. However, the type of tumor cells may be relevant to the use of the invention in combination with tertiary therapeutic agents, particularly chemotherapeutics and anti-tumor cell immunotoxins. As the present invention includes within its modes of action the targeting and destruction of tumor vasculature, and as the vasculature is substantially or entirely the same in all solid tumors, it will be understood that the present methodology is widely or entirely applicable to the treatment of all solid tumors, irrespective of the particular phenotype or genotype of the tumor cells themselves. The data presented herein is compelling as it shows impressive results in a wide range of different tumor models.

Therapeutically effective doses are readily determinable using data from an animal model, as shown in the studies detailed herein, and from clinical data using a range of therapeutic agents. Experimental animals bearing solid tumors are frequently used to optimize appropriate therapeutic doses prior to translating to a clinical environment. Such models are known to be very reliable in predicting effective anti-cancer strategies. For example, mice bearing solid tumors, such as used in the Examples, are widely used in pre-clinical testing. The inventors have used such art-accepted mouse models to determine working ranges of therapeutic agents that give beneficial anti-tumor effects with minimal toxicity.

In terms of tumor therapy, bearing in mind the attendant safety benefits associated with the overall invention, one may refer to the scientific and patent literature on the success of using other anti-vascular therapies. By way of example, U.S. Pat. Nos. 5,855,866; 5,877,289; 5,965,132; 6,051,230; 6,004,555; 5,776,427; 6,004,554; 6,036,955; and 6,093,399 are incorporated herein by reference for the purpose of further describing the use of such agents as may be applied to those of the present invention. U.S. Pat. Nos. 6,312,694 and 6,406,693 are further specifically incorporated herein by reference for guidance on dosing and treatment using unconjugated antibodies to PS and PE and related immunoconjugates.

As is known in the art, there are realistic objectives that may be used as a guideline in connection with pre-clinical testing before proceeding to clinical treatment. However, due to the safety already demonstrated in accepted models, pre-clinical testing of the present invention will be more a matter of optimization, rather than to confirm effectiveness. Thus, pre-clinical testing may be employed to select the most advantageous agents, doses or combinations.

Any antibody dose, combined method or medicament that results in any consistently detectable anti-tumor effect, including detectable tumor vasculature regression, thrombosis and/or destruction and tumor necrosis, will still define a useful invention. Regressive, thrombotic, destructive and necrotic effects should preferably be observed in between about 10% and about 40-50% of the tumor blood vessels and tumor tissues, upwards to between about 50% and about 99% of such effects being observed. The present invention may also be effective against vessels downstream of the tumor, i.e., target at least a sub-set of the draining vessels, particularly as cytokines released from the tumor will be acting on these vessels, changing their antigenic profile.

It will also be understood that even in such circumstances where the anti-tumor effects of the therapy are towards the low end of this range, it may be that this therapy is still equally or even more effective than all other known therapies in the context of the particular tumor. It is unfortunately evident to a clinician that certain tumors cannot be effectively treated in the intermediate or long term, but that does not negate the usefulness of the present therapy, particularly where it is at least about as effective as the other strategies generally proposed.

In designing appropriate doses of anti-aminophospholipid or anti-anionic phospholipid antibodies, PE-binding peptide derivatives or combined therapeutics for the treatment of vascularized tumors, one may readily extrapolate from the animal studies described herein in order to arrive at appropriate doses for clinical administration. To achieve this conversion, one would account for the mass of the agents administered per unit mass of the experimental animal and, preferably, account for the differences in the body surface area between the experimental animal and the human patient. All such calculations are well known and routine to those of ordinary skill in the art.

For example, in taking the successful doses of therapeutics used in the mouse studies, and applying standard calculations based upon mass and surface area, effective doses of agents for use in human patients would be between about 1 mg and about 500 mgs antibody per patient, and preferably, between about 10 mgs and about 100 mgs antibody per patient.

Accordingly, using this information, the inventors contemplate that useful low doses for human administration will be about 1, 2, 3, 4, 5, 6, 7, 8, 9, 10, 15, 20, 25 or about 30 mgs or so per patient; and useful high doses for human administration will be about 250, 275, 300, 325, 350, 375, 400, 425, 450, 475 or about 500 mgs or so per patient. Useful intermediate doses for human administration are contemplated to be about 35, 40, 50, 60, 70, 80, 90, 100, 125, 150, 175, 200 or about 225 mgs or so per patient. In general, dosage ranges of between about 5-100 mgs, about 10-80 mgs, about 20-70 mgs, about 25-60 mgs, or about 30-50 mgs per patient will be preferred. However, any particular range using any of the foregoing recited exemplary doses or any value intermediate between the particular stated ranges is contemplated.

Notwithstanding the stated ranges, it will be understood that, given the parameters and detailed guidance presented herein, further variations in the active or optimal ranges will be encompassed within the present invention. It will thus be understood that lower doses may be more appropriate in combination with certain agents, and that high doses can still be tolerated, particularly given the enhanced safety of the present constructs. The use of human or humanized antibodies and human effectors renders the present invention even safer for clinical use, further reducing the chances of significant toxicity or side effects in healthy tissues.

The intention of the therapeutic regimens of the present invention is generally to produce significant anti-tumor effects whilst still keeping the dose below the levels associated with unacceptable toxicity. In addition to varying the dose itself, the administration regimen can also be adapted to optimize the treatment strategy. A currently preferred treatment strategy is to administer between about 1-500 mgs, and preferably, between about 10-100 mgs of the antibody, or therapeutic cocktail containing such, about 3 times within about a 7 day period. For example, doses would be given on about day 1, day 3 or 4 and day 6 or 7.

In administering the particular doses themselves, one would preferably provide a pharmaceutically acceptable composition (according to FDA standards of sterility, pyrogenicity, purity and general safety) to the patient systemically. Intravenous injection is generally preferred, and the most preferred method is to employ a continuous infusion over a time period of about 1 or 2 hours or so. Although it is not required to determine such parameters prior to treatment using the present invention, it should be noted that the studies detailed herein result in at least some thrombosis being observed specifically in the blood vessels of a solid tumor within about 12-24 hours of injection, and that the tumor cells themselves begin to die within about 24 to 72 hours. Widespread tumor necrosis is generally observed in the next about 48-96 hours, up to and including greater than 60% necrosis being observed.

Naturally, before wide-spread use, clinical trials will be conducted. The various elements of conducting a clinical trial, including patient treatment and monitoring, will be known to those of skill in the art in light of the present disclosure. The following information is being presented as a general guideline for use in establishing such trials.

Patients chosen for the first treatment studies will have failed to respond to at least one course of conventional therapy, and will have objectively measurable disease as determined by physical examination, laboratory techniques, and/or radiographic procedures. Any chemotherapy should be stopped at least 2 weeks before entry into the study. Where murine monoclonal antibodies or antibody portions are employed, the patients should have no history of allergy to mouse immunoglobulin.

Certain advantages will be found in the use of an indwelling central venous catheter with a triple lumen port. The therapeutics should be filtered, for example, using a 0.22μ filter, and diluted appropriately, such as with saline, to a final volume of 100 ml. Before use, the test sample should also be filtered in a similar manner, and its concentration assessed before and after filtration by determining the $A_{280}$. The expected recovery should be within the range of 87% to 99%, and adjustments for protein loss can then be accounted for.

The constructs may be administered over a period of approximately 4-24 hours, with each patient receiving 2-4 infusions at 2-7 day intervals. Administration can also be performed by a steady rate of infusion over a 7 day period. The infusion given at any dose level should be dependent upon any toxicity observed. Hence, if Grade II toxicity was reached after any single infusion, or at a particular period of time for a steady rate infusion, further doses should be withheld or the steady rate infusion stopped unless toxicity improved. Increasing doses should be administered to groups of patients until approximately 60% of patients showed unacceptable Grade III or IV toxicity in any category. Doses that are ⅔ of this value are defined as the safe dose.

Physical examination, tumor measurements, and laboratory tests should, of course, be performed before treatment and at intervals up to 1 month later. Laboratory tests should include complete blood counts, serum creatinine, creatine kinase, electrolytes, urea, nitrogen, SGOT, bilirubin, albumin, and total serum protein. Serum samples taken up to 60 days after treatment should be evaluated by radioimmunoassay for the presence of the administered construct, and antibodies against any portions thereof. Immunological analyses of sera, using any standard assay such as, for example, an ELISA or RIA, will allow the pharmacokinetics and clearance of the therapeutics to be evaluated.

To evaluate the anti-tumor responses, the patients should be examined at 48 hours to 1 week and again at 30 days after the last infusion. When palpable disease was present, two perpendicular diameters of all masses should be measured daily during treatment, within 1 week after completion of therapy, and at 30 days. To measure nonpalpable disease, serial CT scans could be performed at 1-cm intervals throughout the chest, abdomen, and pelvis at 48 hours to 1 week and again at 30 days. Tissue samples should also be evaluated histologically, and/or by flow cytometry, using biopsies from the disease sites or even blood or fluid samples if appropriate.

Clinical responses may be defined by acceptable measure. For example, a complete response may be defined by the disappearance of all measurable tumor 1 month after treatment. Whereas a partial response may be defined by a 50% or greater reduction of the sum of the products of perpendicular diameters of all evaluable tumor nodules 1 month after treatment, with no tumor sites showing enlargement. Similarly, a mixed response may be defined by a reduction of the product of perpendicular diameters of all measurable lesions by 50% or greater 1 month after treatment, with progression in one or more sites.

In light of results from clinical trials, such as those described above, an even more precise treatment regimen may be formulated. Even so, some variation in dosage may later be necessary depending on the condition of the subject being treated. The physician responsible for administration will, in light of the present disclosure, be able to determine the appropriate dose for the individual subject. Such optimization and adjustment is routinely carried out in the art, and by no means reflects an undue amount of experimentation.

N. Combination Tumor Therapies

The treatment methods of the present invention may be combined with any other methods generally employed in the treatment of the particular tumor, disease or disorder that the patient exhibits. So long as a particular therapeutic approach is not known to be detrimental to the patient's condition in itself, and does not significantly counteract the anti-aminophospholipid or anti-anionic phospholipid-based treatment of the invention, its combination with the present invention is contemplated.

Combination therapy for non malignant diseases is also contemplated. A particular example of such is benign prostatic hyperplasia (BPH), which may be treated in combination other treatments currently practiced in the art. For example, targeting of immunotoxins to markers localized within BPH, such as PSA.

In connection solid tumor treatment, the present invention may be used in combination with classical approaches, such as surgery, chemotherapy, radiotherapy, cytokine therapy, anti-angiogenesis and the like. The invention therefore provides combined therapies in which the antibodies, immunoconjugates or peptide conjugates are used simultaneously with, before, or after surgery or radiation treatment; or are administered to patients with, before, or after conventional chemotherapeutic or radiotherapeutic agents, cytokines, anti-angiogenic agents, apoptosis-inducing agents, targeted immunotoxins or coaguligands or such like. Many examples of suitable therapeutic agents have been described above in connection with the immunoconjugate aspects of the present invention. Any of the agents initially described for use as one part of a therapeutic conjugate may also be used separately, in the combination therapies of the present invention.

In terms of surgery, any surgical intervention may be practiced in combination with the present invention. In connection with radiotherapy, any mechanism for inducing DNA damage locally within tumor cells is contemplated, such as γ-irradiation, X-rays, UV-irradiation, microwaves and even electronic emissions and the like. The directed delivery of radioisotopes to tumor cells is also contemplated, and this may be used in connection with a targeting antibody or other targeting means.

The general use of combinations of substances in cancer treatment is well known. For example, U.S. Pat. No. 5,710, 134 (incorporated herein by reference) discloses components that induce necrosis in tumors in combination with non-toxic substances or "prodrugs". The enzymes set free by necrotic processes cleave the non-toxic "prodrug" into the toxic "drug", which leads to tumor cell death. Also, U.S. Pat. No. 5,747,469 (incorporated herein by reference) discloses the combined use of viral vectors encoding p53 and DNA damaging agents. Any such similar approaches can be used with the present invention.

When one or more agents are used in combination with the antibodies, immunoconjugates and peptide-based therapeutics of the present invention, there is no requirement for the combined results to be additive of the effects observed when each treatment is conducted separately. Although at least additive effects are generally desirable, any increased anti-tumor effect above one of the single therapies would be of benefit. Also, there is no particular requirement for the combined treatment to exhibit synergistic effects, although this is certainly possible and advantageous.

N1. Selection of Second Anti-Cancer Agents

The "primary therapeutic agents" of the present invention, as used herein, are anti-aminophospholipid or anti-anionic phospholipid antibodies, immunoconjugates or PE-binding peptide derivatives and conjugates. The "secondary therapeutic agents", as used herein, are second, distinct therapeutic agents or anti-cancer agents, i.e., therapeutic agents or anti-cancer agents "other than" the primary therapeutic agent. Any secondary therapeutic agent may be used in the combination therapies of the present invention. Also, secondary therapeutic agents or "second anti-cancer agents" may be selected with a view to achieving additive, greater than additive and potentially synergistic effects, according to the following guidance.

To practice combined anti-tumor therapy, one would simply administer to an animal or patient an anti-aminophospholipid or anti-anionic phospholipid antibody, immunoconjugate or PE-binding peptide-based therapeutic of the present invention in combination with another, i.e., a second, distinct anti-cancer agent in a manner effective to result in their combined anti-tumor actions within the animal or patient. The agents would therefore be provided in amounts effective and for periods of time effective to result in their combined presence within the tumor or tumor vasculature and their combined actions in the tumor environment. To achieve this goal, the primary therapeutics of the present invention and the second, distinct anti-cancer agents may be administered to the animal substantially simultaneously, either in a single composition, or as two distinct compositions using different administration routes.

Alternatively, the anti-aminophospholipid or anti-anionic phospholipid antibody, immunoconjugate or PE-binding peptide-based therapeutic of the present invention may precede, or follow, the second, distinct anti-cancer agent by, e.g., intervals ranging from minutes to weeks. In certain embodiments where the primary therapeutics of the present invention and the second, distinct anti-cancer agents are applied separately to the animal, one would ensure that a significant period of time did not expire between the time of each delivery, such that each agent would still be able to exert an advantageously combined effect on the tumor. In such instances, it is contemplated that one would contact the tumor with both agents within about 5 minutes to about one week of each other and, more preferably, within about 12-72 hours of each other, with a delay time of only about 12-48 hours being most preferred.

The secondary therapeutic agents for separately timed combination therapies may be selected based upon certain criteria, including those discussed below. However, a preference for selecting one or more second, distinct anti-cancer agents for prior or subsequent administration does not preclude their use in substantially simultaneous administration if desired.

Second, distinct anti-cancer agents selected for administration "prior to" the primary therapeutic agents of the present invention, and designed to achieve increased and potentially synergistic effects, include agents that induce the expression of aminophospholipids or anionic phospholipids within the tumor vasculature. For example, agents that stimulate localized calcium production, activate membrane transporters that move PS and other phospholipids to the outer surface of the plasma membrane, injure the tumor endothelium, cause preapoptotic changes and/or induce apoptosis in the tumor endothelium will generally result in increased aminophospholipid and anionic phospholipid expression. Examples of such agents are docetaxel and paclitaxol. The aminophospholipids and anionic phospholipids can then be targeted using an antibody of the invention, thus amplifying the overall therapeutic effect, and also giving increased attack via host effectors (complement, ADCC, antibody-mediated phagocytosis, CDC).

Drugs that have selectivity for angiogenic, remodeling or activated endothelial cells, such as are present in tumor blood vessels, but not in normal resting blood vessels, can also be used to selectively causes exposure of PS and other phospholipids on the surface of tumor endothelial cells. Examples of such agents are combretastatins and docetaxel. This again would lead to increased antibody binding and enhanced initiation of host effector mechanisms.

Second, distinct anti-cancer agents selected for administration "subsequent to" the primary therapeutic agents of the present invention, and designed to achieve increased and potentially synergistic effects, include agents that benefit from the effects of the primary therapeutic agent. The anti-aminophospholipid or anti-anionic phospholipid antibody, immunoconjugate or peptide-based therapeutic of the present invention will cause tumor destruction. Accordingly, effective second, distinct anti-cancer agents for subsequent administration include anti-angiogenic agents, which inhibit metastasis; agents targeting necrotic tumor cells, such as antibodies specific for intracellular antigens that become accessible from malignant cells in vivo (U.S. Pat. Nos. 5,019,368, 4,861,581 and 5,882,626, each specifically incorporated herein by reference); and chemotherapeutic agents and anti-tumor cell immunoconjugates, which attack any tumor cells that may survive at the periphery.

In some situations, it may be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as the primary therapeutic agent of the present invention, and another treatment was intended to prevent micrometastasis or tumor re-growth, such as the administration of an anti-angiogenic agent. Anti-angiogenics should be administered at a careful time after surgery, however, to allow effective wound healing. Anti-angiogenic agents may then be administered for the lifetime of the patient.

It is also envisioned that more than one administration of either the primary therapeutic agent or the second, distinct anti-cancer agent will be utilized. The primary therapeutic agent and the second, distinct anti-cancer agent may be administered interchangeably, on alternate days or weeks; or a sequence of one agent treatment may be given, followed by a sequence of the other treatment. In any event, to achieve tumor regression using a combined therapy, all that is required is to deliver both agents in a combined amount effective to exert an anti-tumor effect, irrespective of the times for administration.

Whether administered substantially simultaneously or sequentially, the anti-aminophospholipid and anti-anionic phospholipid antibodies and therapeutics of the present invention may be administered in combination with one or more chemotherapeutic agents or drugs. Chemotherapeutic drugs can kill proliferating tumor cells, enhancing the necrotic areas created by the overall treatment. The drugs can thus enhance the thrombotic action of the primary therapeutic agents of the invention.

Most cancer chemotherapeutic drugs are selective for dividing, oxygenated cells. These have advantages in combined therapy as the chemotherapeutic drug acts on different targets from the primary therapeutic agents of the invention, leading to a more complete anti-vascular or anti-tumor effect. For example, chemotherapeutic drugs are selectively active against the rapidly dividing, oxygenated tumor cells in the tumor periphery, whereas the agents of the invention act primarily on vessels or tumor cells in the 'stressed' tumor core, where activating reactive oxygen species are abundant. Anti-angiogenic drugs that are selective for well-oxygenated, angiogenic vessels in the tumor periphery would also be effective in combination, as the agents of the invention act on the relatively hypoxic, quiescent vessels in the tumor core.

By inducing the formation of thrombi in tumor vessels, the primary therapeutic agents of the present invention can also enhance the action of the chemotherapeutic drugs by retaining or trapping the drugs within the tumor. The chemotherapeutics are thus retained within the tumor, while the rest of the drug is cleared from the body. Tumor cells are thus exposed to a higher concentration of drug for a longer period of time. This entrapment of drug within the tumor makes it possible to reduce the dose of drug, making the treatment safer as well as more effective.

Further drugs for combined use in the present invention are those that act on cells that are "sensitized" to the drug by the action of the primary therapeutic agent, such that reduced doses of the second drug are needed to achieve its anti-tumor effect. For example, this could occur where a major component of the second drug's action is exerted on tumor vessels and the antibodies or agents of the invention sensitize the cells to the drug. The same is true where the primary therapeutic agent of the invention sensitizes tumor cells to a second drug, either directly or through stimulation of cytokine release.

Other suitable second anti-cancer agents for combination therapy are those that enhance the activity of host effector cells, e.g., by selectively inhibiting the activity of immunosuppressive components of the immune system. Such agents enable the primary therapeutic agents of the invention, which stimulate attack by effector cells as part of their mechanism, to work more aggressively. An example of such an agent is docetaxel.

Although an understanding of the precise mechanism(s) of action of the primary therapeutic agents is not necessary to practice the treatment of the invention, data and reasoned deductions concerning such mechanisms can be used to select particular second anti-cancer agents for combined use in the present invention. The effectiveness of the chosen combination therapy, in turn, supports the original data and proposed mechanisms of action, and also leads to preferred categories of second anti-cancer agents for practicing combination therapy.

Drugs that induce apoptosis are preferred for use in the combination therapies. Docetaxel, for example, induces apoptosis and therefore PS exposure by binding to microtubules and disrupting cell mitosis (Hotchkiss et al., 2002). Treatment of endothelial cells, which line tumor blood vessels, and tumor cells with docetaxel at subclinical concentrations is herein shown to induce PS expression at the cell surface, as demonstrated by strong binding of the 3G4 antibody in vitro.

The present inventors have also determined that the anti-tumor effects of the antibodies of the invention include Fc domain-mediated augmentation of immune effector functions, as shown by increased antibody-mediated phagocytosis. Therefore, the antibodies should also exert other Fc domain-mediated functions, such as ADCC, CDC, stimulation of cytokine production, and such mechanisms in combination. This is also relevant to docetaxel, as other studies have shown that the treatment of breast cancer patients with docetaxel leads to increases in serum IFN-γ, IL-2, IL-6 and GM-CSF cytokine levels, augmenting the anti-tumor immune responses in these patients by enhancing the activity of natural killer (NK) and lymphokine activated killer (LAK) cells (Tsavaris et al., 2002).

Therefore, the inventors reasoned that docetaxel will both induce PS expression and binding of the administered antibody, and also enhances the activities of immune effectors, which mediate anti-tumor effects. Based upon the foregoing considerations, the inventors have shown that combination of the antibodies of the present invention, as exemplified by the 3G4 antibody, with docetaxel was significantly superior to either docetaxel or 3G4 alone in mice bearing orthotopic MDA-MB-435 human breast cancer xenografts (Example XX).

Accordingly, docetaxel and other chemotherapeutic agents that induce apoptosis are preferred agents for use in the combination treatments of the present invention. Combinations of antibodies to aminophospholipids and/or anionic phospholipids with chemotherapeutics drugs that induce apoptosis, such as docetaxel, should synergistically attack tumor vasculature endothelial cell and tumor cell compartments, leading to not only significantly enhanced treatment efficacy but also lower toxicity. These combinations are contemplated for use in breast cancer treatment, particularly the combination of metronomic chemotherapy using docetaxel with an antibody of the present invention.

N2. Endotoxin

Endotoxin and detoxified endotoxin derivatives may be used in the combination treatment, preferably at low doses (PCT Publication No. WO 03/028840, specifically incorporated herein by reference). Various detoxified endotoxins are available, which are preferred for use in animals and particularly for use in humans. Detoxified and refined endotoxins, and combinations thereof, are described in U.S. Pat. Nos. 4,866,034; 4,435,386; 4,505,899; 4,436,727; 4,436,728; 4,505,900, each specifically incorporated herein by reference.

The non-toxic derivative monophosphoryl lipid A (MPL) is one example of a detoxified endotoxin that may be used in the present invention. MPL is known to be safe for humans; clinical trials using MPL as an adjuvant have shown 100 μg/m$^2$ to be safe for human use, even on an outpatient basis.

N3. Cytokines

Cytokine therapy has proven to be an effective partner for combined therapeutic regimens. Various cytokines may be employed in the combined approaches of the present invention. Examples of cytokines include IL-1α, IL-1β, IL-2, IL-3, IL-4, IL-5, IL-6, IL-7, IL-8, IL-9, IL-10, IL-11, IL-12, IL-13, TGF-β, GM-CSF, M-CSF, G-CSF, TNFα, TNFβ, LAF, TCGF, BCGF, TRF, BAF, BDG, MP, LIF, OSM, TMF, PDGF, IFN-α, IFN-β, IFN-γ. Cytokines are administered according to standard regimens, consistent with clinical indications such as the condition of the patient and relative toxicity of the cytokine. Uteroglobins may also be used to prevent or inhibit metastases (U.S. Pat. No. 5,696,092; incorporated herein by reference).

N4. TNFα and Inducers of TNFα

TNFα and inducers of TNFα may also be used in combination with the present invention. TNFα increases vascular permeability, and is therefore useful in facilitating the penetration of anti-cancer agents into the tumor. Although antibody localization is by no means a problem when targeting aminophospholipid and anionic phospholipids, as in the present invention, the combined use of TNFα can facilitate access of other chemotherapeutics and immunoconjugates to the tumor, and even increase binding of the antibodies of the invention to far distant tumor cells.

Low levels of endotoxin, Rac1 antagonists, such as an attenuated or engineered adenovirus, DMXAA (and FAA), CM101 and thalidomide may also be used. Rac1 antagonists may be used in the combined treatment of the present invention, as about 5000 DNA particles per cell cause TNF upregulation independent of CD14 (Sanlioglu et al., 2001). CM101, thalidomide and DMXAA can also be used in combination herewith, at standard or reduced doses.

N5. Chemotherapeutics

Irrespective of the underlying mechanism(s), a variety of chemotherapeutic agents may be used in the combined treatment methods disclosed herein. Chemotherapeutic agents contemplated for combined use include, e.g., tamoxifen, taxol, vinblastine, etoposide (VP-16), adriamycin, 5-fluorouracil (5FU), camptothecin, actinomycin-D, mitomycin C, combretastatin(s), more particularly docetaxel (taxotere), cisplatin (CDDP), cyclophosphamide, doxorubicin, methotrexate, paclitaxel and vincristine, and derivatives and prodrugs thereof.

As will be understood by those of ordinary skill in the art, appropriate doses of chemotherapeutic agents include those already employed in clinical therapies wherein the chemotherapeutics are administered alone or in combination with other chemotherapeutics. However, lower doses are now possible due to the advantages provided by the present invention. By way of example only, agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis, chromosomal segregation and/or tubulin activity. Such chemotherapeutic compounds include adriamycin, also known as doxorubicin, etoposide, verapamil, podophyllotoxin(s), combretastatin(s) and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Exemplary chemotherapeutic agents that are useful in connection with combined therapy are listed in Table D. Each of the agents listed therein are exemplary and by no means limiting. The skilled artisan is directed to "Remington's Pharmaceutical Sciences" 15th Edition, chapter 33, in particular pages 624-652. Some variation in dosage will necessarily occur depending on the condition of the subject being treated. The physician responsible for administration will be able to determine the appropriate dose for the individual subject.

TABLE D

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan (L-sarcolysin) | Multiple myeloma, breast, ovary |
| | | Chlorambucil | Chronic lymphocytic leukemia, primary macroglobulinemia, Hodgkin's disease, non-Hodgkin's lymphomas |
| | Ethylenimenes and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) | Malignant pancreatic insulinoma, malignant carcinoid |
| | Triazines | Dacarbazine (DTIC; dimethyltriazenoimidazolecarboxamide) | Malignant melanoma, Hodgkin's disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Analogs | Fluouracil (5-fluorouracil; 5-FU) | Breast, colon, stomach, pancreas, ovary, head and neck, urinary bladder, premalignant skin lesions (topical) |
| | | Floxuridine (fluorodeoxyuridine; FUdR) | |
| | | Cytarabine (cytosine arabinoside) | Acute granulocytic and acute lymphocytic leukemias |
| | | Mercaptopurine | Acute lymphocytic, acute granulocytic |

TABLE D-continued

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
|---|---|---|---|
| | | (6-mercaptopurine; 6-MP) | and chronic granulocytic leukemias |
| | Purine Analogs and Related Inhibitors | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide | Testis, small-cell lung and other lung, breast, Hodgkin's disease, non-Hodgkin's lymphomas, acute granulocytic leukemia, Kaposi's sarcoma |
| | | Tertiposide | |
| | Antibiotics | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung and genitourinary tract; Hodgkin's disease, non-Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia., Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) | Testis, ovary, bladder, head and neck, lung, thyroid, cervix, endometrium, neuroblastoma, osteogenic sarcoma |
| | | Carboplatin | |
| | Anthracenedione | Mitoxantrone | Acute granulocytic leukemia, breast |
| | Substituted Urea | Hydroxyurea | Chronic granulocytic leukemia, polycythemia vera, essential thrombocytosis, malignant melanoma |
| | Methyl Hydrazine Derivative | Procarbazine (N-methylhydrazine, MIH) | Hodgkin's disease |
| | Adrenocortical Suppressant | Mitotane (o,p'-DDD) | Adrenal cortex |
| | | Aminoglutethimide | Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |
| | Progestins | Hydroxyprogesterone caproate | Endometrium, breast |
| | | Medroxyprogesterone acetate | |
| | | Megestrol acetate | |
| | Estrogens | Diethylstilbestrol | Breast, prostate |
| | | Ethinyl estradiol (other preparations available) | |
| | Antiestrogen | Tamoxifen | Breast |
| | Androgens | Testosterone propionate | Breast |
| | | Fluoxymesterone (other preparations available) | |

TABLE D-continued

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
|---|---|---|---|
| | Antiandrogen | Flutamide | Prostate |
| | Gonadotropin-releasing hormone analog | Leuprolide | Prostate |

N6. Anti-Angiogenics

The term "angiogenesis" refers to the generation of new blood vessels, generally into a tissue or organ. Under normal physiological conditions, humans or animals undergo angiogenesis only in specific restricted situations. For example, angiogenesis is normally observed in wound healing, fetal and embryonic development and formation of the corpus luteum, endometrium and placenta. New evidence, however, shows that angiogenesis is important in certain normal situations, such as in adrenal tissue, prostate and ovary. The therapeutic agents of the present invention, in which anti-angiogenesis is not the only mode of action, thus have advantages over prominent anti-angiogenic therapies, such as antibody A4.6.1 (Brem, 1998; Baca et al., 1997; Presta et al., 1997), in that desirable or "physiological" angiogenesis will not be inhibited when using the present invention.

Uncontrolled (persistent and/or unregulated) angiogenesis is related to various disease states, and occurs during tumor development and metastasis. Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Despite the new evidence that angiogenesis is required in some normal tissues, anti-angiogenic therapies are still important in the treatment of tumors and other diseases. Anti-angiogenic therapies are therefore intended for use in the combination treatments of the present invention. The combination of a low, relatively frequent dose of a therapeutic agent of the present invention in combination with an agent that inhibits angiogenesis is particularly contemplated. Exemplary anti-angiogenic agents that are useful in connection with combined therapy are listed above (in connection with immunoconjugates). Any one or more of such agents, including those in Table B, may be used in combination therapy with the invention. Angiostatin, endostatin, vasculostatin, canstatin and maspin are currently preferred.

Many known anti-cancer agents also have an anti-angiogenic effect as part of their mechanism of action. These agents, as exemplified by those in Table E, are particularly contemplated for use in the combination therapy aspects of the present invention (they may also be conjugated to an antibody of the invention, as described above).

TABLE E

Anti-Cancer Agents with Anti-Angiogenic Activity

| Class or Type of Agent | Examples |
|---|---|
| Alkylators | Cyclophosphamide, edelfosine, estramustine, melphalan |
| Antimetabolites | Fluorouracil, methotrexate, mercaptopurine, UFT, tegafur, uracil, cytarabine |
| Anti-Tumor Antibiotics | Bleomycin, daunorubicin, doxorubicin, epirubicin, mitomycin, mitoxantrone |
| Topoisomerase Inhibitors | Camptothecin, irinotecan, etoposide, topotecan |
| Taxanes | Docetaxel, paclitxael |
| Vinca Alkaloids | Vinblastine, vincristine |
| Miscellaneous | Cisplatin, octreotide |

In addition, the antibody LM609 against the $\alpha_v\beta_3$ integrin also induces tumor regressions and may be used in combination therapies. Integrin $\alpha_v\beta_3$ antagonists, such as LM609, induce apoptosis of angiogenic endothelial cells leaving the quiescent blood vessels unaffected. LM609 or other $\alpha_v\beta_3$ antagonists may also work by inhibiting the interaction of $\alpha_v\beta_3$ and MMP-2, a proteolytic enzyme thought to play an important role in migration of endothelial cells and fibroblasts.

Apoptosis of the angiogenic endothelium by LM609 may have a cascade effect on the rest of the vascular network. Inhibiting the tumor vascular network from completely responding to the tumor's signal to expand may, in fact, initiate the partial or full collapse of the network resulting in tumor cell death and loss of tumor volume. It is possible that endostatin and angiostatin function in a similar fashion. The fact that LM609 does not affect quiescent vessels but is able to cause tumor regressions suggests strongly that not all blood vessels in a tumor need to be targeted for treatment in order to obtain an anti-tumor effect.

Antibodies to angiogenin may also be employed, as described in U.S. Pat. No. 5,520,914, specifically incorporated herein by reference. As FGF is connected with angiogenesis, FGF inhibitors may also be used. Certain examples are the compounds having N-acetylglucosamine alternating in sequence with 2-O-sulfated uronic acid as their major repeating units, including glycosaminoglycans, such as archaran sulfate. Such compounds are described in U.S. Pat. No. 6,028,061, specifically incorporated herein by reference, and may be used in combination herewith.

N7. VEGF Inhibitors

VEGF is a multifunctional cytokine that is induced by hypoxia and oncogenic mutations. VEGF is a primary stimulant of the development and maintenance of a vascular network in embryogenesis. It functions as a potent permeability-inducing agent, an endothelial cell chemotactic agent, an endothelial survival factor, and endothelial cell proliferation factor. Its activity is required for normal embryonic development, as targeted disruption of one or both alleles of VEGF results in embryonic lethality.

The use of one or more VEGF inhibition methods is a preferred aspect of the combination therapies of the present invention. The recognition of VEGF as a primary stimulus of angiogenesis in pathological conditions has led to various methods to block VEGF activity. Any of the VEGF inhibitors developed may now be advantageously employed herewith. Accordingly, any one or more of the following neutralizing anti-VEGF antibodies, soluble receptor constructs, antisense strategies, RNA aptamers and tyrosine kinase inhibitors designed to interfere with VEGF signaling may thus be used.

Suitable agents include neutralizing antibodies (Kim et al., 1992; Presta et al., 1997; Sioussat et al., 1993; Kondo et al., 1993; Asano et al., 1995), soluble receptor constructs (Kendall and Thomas, 1993; Aiello et al., 1995; Lin et al., 1998; Millauer et al., 1996), tyrosine kinase inhibitors (Siemeister et al., 1998), antisense strategies, RNA aptamers and ribozymes against VEGF or VEGF receptors (Saleh et al., 1996; Cheng et al., 1996). Variants of VEGF with antagonistic properties may also be employed, as described in WO 98/16551. Each of the foregoing references are specifically incorporated herein by reference.

Blocking antibodies against VEGF will be preferred in certain embodiments, particularly for simplicity. Monoclonal antibodies against VEGF have been shown to inhibit human tumor xenograft growth and ascites formation in mice (Kim et al., 1993; Mesiano et al., 1998; Luo et al., 1998a; 1998b; Borgstrom et al., 1996; 1998; each incorporated herein by reference). The antibody A4.6.1 is a high affinity anti-VEGF antibody capable of blocking VEGF binding to both VEGFR1 and VEGFR2 (Kim et al., 1992; Wiesmann et al., 1997; Muller et al., 1998; Keyt et al., 1996; each incorporated herein by reference). A4.6.1 has recently been humanized by monovalent phage display techniques and is currently in Phase I clinical trials as an anti-cancer agent (Brem, 1998; Baca et al., 1997; Presta et al., 1997; each incorporated herein by reference).

Alanine scanning mutagenesis and X-ray crystallography of VEGF bound by the Fab fragment of A4.6.1 showed that the epitope on VEGF that A4.6.1 binds is centered around amino acids 89-94. This structural data demonstrates that A4.6.1 competitively inhibits VEGF from binding to VEGFR2, but inhibits VEGF from binding to VEGFR1 most likely by steric hindrance (Muller et al., 1998; Keyt et al., 1996; each incorporated herein by reference)

A4.6.1 may be used in combination with the present invention. However, a new antibody termed 2C3 (4545) is currently preferred, which selectively blocks the interaction of VEGF with only one of the two VEGF receptors. 2C3 inhibits VEGF-mediated growth of endothelial cells, has potent anti-tumor activity and selectively blocks the interaction of VEGF with VEGFR2 (KDR/Flk-1), but not VEGFR1 (FLT-1). In contrast to A4.6.1, 2C3 allows specific inhibition of VEGFR2-induced angiogenesis, without concomitant inhibition of macrophage chemotaxis (mediated by VEGFR1), and is thus contemplated to be a safer therapeutic. U.S. Pat. Nos. 6,342,219, 6,342,221, 6,416,758 and 6,416,758, are specifically incorporated herein by reference for the purposes of even further describing the 2C3 antibody and its uses in anti-angiogenic therapy and VEGF inhibition.

N8. Apoptosis-Inducing Agents

The therapeutic agents of the present invention are also preferably combined with treatment methods that induce apoptosis in any cells within the tumor, including tumor cells and tumor vascular endothelial cells. Exemplary agents that induce apoptosis are listed above (in connection with immunoconjugates). Any one or more of such apoptosis-inducing agents may be used in the combination therapies of the present invention, without being linked to an antibody of the invention.

Many known anti-cancer agents also have an apoptosis-inducing effect as part of their mechanism of action. These agents, as exemplified by those in Table F, are particularly contemplated for use in the combination therapy aspects of the present invention (they may also be conjugated to an antibody of the invention, as described above).

TABLE F

Anti-Cancer Agents that Induce Apoptosis

| Class or Type of Agent | Examples |
| --- | --- |
| Antimetabolites | Cytarabine, fludarabine, 5-fluoro-29-deoxyuridine, gemcitabine, hydroxyurea, methotrexate |
| DNA Cross-Linking Agents | Chlorambucil, cisplatin, cyclophosphamide, nitrogen mustard |
| Intercalating Agents | Adriamycin (doxorubicin), mitixantrone |
| Topoisomerase II Poisons | Etoposide, teniposide |
| Microtubule-Directed Agents | Colcemid, colchicine, docetaxel, vincristine |
| Kinase Inhibitors | Flavopiridol, staurosporine, STI571 (CPG 57148B), UCN-01 (7-hydroxystaurosporine) |
| Farnesyl Transferase Inhibitors | L-739749, L-744832 |
| Hormones | Glucocorticoids, fenretinide |
| DNA Fragmenting Agents | Bleomycin |
| Hormone Antagonists | Tamoxifen, finasteride, LHRH antagonists |
| Biologicals | TNF-α, TRAIL, anti-CD20 |
| Protein Synthesis Inhibitors | L-asparaginase, cycloheximide, puromycin, diphtheria toxin |
| Topoisomerase II Poisons | Camptothecin, toptecan |

N9. Immunotoxins and Coaguligands

The present invention may also be used in combination with other immunotoxins or coaguligands in which the targeting portion is directed to a marker of tumor cells, tumor vasculature or tumor stroma. Any of the targeting agents described herein for use in targeting a PE-binding peptide to a tumor cell, tumor vasculature or tumor stroma may be used in these embodiments. In the immunotoxins, the attached agents include anti-cellular or cytotoxic agents, cytokines, radiotherapeutic agents, anti-angiogenic agents, apoptosis-inducing agents and anti-tubulin drugs. In the coaguligands, the attached agents are coagulants. U.S. Pat. Nos. 5,855,866, 5,965,132, 6,261,535, 6,051,230, 6,451,312 (immunotoxins), 6,093,399, 6,004,555, 5,877,289, and 6,036,955 (coaguligands) are specifically incorporated herein by reference to exemplify such constructs.

N10. ADEPT and Prodrug Therapy

The antibodies of the present invention, including the 9D2, 3G4 (ATCC 4545) and like antibodies, may also be used in conjunction with prodrugs, wherein the antibody is operatively associated with a prodrug-activating component, such as a prodrug-activating enzyme, which converts a prodrug to the more active form only upon contact with the antibody. This technology is generally termed "ADEPT", and is described in, e.g., WO 95/13095; WO 97/26918, WO 97/24143, and U.S. Pat. Nos. 4,975,278 and 5,658,568, each specifically incorporated herein by reference.

The term "prodrug", as used herein, refers to a precursor or derivative form of a biologically or pharmaceutically active substance that exerts reduced cytotoxic or otherwise anticellular effects on targets cells, including tumor vascular endothelial cells, in comparison to the parent drug upon which it is based. Preferably, the prodrug or precursor form exerts significantly reduced, or more preferably, negligible, cytotoxic or anticellular effects in comparison to the "native" or parent form. "Prodrugs" are capable of being activated or converted to yield the more active, parent form of the drug.

The technical capability to make and use prodrugs exists within the skill of the ordinary artisan. Willman et al. (1986) and Stella et al. (1985) are each specifically incorporated herein by reference for purposes of further supplementing the description and teaching concerning how to make and use various prodrugs. Exemplary prodrug constructs that may be used in the context of the present invention include, but are not limited to, phosphate-containing prodrugs (U.S. Pat. No. 4,975,278), thiophosphate-containing prodrugs, sulfate-containing prodrugs, peptide-based prodrugs (U.S. Pat. Nos. 5,660,829; 5,587,161; 5,405,990; WO 97/07118), D-amino acid-modified prodrugs, glycosylated prodrugs (U.S. Pat. Nos. 5,561,119; 5,646,298; 4,904,768, 5,041,424), β-lactam-containing prodrugs, optionally substituted phenoxyacetamide-containing prodrugs (U.S. Pat. No. 4,975,278), optionally substituted phenylacetamide-containing prodrugs, and even 5-fluorocytosine (U.S. Pat. No. 4,975,278) and 5-fluorouridine prodrugs and the like, wherein each of the patents are specifically incorporated herein by reference.

The type of therapeutic agent or cytotoxic drug that can be used in prodrug form is virtually limitless. The more cytotoxic agents will be preferred for such a form of delivery, over, e.g., the delivery of coagulants, which are less preferred for use as prodrugs. All that is required in forming the prodrug is to design the construct so that the prodrug is substantially inactive and the "released" or activated drug has substantial, or at least sufficient, activity for the intended purpose.

Various improvements on the original prodrugs are also known and contemplated for use herewith, as disclosed in WO 95/03830; EP 751,144 (anthracyclines); WO 97/07097 (cyclopropylindoles); and WO 96/20169. For example, prodrugs with reduced Km are described in U.S. Pat. No. 5,621,002, specifically incorporated herein by reference, which may be used in the context of the present invention. Prodrug therapy that be conducted intracellularly is also known, as exemplified by WO 96/03151, specifically incorporated herein by reference, and can be practiced herewith.

For use in ADEPT, the agent that activates or converts the prodrug into the more active drug is operatively attached to an antibody of the invention. The antibody thus localizes the prodrug converting capability within the angiogenic or tumor site, so that active drug is only produced in such regions and not in circulation or in healthy tissues.

Enzymes that may be attached to the antibodies of the invention to function in prodrug activation include, but are not limited to, alkaline phosphatase for use in combination with phosphate-containing prodrugs (U.S. Pat. No. 4,975,278); arylsulfatase for use in combination with sulfate-containing prodrugs (U.S. Pat. No. 5,270,196); peptidases and proteases, such as serratia protease, thermolysin, subtilisin, carboxypeptidase (U.S. Pat. Nos. 5,660,829; 5,587,161; 5,405,990) and cathepsins (including cathepsin B and L), for use in combination with peptide-based prodrugs; D-alanylcarboxypeptidases for use in combination with D-amino acid-modified prodrugs; carbohydrate-cleaving enzymes such as β-galactosidase and neuraminidase for use in combination with glycosylated prodrugs (U.S. Pat. Nos. 5,561,119; 5,646,298); β-lactamase for use in combination with β-lactam-containing prodrugs; penicillin amidases, such as penicillin V amidase (U.S. Pat. No. 4,975,278) or penicillin G amidase, for use in combination with drugs derivatized at their amino nitrogens with phenoxyacetamide or phenylacetamide groups; and cytosine deaminase (U.S. Pat. Nos. 5,338,678; 5,545,548) for use in combination with 5-fluorocytosine-based prodrugs (U.S. Pat. No. 4,975,278), wherein each of the patents are specifically incorporated herein by reference.

Antibodies with enzymatic activity, known as catalytic antibodies or "abzymes", can also be employed to convert prodrugs into active drugs. Abzymes based upon the antibodies of the invention, preferably the 9D2 and 3G4 and like antibodies, thus form another aspect of the present invention. The technical capacity to make abzymes also exists within those of ordinary skill in the art, as exemplified by Massey et al. (1987), specifically incorporated herein by reference for purposes of supplementing the abzyme teaching. Catalytic antibodies capable of catalyzing the breakdown of a prodrug at the carbamate position, such as a nitrogen mustard aryl carbamate, are further contemplated, as described in EP 745,673, specifically incorporated herein by reference.

O. Antibody-Coated Liposomes and Therapeutics

Liposomal formulations are often used in therapeutics and pharmaceuticals. However, the biodistribution of liposomes in initial studies meant that such formulations were not widely applicable for use in humans. Liposomes are rapidly taken up by the phagocytic cells of the reticuloendothelial system (RES), including the circulating mononuclear phagocytic cells and those located in the liver and spleen. Thus, the blood circulation half-lives can be as short as a few minutes.

The technology of "stealth or stealthed" liposomes and formulations was thus developed, which allows liposomes to evade uptake by the RES and circulate for longer (Hristova and Needham, 1993). A preferred agent for use in stealthing liposomes is polyethylene glycol (PEG), and the resultant liposomes are also termed PEGylated liposomes. Other stealthing agents include poly(2-methyl-2-oxazoline) and poly(2-ethyl-2-oxazoline) conjugates (Woodle et al., 1994). A range of improved stealthed liposomes are described in U.S. Pat. No. 6,284,267, specifically incorporated herein by reference, which may be used in combination with the present invention.

Liposomes smaller in diameter than the average diameter of the fenestrae in capillaries leak out from the circulation. The average diameter of the fenestrae in rapidly growing tumors is larger than in normal tissues and therefore liposomes smaller than about 100 nm in diameter migrate into tumors. Stealth liposomes have thus been proposed for use in delivering cytotoxic agents to tumors in cancer patients. A range of drugs have been incorporated into stealth liposomes, including cisplatin (Rosenthal et al., 2002), TNFα (Kim et al., 2002), doxorubicin (Symon et al., 1999) and adriamycin (Singh et al., 1999), each reference being specifically incorporated herein by reference. However, recent reports have indicated unexpected low efficacy of stealth liposomal doxorubicin and vinorelbine in the treatment of metastatic breast cancer (Rimassa et al., 2003).

The present invention provides improved stealthed liposome formulations, overcoming various of the drawbacks in the art, in which the stealthed liposomes are functionally associated or "coated" with an antibody that binds to an aminophospholipid or anionic phospholipid, preferably to PS or PE. The 9D2, 3G4 (ATCC 4545) and like, competing antibodies of the invention are preferred for such uses, although any antibody, or antigen binding region thereof, which binds to an aminophospholipid or anionic phospholipid may be used. A divalent antibody or antibody portion is not required in these aspects of the invention.

Any stealthed liposome may form the basis of the new liposomal formulations, and preferably a PEGylated liposome will be employed. The stealthed liposomes are "coated", i.e., operatively or functionally associated with the antibody that binds to an aminophospholipid or anionic phospholipid. The operative or functional association is made such that the antibody retains the ability to specifically bind to the target aminophospholipid or anionic phospholipid, preferably PS or PE, thereby delivering or targeting the stealthed liposome and any contents thereof to PS-and/or PE-positive cells, such as tumor cells and tumor vascular endothelial cells.

The antibody-coated stealthed liposomes of the invention may be used alone. Preferably, however, such liposomes will also contain one or more second therapeutic agents, such as anti-cancer or chemotherapeutic agents (the first therapeutic agent being the antibody itself). The second therapeutic agents are generally described as being within the "core" of the liposome. Any one or more of the second, anti-cancer or chemotherapeutic agents known in the art and/or described herein for conjugation to antibodies, or for combination therapies, may be used in the antibody-coated stealthed liposomes of the invention. For example, any chemotherapeutic or radiotherapeutic agent, cytokine, anti-angiogenic agent or apoptosis-inducing agent. Currently preferred within the chemotherapeutic agents are anti-tubulin drugs, docetaxel and paclitaxel.

Moreover, the antibody-coated stealthed liposomes of the invention may also be loaded with one or more anti-viral drugs for use in treating viral infections and diseases. As with the anti-cancer agents, any one or more of the second, anti-viral drugs known in the art and/or described herein for conjugation to antibodies, or for combination therapies, may be used in the antibody-coated stealthed liposomes of the invention. Cidofovir and AZT are currently preferred examples.

P. Anti-Vascular, Anti-Angiogenic and Other Therapies

The present invention may also be used in the treatment of other diseases in which aberrant vasculature is involved, including diseases and disorders having prothrombotic blood vessels. Although not the only therapeutic mechanism, the antibodies, immunoconjugates and peptide-based therapeutics of the present invention may also be used to treat animals and patients with aberrant angiogenesis, such as that contributing to a variety of diseases and disorders.

Whether based upon anti-angiogenesis, prothrombotic vasculature or other anti-vascular mechanisms, the present invention may thus be used to treat prevalent and/or clinically important diseases outside the field of cancer, including arthritis, rheumatoid arthritis, psoriasis, atherosclerosis, diabetic retinopathy, age-related macular degeneration, Grave's disease, vascular restenosis, including restenosis following angioplasty, arteriovenous malformations (AVM), meningioma, hemangioma and neovascular glaucoma. Other targets for intervention include angiofibroma, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis, various other inflammatory diseases and disorders, and even endometriosis. Further diseases and disorders that are treatable by the invention, and the unifying basis of such disorders, are set forth below.

One prominent disease in which aberrant vasculature and angiogenesis is involved is rheumatoid arthritis, wherein the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Factors associated with angiogenesis also have a role in osteoarthritis, contributing to the destruction of the joint. Various factors, including VEGF, have been shown to be involved in the pathogenesis of rheumatoid arthritis and osteoarthritis.

Another important example of a disease involving aberrant vasculature and angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia.

Other diseases associated with corneal neovascularization that can be treated according to the present invention include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

Other diseases that can be treated according to the present invention include, but are not limited to, diseases associated with rubeosis (neovascularization of the angle) and diseases caused by the abnormal proliferation of fibrovascular or fibrous tissue including all forms of proliferative vitreoretinopathy, whether or not associated with diabetes.

Chronic inflammation also involves aberrant vasculature and pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells.

Another pathological role associated with aberrant vasculature and angiogenesis is found in atherosclerosis. The plaques formed within the lumen of blood vessels have been shown to have angiogenic stimulatory activity. There is particular evidence of the pathophysiological significance of angiogenic markers, such as VEGF, in the progression of human coronary atherosclerosis, as well as in recanalization processes in obstructive coronary diseases. The present invention provides an effective treatment for such conditions.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use, but are addressed by the invention.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is also involved in normal physiological processes such as reproduction and wound healing. Angiogenesis is an important step in ovulation and also in implantation of the blastula after fertilization. Prevention of angiogenesis according to the present invention could be used to induce amenorrhea, to block ovulation or to prevent implantation by the blastula. In wound healing, excessive repair or fibroplasia can be a detrimental side effect of surgical procedures and may be caused or exacerbated by angiogenesis. Adhesions are a frequent complication of surgery and lead to problems such as small bowel obstruction. This can also be treated by the invention.

Each of the foregoing diseases and disorders, along with all types of tumors, are also contemplated for treatment according to the present invention. U.S. Pat. No. 5,712,291 is specifically incorporated herein by reference to further demonstrate the knowledge in the art that once the inhibition of angiogenesis has been shown using a particular agent, the treatment of an extensive range of diseases associated with aberrant angiogenesis using that and like agents can reasonably be carried out. U.S. Pat. No. 6,524,583 is also specifically incorporated herein by reference for similar purposes and to particularly demonstrate that this principle applies to the inhibition of angiogenesis and the treatment of angiogenic diseases using antibody-based therapeutics. The anti-angiogenic effects of the 3G4 antibody (ATCC 4545) in tumor-bearing mice (FIG. 17A) is thus important evidence that 3G4 and like antibodies are suitable for treating a wide range of angiogenic diseases.

The invention further provides compositions and methods for use in treating other diseases in which aminophospholipids and/or anionic phospholipids, particularly PS and PE, play a role. For example, as PS is involved in cell adhesion, inflammatory responses and septic shock, antibodies to PS can be used in the treatment of inflammation and septic shock. The use of the 3G4 (ATCC 4545) or like antibodies is preferred for such embodiments, particularly an Fab dimer of such an antibody. A duramycin Fab dimer is also particularly contemplated for use in treating septic shock.

Aminophospholipids and/or anionic phospholipids, particularly PS, are also involved in sickle cell anaemia, in particular, as part of the clearance mechanism. Antibodies to PS can therefore be used to treat or ameliorate sickle cell anaemia. The use of the 3G4 (ATCC 4545) or like antibodies is preferred, particularly an Fab dimer thereof.

Most bacteria express the anionic phospholipid, PA. Antibodies that bind to PA, optionally with binding to other anionic phospholipids, can therefore be used as anti-bacterial agents. Although the antibodies of the invention can be prepared in E. coli, and are thus not bacteriocidal in all circumstances, an anti-bacterial role in vivo is believed to result from the ability to fix complement. An intact antibody rather than an antibody fragment should therefore be used as an anti-bacterial agent. The 3G4 (ATCC 4545) and like antibodies are preferred for use in such embodiments, although any antibody that fixes complement and binds to PA may be employed, such as other PA-binding antibodies from Table 4.

Antiphospholipid syndrome and lupus, autoimmune disorders in which antibodies are produced against the body's own phospholipids, are associated with coagulation disorders, including miscarriages and thrombocytopenia (low platelet counts). Accordingly, the anti-phospholipid antibodies in these patients are pathogenic antibodies, which cause thrombosis. The antibodies of the present invention, however, bind to aminophospholipids and anionic phospholipids without exhibiting such side effects. Accordingly, the antibodies of the invention are contemplated for use in treating antiphospholipid syndrome, associated diseases and complications thereof.

The pathogenic anti-phospholipid antibodies that circulate in patients with antiphospholipid syndrome are believed to bind to PS, PE and other phospholipids in combination with proteins, such as $\beta_2$-glycoprotein I, prothrombin, kininogens, prekallikrein and factor XI (Rote, 1996; Sugi and McIntyre, 1995; 1996a; 1996b). $\beta_2$-glycoprotein I and prothrombin bound to PS are reported to be the primary antigens for anti-cardiolipin antibodies and lupus antibodies, respectively. The antibodies of the present invention have been particularly selected on the basis of not binding to aminophospholipids and anionic phospholipids only in the presence of serum proteins. Therefore, by binding to the phospholipid component, the antibodies of the invention are contemplated for use in antagonizing or competing with the pathogenic antibodies in such patients, thus displacing the pathogenic antibodies from their phospholipid-protein targets in the body.

Q. PE-Binding Peptide Derivatives and Conjugates

In addition to antibodies and immunoconjugates, the present invention further provides PE-binding peptide derivatives and various uses, particularly in the treatment of tumors and viral diseases. Currently preferred PE-binding peptide constructs and derivatives are those based upon the peptide termed duramycin. Three general categories of PE-binding peptide and duramycin derivatives are provided by the invention, two of which use the PE-binding peptide or duramycin as the targeting portion of the construct, and the other uses the duramycin or like agent mainly as the effector portion of the construct.

The use of PE-binding peptides, preferably duramycin, as targeting agents is based on their ability to impart a selective binding capacity to a resultant construct. Accordingly, a construct or conjugate containing a PE-binding peptide, preferably duramycin, will specifically bind to PE-expressing cells, such as tumor vascular endothelial cells, malignant tumor cells, proliferating cells and/or virally infected cells.

As PE-binding peptides such as duramycin have biological activity in addition to the PE targeting function, it is not necessary to conjugate a PE-binding peptide such as duramycin to a therapeutic agent to achieve a therapeutic conjugate. However, as PE-binding peptides such as duramycin have associated toxicities in their natural form, the peptide should be modified to reduce toxicity. The toxicities are connected with the ability of the peptides to form clusters, form pores in cell membranes, and to generally permeate or penetrate into the cells. Accordingly, these functions should be attenuated, to significantly or substantially prevent the PE-binding peptide from forming clusters, permeating into the cells and being non-specifically toxic. Preferably, whilst the ability to bind to PE is substantially maintained, the ability of the PE-binding peptides to form clusters and penetrate cells is substantially inhibited, thus significantly reducing or abolishing cytotoxicity.

The first category of PE-binding peptide derivatives with reduced toxicity provided by the present invention is that in which the PE-binding peptide, preferably duramycin, is rendered relatively or substantially cell impermeant. This is preferably achieved by attaching to a cell impermeant group, which can be a small group with positive or negative charge or a polar group, or can be in the form of an inert carrier. The terms "cell impermeant group" and "cell impermeant PE-binding peptide", as used herein, are relative rather than absolute, and refer to modified PE-binding peptides, preferably duramycin, in which the ability to form clusters and permeate cells has been significantly, and preferably substantially, reduced. The resultant cell impermeant PE-binding peptides may function by trapping PE, and associated membrane molecules, on the exterior of cells and/or by bringing host defenses to bear on the peptide-coated cells.

Within this category of PE-binding peptide derivatives, certain constructs will emphasize the recruitment of host defenses, thus enhancing their therapeutic activity. For example, where a PE-binding peptide, preferably duramycin, is attached to an immunoglobulin, the immunoglobulin can function both as an inert carrier and as an immune effector. This applies to immunoglobulins of so-called "irrelevant specificity" and to immunoglobulin derivatives without antigen binding capacity, such as Fc regions. By virtue of the attached immunoglobulin or immunoglobulin derivative, such constructs will be able to redirect host defenses against PE-expressing cells, e.g. by attracting and/or activating immune effector cells.

In the second general category of PE-binding peptide derivatives of the invention, the peptides are still modified to reduce cell penetration and resultant toxicity, but rather than using a small cell impermeant group or inert carrier, an agent is used that changes the blood and tissue distribution of the resultant construct. Preferred examples are those in which a PE-binding peptide, preferably duramycin, is attached to a targeting agent that binds to a component of a tumor cell, tumor or intratumoral vasculature or tumor stroma. Although the PE-binding peptide itself still has a targeting property, in these aspects of the invention, the targeting agent primarily directs the construct to the target tissue, such as to the tumor environment, and the attached PE-binding peptide such as duramycin exerts a therapeutic effect upon delivery.

The third general category of PE-binding peptide derivatives returns to the use of the PE-binding peptide, preferably duramycin, as a targeting agent to localize the derivative to PE-expressing cells. As virally infected cells express PE at the cell surface, as opposed to normal, uninfected cells, linking a PE-binding peptide such as duramycin to an anti-viral agent will provide an effective, targeted anti-viral agent. Although the PE-binding peptide portion, preferably duramycin, may have additional therapeutic effects, the attached anti-viral agent is designed to be the primary therapeutic agent within such constructs.

Any of the conjugation techniques described above may be used to prepare duramycin derivatives in accordance with the invention, including cross-linkers, peptide spacers, biotin: avidin constructs and recombinant expression. An advantageous site of attachment within the duramycin molecule, for example, is to the lysine residue at amino acid position 2 in the duramycin sequence (SEQ ID NO:9; FIG. 13P; Hayashi et al., 1990). However, linkage at this site is not a requirement of the invention.

Accordingly, PE-binding peptides, preferably duramycin, can be derivatized to have a functional group available for cross-linking purposes. A wide variety of groups can be used in this manner, for example, primary or secondary amine groups, hydrazide or hydrazine groups, carboxyl alcohol, phosphate, carbamate and alkylating groups. The agents for attachment, including anti-viral agents, may thus be conjugated through a Schiff's base linkage, a hydrazone or acyl hydrazone bond or a hydrazide linker (U.S. Pat. Nos. 5,474, 765 and 5,762,918, each specifically incorporated herein by reference).

Q1. PE-Binding and Anti-Microbial Peptides

Any PE-binding peptide may be used in these aspects of the invention. For example, low and high molecular weight kininogens are known to bind PE. The protein and DNA sequences for a variety of such binding proteins, including the human proteins, are known in the art, facilitating the use of PE-binding peptides therefrom. For example, the human genes and proteins for high and low molecular weight kininogens are described in Kitamura et al. (1985) and Kellermann et al. (1986), each specifically incorporated herein by reference.

U.S. Pat. No. 6,312,694 describes certain PE-binding conjugates using PE-binding proteins, such as kininogens, and PE-binding fragments thereof. In U.S. Pat. No. 6,312,694, the PE-binding proteins or PE-binding fragments thereof are operatively attached to anti-cellular agents, toxins and coagulation factors. In the present case, PE-binding peptides are attached to inert carriers, tumor targeting agents or anti-viral agents. Although the present agents for attachment and their methods of use represent surprising advances, U.S. Pat. No. 6,312,694 is specifically incorporated herein by reference for purposes of further describing and enabling PE-binding peptides, such as PE-binding peptide fragments of kininogens.

Currently preferred PE-binding peptides for use in the invention are those based upon the PE-binding molecule, duramycin. Duramycin (2622U90, Moli1901) is an antimicrobial peptide from the lantibiotic family (U.S. Pat. No. 4,452,782; Shotwell et al., 1958; Nakamura and Racker, 1984), and other members of the lantibiotic family may be used in the present invention. Where the PE-binding peptides are used as the targeting agent of the construct, for example, when linked to an inert carrier or to an anti-viral agent, a lantibiotic PE-binding peptide should substantially retain PE binding activity. When used as the therapeutic agent in a construct, particularly when attached to a tumor-targeting agent, there is more tolerance for some loss of PE binding activity.

Testing a candidate peptide to confirm or identify those that substantially bind to PE is a straightforward matter in light of the present disclosure and can be achieved, for example, using any one or more of the ELISAs described herein. Lantibiotics for use as PE-binding peptides herein will preferably exhibit substantially the same PE binding activity as duramycin, and even more preferably, will also exhibit substantially the same specificity for PE over other phospholipids as duramycin. Such properties can also be readily determined in light of the present disclosure, particularly the working examples.

Based upon the criteria above, the following lantibiotics may be used as part of the constructs and conjugates of the present invention: duramycin, cinnamycin, actagardine, ancovenin, epidermin, gallidermin, lanthiopeptin, mersacidin, nisin, Pep5 and subtilin. Duramycin is the most preferred PE-binding peptide for use in all aspects of the invention. Duramycin is an antimicrobial, which has also been suggested for use in treating asthma, chronic bronchitis and *Mycobacterium tuberculosis* infection (U.S. Pat. Nos. 5,849,706; 5,716,931; 5,683,675; 5,651,957; and 5,512,269; each specifically incorporated herein by reference) and cystic fibrosis (McNulty et al., 2003). However, duramycin has not previously been described or suggested for conjugation to a cell impermeant group, particularly not for use in treating viral infections.

Cinnamycin (Ro09-0198) is a related molecule that binds to PE (Wakamatsu et al., 1986; Choung et al., 1988a; 1988b). Labeled cinnamycin has been used as a probe to study the transbilayer movement of PE (Aoki et al., 1994; Emoto et al., 1996) and PE exposure during apoptosis of T cells in vitro (Emoto et al., 1997; Umeda and Emoto, 1999). However, therapeutic uses of cinnamycin derivatives in accordance with the present invention have not been previously described or suggested. Pharmaceutical compositions containing PE-binding peptide derivatives of the invention based upon cinnamycin, and various medical uses thereof, therefore represent an advance in the art, particularly where such compositions are intended for use in treating viral infections.

The following anti-microbial peptides may also be used in the conjugates of the invention, particularly as therapeutic agents attached to tumor targeting agents: cystibiotics, such as pediocin AcH/PA1, leucocin A/Ual 187, mesentericin Y 105, sakacin A, sakacin P, lactacin F, cerein 7/8 and carnobacteriocins, such as carnobacteriocin A, BM1 and B2; and thiolbiotics, particularly lactococcins, such as lactococcin B, A, $M^a$, $N^a$, $G^a$ and G.

Q2. Cell Impermeant Groups

Attaching a PE-binding peptide, preferably duramycin, to a cell impermeant group will reduce the ability of the peptides to form clusters, substantially preventing the PE-binding peptide from permeating into normal cells and thus reducing the toxicity. The PE binding property is maintained, however, so that the peptides can localize to aberrant or infected cells, which have PE exposed on the surface.

Exemplary cell impermeant groups include groups that bear positive or negative charge at physiological pH, such as sulfate, sulfonate, phosphate, carboxyl, phenolic, quaternary ammonium ions and amine groups. Further examples are polar groups, such as simple sugars and polysaccharides, amino acids and polyalcohols. Duramycin, in particular, may be linked to biotin to form biotinylated PE-binding peptides, which can be dispersed in a pharmaceutical composition or medicament, particularly one intended for treating a viral infection. The cell impermeant group can also be a polypeptide, protein or immunoglobulin, any of can function as an inert carrier or as a targeting agent.

Q3. Inert Carriers

PE-binding peptides, preferably duramycin, can be rendered cell impermeant by attachment to an inert, cell impermeant carrier. A wide range of inert, cell impermeant carriers can be conjugated to a PE-binding peptide, preferably duramycin, to prepare a cell impermeant PE-binding peptide, so long as PE binding activity is not substantially destroyed. The inert carriers should preferably be biologically compatible, such that they do not result in any significant untoward effects upon administration to an animal or patient.

Carrier proteins can be used, and exemplary proteins are albumins and globulins. Neutravidin and streptavidin will often be preferred. Non-protein carriers can also be used, such as natural or synthetic polymers, including polysaccharides and PEG.

In certain embodiments, the carrier will be an immunoglobulin or portion thereof. Human immunoglobulins (HIgG) will be preferred for human administration. Immunoglobulins can also impart targeting functions, as discussed below. As an inert carrier, an immunoglobulin is one of "irrelevant specificity", in that it does not impart a targeting function to the conjugate. However, certain advantages may still be achieved through the selection of particular types of immunoglobulin. For example, the Fc portion of an immunoglobulin may be used to recruit host immune cells and thus further stimulate host defenses.

Q4. Targeting Agents

Rather than attaching to an inert carrier, PE-binding peptides, preferably duramycin, can be rendered cell impermeant by attachment to a targeting agent, in particular, one that binds to a component of a tumor cell, tumor or intratumoral vasculature or tumor stroma. The targeting agent directs the construct to the target tissue, preferably the tumor environment, and the attached PE-binding peptide, preferably duramycin, exerts a therapeutic effect upon delivery.

Suitable targeting agents are components, such as antibodies and other agents, which bind to a tumor cell. Agents that "bind to a tumor cell" are defined herein as targeting agents that bind to any accessible component or components of a tumor cell, or that bind to a component that is itself bound to, or otherwise associated with, a tumor cell, as further described herein.

The majority of such tumor cell-targeting agents and binding ligands are contemplated to be agents, particularly antibodies, that bind to a cell surface tumor antigen or marker. Many such antigens are known, as are a variety of antibodies for use in antigen binding and tumor targeting. The invention thus includes targeting agents that bind to an identified tumor cell surface antigen and/or that bind to an intact tumor cell. The identified tumor cell surface antigens and intact tumor cells of Table I and Table II of U.S. Pat. Nos. 5,877,289; 6,004,555; 6,036,955; 6,093,399 are specifically incorporated herein by reference for the purpose of exemplifying suitable tumor cell surface antigens.

Examples of tumor cell binding regions are those that comprise an antigen binding region of an antibody that binds to the cell surface tumor antigen p185$^{HER2}$, milk mucin core protein, TAG-72, Lewis a or carcinoembryonic antigen (CEA). Another group of tumor cell binding regions are those that comprise an antigen binding region of an antibody that binds to a tumor-associated antigen that binds to the antibody 9.2.27, OV-TL3, MOv18, B3 (ATCC HB 10573), KS1/4 (obtained from a cell comprising the vector pGKC2310 (NRRL B-18356) or the vector pG2A52 (NRRL B-18357), 260F9 (ATCC HB 8488) or D612 (ATCC HB 9796). D612 is described in U.S. Pat. No. 5,183,756, and has ATCC Accession No. HB 9796; B3 is described in U.S. Pat. No. 5,242,813, and has ATCC Accession No. HB 10573; and recombinant and chimeric KS1/4 antibodies are described in U.S. Pat. No. 4,975,369; each incorporated herein by reference.

Targetable components of tumor cells further include components released from necrotic or otherwise damaged tumor cells, including cytosolic and/or nuclear tumor cell antigens. These are preferably insoluble intracellular antigen(s) present in cells that may be induced to be permeable, or in cell ghosts of substantially all neoplastic and normal cells, that are not present or accessible on the exterior of normal living cells of a mammal.

U.S. Pat. Nos. 5,019,368, 4,861,581 and 5,882,626, issued to Alan Epstein and colleagues, are each specifically incorporated herein by reference for purposes of even further describing and teaching how to make and use antibodies specific for intracellular antigens that become accessible from malignant cells in vivo. The antibodies described are sufficiently specific to internal cellular components of mammalian malignant cells, but not to external cellular components. Exemplary targets include histones, but all intracellular components specifically released from necrotic tumor cells are encompassed.

Upon administration to an animal or patient with a vascularized tumor, such antibodies localize to the malignant cells by virtue of the fact that vascularized tumors naturally contain necrotic tumor cells, due to the process(es) of tumor remodeling that occur in vivo and cause at least a proportion of malignant cells to become necrotic. In addition, the use of such antibodies in combination with other therapies that enhance tumor necrosis serves to enhance the effectiveness of targeting and subsequent therapy. These types of antibodies may thus be used as targeting agents as disclosed herein.

A range of suitable targeting agents are available that bind to markers present on tumor endothelium and stroma, but largely absent from normal cells, endothelium and stroma. For tumor vasculature targeting, the targeting antibody or ligand will often bind to a marker expressed by, adsorbed to, induced on or otherwise localized to the intratumoral blood vessels of a vascularized tumor. "Components of tumor vasculature" thus include both tumor vasculature endothelial cell surface molecules and any components, such as growth factors, that may be bound to these cell surface receptors or molecules. The following patents are specifically incorporated herein by reference for the purposes of even further supplementing the present teachings regarding the preparation and use of targeting agents directed against expressed, adsorbed, induced or localized markers of tumor vasculature: U.S. Pat. Nos. 5,855,866; 5,776,427; 5,863,538; 5,660,827; 5,855,866; 5,877,289; 6,004,554; 5,965,132; 6,036,955; 6,093,399; 6,004,555.

Examples of surface-expressed targets of tumor and intratumoral blood vessels include vascular cell surface receptors and cell adhesion molecules (Thorpe and Ran, 2000, specifically incorporated herein by reference, see Table 1). Suitable examples include endoglin, targeted by, e.g., TEC-4, TEC-11, E-9 and Snef antibodies; E-selectin, targeted by, e.g., H4/18 antibodies; VCAM-1, targeted by, e.g., E1/6 and 1.4c3 antibodies; endosialin, targeted by, e.g., FB5 antibodies; $\alpha_v\beta_3$ integrin, targeted by, e.g., LM609 and peptide targeting agents; the VEGF receptor VEGFR1, targeted by a number of antibodies, and particularly by VEGF; the VEGF receptor complex, also targeted by a number of antibodies, such as 3E7 and GV39; and PSMA, targeted by antibodies such as J591. Examples such as endoglin, TGFβ receptors, E-selectin, P-selectin, VCAM-1, ICAM-1, a ligand reactive with LAM-1, a VEGF/VPF receptor, an FGF receptor, $\alpha_v\beta_3$ integrin, pleiotropin, endosialin are further described and enabled in U.S. Pat. Nos. 5,855,866; 5,877,289; 6,004,555; 6,093,399; each incorporated herein by reference.

Further suitable examples include proteoglycans, such as NG2, and matrix metalloproteinases (MMPs), such as MMP2 and MMP9, each targeted by particular peptide targeting agents (Thorpe and Ran, 2000). These are examples of remodeling enzymes that are expressed as targetable entities in the tumor, which is a site of vascular remodeling. Further suitable targets are thrombomodulin, Thy-1 and cystatin. Studies identifying sequences elevated in tumor endothelium have also identified thrombomodulin, MMP 11 (stromelysin), MMP 2 (gelatinase) and various collagens as targetable tumor vascular markers, which is also in accordance with U.S. Pat. Nos. 6,004,555 and 6,093,399, specifically incorporated herein by reference.

Another suitable target is PSMA (prostate-specific membrane antigen). PSMA, initially defined by monoclonal antibody 7E11, was originally identified as a marker of prostate cancer and is known to be a type 2 integral membrane glycoprotein. The 7E11 antibody binds to an intracellular epitope of PSMA that, in viable cells, is not available for binding. In the context of the present invention, PSMA is thus targeted using antibodies to the extracellular domain. Such antibodies react with tumor vascular endothelium in a variety of carcinomas, including lung, colon and breast, but not with normal vascular endothelium.

Many antibodies that bind to the external domain of PSMA are readily available and may be used in the present invention. Monoclonal antibodies 3E11, 3C2, 4E10-1.14, 3C9 and 1G3 display specificities for differing regions of the extracellular domain of the PSMA protein and are suitable for use herein. Three additional antibodies to the extracellular domain of PSMA are J591, J415 and PEQ226.5, which confirm PSMA expression in tumor-associated vasculature and may be used in the invention. As the nucleic acids encoding PSMA and variants thereof are also readily available, U.S. Pat. Nos. 5,935,818 and 5,538,866, additional antibodies can be generated if desired.

U.S. Pat. No. 6,150,508, specifically incorporated herein by reference, describes various other monoclonal antibodies that bind to the extracellular domain of PSMA, which may be used in the present invention. Any one or more of the thirty-five exemplary monoclonal antibodies reactive with PSMA expressed on the cell surface may be used. These include, 3F5.4G6 (ATCC HB12060); 3D7-1.I. (ATCC HB12309); 4E10-1.14 (ATCC HB12310); 3E11 (ATCC HB12488); 4D8 (ATCC HB12487); 3E6 (ATCC HB12486); 3C9 (ATCC HB12484); 2C7 (ATCC HB12490); 1G3 (ATCC HB12489); 3C4 (ATCC HB12494); 3C6 (ATCC HB12491); 4D4 (ATCC HB12493); 1G9 (ATCC HB12495); 5C8B9 (ATCC HB12492); 3G6 (ATCC HB12485); and 4C8B9 (ATCC HB12492).

Further antibodies, or binding portions thereof, that recognize an extracellular domain of PSMA are described in U.S. Pat. Nos. 6,107,090 and 6,136,311, each specifically incorporated herein by reference. Four hybridoma cell lines in particular are described, being E99, J415, J533, and J591 (ATCC HB-12101, HB-12109, HB-12127, and HB-12126), any one or more of which may thus be used as a targeting agent in accordance with the claimed invention.

Targeting agents that bind to "adsorbed" targets are another suitable group, such as those that bind to ligands or growth factors that bind to tumor or intratumoral vasculature cell surface receptors. Such antibodies include those that bind to VEGF, FGF, TGFβ, HGF, PF4, PDGF, TIMP or a tumor-associated fibronectin isoform (U.S. Pat. Nos. 5,877,289; 5,965,132; 6,093,399 and 6,004,555; each incorporated herein by reference).

Other suitable targeting antibodies, or fragments thereof, are those that bind to epitopes that are present on ligand-receptor complexes or growth factor-receptor complexes, but absent from both the individual ligand or growth factor and the receptor. Such antibodies will recognize and bind to a ligand-receptor or growth factor-receptor complex, as presented at the cell surface, but will not bind to the free ligand or growth factor or the uncomplexed receptor. A "bound receptor complex", as used herein, therefore refers to the resultant complex produced when a ligand or growth factor specifically binds to its receptor, such as a growth factor receptor.

These aspects are exemplified by the VEGF/VEGF receptor complex. Such ligand-receptor complexes will be present in a significantly higher number on tumor-associated endothelial cells than on non-tumor associated endothelial cells, and may thus be targeted by anti-complex antibodies. Anti-complex antibodies include the monoclonal antibodies 2E5, 3E5 and 4E5 and fragments thereof.

Antigens naturally and artificially inducible by cytokines and coagulants may also be targeted. Exemplary cytokine-inducible antigens are E-selectin, VCAM-1, ICAM-1, endoglin, a ligand reactive with LAM-1, and even MHC Class II antigens, which are induced by, e.g., IL-1, IL-4, TNF-α, TNF-β or IFN-γ, as may be released by monocytes, macrophages, mast cells, helper T cells, CD8-positive T-cells, NK cells or even tumor cells.

Further inducible antigens include those inducible by a coagulant, such as by thrombin, Factor IX/IXa, Factor X/Xa, plasmin or a metalloproteinase (matrix metalloproteinase, MMP). Generally, antigens inducible by thrombin will be used. This group of antigens includes P-selectin, E-selectin, PDGF and ICAM-1, with the induction and targeting of P-selectin and/or E-selectin being generally preferred.

In other embodiments, the vasculature and stroma targeting agents (see below) of the invention will be targeting agents that are themselves biological ligands, or portions thereof, rather than an antibodies. "Biological ligands" in this sense will be those molecules that bind to or associate with cell surface molecules, such as receptors, that are accessible in the stroma or on vascular cells; as exemplified by cytokines, hormones, growth factors, and the like. Any such growth factor or ligand may be used so long as it binds to the disease-associated stroma or vasculature, e.g., to a specific biological receptor present on the surface of a tumor vasculature endothelial cell.

Suitable growth factors for use in these aspects of the invention include, for example, VEGF/VPF (vascular endothelial growth factor/vascular permeability factor), FGF (the fibroblast growth factor family of proteins), TGFβ (transforming growth factor B), a tumor-associated fibronectin isoform, scatter factor/hepatocyte growth factor (HGF), platelet factor 4 (PF4), PDGF (platelet derived growth factor), TIMP or even IL-8, IL-6 or Factor XIIIa. VEGF/VPF and FGF will often be preferred.

Further suitable targeting agents are those that bind to tumor-associated stroma. During tumor progression, the extracellular matrix of the surrounding tissue is remodeled through two main processes: the proteolytic degradation of extracellular matrix components of normal tissue; and the de novo synthesis of extracellular matrix components by tumor cells and stromal cells activated by tumor-induced cytokines. These two processes generate a "tumor extracellular matrix" or "tumor stroma", which is permissive for tumor progression and is qualitatively and quantitatively distinct from the extracellular matrices or stroma of normal tissues.

The "tumor stroma" thus has targetable components that are not present in formal tissues. Certain preferred tumor stromal targeting agents for use in the invention are those that bind to basement membrane markers, type IV collagen, laminin, heparan sulfate, proteoglycan, fibronectins, activated platelets, LIBS, RIBS and tenascin. The following patents are specifically incorporated herein by reference for the purposes of even further supplementing the present teachings regarding the preparation and use of tumor stromal targeting agents: U.S. Pat. Nos. 5,877,289; 6,093,399; 6,004,555; and 6,036,955.

Components of tumor-associated stroma include structural and functional components of the stroma, extracellular matrix and connective tissues. Tumor stroma targeting agents thus include those that bind to components such as basement membrane markers, type IV collagens, laminin, fibrin, heparan sulfate, proteoglycans, glycoproteins, anionic polysaccharides such as heparin and heparin-like compounds and fibronectins.

Exemplary useful antibodies are those that bind to tenascin, a large molecular weight extracellular glycoprotein expressed in the stroma of various benign and malignant tumors. Anti-tenascin antibodies may thus be used as targeting agents (U.S. Pat. Nos. 6,093,399 and 6,004,555, specifically incorporated herein by reference).

Further suitable targeting agents include antibodies and ligands that bind to a smooth muscle cell, a pericyte, a fibroblast, a macrophage, and an infiltrating lymphocyte or leucocyte. "Activated platelets" are further components of tumor stroma, as platelets bind to the stroma when activated, and such platelets may thus be targeted by the invention.

Further suitable stromal targeting agents, antibodies and antigen binding regions thereof bind to "inducible" tumor stroma components, such as those inducible by cytokines, and especially those inducible by coagulants, such as thrombin. A group of preferred anti-stromal antibodies are those that bind to RIBS, the receptor-induced binding site, on fibrinogen. "RIBS" is thus a targetable antigen, the expression of which in stroma is dictated by activated platelets. Antibodies that bind to LIBS, the ligand-induced binding site, on activated platelets are also useful.

Particularly preferred targetable elements of tumor-associated stroma are currently the tumor-associated fibronectin (FN) isoforms. Fibronectins are multifunctional, high molecular weight glycoprotein constituents of both extracellular matrices and body fluids. They are involved in many different biological processes, such as the establishment and maintenance of normal cell morphology, cell migration, haemostasis and thrombosis, wound healing and oncogenic transformation.

Fibronectin isoforms are ligands that bind to the integrin family of receptors. "Tumor-associated fibronectin isoforms" may be considered to be part of the tumor vasculature and/or the tumor stroma. Fibronectin isoforms have extensive structural heterogeneity, which is brought about at the transcriptional, post-transcriptional and post-translational levels.

Structural diversity in fibronectins is first brought about by alternative splicing of three regions (ED-A, Ed-B and IIICS) of the primary fibronectin transcript to generate at least 20 different isoforms. As well as being regulated in a tissue- and developmentally-specific manner, it is known that the splicing pattern of fibronectin-pre-mRNA is deregulated in transformed cells and in malignancies. In fact, the fibronectin isoforms containing the ED-A, ED-B and IIICS sequences are expressed to a greater extent in transformed and malignant tumor cells than in normal cells.

In particular, the fibronectin isoform containing the ED-B sequence (B+ isoform), is highly expressed in foetal and tumor tissues as well as during wound healing, but restricted in expression in normal adult tissues. B+ fibronectin molecules are undetectable in mature vessels, but upregulated in angiogenic blood vessels in normal situations (e.g., development of the endometrium), pathological angiogenesis (e.g., in diabetic retinopathy) and in tumor development. The so-called B+ isoform of fibronectin (B-FN) is thus particularly suitable for use with the present invention.

The ED-B sequence is a complete type III-homology repeat encoded by a single exon and comprising 91 amino acids. The presence of B+ isoform itself constitutes a tumor-induced neoantigen, but in addition, ED-expression exposes a normally cryptic antigen within the type III repeat 7 (preceding ED-B); since this epitope is not exposed in fibronectin molecules lacking ED-B, it follows that ED-B expression induces the expression of neoantigens both directly and indirectly. This cryptic antigenic site forms the target of the monoclonal antibody, BC-1 (European Collection of Animal Cell Cultures, Porton Down, Salisbury, UK, number 88042101). The BC1 antibody may be used as a vascular targeting component of the present invention.

Improved antibodies with specificity for the ED-B isoform are described in WO 97/45544, specifically incorporated herein by reference. Such antibodies have been obtained as single chain Fvs (scFvs) from libraries of human antibody variable regions displayed on the surface of filamentous bacteriophage (see also WO 92/01047, WO 92/20791, WO 93/06213, WO 93/11236 and WO 93/19172).

Using an antibody phage library, specific scFvs can be isolated both by direct selection on recombinant fibronectin-fragments containing the ED-B domain and on recombinant ED-B itself when these antigens are coated onto a solid surface ("panning"). These same sources of antigen have also been successfully used to produce "second generation" scFvs with improved properties relative to the parent clones in a process of "affinity maturation". The isolated scFvs react strongly and specifically with the B+ isoform of human fibronectin, preferably without prior treatment with N-glycanase.

The antibodies of WO 97/45544 are thus particularly contemplated for use herewith. In anti-tumor applications, these human antibody antigen-binding domains are advantageous as they have less side-effects upon human administration. The referenced antibodies bind the ED-B domain directly. Preferably, the antibodies bind both human fibronectin ED-B and a non-human fibronectin ED-B, such as that of a mouse, allowing for testing and analysis in animal models. The antibody fragments extend to single chain Fv (scFv), Fab, Fab', F(ab')$_2$, Fabc, Facb and diabodies.

Even further improved antibodies specific for the ED-domain of fibronectin have been produced with sub-nanomolar dissociation constants, as described in WO 99/58570, and are thus even more preferred for use herewith. These targeting agents are exemplified by the L19 antibody, described in WO 99/58570, specifically incorporated herein by reference for the purpose of teaching how to make and use this and related antibodies. These antibodies have specific affinity for a characteristic epitope of the ED-B domain of fibronectin and have improved affinity to the ED-B epitope.

Such improved recombinant antibodies are available in scFv format, from an antibody phage display library. In addition to H10 and L19, the latter of which has a dissociation constant for the ED-B domain of fibronectin in the sub-nanomolar concentration range, the techniques of WO 99/58570, specifically incorporated herein by reference, may be used to prepare like antibodies. The isolation of human scFv antibody fragments specific for the ED-B domain of fibronectin from antibody phase-display libraries and the isolation of a human scFv antibody fragment binding to the ED-B with sub-nanomolar affinity are particularly described in Examples 1 and 2 of WO 99/58570.

Preferred antibodies thus include those with specific affinity for a characteristic epitope of the ED-B domain of fibronectin, wherein the antibody has improved affinity for the ED-B epitope, wherein the affinity is in the subnanomolar range, and wherein the antibody recognizes ED-B(+) fibronectin. Other preferred formats are wherein the antibody is a scFv or recombinant antibody and wherein the affinity is improved by introduction of a limited number of mutations in its CDR residues. Exemplary residues to be mutated include 31-33, 50, 52 and 54 of the VH domain and residues 32 and 50 of its VL domain. Such antibodies are able to bind the ED-B domain of fibronectin with a Kd of 27 to 54 pM; as exemplified by the L19 antibody or functionally equivalent variants form of L19.

Q5. Anti-Viral Conjugates

Under normal conditions, PE is not exposed at the cell surface. However, in various disease states, PE becomes exposed at the cell surface of one or more cell types. For example, endothelial cells within tumor vasculature become PE-positive and can be targeted by PE-directed therapeutics, as shown herein by the successful tumor treatment using duramycin conjugated to HuIgG. PE also becomes exposed at the cell surface of virally infected cells, which are thus additional targets for therapeutic intervention using the PE-binding peptide derivatives of the present invention. Indeed, the present application shows that duramycin derivatives, as exemplified by those linked to biotin and HuIgG, are effective anti-viral agents, both in vitro and in vivo.

Several anti-viral drugs, including AZT, acyclovir, gancyclovir, cidofovir (cytosine derivative) and new anti-viral drugs are limited by toxicity/efficacy. Based on their observations regarding changes in PE during viral infection, and further in light of the effectiveness of the original PE-binding peptide derivatives, the present inventors have addressed problems in the anti-viral field by designing new anti-viral therapeutics with reduced toxicity and increased efficacy. In the new anti-viral therapeutics of the invention, anti-viral drugs are linked to PE-binding peptides, which function to deliver the attached anti-viral drugs to virally infected cells.

In addition, the inventors have the following observations in regard to the development of the PE-binding peptide, anti-viral derivatives of the present invention. Data are presented herein to show that PE-binding peptide derivatives, e.g., duramycin-L-biotin, are taken up by macrophages in vivo, especially in the lung, even after systemic administration. On infection, many viruses first pass through cells of the reticuloendothelial cell system (RES), and the macrophage is the main cell for viral uptake. Therefore, by linking anti-viral drugs to PE-binding peptides such as duramycin, the anti-viral effect of the drug is directed to the primary cell type (macrophage) responsible for clearing invading viruses.

As the PE-binding peptide derivatives localize to macrophages in the lung after systemic administration will naturally be effective. Administration to the lung by more direct means, including via aerosol, is also envisioned. The present invention therefore solves important deficiencies in the viral treatment field by providing widely applicable and practical anti-viral remedies.

The new anti-viral therapeutics of the present invention thus comprise a PE-binding peptide, such as duramycin, linked to an anti-viral drug, preferably using a biologically releasable or hydrolytically labile bond to link the two agents. Any of a range of anti-viral agents, including any agent developed as an anti-viral in the future, may be linked to a PE-binding peptide to form an advantageous anti-viral therapeutic in accordance with this invention. In addition to so-called classic anti-viral agents, other DNA/RNA inhibitors may also be attached to a PE-binding peptide to form an anti-viral therapeutic. Exemplary anti-viral agents are listed in Table G, any one or more of which may be attached to a PE-binding peptide to prepare an anti-viral conjugate of the invention, or can be used separately in the anti-viral combination therapies of the invention.

R. Anti-Viral Treatment Methods

The present invention further provides a range of antibodies, immunoconjugates and PE-binding peptide derivatives, optionally conjugated to anti-viral agents, for use in treating viral infections. The treatment regimens, and particularly the doses, are generally as described above for the cancer treat-

TABLE G

Common Disease-Causing Viruses and Anti-Viral Drugs

| Disease-Causing Viruses | Drug Categories | Exemplary Anti-Viral Drugs |
|---|---|---|
| Herpes virus | | Cidofovir, acyclovir, penciclovir (famciclovir), gancyclovir (ganciclovir), deoxyguanosine, foscarnet, idoxuridine, trifluorothymidine, vidarabine, sorivudine |
| Retroviruses | Nucleoside reverse transcriptase (RT) inhibitors | Zidovudine, didanosine, zalcitabine, lamivudine, stavudine, abacavir, multinucleoside resistance A, multinucleoside resistance B |
| | Non-nucleoside RT inhibitors | Nevirapine, delavirdine, efavirenz, Adefovir Dipivoxil |
| | Protease Inhibitors | Indinavir, ritonavir, saquinavir, nelfinavir, amprenavir |
| | Cell cycle phase specific antineoplastic | Hydroxyurea (Hydrea ™, Bristol Myers-Squibb) |
| Hepatitis B | | Deoxycytosine iphosphate, lamivudine triphosphate, emticitabine triphosphate, adefovir diphosphate, penciclovir triphosphate, lobucavir triphosphate |
| Hepatitis C | | Interferon alpha, ribavirin |
| Influenza A and B | | Amantadine, rimantadine, zanamivir, oseltamivir |

Within the range of anti-viral agents and drugs, AZT and cidofovir are currently preferred for linking to a PE-binding peptide. Irrespective of the chosen anti-viral drug, the PE-binding peptide, anti-viral conjugate will bind to macrophages in the lungs, to virally infected cells and mechanisms. For example, the present examples demonstrate block of herpes virus (CMV), which escapes from Golgi-derived exocytotic vesicles, and block of arenavirus (Pichinde virus) and paramyxovirus (RSV), which bud out directly from the plasma membrane.

Virally infected cells externalize anionic phospholipids and aminophospholipids, particularly PS and PE, which are normally intracellular, i.e., confined to the inner surface of plasma membrane. During escape of the virus, phospholipids redistribute at the site of escape, accommodating membrane bending during viral budding or exocytosis from the plasma membrane, and anionic phospholipids and aminophospholipids are externalized during this process. The antibodies, peptide derivatives and conjugates of the invention can thus bind to the externalized anionic phospholipids and aminophospholipids, particularly PS and PE, and block the escape of the virus from the infected cell. Binding of the constructs of the invention to virally infected cells is also shown in the present examples.

The antibodies, peptide derivatives and conjugates of the invention may further bind to the externalized anionic phospholipids and aminophospholipids, particularly PS and PE, and interfere with one or more signaling pathways necessary for viral gene expression and/or replication.

Moreover, enveloped virions themselves likely have anionic phospholipids and aminophospholipids, such as PS and PE, on their external surface. Since viruses lack a translocase to maintain or restore phospholipid asymmetry, continued exposure of phospholipids such as PS and PE is expected. The antibodies, peptide derivatives and conjugates of the invention may thus cause opsonization, complement binding, phagocytosis by host cells such as macrophages and clearance of free virus particles.

In a further aspect of the invention, viruses likely need anionic phospholipids and aminophospholipids for infection and/or syncitia formation. The antibodies, peptide derivatives and conjugates of the invention may further block these aspects of the viral life cycle by binding to anionic phospholipids and aminophospholipids.

According to the foregoing insights, and in light of the present examples, the spectrum of viral treatment for the present invention extends to any virus, whether enveloped or not, DNA or RNA. As the anionic phospholipid- and aminophospholipid-binding antibodies, peptide derivatives and conjugates of the invention at least in part block viral replication inside the cell, and/or prevent escape of virus from cells, the invention is not limited to the treatment of enveloped viruses alone, nor to any particular virus, which is an important advantage. For example, work published subsequent to the invention reports that annexin V and PS vesicles can inhibit HIV-1 infection of macrophages, but cannot inhibit HIV-1 infection of T cells or inhibit other viruses, such as vesicular stomatitis virus G and amphotropic murine leukemia virus (Callahan et al., 2003).

Naturally, the antibodies, peptide derivatives and conjugates of the invention do act on enveloped viruses, particularly those viruses that have anionic phospholipids and aminophospholipids, of PS and PE, on the outer surface of the envelope, wherein the antibodies, peptide derivatives and conjugates cause viral clearance and/or inhibiting viral entry of target cells.

An important aspect of the present invention is therefore that it is universally applicable, being suitable for the treatment of recombinant, engineered and synthetic viruses, e.g., created as part of bio-terrorism. Indeed, the invention is not limited to the treatment of animals and humans. As the categories of hosts found in the virus taxa include algae, archaea, bacteria, fungi, invertebrates, mycoplasma, plants, protozoa, spiroplasma and vertebrates, the invention can be used to inhibit viral infection and replication in any such setting, including in viruses of agricultural importance. The treatment of viral infection and associated diseases in vertebrates is currently preferred, and any one or more of the viruses in Table H, which infect vertebrate animals, may be inhibited, and the resultant infection treated, using the present invention.

TABLE H

Viruses of Vertebrates

| Family | Genus | Type Species |
| --- | --- | --- |
| Adenoviridae | Mastadenovirus | Human adenovirus 2 |
|  | Aviadenovirus | Fowl adenovirus 1 |
|  | African Swine Fever-like Viruses | African swine fever virus |
| Arenaviridae | Arenavirus | Lymphocytic choriomeningitis virus |
|  | Arterivirus | Equine arteritis virus |
| Astroviridae | Astrovirus | Human astrovirus 1 |
| Birnaviridae | Aquabirnavirus | Infectious pancreatic necrosis virus |
|  | Avibirnavirus | Infectious bursal disease virus |
| Bunyaviridae | Bunyavirus | Bunyamwera virus |
|  | Hantavirus | Hantaan virus |
|  | Nairovirus | Nabrobi sheep disease virus |
|  | Phlebovirus | Sandfly fever Sicilian virus |
| Caliciviridae | Calicivirus | Vesicular exanthema of swine virus |
| Circoviridae | Circovirus | Chicken anemia virus |
| Coronaviridae | Coronavirus | Avian infectious bronchitis virus |
|  | Torovirus | Berne virus |
|  | Deltavirus | Hepatitis delta virus |
| Filoviridae | Filovirus | Marburg virus |
| Flaviviridae | Flavivirus | Yellow fever virus |
|  | Pestivirus | Bovine diarrhea virus |
|  | Hepatitis C - like viruses | Hepatitis C virus |
| Hepadnaviridae | Orthohepadnavirus | Hepatitis B virus |
|  | Avihepadnavirus | Duck hepatitis B virus |
| Herpesviridae Subfamily |  |  |
| Alphaherpesvirinae | Simplexvirus | Human herpesvirus 1 |
|  | Varicellovirus | Human herpesvirus 3 |

TABLE H-continued

Viruses of Vertebrates

| Family | Genus | Type Species |
|---|---|---|
| Subfamily: | | |
| Betaherpesvirinae | Cytomegalovirus | Human herpesvirus 5 |
| | Muromegalovirus | Mouse cytomegalovirus 1 |
| Subfamily | | |
| Gammaherpesvirinae | Roseolovirus | Human herpesvirus 6 |
| | Lymphocryptovirus | Human herpesvirus 4 |
| | Rhadinovirus | Ateline herpesvirus 2 |
| Iridoviridae | Ranavirus | Frog virus 3 |
| | Lymphocystivirus | Flounder virus |
| | Goldfish virus - like viruses | Goldfish virus 1 |
| Orthomyxoviridae | Influenzavirus A, B | Influenza A virus |
| | Influenzavirus C | Influenza C virus |
| | Thogoto-Like viruses | Thogoto virus |
| Papovaviridae | Polyomavirus | Murine polyomavirus |
| | Papillomavirus | Cottontail rabbit papillomavirus (Shope) |
| Paramyxoviridae Subfamily | | |
| Paramyxovirinae | Parayxovirus | Human parainfluenza virus 1 |
| | Morbillivirus | Measles virus |
| | Rubulavirus | Mumps virus |
| Subfamily | | |
| Pneumovirinae | Pneumovirus | Human respiratory syncytial virus |
| Parvoviridae Subfamily | | |
| Parovirinae | Parvovirus | Mice minute virus |
| | Erythovirus | B19 virus |
| | Dependovirus | Adeno-associated virus 2 |
| Picornaviridae | Enterovirus | Poliovirus 1 |
| | Rhinovirus | Human rhinovirus 1A |
| | Hepatovirus | Hepatitis A virus |
| | Cardiovirus | Encephalomyocarditis virus |
| | Aphthovirus | Foot-and-mouth disease virus O |
| Poxviridae Subfamily | | |
| Chordopoxvirinae | Orthopoxvirus | Vaccinia virus |
| | Parapoxvirus | Orf virus |
| | Avipoxvirus | Fowlpox virus |
| | Capripoxvirus | Sheeppox virus |
| | Leporipoxvirus | Myxoma virus |
| | Suipoxvirus | Swinepox virus |
| | Molluscipoxvirus | Molluscum contagiosum virus |
| | Yatapoxvirus | Yaba monkey tumor virus |
| Reoviridae | Orthoreovirus | Reovirus 3 |
| | Orbivirus | Bluetongue virus 1 |
| | Rotavirus | Simian rotavirus SA11 |
| | Coltivirus | Colorado tick fever virus |
| | Aquareovirus | Golden shiner virus |
| Retroviridae | Mammalian type B retroviruses | Mouse mammary tumor virus |
| | Mammalian type C retroviruses | Murine leukemia virus |
| | Avian type C retroviruses | Avian leukosis virus |
| | Type D retroviruses | Mason-Pfizer monkey virus |
| | Blv-htlv retroviruses | Bovine leukemia virus |
| | Lentivirus | Human immunodeficiency virus 1 |
| | Spumavirus | Human spumavirus |
| Rhabdoviridae | Vesiculovirus | Vesicular stomatitis Indiana virus |
| | Lyssavirus | Rabies virus |
| | Ephemerovirus | Bovine ephemeral fever |
| Togaviridae | Alphavirus | Sindbis virus |
| | Rubivirus | Rubella virus |

The use of the invention in treating viral infections and associated diseases in mammals is preferred, particularly in terms of valuable or valued animals, such as racehorses and domestic pets, and animals and birds used to directly produce (e.g., meat) or indirectly produce (e.g. milk and eggs) food for human consumption. In addition to human treatment, exemplary embodiments of the invention include the treatment of horses, dogs, cats and the like; the treatment of cows, pigs, boar, sheep, goat, buffalo, bison, llama, deer, elk, and other large animals, as well as their young, including calves and lambs.

The treatment of humans is particularly preferred, whether for naturally occurring viruses or for those created by bioterrorism. In terms of naturally occurring viruses and the resultant diseases, the invention is again unlimited in its applications. Accordingly, any one or more of the viruses in Table J may be inhibited using the present invention, and the resultant infections and diseases thus treated.

TABLE J

Viral Diseases in Humans

| Disease | Virus | Type of Virus |
| --- | --- | --- |
| AIDS | Human Immunodeficiency Virus (HIV) | Retrovirus |
| Bronchiolitis and viral pneumonia | Respiratory syncytial virus | Paramyxovirus |
| Bronchiolitis | Parainfluenza virus | Paramyxovirus |
| Cervical cancer | Human papilloma virus | Papovavirus |
| Chicken pox | Varicella Zoster virus | Herpesvirus |
| Dengue | Dengue virus | Flavivirus |
| Ebola hemorrhagic fever | Ebola virus | Filovirus |
| Genital Herpes | Herpes Simplex virus-2 | Herpesvirus |
| Hantavirus hemorrhagic fever | Hantavirus | Bunyavirus |
| Hepatitis | Hepatitis A | Picornavirus |
|  | Hepatitis B | Hepadavirus |
|  | Hepatitis C | Flavivirus |
|  | Hepatitis D | Deltavirus |
|  | Hepatitis E | Calcivirus |
| Influenza | Influenza viruses A, B and C | Orthomyxovirus |
| Junin Argentinian Hemorrhagic Fever | Junin virus | Arenavirus |
| Lassa hemorrhagic fever | Lassa virus | Arenavirus |
| Machupo hemorrhagic fever | Machupo virus | Arenavirus |
| Measles | Rubeola virus | Paramyxovirus |
| Mononucleosis | Epstein Barr virus | Herpesvirus |
| CMV disease (viral pneumonia, mononucleosis like syndrome) | Cytomegalovirus | Herpesvirus |
| Severe Acute Respiratory Syndrome (SARS) | Human coronavirus | Coronavirus |
| Shingles | Varicella zoster virus | Herpesvirus |
| Smallpox | Variola virus | Poxvirus |
| Yellow fever | Yellow fever virus | Flavivirus |
| West Nile Disease | West Nile virus |  |
| Western equine encephalitis | Western EE virus | Togavirus |
| Pneumonia, Hepatitis, acute respiratory disease | Adenovirus | Adenovirus |
| Gastroenteritis | Rotavirus | Rotavirus |
| Encephalitis | Semliki Forest virus | Alphavirus |
| Cowpox | Vaccima virus | Poxvirus |
| Encephalitis | Venezuelan EE | Alphavirus |
| Meningitis, encephalitis, meningoencephalitis | Lymphocytic choriomeningitis | Arenavirus |
| Venezuelan hemorrhagic fever | Guanarito virus | Arenavirus |
| Rift valley fever (hemorrhagic fever, encephalitis) | Rift valley fever virus | Bunyavirus |
| Marburg Hemorrhagic fever | Marburg virus | Filovirus |
| Tick borne encephalitis | Tick borne encephalitis virus (TBEV) | Flavivirus |
| Encephalitis | Hendra virus | Paramyxovirus |
| Encephalitis | Nipah virus | Paramyxovirus |
| Crimean-Congo hemorrhagic fever | Crimean-Congo hemorrhagic fever virus | Bunyavirus |
| Brazilian hemorrhagic fever | Sabia virus | Arenavirus |

The invention is particularly contemplated for use in the treatment of CMV related diseases such as viral pneumonia, mononucleosis like syndrome, and associated congenital malformations (deafness and mental retardation); respiratory diseases, such as those caused by RSV, including bronchiolitis and viral pneumonia, influenza, the common cold and SARS; AIDS; hepatitis; cancers associated with viral infections; mononucleosis; and smallpox.

In other embodiments, the inventors particularly contemplate the inhibition of arenaviruses, which are pathogenic in man. The arenaviruses include the Old World viruses responsible for Lassa fever (Lassa virus) and lymphocytic choriomeningitis (LCMV). Lassa fever is endemic in West Africa, affecting up to 300,000 people annually and causing up to 3000 deaths. Infection with Lassa fever leads to fever and malaise within about 10 days. Abdominal pain, nausea, vomiting and diarrhea are common. Pharyngitis and cough may develop. Neurological symptoms are usually mild. Vascular leak syndromes, such as edema and pleural effusions, are present in more severe cases. Bleeding is seen about one quarter of patients. The disease can cause changes in the cardiovascular system that culminate in shock and death.

Arenaviruses also include and the antigenically-distinct New World viruses responsible for Argentine hemorrhagic fever (Junin virus), Bolivian hemorrhagic fever (Machupo virus) and Venezuelan hemorrhagic fever (Guanarito virus). All of these viruses are on the CDC Category A list of potential bioterrorism weapons.

Although not connected with aminophospholipids or anionic phospholipids, other antibodies that bind to viruses directly have been developed into approved drugs. This is true of CytoGam, which is used for suppressing CMV infections in immunosuppressed patients, and Synagis, which is used to protect newborn infants from respiratory syncitial virus. Thus, there are no problems in the use of monoclonal antibodies to access and neutralize viruses in tissues.

The doses that are suitable for the anti-tumor embodiments are also suitable for the anti-viral treatments. Similarly, multiple administration may be used for chronic infections, and high doses may be used for acute infections. Any suitable route of administration may be employed, again as disclosed for the cancer treatment aspects, including IV, IM, SC, as an aerosol to lungs or airways and such like.

The therapeutics provided by the invention are valuable agents having broad-spectrum anti-viral activity. In addition to being effective against a large number of potentially lethal viruses, the agents can also be administered after exposure to the virus, even in settings where the exact nature of the virus is not known. Thus, the anti-viral therapeutics of the present invention do not require a prolonged period of time between identification of the pathogen and delivery of the therapy, in marked contrast with the time and expense entailed by the development, production or delivery of specific vaccines.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Tumor Treatment with Anti-VCAM-1-tTF Coaguligand

The present example shows the specific coagulation of tumor vasculature in vivo that results following the administration of a tumor vasculature-targeted coagulant ("coaguligand") to tumor-bearing animals and the resultant anti-tumor effects. In this coaguligand, an antibody directed to VCAM-1 (vascular endothelial adhesion molecule-1, VCAM-1) is used as a targeting agent to deliver truncated Tissue Factor (tTF), a modified form of a human coagulant, to tumor vasculature.

The MK2.7 hybridoma, secreting a rat $IgG_1$ antibody against murine VCAM-1, was obtained from the American Type Culture Collection (ATCC, Rockville, Md.; ATCC CRL 1909). The R187 hybridoma, secreting a rat $IgG_1$ antibody against murine viral protein p30 gag, was also obtained from the ATCC, and was used as an isotype matched control for the anti-VCAM-1 antibody.

The blood vessels of the major organs and a tumor from mice bearing subcutaneous L540 human Hodgkin's tumors were examined immunohistochemically for VCAM-1 expression using an anti-VCAM-1 antibody. Overall, VCAM-1 expression was observed on 20-30% of total tumor blood vessels stained by the anti-endoglin antibody, MJ 7/18, used as a positive control. Constitutive vascular expression of VCAM-1 was found in heart and lungs in both tumor-bearing and normal animals. Strong stromal staining was observed in testis where VCAM-1 expression was strictly extravascular.

Mice bearing subcutaneous L540 tumors were injected intravenously with anti-VCAM-1 antibody and, two hours later, the mice were exsanguinated. The tumor and normal organs were removed and frozen sections were prepared and examined immunohistochemically to determine the location of the antibody. Anti-VCAM-1 antibody was detected on endothelium of tumor, heart and lung. Staining was specific as no staining of endothelium was observed in the tumor and organs of mice injected with a species isotype matched antibody of irrelevant specificity, R187. No localization of anti-VCAM-1 antibody was found in testis or any normal organ except heart and lung.

An anti-VCAM-1•tTF conjugate or "coaguligand" was prepared using truncated tissue factor (tTF). Intravenous administration of the anti-VCAM-1•tTF coaguligand induces selective thrombosis of tumor blood vessels, as opposed to vessels in normal tissues, in tumor-bearing mice.

The anti-VCAM-1•tTF coaguligand was administered to mice bearing subcutaneous L540 tumors of 0.4 to 0.6 cm in diameter. Before coaguligand injection, tumors were healthy, having a uniform morphology lacking regions of necrosis. The tumors were well vascularized and had a complete absence of spontaneously thrombosed vessels or hemorrhages. Within four hours of coaguligand injection, 40-70% of blood vessels were thrombosed, despite the initial staining of only 20-30% of tumor blood vessels. The thrombosed vessels contained occlusive platelet aggregates, packed erythrocytes and fibrin. In several regions, the blood vessels had ruptured, spilling erythrocytes into the tumor interstitium.

By 24 h after coaguligand injection, the blood vessels were still occluded and extensive hemorrhage had spread throughout the tumor. Tumor cells had separated from one another, had pyknotic nuclei and were undergoing cytolysis. By 72 h. advanced necrosis was evident throughout the tumor. It is likely that the initial coaguligand-induced thrombin deposition results in increased induction of the VCAM-1 target antigen on central vessels, thus amplifying targeting and tumor destruction.

The thrombotic action of anti-VCAM-1•tTF on tumor vessels was antigen specific. None of the control reagents administered at equivalent quantities (tTF alone, anti-VCAM-1 antibody alone. tTF plus anti-VCAM-1 antibody or the control coaguligand of irrelevant specificity) caused thrombosis.

In addition to the thrombosis of tumor blood vessels, this study also shows that intravenous administration of the anti-VCAM-1•tTF coaguligand does not induce thrombosis of blood vessels in normal organs. Despite expression of VCAM-1 on vessels in the heart and lung of normal or L540 tumor-bearing mice, thrombosis did not occur after anti-VCAM-1•tTF coaguligand administration. No signs of thrombosis, tissue damage or altered morphology were seen in 25 mice injected with 5 to 45 µg of coaguligand 4 or 24 h earlier. There was a normal histological appearance of the heart and lung from the same mouse that had major tumor thrombosis. All other major organs (brain, liver, kidney, spleen, pancreas, intestine, testis) also had unaltered morphology.

Frozen sections of organs and tumors from coaguligand-treated mice gave coincident staining patterns when developed with either the anti-TF antibody, 10H10, or an anti-rat IgG antibody and confirmed that the coaguligand had localized to vessels in the heart, lung and tumor. The intensity of staining was equal to that seen when coaguligand was applied directly to the sections at high concentrations followed by development with anti-TF or anti-rat IgG, indicating that saturation of binding had been attained in vivo.

These studies show that binding of coaguligand to VCAM-1 on normal vasculature in heart and lung is not sufficient to induce thrombosis, and that tumor vasculature provides additional factors to support coagulation.

The anti-tumor activity of anti-VCAM-1•tTF coaguligand was determined in SCID mice bearing 0.3-0.4 $cm^3$ L540 tumors. The drug was administered i.v. 3 times at intervals of 4 days. Mean tumor volume of anti-VCAM-1•tTF treated mice was significantly reduced at 21 days of treatment (P<0.001) in comparison to all other groups. Nine of a total of 15 mice treated with the specific coaguligand showed more than 50% reduction in tumor volume. This effect was specific since unconjugated tTF, control IgG coaguligand and mixture of free anti-VCAM-1 antibody and tTF did not affect tumor growth.

EXAMPLE II

Phosphatidylserine Expression on Tumor Blood Vessels

To explain the lack of thrombotic effect of anti-VCAM-1•tTF on VCAM-1 positive vasculature in heart and lungs, certain of the inventors developed a concept of differential aminophospholipid and anionic phospholipid, e.g. PS and PE, localization between normal and tumor blood vessels. Specifically, they hypothesized that endothelial cells in normal tissues segregate aminophospholipids and anionic phospholipids, e.g. PS and PE, to the inner surface of the plasma membrane phospholipid bilayer, where PS is unable to participate in thrombotic reactions; whereas endothelial cells in tumors translocate aminophospholipids and anionic phospholipids to the external surface of the plasma membrane, where PS can support the coagulation action of the coaguligand. PS expression on the cell surface allows coagulation because it enables the attachment of coagulation factors to the membrane and coordinates the assembly of coagulation initiation complexes.

The inventors' model of aminophospholipid and anionic phospholipid translocation to the surface of tumor blood vessel endothelial cells, as developed herein, is surprising in that PS expression does not occur after, and does not inevitably trigger, cell death. Aminophospholipid and anionic phospholipid expression at the tumor endothelial cell surface is thus sufficiently stable to allow aminophospholipids and anionic phospholipids. e.g. PS and PE, to serve as targetable entities for therapeutic intervention.

To confirm the hypothesis that tumor blood vessel endothelium expresses PS on the luminal surface of the plasma membrane, the inventors used the following immunohistochemical study to determine the distribution of anti-PS antibody after intravenous injection into L540 tumor bearing mice.

A. Methods

Anti-PS and anti-cardiolipin antibodies, both mouse monoclonal IgM antibodies, were produced and characterized by Rote et al. (1993, incorporated herein by reference) as described in Example IV. The major reactivity of 3SB is with PS, but it also has reactivity with the anionic phospholipid, phosphatidic acid, a relatively minor component of the plasma membrane also tightly segregated to the internal leaflet in normal cells.

L540 tumor-bearing mice were injected i.v. with 20 µg of either anti-PS or anti-cardiolipin mouse IgM antibodies. After 10 min., mice were anesthetized and their blood circulations were perfused with heparinized saline. Tumors and normal tissues were removed and snap-frozen. Serial sections of organs and tumors were stained with either HRP-labeled anti-mouse IgM for detection of anti-PS antibody or with anti-VCAM-1 antibody followed by HRP-labeled anti-rat Ig.

To preserve membrane phospholipids on frozen sections, the following protocol was developed. Animals were perfused with DPBS containing 2.5 mM $Ca^{2+}$. Tissues were mounted on 3-aminopropyltriethoxysilane-coated slides and were stained within 24 h. No organic solvents, formaldehyde or detergents were used for fixation or washing of the slides.

Slides were re-hydrated by DPBS containing 2.5 mM $Ca^{2+}$ and 0.2% gelatin. The same solution was also used to wash sections to remove the excess of reagents. Sections were incubated with HRP-labeled anti-mouse IgM for 3.5 h at room temperature to detect anti-PS IgM.

B. Results

This immunohistochemical study showed that anti-PS antibody localized within 10 min. to the majority of tumor blood vessels, including vessels in the central region of the tumor that can lack VCAM-1. Vessels that were positive for VCAM-1 were also positive for PS. Thus, there is coincident expression of PS on VCAM-1-expressing vessels in tumors.

In the in vivo localization studies, none of the vessels in normal organs, including VCAM-1-positive vasculature of heart and lung, were stained, indicating that PS is absent from the external surface of the endothelial cells. In contrast, when sections of normal tissues and tumors were directly stained with anti-PS antibody in vitro, no differences were visible between normal and tumor, endothelial or other cell types, showing that PS is present within these cells but only becomes expressed on the surface of endothelial cells in tumors.

The specificity of PS detection was confirmed by two independent studies. First, a mouse IgM monoclonal antibody directed against a different negatively charged lipid, cardiolipin did not home to tumor or any organs in vivo. Second, pretreatment of frozen sections with acetone abolished staining with anti-PS antibody, presumably because it extracted the lipids together with the bound anti-PS antibody.

EXAMPLE III

Annexin V Blocks Coaguligand Activity

The present example provides further evidence of the role of surface PS expression in coaguligand activity from studies using the high affinity PS binding ligand, annexin V, to block PS function in vitro and in vivo.

A. Annexin V Blocks Coaguligand Activation of Factor X In Vitro

The ability of Annexin V to affect Factor Xa formation induced by coaguligand was determined by a chromogenic assay. IL-1α-stimulated bEnd.3 cells were incubated with anti-VCAM-•tTF and permeabilized by saponin. Annexin V was added at concentrations ranging from 0.1 to 10 µg/ml and cells were incubated for 30 min. before addition of diluted Proplex T. The amount of Factor Xa generated in the presence or absence of Annexin V was determined. Each treatment was performed in duplicate and repeated at least twice.

The need for surface PS expression in coaguligand action is further indicated by the inventors' finding that annexin V, which binds to PS with high affinity, blocks the ability of anti-VCAM-1•tTF bound to bEnd.3 cells to generate factor Xa in vitro.

Annexin V added to permeabilized cells preincubated with anti-VCAM-1•tTF inhibited the formation of factor Xa in a dose-dependent manner. In the absence of Annexin V, cell-bound coaguligand produced 95 ng of factor Xa per 10,000 cells per 60 min. The addition of increasing amounts of Annexin V (in the µg per ml range) inhibited factor Xa production. At 10 µg per ml, Annexin V inhibited factor Xa production by 58%. No further inhibition was observed by increasing the concentration of Annexin V during the assay, indicating that annexin V saturated all available binding sites at 10 µg per ml.

B. Annexin V Blocks Coaguligand Activity In Vivo

The ability of Annexin V to inhibit coaguligand-induced thrombosis in vivo was examined in L540 Hodgkin-bearing SCID mice. Tumors were grown in mice and two mice per group (tumor size 0.5 cm in diameter) were injected intravenously via the tail vein with one of the following reagents: a) saline; b) 100 µg of Annexin V; c) 40 µg of anti-VCAM-1•tTF; d) 100 µg of Annexin V followed 2 hours later by 40 µg of anti-VCAM-1•tTF.

Four hours after the last injection mice were anesthetized and perfused with heparinized saline. Tumors were removed, fixed with 4% formalin, paraffin-embedded and stained with hematoxylene-eosin. The number of thrombosed and non-thrombosed blood vessels was counted and the percentage of thrombosis was calculated.

Annexin V also blocks the activity of the anti-VCAM-1•tTF coaguligand in vivo. Groups of tumor-bearing mice were treated with one of the control or test reagents. The mice were given (a) saline; (b) 100 µg of Annexin V; (c) 40 µg of anti-VCAM-1•tTF coaguligand; or (d) 100 µg of Annexin V followed 2 hours later by 40 µg of anti-VCAM-1•tTF coaguligand. Identical results were obtained in both mice per group.

No spontaneous thrombosis, hemorrhages or necrosis were observed in tumors derived from saline-injected mice. Treatment with Annexin V alone did not alter tumor morphology.

In accordance with other data presented herein, 40 µg of anti-VCAM-1•tTF coaguligand caused thrombosis in 70% of total tumor blood vessels. The majority of blood vessels were occluded with packed erythrocytes and clots, and tumor cells were separated from one another. Both coaguligand-induced anti-tumor effects, i.e., intravascular thrombosis and changes in tumor cell morphology, were completely abolished by pre-treating the mice with Annexin V.

These findings confirm that the anti-tumor effects of coaguligands are mediated through the blockage of tumor vasculature. These data also demonstrate that PS is essential for coaguligand-induced thrombosis in vivo.

EXAMPLE IV

Generation of Antibodies to Aminophospholipids and Anionic Phospholipids

This example describes an immunization protocol designed by the inventors in light of their observations on aminophospholipid and anionic phospholipid translocation in tumor vascular endothelial cells, and discovered to function well in the generation of antibodies against aminophospholipids and anionic phospholipids. A number of antibodies reactive with aminophospholipids and anionic phospholipids, such as PS and PE, were obtained. In the present and following examples, for simplicity, antibodies reactive with PS can be termed "anti-PS antibodies", although the binding of certain of these antibodies is not restricted to PS but extends to certain other aminophospholipids and anionic phospholipids as shown herein.

A. Immunization Protocol

To present aminophospholipids and anionic phospholipids to the immune system as stronger immunogens, the aminophospholipids and anionic phospholipids were formulated as aminophospholipid-positive and anionic phospholipid-positive cells. The membrane-inserted aminophospholipids and anionic phospholipids, surrounded by other membrane components, have a better conformation and clearance rate for raising antibodies.

The intent is to immunize immunocompetent animals with autologous cells expressing aminophospholipids and anionic phospholipids, as exemplified in this instance by PS, wherein the animals would not produce antibodies against all self surface antigens, but would recognize membrane-exposed phospholipids, e.g. PS, as a foreign element. The procedure is applicable to the use of any standard laboratory animals, such as immunocompetent BALB/c mice and Lewis rats, with any aminophospholipid-positive or anionic phospholipid-positive cells.

BALB/c mice and mouse endothelioma cells, bEnd.3 (immortalized mouse (BALB/c strain) endothelial cells), were first chosen. bEnd.3 were cultured in 10% DMEM with 9 ml/500 ml HEPES Buffer, in 10% $CO_2$ incubator. The bEnd.3 cells were expanded in T175 TC flasks until the desired number of cells were obtained. Typically, each flask at ~70-80% confluency has about $3 \times 10^6$ cells, and each mouse should receive from $1 \times 10^6$ to $20 \times 10^6$ cells, up to $1 \times 10^7$ cells.

bEnd.3 cells are treated with 50 µM to 200 µM of hydrogen peroxide for 1 or 2 hours at 37° C. to expose anionic phospholipids, such as PS, before immunization. The stock of $H_2O_2$ is [9.8M]; 30% (v/v). This is diluted 1:1000, then 0.4 ml is add into the T175 TC flask with 40 ml media to a final concentration of 100 µM $H_2O_2$. The cells were maintained for 1 hour at 37° C. To harvest, the cells were washed 3× with warm PBS, +10 mM EDTA, to remove all BSA or serum protein in the medium. The cells were removed with gentle trypsin treatment, washed and centrifuged for 5 minutes at 1000 rpm. The supernatant was aspirated and the cells resuspended in DMEM without additives to the appropriate volume (each mouse receives about $1 \times 10^7$ cells in 200 µl) and kept on ice.

Cells treated in this manner were injected (200 µl of cell suspension) into each mouse IP using 1 ml syringe and 23 gauge needle. Mice were immunized from three to seven times at intervals of 3 to 4 weeks. Immune sera were collected by bleeding the mice ten days after each boost, starting from the second boost. The serum titer for anti-PS was tested by ELISA.

These immunizations with autologous PS-positive cells did not result in unrestricted production of autoantibodies, but were limited to the production of antibodies reactive with PS or reactive with PS in combination with other aminophospholipids and anionic phospholipids.

In another study, female Lewis rats were immunized with bEnd.3 endothelial cells that had been treated with 200 µM of hydrogen peroxide for 2 h. The treatment caused translocation of anionic phospholipids to the external surface in 70-90% of cells as detected by $^{125}$I-labeled annexin V. Treated cells were washed, detached and counted. Two million cells were suspended in sterile PBS and injected 5 times i.p. with the interval of 3 wk between injections. The titer of polyclonal antibodies to anionic phospholipids was determined 2 days after each immunization.

B. High Titer Antisera

Mice with extremely high titers of antibodies reactive with anionic phospholipids such as PS were obtained (Table 1). The mice did not show any signs of toxicity. Although this immunization protocol was more effective in mice than rats overall, immunization of rats was effective and produced the 9D2 antibody (see below).

TABLE 1

Anti-PS IgG Antibody Generation

| Titer Range | Number of Mice per Group (% of total) |
|---|---|
| 1:100-1:1,000 | 2/30 (6.66%) |
| 1:1000-1:10,000 | 5/30 (16.6%) |
| 1:10,000-1:100,000 | 18/30 (60%) |
| 1:100,000-1,000,000 | 5/30 (16.6%) |

In further immunizations, various mice were immunized three times with hydrogen peroxide-treated bEnd.3 cells and the serum was tested 54 days after the first immunization. IgG antibodies reactive with PS within serum were detected with an anti-mouse IgG. Fc specific secondary antibody, and IgM antibodies within serum were detected with an anti-mouse IgG mu specific secondary antibody. A number of effective antisera with IgG and IgM antibodies reactive with PS were obtained using this immunization protocol, of which the antisera with IgG antibodies were generally more effective.

These methods can now be used to generate further particular anti-PS antibodies, e.g. including those screened for effectively competition with the 3G4 antibody described below. Typically, when the IgG titer of the desired antisera for PS reaches >200,000, but PC titer is <50,000, fusion can be performed to generate the monoclonal antibody.

Also, these methods are not limited to initial cell treatment with $H_2O_2$, as other methods to induce expression of aminophospholipids and anionic phospholipids can be used. For example, treatment with TNF and actinomycin D is another useful method. In one case, subconfluent (~85% confluence) bEnd.3 cells were treated with 10 ng/ml mouse TNF and 1 µg/ml actinomycin D for 16 hrs at 37° C. in the incubator. The cells were then taken through the immunization procedure as outlined above.

C. IgG and IgM Monoclonal Antibodies

Hybridomas were obtained by fusing splenocytes from immunized animals with myeloma partner P3X63AG8.653 cells (ATCC, Rockville, Md.).

An important aspect of the inventors' technique to prepare monoclonal antibodies useful in tumor treatment is the selection strategy, which involves screening to select antibodies that bind to aminophospholipids or anionic phospholipids, but not to neutral phospholipids. Another important aspect is to select antibodies that bind to PS-coated plates as strongly in the presence of serum as in the absence of serum. This is carried out to exclude antibodies that recognize complexes of PS and serum proteins, which are believed to cause or contribute to anti-phospholipid syndrome.

The strategy to isolate monoclonal antibodies reactive with PS, for example, involved screening hybridoma supernatants on PS-coated plates using an anti-mouse IgG, Fc gamma specific secondary antibody. Screening was first conducted against four phospholipids (PS, phosphatidylserine; PE, phosphatidylethanolamine; CL, cardiolipin; and PC, phosphatidylcholine), as well as bEnd3 cells. Clones reactive with the neutral phospholipid, PC were discarded, as were clones non-reactive with bEnd3 cells. High binding anti-PS clones were selected. The wells that had PS only reactivity, or strong preference for PS were sub-cloned first, and wells that exhibited PS reactivity in combination with binding to other anionic phospholipids were sub-cloned second.

In certain in the following studies, mouse monoclonal IgM antibodies termed 3SB, D11 and BA3, produced as described by Rote et al. (1993), were also included. The 3SB antibody is described in the literature as an anti-PS antibody and the D11 antibody is described in the literature as an anti-cardiolipin (anti-CL) antibody. Details of the generation and characterization of these antibodies were reported by Rote et al. (1993, incorporated herein by reference).

The isotype of each selected hybridoma generated by the inventors was determined. As antibodies of IgG class have numerous advantages over IgM, including typically higher affinity, lower clearance rate in vivo and simplicity of purification, modification and handling, their generation was particularly desired. To focus on wells with homogeneous IgG isotype wells containing IgM or a mixture of different Igs were discarded or re-cloned. Sub-cloning of highly positive clones was repeated three to four times.

The isotype of representative IgG and IgM antibodies, as determined by ELISA, is shown in Table 2. The inventors initially termed the 3G4 antibody "F3-G4", before changing the designation to 3G4. This does not reflect any change in biological material. The serum dependence or independence of the antibodies is also set forth in Table 2.

TABLE 2

Isotype and Serum-Dependence of Anti-PS Antibodies

| Name | Origin | Species/Isotype | Serum-dependence |
|---|---|---|---|
| 3SB | Rote et al., 1993 | Mouse IgM kappa | None |
| D11 | N. Rote | Mouse IgM kappa | |
| BA3 | Rote et al., 1993 | Mouse IgM kappa | |
| 9D2 | This study | Rat IgM kappa | None |
| 1B12 | This study | Mouse IgG$_1$ kappa | |
| 3G4 | This study | Mouse IgG$_3$ kappa | None |
| 1B9 | This study | Mouse IgG$_1$ kappa | Absolute |
| 3B10 | This study | Mouse IgG$_3$ kappa | None |
| 2G7 | This study | Mouse IgG$_1$ kappa | Absolute |
| 7C5 | This study | Mouse IgG$_1$ kappa | Absolute |

D. ELISA Protocol and Monoclonal Antibody Characterization

The antibodies were studied further by ELISA and compared to 3SB and D11. The anti-PS ELISA used in the present studies is conducted as follows. Unless particular differences are specified, this is the format of the ELISA used throughout the studies of the present application.

The ELISA is exemplified using the antigen PS (P-6641 25 mg 10 mg/ml (solvent is Chloroform:MeOH 95:5) in 2.5 ml bottle). Other phospholipids can be used using the same protocol. The PS (or other phospholipids) stock solution should be aliquoted and stored in an airtight container at –30° C. The preferred 96 well plates are Dynatech U bottom Immulon 1 (from Dynatech Labs, Cat# 011-010-3550).

The standard blocking buffer used herein is 10% bovine serum dissolved in PBS. Other blocking solutions are suitable, but any detergents should be excluded from block and wash solutions. The primary antibody is the test sample or admixture. The preferred secondary antibody is goat, anti-mouse IgG-HRP. The developing solutions are: 10 ml of 0.2M $Na_2PO_4$, 10 ml of 0.1M citric acid, one 10 mg tablet of OPD, and 10 µl of hydrogen peroxide. The stop solution is 0.18 M $H_2SO_4$.

The protocol entails coating 96-well plate with PS as follows: dilute the PS stock solution in n-hexane to 10 µg/ml and mix well. Add 50 µl to each well and allow this to evaporate for one hour. Add 200 µl of 10% serum (or other blocking buffer) to each well, cover and maintain at room temperature for 2 hours or overnight at 4° C. Wash the plate three times with PBS. Add the primary antibody (dilute in blocking buffer) and incubate for 2 hours at 37° C. Wash three times with PBS. Add 100 µl/well of secondary antibody (typically goat, anti-mouse IgG-HRP or other appropriate secondary antibody) and incubate for 1 hour at 37° C. Wash the plate three times with PBS. Develop the ELISA by adding 100 µl of developing solution to each of the wells, develop for 10 minutes, then add 100 µl of stop solution to each plate and read the O.D. at 490 nm.

The following results are presented for 9D2, 1B12, 3G4 and 1B9. The affinity of these antibodies for PS was determined and compared to 3SB. Certain of the relative affinities of the new antibodies are much improved compared to 3SB (Table 3).

TABLE 3

Relative Affinity of Anti-PS Antibodies

| Name | $EC_{50}$ (µg/ml)[1] | Binding vs. 3SB (-fold increased) | $EC_{50}$ (nM)[2] | Affinity vs. 3SB (-fold increased) |
| --- | --- | --- | --- | --- |
| 3SB | 0.468 | 1 | 0.518 | 1 |
| D11 | >40.0 | 0.011 | >44.4 | 0.011 |
| 9D2 | 0.104 | 4.50 | 0.115 | 4.50 |
| 1B12 | 0.312 | 1.50 | 2.07 | 0.25 |
| 3G4 | 0.040 | 11.7 | 0.266 | 1.94 |
| 1B9 | 0.019 | 24.6 | 0.126 | 4.11 |
| Annexin V[3] | 0.100 | 4.68 | 2.77 | 0.18 |

[1]Based on dilutions of Tissue Culture supernatants; concentration of IgG and IgM were determined by sandwich ELISA using either anti-mouse or rat Igs as capturing Antibodies. All clones secrete in average 10 to 15 µg/ml of Ig.
[2]MW used for conversion: IgM - 900 kDa, IgG - 150 kDa, Annexin V - 36 kDa
[3]Affinity of Annexin V to PS is in the range of 0.1 nM to 1 nM. The value in this table represents binding of commercial biotinylated Annexin V detected by streptavidin-HRP using the same ELISA conditions as for anti-PS antibodies.

The specificity of the antibodies was determined by ELISA using plates coated with the following phospholipids: PS, phosphatidylserine; PE, phosphatidylethanolamine; PI, phosphatidylinositol: PA, phosphatidic acid; PG, phosphatidylglycerol; PC, phosphatidylcholine: CL, cardiolipin; and SM, sphingomyelin. The specificity profiles of 9D2, 1B12, 3G4 and 1B9, as compared to 3SB and D11, are shown in Table 4.

TABLE 4

Phospholipid Specificity of Anti-PS Antibodies

| Name | Relative Strength of Reactivity on ELISA[1,2] |
| --- | --- |
| 3SB | PS = PA >> CL, PI, PE, PG |
| D11 | CL = PA >> PS, PI, PE, PG |
| 9D2 | PA > PS = CL > PG = PI >> PE |
| 1B12 | PS = PA > CL > PE = PI, PG |
| 3G4 | PS = PA = PI = PG = CL >> PE |
| 3B10 | PS = PA = PI >> PE |
| 1B9 | PS only |
| 2G7 | PS only |
| 7C5 | PS only |
| Annexin V | PS = PE = PI = PA > CL > PG |

[1]The symbol > indicates at least 2-fold difference in binding to various phospholipids tested at identical antibody concentration.
[2]The symbol >> indicates at least 10-fold difference in binding to various phospholipids tested at identical antibody concentration.

The 1B9, 2G7 and 7C5 antibodies behave essentially the same. These antibodies recognize only PS and require serum or serum proteins for binding to PS. The binding of 1B9, 2G7 and 7C5 to various phospholipids was assayed only in the presence of 10% bovine serum, whereas binding of the other antibodies was tested either in the absence or in the presence of serum. For antibodies other than 1B9, 2G7 and 7C5, the presence of serum does not change preference in binding to a particular phospholipid. This latter group, including 3G4, 3B10 and 9D2, have the preferred property of binding to PS in the absence of serum.

The 3SB antibody recognizes PS on intact cells in the presence and absence of serum. The major reactivity of 3SB is with PS, but it also has reactivity with phosphatidic acid, which is a relatively minor component of the plasma membrane (Hinkovska-Galcheva et al., 1989). 3SB is essentially devoid of reactivity with phosphatidylethanolamine and phosphatidylinositol, as well as phosphatidylcholine and sphingomyelin (Table 4).

PS is the most abundant anionic phospholipid of the plasma membrane and is tightly segregated to the internal leaflet of the plasma membrane in normal cells under normal conditions. PS is an aminophospholipid. PE is also an aminophospholipid, but PE is neutral, not anionic. Other than being a neutral aminophospholipid, PE behaves similarly to PS and is normally tightly segregated to the internal leaflet of the plasma membrane.

PI is another major anionic phospholipid of the plasma membrane, which is further tightly segregated to the internal leaflet in normal cells under normal conditions. PA and PG are minor anionic phospholipids of the plasma membrane, which are also normally segregated to the internal leaflet. CL is an anionic phospholipid present in mitochondrial membranes, and typically absent from the plasma membrane.

PC and SM are choline-containing, neutral phospholipids of the plasma membrane. Each of PC and SM are predominantly located on the external leaflet under normal conditions.

In keeping with the inventors' model for differential aminophospholipid and anionic phospholipid expression between normal and tumor blood vessels, none of the antibodies developed using the selected protocol reacted with the neutral phospholipids, PC and SM. The 1B9 antibody was specific for PS, whereas 9D2, 1B12 and 3G4 bound to anionic phospholipids and aminophospholipids with the preferences shown in Table 4. The 9D2 antibody is also described in Example VI.

EXAMPLE V

Externalized Phosphatidylserine is a Global Marker of Tumor Blood Vessels

The present example shows that the exposure of PS occurs on endothelial cells in each of ten different solid tumors growing in mice and is not limited to the L540 tumor model described in Example II.

Externalized PS in vivo was detected by injecting a monoclonal antibody directed against PS intravenously into mice bearing various types of human or murine tumors. Anti-PS antibodies are shown to bind specifically to vascular endothelium in all ten different tumor models. Vascular endothelium in normal organs derived from the same mice were unstained. An isotype-matched control monoclonal antibody did not localize to either tumor or normal cells. Apoptotic cells were also identified immunohistochemically, wherein very few endothelial cells in tumors expressed markers of apoptosis.

The present example therefore shows that vascular endothelial cells in tumors but not in normal vessels externalize PS. Most of the tumor endothelial cells having exposed PS were not apoptotic. PS is thus an abundant and accessible marker of tumor vasculature that can be used for tumor vessel imaging and therapy.

A. L540, H358 and HT29 Tumors

The anti-PS antibody used in these studies was the mouse monoclonal IgM antibody termed 3SB (Example IV, Rote et al., 1993). 3SB mainly binds to PS, but also reacts with PA, a relatively minor anionic phospholipid with a distribution like PS. The anti-CL antibody used was the mouse monoclonal IgM antibody termed D11 (Example IV, Rote et al., 1993).

PS exposure on tumor and normal vascular endothelium was first examined in three animal tumor models: L540 human Hodgkin's lymphomas, NCI H358 human non-small cell lung carcinoma (NSCLC) and HT29 human colorectal carcinomas. To grow the tumors in vivo. $2 \times 10^6$ cells were injected into the right flank of SCID mice and tumors allowed to reach 0.8-1.2 cm in diameter.

Mice bearing large tumors (volume above 800 mm$^3$) were injected intravenously via the tail vein with 20 µg of either anti-PS or anti-CL antibodies. One hour after injection, mice were anesthetized and their blood circulation was perfused with heparinized saline. Tumors and normal organs were removed and snap-frozen for preparation of cryosections. Mouse IgM was detected using goat anti mouse IgM (µ specific)-HRP conjugate followed by development with carbazole. At least 10 random fields per section were examined at ×40 magnification and the average percentage of positive vessels was calculated.

The anti-PS antibodies specifically homed to the vasculature of all three tumors (HT 29, L540 and NCI-H358) in vivo, as indicated by detection of the mouse IgM. In this first study, the average percentages of vessels stained in the tumors were 80% for HT 29.30% for L540 and 50% for NCI-H358. Vessels in all regions of the tumors were stained and there was staining both of small capillaries and larger vessels.

No vessel staining was observed with anti-PS antibodies in any normal tissues. In the kidney, tubules were stained in both anti-PS and anti-CL recipients, and this relates to the secretion of IgM through this organ. Anti-CL antibodies were not detected in any tumors or normal tissues, except kidney. These findings indicate that only tumor endothelium exposes PS to the outer site of the plasma membrane.

B. Small and Large L540 Tumors

To estimate the time at which tumor vasculature loses the ability to segregate PS to the inner side of the membrane, anti-PS localization was examined in L540 tumors ranging in volume from 140 to 1,600 mm$^3$.

Mice were divided into 3 groups according to their tumor size: 140-300, 350-800 and 800-1,600 mm$^3$. Anti-PS Ab was not detected in three mice bearing small L540 tumors (up to 300 mm$^3$). Anti-PS Ab localized in 3 animals of 5 in the group of intermediate size L540 tumors and in all mice (4 out of 4) bearing large L540 tumors (Table 5). Percent of PS-positive blood vessels from total (identified by pan endothelial marker Meca 32) was 10-20% in the L540 intermediate group and 20-40% in the group of large L540 tumors (Table 5).

TABLE 5

PS Externalization Detected in Mid and Large Sized Tumors

| Tumor Size (mm$^3$) | No. Positive Tumors/Total* | % PS-Positive Vessels/Total† |
|---|---|---|
| 350-800 | 3/5 | 10-20 |
| 850-1,600 | 4/4 | 20-40 |

*Mice bearing L540 Cy tumors were divided into three groups according to tumor size. 20 µg of anti-PS antibodies were injected i.v. and allowed to circulate for 1 hour. Mouse antibodies were detected on frozen sections using anti-mouse IgM-peroxidase conjugate.
†Total number of blood vessels was determined using pan-endothelial Ab Meca 32. PS-positive and Meca-positive vessels were counted in 4 fields per cross section of tumor. Range of % PS-positive vessels within the same group is shown.

C. L540, H358, HT29, Colo26, B16 and 3LL Tumors

Using the same anti-PS (3SB) and anti-CL (D11) antibodies, PS exposure on tumor and normal vascular endothelium was examined in further studies using an additional three animal tumor models (six in total): L540 human Hodgkin's lymphomas, NCI H358 human non-small cell lung carcinoma (NSCLC), HT29 human colorectal carcinomas, Colo26 mouse colon carcinomas, B16 mouse melanomas and 3LL mouse lung tumors.

In these studies, tumors were grown subcutaneously in SCID mice and allowed to reach a volume of 0.4-0.7 cm$^3$. Three or more mice were used per group. Anti-PS or anti-CL mouse IgM antibodies (30 µg/mouse) were injected intravenously in 200 µl of saline. Thirty minutes later, the mice were sacrificed, exsanguinated and their blood circulation perfused with heparinized saline. Major organs and tumors were harvested and snap-frozen for preparation of cryosections. Mouse IgM was detected using goat anti mouse IgM (µ specific)-HRP conjugate followed by development with carbazole.

Serial sections of tumor were stained with a monoclonal antibody. MECA 32, directed against a pan-endothelial marker of mouse vessels. PS-positive vessels were identified morphologically and by their coincident staining with anti-mouse IgM and MECA 32. At least 10 random fields per section (0.317 mm$^2$/field) were examined in blinded fashion by two independent observers. The percentage of MECA 32-positive vessels that stained positively for PS was calculated. Three tumors of each type were examined in each of two separate studies. The mean values and standard errors (SE) were calculated. Inter-tumor variation in the number of total and PS-positive vessels in each group was approximately 10%.

Figure 1:
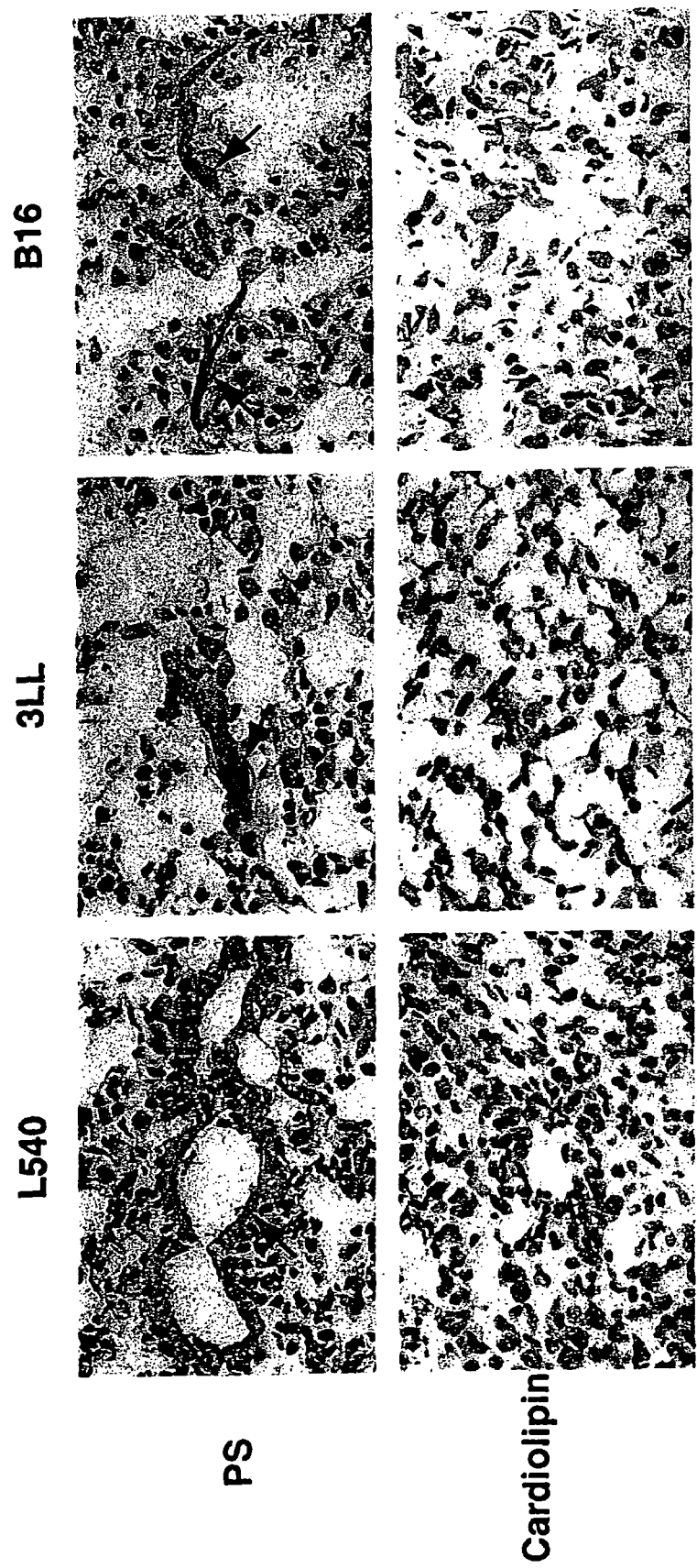
FIG. 1. Localization of anti-PS antibody (3SB) to vascular endothelial cells in L540 human Hodgkin's lymphoma, 3LL murine lung carcinoma and B16 murine melanoma tumors in mice. Tumor-bearing SCID mice were injected intravenously with 20 μg of anti-PS (3SB) or anti-CL (D11) mouse IgM. The blood circulation was perfused with saline 1 h later. Mice were sacrificed 1 h later and tumor and organs were harvested and snap-frozen. Mouse IgM was detected on frozen sections using goat anti-mouse IgM-peroxidase conjugate. Anti-PS antibody specifically localized to blood vessels (indicated by arrows) in all tumors. No localization was observed in mice injected with control, anti-CL IgM.

All six tumors in this study contained PS-positive vessels (Table 6). Detection of PS by 3SB was specific since no staining of tumor endothelium was observed with the anti-CL antibody (Table 6; FIG. 1). No vascular localization of anti-PS or anti-CL antibodies was observed in normal organs other than the kidneys (tubule staining in both anti-PS and anti-CL recipients reflects secretion of IgM through this organ).

TABLE 6

Specific Localization of Anti-PS Antibodies to Tumor Vessels

| Tissue | Anti-PS* | Anti-CL |
|---|---|---|
| L540 tumor | 19.3 ± 3.3 | 0 |
| H358 tumor | 15.6 ± 4.1 | 0 |
| HT29 tumor | 4.2 ± 1.6 | 0 |
| B16 tumor | 40.6 ± 5.4 | 0 |
| 3LL tumor | 5.3 ± 3.7 | 0 |
| Colo 26 tumor | 12.4 ± 2.4 | 0 |
| Adrenal | 0 | 0 |
| Brain | 0 | 0 |
| Heart | 0 | 0 |
| Kidney | 0† | 0† |
| Intestine | 0 | 0 |
| Liver | 0 | 0 |
| Lung | 0 | 0 |
| Pancreas | 0 | 0 |
| Spleen | 0 | 0 |
| Testis | 0 | 0 |

*The results are presented as the mean (±SE) percentage of PS-positive vessels of MECA 32-stained vessels per field of 0.317 mm$^2$. Six tumors of each type were analyzed. The average number of MECA 32-positive vessels per 0.317 mm$^2$ field was 25, 21, 17, 18, 27 and 22 ± 10% vessels for L540, H358, HT29, B16, 3LL and Colo 26 tumors, respectively
†Non-antigen specific tubular staining was visible in both anti-PS and anti-CL recipients.

In these studies, the percentage of PS-positive vessels ranged from 10% in Colo 26 tumors to 40% in B16 tumors. Anti-PS IgM was present on the luminal surface of capillaries and venules in all regions of the tumors. PS-positive vessels appeared to be particularly prevalent in and around regions of necrosis. Positive vessels usually did not show morphological abnormalities that were apparent by light microscopy. Occasional vessels located in necrotic areas showed morphological signs of deterioration. Anti-PS antibody (but not anti-CL antibody) also localized to necrotic and apoptotic tumor cells.

These controlled studies demonstrate that PS is consistently exposed on the luminal surface of vascular endothelial in various tumors, but not in normal tissues, and that the tumor vasculature expression is not model-specific.

D. The Majority of PS-Positive Tumor Vessels are not Apoptotic

A double labeling technique was used to identify apoptotic endothelial cells in tumor sections. Endothelial cells were identified with the pan-endothelial cell marker, MECA 32. Apoptotic cells were identified immunohistochemically using two independent markers: an active form of caspase-3, which identifies cytosolic changes in dying cells (Krajewska et al., 1997), and fragmented DNA, which identifies cells having nuclear alterations (Gavrieli et al., 1992).

Active caspase-3 was detected by a rabbit anti-caspase-3 specific antibody (R&D. Minneapolis, Minn.) followed by incubation with anti-rabbit IgG conjugated to alkaline phosphatase (AP, Pierce, Rockford, Ill.). Other tumor sections were analyzed by Tunel assay (ApopTag™ kit, Oncor, Md.) using anti-digoxigenin-alkaline phosphatase conjugate as a detecting reagent. Sections were double stained for apoptosis markers (pink) and the endothelial cell marker, MECA 32 (brown). Both colors were clearly visible on the same cells, if markers of endothelial cells and apoptotic cells coincided.

Endothelial cells in five out of six types of tumors (HT29, H358, B16, Colo 26, L540) did not display either of the apoptosis markers (Table 7). The sixth type of tumor, 3LL, displayed a few apoptotic endothelial cells that were located in necrotic areas. In contrast, apoptotic malignant cells were common in all types of tumors. The percentage of apoptotic tumor cells ranged from 1-2% in L540 tumors to 12.6-19.6% in 3LL tumors.

TABLE 7

Expression of Apoptotic Markers in Tumors

| Tumor type | Active caspase-3 | | Tunel assay | |
|---|---|---|---|---|
| | Tumor cells (% of total)* | Tumor vessels | Tumor cells (% of total) | Tumor vessels |
| 3LL | 19.8 ± 4.3 | <1.0† | 12.6 ± 3.6 | 0 |
| HT29 | 13.7 ± 2.3 | 0 | 7.8 ± 2.5 | 0 |
| H358 | 5.8 ± 2.0 | 0 | 4.3 ± 1.6 | 0 |
| Colo 26 | 5.3 ± 1.5 | 0 | 4.1 ± 1.5 | 0 |
| B16 | 4.2 ± 1.8 | 0 | 3.5 ± 1.6 | 0 |
| L540 | 2.3 ± 1.0 | 0 | 1.6 ± 0.5 | 0 |

*The percentage of tumor cells or tumor blood vessels that were positive for either caspase-3 or Tunel was determined in ten high power fields per section. The fields were randomly selected along two perpendicular directions from the edges through the center of the tumor. The mean (±SE) of the percentage of positive cells or vessels in tumors from 6 mice is presented.
†Occasional vessels (1 of >100) in the necrotic area of 3LL tumor displayed both markers of apoptosis.

E. MDA-MB-231 and Meth A Tumors

PS exposure on tumor vascular endothelium was also examined in MDA-MB-231 human breast tumors growing in mice and in mouse Meth A fibrosarcoma growing subcutaneously. The antibody used in these studies was the 9D2 antibody, generated as described in Example IV, which is reactive with anionic phospholipids.

As described in detail in Example VI, 9D2 localized to tumor vessels in L540. NCI-H358 and B16 tumors, as well as in models of MDA-MB-231 breast tumor growing orthotopically in the mammary fat pads of SCID mice and mouse Meth A fibrosarcoma growing subcutaneously. 9D2 localized to tumor vessels in all of five tumors. Vascular endothelium in the tumors showed distinct membrane staining. 9D2 antibody also localized to the membrane and cytosol of necrotic and apoptotic tumor cells. No vascular localization of 9D2 antibody was observed in 9 of the 10 normal organs that were examined, with non-specific staining of the tubules in the kidney being observed.

Double-staining studies were also performed in which mice bearing orthotopic MDA-MB-231 breast tumors were injected i.v. with biotinylated 9D2 antibody and frozen sections later stained with FITC-conjugated MECA32 (Example VI). About 40% of MECA 32-positive vessels bound 9D2.

F. MD-MBA-435 Tumors

In a further breast cancer model, PS exposure on tumor vascular endothelium was examined in MDA-MB-435 human breast cancer cells growing in mice. The antibody used in these studies is a chimeric version of the 3G4 antibody (ch3G4). The 3G4 antibody generation is described in Example IV, and the production of the chimeric 3G4 antibody is detailed in Example XIX. The localization of ch3G4 to tumor vascular endothelium in the MDA-MB-435 model is described in more detail in Example XIX and shown in FIG. 22.

Briefly, tumors were established using MD-MBA-435s cells and biotinylated versions of the chimeric 3G4 antibody and a control IgG of irrelevant specificity were administered. Tumor sections were stained with Cy3-conjugated streptavidin to detect the biotinylated proteins. Double staining with the MECA 32 antibody followed by FITC-tagged anti-rat IgG secondary antibody was conducted to detect vascular endothelium. This detection method labeled the biotinylated proteins and the vascular endothelium using red and green, so that biotinylated proteins bound to the endothelium appear yellow in a converged image (FIG. 22). This study showed specific localization of the chimeric 3G4 antibody to tumor vascular endothelium.

G. RIP-Tag Tumors

For the tenth model, PS exposure on tumor vascular endothelium was examined in a "RIP-Tag" transgenic mouse model (RIP1-Tag 2) of multistage carcinogenesis. In this transgenic mouse model, every mouse develops islet tumors of the pancreas by 12-14 weeks of age as a result of expression of the SV40 T antigen (Tag) oncogene in insulin-producing beta-cells. Tumors develop in multiple stages from hyperproliferative islets, and require an angiogenic switch in order to progress towards malignancy. Matrix metalloproteinase-9 controls the angiogenic switch (REF).

9D2 localization studies were conducted in the RIP1-Tag2 model in collaboration with Dr. Donald McDonald, Professor of Pathology at UCSF. 9D2 was injected intravenously into RIP1-Tag2 mice starting at 10 weeks of age, when all mice have small, highly vascularized, solid tumors. Double staining of thick (80 µm) tumor sections was performed to identify localized 9D2 and CD31 in tumors and normal pancreas. Approximately 50% of vessels (CD31 positive) in pancreatic tumors had localized 9D2, whereas vessels in normal islets were unstained. Mice injected with control rat IgM had weak and infrequent staining of tumor vessels. Some leakage of 9D2 and control rat IgM into extravascular tissues beyond the endothelium was also apparent.

The present example therefore confirms that vascular endothelial cells in tumors externalize PS and anionic phospholipids to their luminal surface, where they can be bound by anti-PS antibodies in vivo. PS is absent from the external surface of vascular endothelial cells in normal tissues, indicating that PS-recognizing antibodies, annexin V and other ligands can be used for delivering cytotoxic drugs, coagulants and radionuclides for the selective imaging or destruction of vessels in solid tumors.

PS-positive tumor endothelium appeared, for the most part, to be viable in the tumors used in this study. It does not display markers of apoptosis, it is morphologically intact and metabolically active, as indicated by its expression of VCAM-1, E-selectin and other rapidly turned-over proteins. Although often regarded as an indicator of apoptosis, PS exposure has been observed in several types of viable cells, including malignant cells (Rao et al., 1992), (Utsugi et al., 1991) activated platelets (Rote et al., 1993), and embryonic trophoblasts at various stages of migration, matrix invasion and fusion (Adler et al., 1995).

Lack of correlation between PS exposure and commitment to cell death has been also shown on pre-apoptotic B lymphoma cells that restore PS asymmetry and grow normally after removal of the pro-apoptotic stimulus (Hammill et al., 1999). In normal viable cells, PS exposure is probably triggered by surface events, such as ligand-receptor interactions, that induce $Ca^{2+}$ fluxes into the cells (Dillon et al., 2000). $Ca^{2+}$ fluxes activate scramblase (Zhao et al., 1998) and simultaneously inhibit aminophospholipid translocase (Comfurius et al. 1990).

PS on tumor vessels is attractive as a target for cancer imaging or therapy for several reasons: it is abundant (approximately $3 \times 10^6$ molecules per cell); it is on the luminal surface of tumor endothelium, which is directly accessible for binding by vascular targeting agents in the blood; it is present on a high percentage of tumor endothelial cells in diverse solid tumors, and it is absent from endothelium in all normal tissues examined to date. Unconjugated antibodies, vascular targeting agents and imaging agents directed against PS or tumor vasculature can therefore be used for the detection and treatment of cancer in man.

EXAMPLE VI

Anionic Phospholipids are Exposed on the Surface of Tumor Blood Vessels

Anionic phospholipids are largely absent from the external leaflet of the plasma membrane of mammalian cells under normal conditions. Exposure of phosphatidylserine, for example, on the cell surface occurs during apoptosis, necrosis, cell injury, cell activation and malignant transformation. The present example shows that anionic phospholipids are upregulated on tumor vasculature in vivo, as demonstrated by localization of both a specific antibody and a natural ligand that binds to anionic phospholipids.

A monoclonal antibody, 9D2, which specifically recognizes anionic phospholipids, was injected into mice bearing a variety of orthotopic or ectopic tumors. Other mice received annexin V, a natural ligand that binds to anionic phospholipids. Both 9D2 and annexin V specifically localized to vascular endothelium in all tumors and also to tumor cells in and around regions of necrosis. Between 15 and 40% of endothelial cells in tumor vessels were stained. No localization was detected on normal endothelium.

Various factors and tumor-associated conditions known to be present in the tumor microenvironment were examined for their ability to cause exposure of anionic phospholipids in cultured endothelial cells, as judged by 9D2 and annexin V binding. Hypoxia/reoxygenation, acidity, thrombin and inflammatory cytokines all induced exposure of anionic phospholipids. Hydrogen peroxide was also a strong inducer. Combined treatment with inflammatory cytokines and hypoxia/reoxygenation had greater than additive effects. The demonstrated exposure of anionic phospholipids on tumor endothelium in vivo is thus likely to be caused by injury and activation by cytokines and reactive oxygen species. Irrespective of the mechanism, anionic phospholipids are markers of tumor vessels that can now be used for tumor vessel targeting, imaging and therapy.

A. Materials and Methods

1. Materials $Na^{125}I$ was obtained from Amersham (Arlington Heights, Ill.). Dulbecco's modified Eagle's tissue culture medium and Dulbecco PBS containing $Ca^{2+}$ and $Mg^{2+}$ were obtained from Gibco (Grand Island, N.Y.). Fetal calf serum was obtained from Hyclone (Logan, Utah). L-α-phosphatidylserine, L-α-phosphatidylcholine, cardiolipin, L-α-phosphatidylethanolamine, L-α-phosphatidylinositol, sphingomyelin, phosphatidic acid, phosphatidylglycerol, O-phenylenediamine, hydrogen peroxide and thrombin were from Sigma (St. Louis, Mo.). Flat bottom plates with 24 wells were obtained from Falcon (Becton Dickinson and Co., Lincoln Park, N.J.).

Recombinant hepatocyte growth factor (HGF or scatter factor) and actinomycin D was from Calbiochem (San Diego, Calif.). Recombinant murine interleukin-1 alpha, beta and tumor necrosis factor alpha (TNF α) were purchased from R&D Systems (Minneapolis, Minn.). Interferon of Universal Type I (hybrid protein that substitutes for all types of interferons) was purchased from PBL Biomedical Laboratories (New Brunswick, N.J.). Recombinant human vascular endothelial growth factor 121 (VEGF), human platelet-derived growth factor-BB, interleukin-6 (IL-6), interleukin-8 (IL-8), interleukin-10 (IL-10) and human fibroblast growth factor-2 (FGF-2) were purchased from PeproTech (Rocky Hill, N.J.).

2. Antibodies

MECA 32, a pan mouse endothelial cell antibody, was obtained from Dr. E. Butcher (Stanford University, Calif.) and served as a positive control for immunohistochemical studies. Details of this antibody have been published (Leppink et al., 1989). Rabbit anti-rat immunoglobulin, rat-anti mouse immunoglobulin and goat-anti mouse and anti-rat secondary antibodies conjugated to horseradish peroxidase (HRP) were purchased either from Daco (Carpinteria, Calif.) or from Jackson Immunoresearch Labs (West Grove, Pa.).

The 9D2 antibody used in these studies was generated as described in Example IV. 9D2 is a rat monoclonal antibody reactive with anionic phospholipids. Further characterization of the phospholipid specificity of 9D2 is given in the results section of this example.

3. Cells

L540Cy Hodgkin lymphoma cells, derived from a patient with end-stage disease, were provided by Prof. V. Diehl (Köln, Germany). NCI-H358 human non-small cell lung carcinoma was provided by Dr. Adi Gazdar (Southwestern Medical Center, Dallas, Tex.). Meth A mouse fibrosarcoma and MDA-MB-231 human breast carcinoma were obtained from American Type Cell Collection (Rockville, Md.). The mouse brain endothelioma line, bEnd.3, was provided by Prof. Werner Risau (Max Plank Institution, Munich, Germany) and was maintained in DMEM with 10% FBS. Adult bovine aortic endothelial (ABAE) cells were purchased from Clonetics (San Diego, Calif.; Walkerville, Md.). ABAE cells were maintained in DMEM with 10% serum and 2 ng/ml of bFGF.

4. Tissue Culture bEnd.3, ABAE cells and all tumor cells except L540Cy lymphoma were maintained in DMEM supplemented with 10% fetal calf serum, 2 mM L-glutamine, 2 units/ml penicillin G and 2 μg/ml streptomycin. L540Cy cells were maintained in RPMI 1640 containing the same additives. Cells were sub-cultured once a wk. Trypsinization of bEnd.3 cells was performed using 0.125% trypsin in PBS containing 0.2%

EDTA. For in vitro studies, endothelial cells were seeded at a density of $10\times10^3$ cells/ml in 1 ml of culture medium in 24 well plates and incubated 48-96 h before being used in the assays. Medium was refreshed 24 h before each study.

5. Reactivity with Plastic-Immobilized Phospholipids

Phospholipids were dissolved in n-hexane to a concentration of 50 µg/ml. 100 µl of this solution was added to wells of 96-well microtiter plates. After evaporation of the solvent in air, the plates were blocked for 2 h with 10% fetal bovine serum diluted in DPBS containing 2 mM $Ca^{2+}$ (binding buffer).

9D2 antibody or annexin V were diluted in the binding buffer in the presence of 10% serum at an initial concentration of 6.7 nM. Serial two-fold dilutions were prepared in the plates (100 µl per well). The plates were then incubated for 2 h at room temperature. The plates were washed and the 9D2 and annexin V were detected by goat anti-rat IgM conjugated to HRP and rabbit anti-human annexin V followed by goat anti-rabbit IgG conjugated to HRP (all diluted 1:1000), respectively. Secondary reagents were detected by using chromogenic substrate OPD followed by reading plates at 490 nm using a microplate reader (Molecular Devices, Palo Alto, Calif.).

The specificity of the 9D2 antibody binding was validated by using control rat IgM of irrelevant specificity (Pharmingen, San Diego, Calif.). The specificity of annexin V binding to phospholipids, which is $Ca^{2+}$-dependent, was determined by diluting the reagent in the DPBS containing 5 mM EDTA. Additional negative controls consisted of washing the plates with the binding buffer containing 0.2% of a detergent Tween 20. This treatment extracts lipids, thus removing the phospholipid that was absorbed to plastic. Neither 9D2 antibody nor annexin V bound to detergent-washed plates.

6. Detection of Anionic Phospholipids on the Surface of Cultured Endothelial Cells Endothelial cells were grown until they reached approximately 70% confluence. To induce PS exposure, cells were treated with $H_2O_2$ (200 µM) for 1 h at 37° C. Control and treated slides were washed with DPBS containing $Ca^{2+}$ and $Mg^{2+}$ and fixed with 0.25% of glutaraldehyde diluted in the same buffer. Excess aldehyde groups were quenched by incubation with 50 mM of $NH_4Cl$ for 5 min. To examine the effect of detergents and organic solvents on detection of phospholipids, some slides were pre-incubated with acetone (5 min) or with PBS containing 1% (v/v) Triton™ X-100.

Cells were washed with DPBS (containing $Ca^{2+}$, $Mg^{2+}$ and 0.2% (w/v) gelatin) and incubated with 1 µg/ml of biotinylated annexin V (Pharmingen, San Diego, Calif.) or with 1 µg/ml of 9D2 antibody. After 2 h of incubation, cells were washed with 0.2% gelatin buffer and were incubated with streptavidin-HRP (1:500 dilution). Rat IgM of irrelevant specificity and streptavidin alone were used as negative controls in these studies. All steps were performed at room temperature. HRP activity was measured by adding O-phenylenediamine (0.5 mg/ml) and hydrogen peroxide (0.03% w/v) in citrate-phosphate buffer, pH 5.5. After 15 min, 100 µl of supernatant were transferred to 96 well plates, 100 µl of 0.18 M $H_2SO_4$ were added and the absorbance was measured at 490 nm. Alternatively, PS-positive cells were detected by addition of carbazole substrate, resulting in insoluble red-brownish precipitate. Each study was performed in duplicate and repeated at least twice.

7. Inhibition of 9D2 and Annexin V Binding to Phospholipids by Liposomes

The specificity of phospholipid recognition was further confirmed by competition assays with various liposomes. Liposomes were prepared from solutions of 5 mg of a single phospholipid in chloroform. The solutions were dried under nitrogen to form a thin layer in a round-bottomed glass flask. Ten ml of Tris buffer (0.1 M, pH 7.4) were then added and the flask was sonicated five times for 2 min. 9D2 or annexin V (6.66 nM) were pre-incubated with 200 µg/ml of liposomal solution for 1 h at room temperature. The mixture was added to phospholipid-coated plates or endothelial cell monolayers. The ability of 9D2 to bind to an immobilized phospholipid or cell surface in the presence or absence of the different liposomes was determined as described above.

8. Competition of 9D2 and Annexin V for Binding to Immobilized PS

Biotinylated 9D2 antibody and annexin V were prepared by incubating purified proteins with a 10-fold molar excess of N-hydroxysuccinimide biotin (Sigma, MO) for 1 h at room temperature. Free biotin was removed by dialysis against PBS. The biotinylation procedure did not impair the PS-binding capacity of either protein. For competition studies, unmodified and biotinylated proteins were premixed with a 10-fold molar excess of unmodified proteins. The mixtures were then added to PS-coated plates. Bound reagents were detected by streptavidin-HRP conjugate diluted 1:1000. The binding to PS of each reagent in the absence of a competitor was taken as the 100% value.

9. Growth of Subcutaneously Implanted Tumors

For localization studies, $2\times10^7$ L540 human Hodgkin's lymphoma cells or $1\times10^7$ cells of other tumor types were injected subcutaneously into the right flank of SCID mice (Charles River, Wilmington, Mass.). Tumors were allowed to reach a volume of 0.4-0.7 $cm^3$. A minimum of three animals per group was used. Studies were replicated at least three times.

10. Orthotopic Model of Human MDA-MB-231 Breast Carcinoma

Female nu/nu or SCID mice were purchased from Charles River. MDA-MB-231 human mammary carcinoma cells were implanted into the mammary fat pad according to a published protocol (Price. 1996). Briefly, mice were anesthetized and a 5-mm incision was made in the skin over the lateral thorax. The mammary pad was exposed to ensure the correct site for injection of $1\times10^7$ MDA-MB-231 cells re-suspended in 0.1 ml of saline.

11. Detection of Anionic Phospholipids in Tumor Bearing Mice In Vivo

Immunohistochemical techniques, in which 9D2 or annexin V are applied directly to sections of frozen tissues, do not discriminate between anionic phospholipids on the inner leaflet and the outer leaflet of the plasma membrane. To detect externally-positioned phospholipids, methods were performed essentially as previously described (Example V; Ran et al., 1998). Tumor-bearing SCID mice were injected intravenously with either 50 µg of 9D2 or biotinylated 9D2 antibody or 100 µg of biotinylated annexin V. Sixty min later mice were sacrificed and their blood circulation was exsanguinated and perfused with heparinized saline as previously described (Burrows et al., 1992). All major organs and tumor were harvested and snap-frozen for preparation of cryosections.

Sections were blocked with PBS containing 10% serum. To prevent loss of phospholipids during slide processing, detergents and organic solvents were omitted from blocking and washing buffers. Rat IgM was detected using goat anti rat IgM (µ specific)-HRP conjugate followed by development with carbazole or DAB (Fries et al., 1993). Biotinylated reagents were detected by streptavidin conjugated to HRP.

Tumor sections derived from mice injected with saline or rat IgM of irrelevant specificity served as negative controls. Additional controls consisted of incubating the slides in 1%

Triton solution or in acetone for 10 min. These treatments extract phospholipids. No signal was detected under these conditions. The number of positive vessels per high power field was determined at magnification of ×100. At least 10 fields per section were examined and the average percentage of positive vessels was calculated. Staining of the sections by this method for the presence of 9D2 or annexin V detects cells having externalized anionic phospholipids that were accessible for binding by the reagents in vivo.

12. Identification and Quantification of PS-Positive Tumor Vessels

Structures with localized 9D2 antibody or annexin V were identified as blood vessels by morphological appearance on DAB-stained sections and by co-incident staining with the pan-endothelial cell marker, MECA 32 on serial sections of frozen tissues. Quantification on DAB-stained sections was done by counting vessels stained by MECA 32, 9D2 or annexin V in serial sections of a tumor. Six slides of each tumor type derived from 6 mice injected with 9D2 antibody, control rat IgM or annexin V were examined. At least 10 random fields per section (0.317 mm²/field) were scored in blinded fashion by two independent observers. The mean numbers and standard errors of vessels stained by 9D2, annexin V or MECA 32 were calculated. The mean number of 9D2 or annexin V-positive vessels determined in each tumor type group was compared to the mean number of MECA 32-positive vessels in the same tumor group. The percentage of 9D2 or annexin V-positive vessels was calculated.

In further studies, mice bearing MDA-MB-231 tumors (0.3-0.7 cm³ in volume) were injected intravenously with 50 μg of biotinylated 9D2, control IgM or annexin V (six mice per group). Biotinylated reagents were first incubated with streptavidin-Cy3 conjugate, washed in PBS, then incubated with MECA 32 antibody followed by FITC-tagged anti-rat IgG secondary antibody. Single images, taken with appropriate filters for Cy3 (red) and FITC (green) fluorescence respectively, were captured by digital camera and transferred to a computer. Images of 10 random fields (0.317 mm²/field) demonstrating yellow color (a product of merged green and red fluorescence) were superimposed with the aid of Metaview software. The same method was used to analyze tumors from mice injected with control rat IgM or saline. The percentage of vessels with localized 9D2 or annexin V was calculated as follows: mean number of yellow vessels per field divided by mean number of green (total) vessels multiplied by 100.

B. Results

1. Phospholipid Specificity of 9D2 Antibody and Annexin V

Figure 2A:
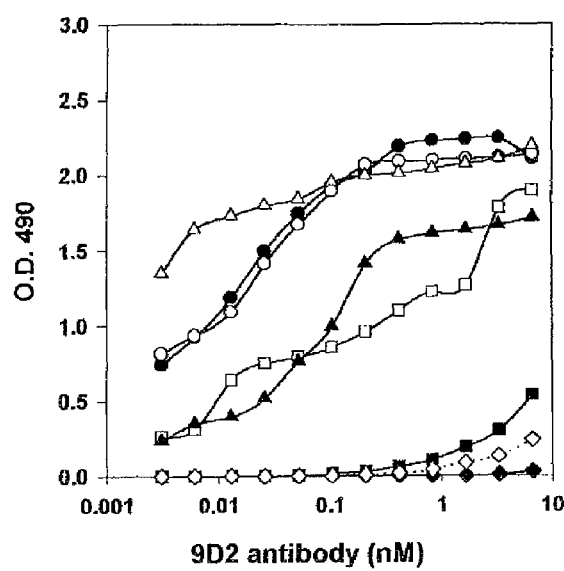
FIG. 2A and FIG. 2B. Binding of 9D2 antibody and annexin V to phospholipids adsorbed to plastic. Phospholipids were adsorbed to plastic of microtiter plates. After blocking with 10% serum, 9D2 antibody (FIG. 2A) or annexin V (FIG. 2B) were added at concentrations ranging from 6.66 nM to 0.005 nM in the presence of 10% serum. The plates were washed and the bound 9D2 antibody and annexin V were detected using goat anti-rat IgM-HRP and rabbit anti-annexin V IgG followed by anti-rabbit-HRP, respectively.

The 9D2 antibody specifically recognized anionic phospholipids (PS, PA, CL, PI, PG) and had no significant reactivity with neutral phospholipids (PE, PC and SM) in ELISA (FIG. 2A; Table 8). The order of strength of binding of 9D2 to phospholipids in ELISA was PA>PS=CL>PG=PI. The binding was antigen-specific since no binding was observed with several control rat IgM of irrelevant specificity. Binding of 9D2 to any of the anionic phospholipids adsorbed to ELISA plates was blocked by liposomes prepared from any of the anionic phospholipids, but not by liposomes prepared from any of the neutral phospholipids.

TABLE 8

Phospholipid Specificity of 9D2 and Annexin V

| Phospholipid | | Abundance and location in the plasma membrane under normal conditions[a] | $EC_{50}$ of binding (pM) | |
|---|---|---|---|---|
| Name | Type | | 9D2 | Annexin V |
| PS | Anionic amino-PL | Major PL (15%), located on inner side | 12 | 100 |
| PA | Anionic PL | Minor PL (less than 1%) | 2 | 100 |
| PG | Anionic PL | Minor PL (less than 1%) | 100 | 250 |
| PI | Anionic PL | Major PL (7%), mainly located on the inner side | 100 | 50 |
| CL | Anionic PL | Absent from the plasma membrane | 15 | 130 |
| PE | Neutral amino-PL | Major PL (22%), mainly located on inner side | >8000 | 100 |
| SM | Neutral choline-PL | Major PL (9%), located on the outer side | >8000 | >8000 |
| PC | Neutral choline-PL | Major PL (46%), located on the outer side | >8000 | >8000 |

[a]Percentage of total phospholipids, taken from Fridrikkson, et al., 1999. Percentages may vary for different cell types.

Annexin V also bound to anionic phospholipids, but its binding was less specific than that of 9D2 in that it also bound strongly to the neutral phospholipid, PE. The order of strength of binding of annexin V to phospholipids in ELISA was PI>PS=PE=PA=CL>PG (Table 8). These findings for annexin V are consistent with earlier data (Andree et al., 1990).

The binding of 9D2 was unaffected by the presence of 5 mM EDTA, showing it did not require $Ca^{2+}$ for binding to anionic phospholipids. In contrast, the binding of annexin V to anionic phospholipids was abolished in the presence of 5 mM EDTA, as expected from its known dependence on $Ca^{2+}$ for binding to anionic phospholipids or PE (Schlaepfer et al., 1987; Blackwood and Ernst, 1990).

Neither 9D2 nor annexin V bound to ELISA plates that had been coated with phospholipids but then washed with 0.2% Tween in saline, confirming that their binding was to the absorbed phospholipids. 9D2 and annexin V did not bind detectably to heparin, heparan sulfate or to double or single stranded DNA.

2. 9D2 Antibody and Annexin V do not Cross-Block Each Other's Binding to PS

To examine whether 9D2 antibody and annexin V compete for binding to PS, cross-blocking studies were performed using biotinylated proteins on PS-coated plates. Binding of biotinylated 9D2 antibody and annexin V was blocked by a 10-fold molar excess of unmodified 9D2 and annexin V, respectively (Table 9). However, unmodified annexin V did not affect the ability of biotinylated 9D2 to bind to the PS plate. Likewise, addition of unmodified 9D2 antibody did not alter the ability of biotinylated annexin V to bind to the PS plate (Table 9).

TABLE 9

9D2 and Annexin V Do Not Cross-Block Binding to PS

| PS-binding protein | Competitor[a] | Binding (% Control)[b] |
|---|---|---|
| Biotinylated annexin V | Annexin V | 8% |
| Biotinylated 9D2 | Annexin V | 93% |

TABLE 9-continued

9D2 and Annexin V Do Not Cross-Block Binding to PS

| PS-binding protein | Competitor[a] | Binding (% Control)[b] |
|---|---|---|
| Biotinylated annexin V | 9D2 | 95% |
| Biotinylated 9D2 | 9D2 | 5% |

[a]Annexin V or 9D2 antibody were pre-mixed in 10-fold molar excess over the biotinylated reagents. Binding of biotinylated reagents to PS on microtiter plates was detected by streptavidin-HRP.
[b]Reactivity of biotinylated reagents in the absence of a competitor was taken as 100%. The mean values of triplicate determinations are presented. SD was less than 10% of the mean value.

These results indicate that 9D2 antibody and annexin V do not cross-block each other binding to PS-coated plates, either because they recognize different epitopes on the PS molecule or different conformations of PS adsorbed on plastic.

3. Binding to Externalized Anionic Phospholipids on Cell Surfaces

The binding of 9D2 antibody and annexin V to cell surfaces was examined using mouse bEnd.3 endothelioma cells or bovine ABAE cells. Neither 9D2 nor annexin V bound to non-permeabilized monolayers of either cell type under quiescent conditions. This indicates that the majority of anionic phospholipids of the plasma membrane are normally sequestered to the cytosolic domain. In contrast, strong staining was observed when cells were pre-incubated with TNFα and actinomycin D under conditions that caused apoptosis in 90-100% of the endothelial cells.

To confirm that 9D2 and annexin V were binding to phospholipids on cell surfaces. $H_2O_2$-treated bEnd.3 cells were incubated with 9D2 antibody or annexin V in the presence or absence of various competing liposomes. Anionic phospholipids become exposed on non-apoptotic, viable bEnd.3 cells when they are pre-treated with a sub-toxic concentration (100-200 μM) of $H_2O_2$ (Ran et al., 2002).

Figure 2B:
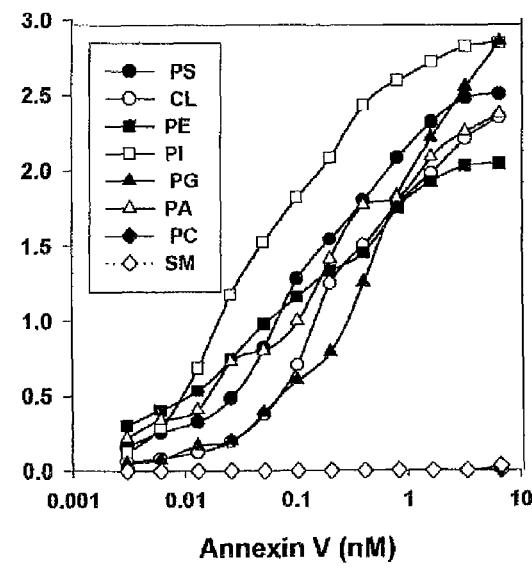
Figure 3:
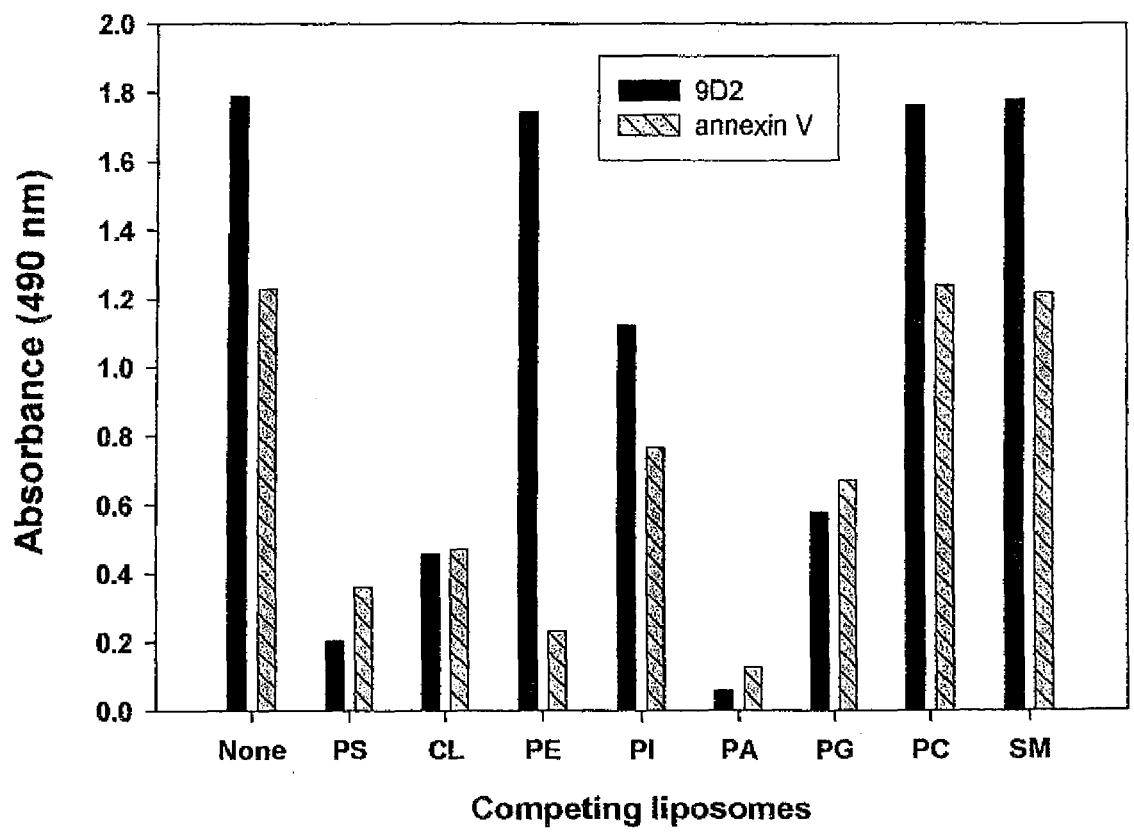
FIG. 3. Inhibition of binding of 9D2 antibody and annexin V to anionic phospholipids on $H_2O_2$-treated endothelial cells with competing phospholipid liposomes. 9D2 antibody and annexin V (6.66 nM) were pre-incubated with various phospholipid liposomes (200 μg/ml) DPBS buffer containing 10% serum. The bound 9D2 antibody and annexin V were detected using goat anti-rat IgM-HRP and rabbit anti-annexin V IgG followed by anti-rabbit-HRP respectively. Binding in the presence or absence of competing liposomes was determined. Standard deviations of triplicate measurements were less than 10% of the mean values.

The binding of 9D2 antibody to $H_2O_2$-treated bend.3 cells was inhibited by liposomes containing anionic phospholipids but not by liposomes containing neutral phospholipids (FIG. 3). The magnitude of inhibition of 9D2 binding to cells varied in the order PA>PS>CL>PG>PI, in close agreement with the results obtained using plastic-immobilized phospholipids (FIG. 2A and FIG. 2B). Similarly, the binding of annexin V to $H_2O_2$-treated cells was blocked by liposomes containing PS, PA, PE, CL and, to a lesser extent, PI and PG. Liposomes containing SM or PC did not block annexin V binding to cells, all in agreement with the results obtained using plastic-immobilized phospholipids.

These results confirm that 9D2 binds to anionic phospholipids in the $H_2O_2$-treated endothelial cells, whereas annexin V binds to PE in addition of anionic phospholipids.

4. Detection of Externalized Anionic Phospholipids on Cells In Vivo

Direct immunohistochemical techniques, in which 9D2 or annexin V are applied directly to sections of frozen tissues, do not discriminate between anionic phospholipids on the inner leaflet and the outer leaflet of the plasma membrane. To detect externally-positioned phospholipids, 9D2 and annexin V were injected intravenously into tumor-bearing mice and localization to tumor vessels was determined by indirect immunohistochemistry.

Mice bearing various types of solid tumors were injected intravenously with 9D2 antibody or biotinylated annexin V, and one hour later, were exsanguinated and the tumors and normal tissues were removed and frozen sections were prepared. Frozen sections of tissues were cut and stained with HRP-labeled anti-rat IgM or with HRP-labeled streptavidin to determine to which cells the 9D2 and annexin V had bound after injection. Blood vessels were identified morphologically, and from their positive staining by the pan-endothelial cell antibody, MECA 32, on serial sections.

5. Biodistribution of 9D2 Antibody and Annexin V in Tumor Bearing Mice

Figure 4:
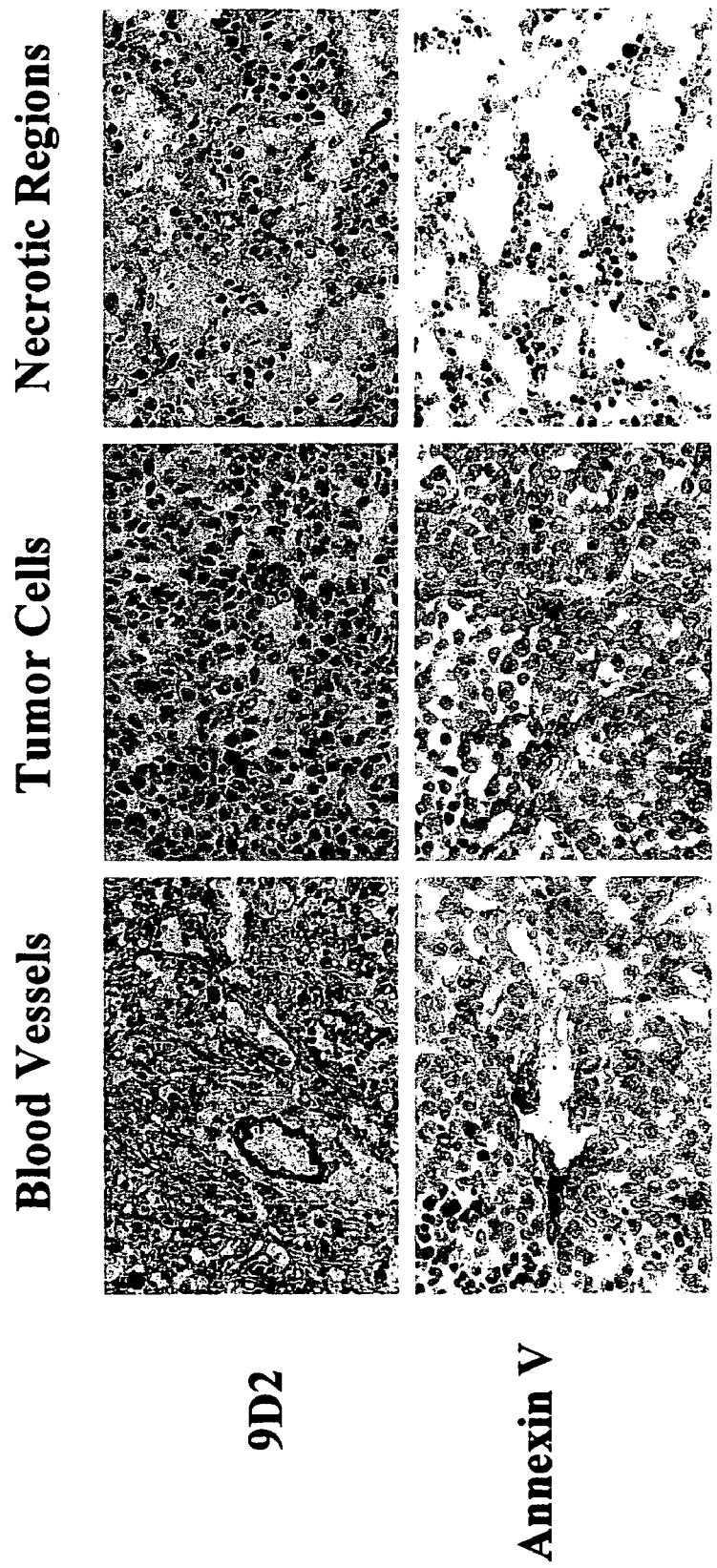
FIG. 4. Localization of biotinylated 9D2 antibody and annexin V to vascular endothelial cells and tumor cells in orthotopic MDA-MB-231 human breast tumors in mice. Nu/nu mice bearing MDA-MB-231 tumors in their mammary fat pads were injected intravenously with 50 μg of biotinylated 9D2 antibody or 100 μg of biotinylated annexin V. One h later, their blood circulation was perfused with saline. Tumor and organs were removed and snap-frozen. Localized 9D2 and annexin V were detected on the frozen sections using streptavidin-HRP conjugate. Tumor sections derived from mice injected with saline or control rat IgM served as negative controls.

9D2 antibody and annexin V localized to tumor vessels in all of five tumors included in this study (FIG. 4; Table 10). The tumors were: human MDA-MB-231 breast tumor growing orthotopically in the mammary fat pads of SCID mice; human L540 Hodgkin's tumor growing subcutaneously; human NCI-H358 NSCLC growing subcutaneously; mouse B16 melanoma growing subcutaneously and mouse Meth A fibrosarcoma growing subcutaneously.

TABLE 10

Specific Localization of 9D2 and Annexin V to Tumor Vessels

| Tissue | 9D2 Antibody[a] | Rat IgM control | Annexin V[b] |
|---|---|---|---|
| Tumors | | | |
| MDA-MB-231 | 40.6 ± 5.4 | — | 45.3 ± 5.6 |
| L540cy | 19.3 ± 3.3 | — | 16.7 ± 3.9 |
| NCI-H358 | 15.6 ± 4.1 | — | ND |
| B16 | 23.4 ± 4.5 | — | 21.3 ± 6.6 |
| Meth A | 25.7 ± 6.8 | — | ND |
| Normal | | | |
| Adrenal | — | — | — |
| Brain | — | — | — |
| Heart | — | — | — |
| Kidney | —[c] | —[c] | — |
| Intestine | — | — | — |
| Liver | — | — | — |
| Lung | — | — | — |
| Pancreas | — | — | — |
| Spleen | — | — | — |
| Testis | — | — | — |

[a]Localization of 9D2 antibody and rat IgM control in tumor bearing mice was determined by injecting the antibody (50 μg), perfusing the blood circulation of the mice with saline and detecting the antibody on sections of the tissues by using an anti-mouse IgM - peroxidase conjugate. The results are presented as the mean (±SE) percentage of PS-positive vessels of MECA 32-stained vessels per field of 0.317 mm². Six samples of each type were analyzed. The mean number of MECA 32-positive vessels per 0.317 mm² field was 23, 25, 21, 18 and 19 ± 10 vessels for MDA-MB-231, L540cy, H358, B16 and Meth A tumors, respectively
[b]Localization of annexin V was determined by injecting biotinylated annexin V followed by detection on frozen sections using streptavidin-peroxidase conjugate.
[c]Non-antigen specific tubular staining was visible in both 9D2 and control antibody recipients.

9D2 and annexin V gave essentially the same patterns of staining. Localization of the 9D2 antibody to tumor vessels was specific since no staining of tumor endothelium was observed with rat IgM of irrelevant specificity. Presumably, leakage of the control rat IgM out of tumor vessels occurred to some extent, but the staining of extravascular IgM was too diffuse or too weak to discern by indirect immunohistochemistry.

No vascular localization of 9D2 antibody or annexin V was observed in nine of the ten normal organs that were examined (Table 10). In the kidney, staining of tubules was observed that appeared not to be antigen specific. Tubules were stained in both 9D2 and control rat IgM recipients, presumably because of secretion of IgM or its metabolites through this organ. The ovaries, a site of physiological angiogenesis, were not examined.

The percentage of 9D2 and annexin V positive vessels ranged from 40% in MDA-MB-231 tumors to 15% in H358 tumors. Anionic phospholipid-positive vessels were present on the luminal surface of capillaries and vessels in all regions of the tumors, but were particularly prevalent in and around regions of necrosis. Most anionic phospholipid-positive vessels did not show morphological abnormalities that were apparent by light microscopy. Occasional vessels, particularly those located in necrotic areas, showed morphological signs of deterioration. 9D2 antibody and annexin V also localized to necrotic and apoptotic tumor cells, whereas localization of the control IgM was not detectable (FIG. 4).

These findings demonstrate that anionic phospholipids are present on the luminal surface of vascular endothelial cells in various tumors but not in normal tissues.

6. Double Staining Studies

Double staining studies were also performed in which mice bearing orthotopic MDA-MB-231 breast tumors were injected intravenously with biotinylated 9D2 antibody, biotinylated control IgM or biotinylated annexin V. One hour later, the mice were exsanguinated, and their tumors were removed and frozen sections were cut. The tumor sections were then stained with Cy3-conjugated streptavidin to detect the biotinylated proteins and with FITC-conjugated MECA32 to detect vascular endothelium. This detection method labeled the biotinylated proteins and the vascular endothelium by red and green. Where the biotinylated proteins are bound to the endothelium, the converged image appears yellow.

In these studies, the biotinylated 9D2 and annexin V appeared mostly to be bound to the vascular endothelium, because their staining patterns converged with that of MECA 32. About 40% of MECA 32 positive vessels bound 9D2 and annexin V, in close agreement with the results obtained by indirect immunohistochemistry. However, leakage of the biotinylated proteins into the tumor interstitium was detected by double staining, whereas it was not apparent by indirect immunohistochemistry.

Biotinylated proteins were visible outside the vascular endothelium around a minority (about 5%) of vessels. In tumors from mice that had been injected with biotinylated rat IgM of irrelevant specificity, the biotinylated IgM had also leaked into the tumor interstitium around a similar percentage (about 5%) of vessels, but mostly appeared not to be bound by the vascular endothelium. Presumably, the detection of extravasated 9D2 and annexin V by the double staining technique, but not by the indirect immunohistochemistry technique, reflects the greater sensitivity of the former technique and the greater precision with which two staining patterns can be compared. Non-injected control tumors were completely unstained by streptavidin-Cy3, indicating that red fluorescence corresponds to a localized protein.

EXAMPLE VII

Anionic Phospholipid Membrane Translocation in a Tumor Environment

The discovery of aminophospholipids and anionic phospholipids as in vivo surface markers unique to tumor vascular endothelial cells prompted the inventors to further investigate the effect of a tumor microenvironment on the translocation and outer membrane expression of such molecules. The present example shows that exposing endothelial cells in vitro to certain conditions that mimic those in a tumor duplicates the earlier observed aminophospholipid and anionic phospholipid surface expression in intact, viable cells.

A. Materials and Methods

1. Iodination of Annexin V

Recombinant human annexin V was purified from *E. coli* transformed with ET12a-Panionic phospholipid1 plasmid (obtained from Dr. J. Tait, University of Washington, Seattle). The purity of the protein and the binding to PS were confirmed on SDS-PAGE and on PS-coated plastic, respectively. Rabbit polyclonal, affinity-purified anti-annexin V antibodies were used to detect annexin V bound to PS. Annexin V was radiolabeled with $^{125}$I using Chloramine T as described by Bocci (1964). The specific activity was approximately $1 \times 10^6$ cpm per µg of protein, as measured by a Bradford assay (1976).

2. Endothelial Cell Treatment

Endothelial cells were treated with cytokines or growth factors at the concentrations listed in Table 11. All reagents were diluted in medium containing 10% serum and incubated with the cells at 37° C. for 24 h.

To study the effect of hypoxia, cells were seeded on 24 well plates and were incubated in a humidified normoxic atmosphere (21% $O_2$, 5% $CO_2$) for 48 h before being transferred to a humidified hypoxic atmosphere (1% $O_2$, 5% $CO_2$, 94% $N_2$) in a sealed chamber (Billups Rothenberg Inc., Del Mar, Calif.). Cells were incubated in a hypoxic chamber for 24 h at 37° C. and were then returned to a normoxic environment for 4 h at 37° C. The cells were compared to a parallel culture from an identical passage, seeded on the same day and maintained entirely under normoxic conditions. In some studies, IL-1α (10 ng/ml) and TNFα (20 ng/ml) were added to the medium before transfer to the hypoxic chamber.

To examine the effect of an acidic microenvironment, cells were exposed to the growth medium lacking bicarbonate, which was adjusted to different pHs (ranging between 7.3 and 6.2) with the required amount of HCl. Cells were incubated at 37° C. in the absence of $CO_2$. It was confirmed that culture media held the assigned pH during the 24 h period of culture. These experimental conditions were not toxic to either bovine or mouse endothelial cells and had no effect on cell morphology or viability of the attached monolayer.

3. Detection of PS on Cultured Endothelial Cells by $^{125}$I-Labeled Annexin V

After treatment with the reagents described above, treated and control cells were incubated with 7.1 pmoles of $^{125}$I-labeled annexin V (200 µl/well) in the binding buffer. After 2 h incubation at room temperature, cells were washed extensively and dissolved in 0.5 M of NaOH. The entire volume of 0.5 ml was transferred to plastic tubes and counted in a gamma counter. Non-specific binding was determined in the presence of 5 mM EDTA and was subtracted from experimental values. The results were expressed as net pmoles of cell-bound annexin V, normalized per $1 \times 10^6$ cells.

Maximal binding of annexin V was determined on cells simultaneously treated with actinomycin D and TNFα (50 ng/ml of each component). As has been previously reported, these agents cause apoptosis and PS exposure in 90-100% of endothelial cells (Lucas et al., 1998). Basal binding of $^{125}$I-annexin V to untreated cells was determined in the presence of medium with 10% serum. The amount of $^{125}$I-annexin V that bound to the untreated cultures was subtracted from that in the treated cultures. Exposure of PS was calculated according to the following formula: cell-bound annexin V (pmoles) under experimental conditions divided by maximal annexin V binding (pmoles), multiplied by 100. Each study was performed in duplicate and was performed at least three times. Mean values were calculated. The SE of the mean values from three separate experiments was less than 5%.

B. Results

1. Induction by $H_2O_2$

Mouse bEnd.3 endothelial cells were seeded at an initial density of 50,000 cells/well. Twenty-fours later cells were incubated with increasing concentrations of $H_2O_2$ (from 10 µM to 500 µM) for 1 hour at 37° C. or left untreated. At the end of the incubation, cells were washed 3 times with PBS containing 0.2% gelatin and fixed with 0.25% glutaraldehyde. Identical wells were either stained with anti-PS IgM or trypsinized and evaluated for viability by the Trypan Blue exclusion test. For the anti-PS staining, after blocking with 2% gelatin for 10 min., cells were incubated with 2 µg/ml of anti-PS antibody, followed by detection with anti-mouse IgM-HRP conjugate.

Exposing endothelial cells to $H_2O_2$ at high concentrations causes PS translocation in ~90% cells. However, this is accompanied by detachment of the cells from the substrate and cell viability decreasing to about 50-60%. The association of surface PS expression with decreasing cell viability is understandable, although it is still interesting to note that ~90% PS translocation is observed with only a 50-60% decrease in cell viability.

Using lower concentrations of $H_2O_2$ resulted in significant PS expression without any appreciable reduction in cell viability. For example, PS was detected at the cell surface of about 50% of cells in all $H_2O_2$ treated wells using $H_2O_2$ at concentrations as low as 20 µM. It is important to note that, under these low $H_2O_2$ concentrations, the cells remained firmly attached to the plastic and to each other, showed no morphological changes and had no signs of cytotoxicity. Detailed analyses revealed essentially 100% cell-cell contact, retention of proper cell shape and an intact cytoskeleton.

The 50% PS surface expression induced by low levels of $H_2O_2$ was thus observed in cell populations in which cell viability was identical to the control, untreated cells (i.e., 95%). The PS expression associated with high $H_2O_2$ concentrations was accompanied by cell damage, and the PS-positive cells exposed to high $H_2O_2$ concentrations were detached, floating and had disrupted cytoskeletons.

The maintenance of cell viability in the presence of low concentrations $H_2O_2$ is consistent with data from other laboratories. For example, Schorer et al. (1985) showed that human umbilical vein endothelial cells (HUVEC) treated with 15 µM $H_2O_2$ averaged 90 to 95% viability (reported as 5% to 10% injury), whilst those exposed to 1500 µM $H_2O_2$ were only 0%-50% viable (50% to 100% injured).

The use of $H_2O_2$ to mimic the tumor environment in vitro is also appropriate in that the tumor environment is rich in inflammatory cells, such as macrophages, PMNs and granulocytes, which produce $H_2O_2$ and other reactive oxygen species. Although never before connected with stable tumor vascular markers, inflammatory cells are known to mediate endothelial cell injury by mechanisms involving reactive oxygen species that require the presence of $H_2O_2$ (Weiss et al., 1981; Yamada et al., 1981; Schorer et al., 1985). In fact, studies have shown that stimulation of PMNs in vitro produces concentrations of $H_2O_2$ sufficient to cause sublethal endothelial cell injury without causing cell death (measured by chromium release assays) or cellular detachment; and that these $H_2O_2$ concentrations are attainable locally in vivo (Schorer et al., 1985).

The present in vitro translocation data correlates with the earlier results showing that anti-PS antibodies localize specifically to tumor vascular endothelial cells in vivo, and do not bind to cells in normal tissues. The finding that in vivo-like concentrations of $H_2O_2$ induce PS translocation to the endothelial cell surface without disrupting cell integrity has important implications in addition to validating the original in vivo data and the inventors' therapeutic approaches.

Human, bovine and murine endothelial cells are all known to be PS-negative under normal conditions. Any previously documented PS expression has always been associated with cell damage and/or cell death. This is not the case in the present studies, where normal viability is maintained. This shows that PS translocation in tumor vascular endothelium is mediated by biochemical mechanisms unconnected to cell damage. This is believed to be the first demonstration of PS surface expression in morphologically intact endothelial cells and the first indication that PS expression can be disconnected from the apoptosis pathway(s). Returning to the operability of the present invention, these observations again confirm that PS is a sustainable, rather than transient, marker of tumor blood vessels and a suitable candidate for therapeutic intervention.

2. Induction by Thrombin

Thrombin was also observed to increase PS expression, although not to the same extent as $H_2O_2$. This data is also an integral part of the tumor-induction model of PS expression developed by the present inventors: thrombin-induced PS surface expression in normal tissues would also further coagulation as PS expression coordinates the assembly of coagulation initiation complexes.

The tumor environment is known to be prothrombotic, such that tumor vasculature is predisposed to coagulation (U.S. Pat. No. 5,877,289). As thrombin is a product of the coagulation cascade, it is present in tumor vasculature. In fact, the presence of thrombin induces VCAM expression, contributing to the inventors' ability to exploit VCAM as a targetable marker of tumor vasculature (U.S. Pat. Nos. 5,855,866; 5,877,289). The present data showing that thrombin also induces PS expression is thus both relevant to targeting aminophospholipids with naked antibodies and therapeutic conjugates, and further explains the beneficial effects of the anti-VCAM coaguligand containing Tissue Factor (Example I).

3. Other Agents of Oxidative Stress

Mouse bEnd.3 or bovine ABAE cells in vitro were treated for 24 h with various concentrations of factors and conditions that are present in the microenvironment of many tumors (Lichtenbeld et al., 1996; Harris et al., 1996), such as hypoxia/reoxygenation, thrombin, acidity, inflammatory cytokines and hydrogen peroxide (Table 11).

Externalization of PS and anionic phospholipids was quantified by measuring $^{125}$I-annexin V binding. The amount of annexin V binding was compared with that of cells in which apoptosis of 90-100% of cells had been induced by combined treatment with actinomycin D and TNF-α. Actinomycin D and TNF-α induced the binding of 6.2 pmoles of annexin V per $10^6$ cells ($3.8 \times 10^6$ molecules of annexin V per cell) on both cell types, in good agreement with literature reports (Rao et al., 1992). This value was taken as the maximal level of externalized anionic phospholipids.

TABLE 11

Induction of PS by Recreating Tumor Environment

| | | $^{125}$I-Annexin V (% of Max binding) | |
|---|---|---|---|
| Treatment | Concentration | ABAE CELLS | bEnd.3 cells |
| Medium with 10% serum | N/A | 0 | 0 |
| Actinomycin D + TNF α | 50 ng/ml each | 100 | 100 |
| VEGF | 20 ng/ml | 0 | 0 |
| FGF-2 | 20 ng/ml | 0 | 0 |
| Scatter factor | 40 ng/ml | 0 | 0 |
| TGF β$_1$ | 20 ng/ml | 0 | 0 |
| PDGF-BB | 20 ng/ml | 0 | 0 |
| IL-10 | 20 ng/ml | 0 | 0 |
| IL-8 | 20 ng/ml | 0 | 0 |
| IL-6 | 20 ng/ml | 0 | 0 |
| IL-1α | 10 ng/ml | 6.4 | 7.5 |
| IL-1β | 10 ng/ml | 5.8 | 5.5 |
| Interferon | 40 ng/ml | 8.6 | 2.8 |
| TNFα | 20 ng/ml | 7.4 | 13.7 |
| Thrombin | 50 nM | 8.8 | 17.4 |
| Hypoxia | 1% O$_2$ | 15.0 to 17.5 | 22.5 |
| Hypoxia + IL-1α | Same as above | 26.0 | 31.0 |

TABLE 11-continued

Induction of PS by Recreating Tumor Environment

|  |  | $^{125}$I-Annexin V (% of Max binding) | |
| --- | --- | --- | --- |
| Treatment | Concentration | ABAE CELLS | bEnd.3 cells |
| Hypoxia + TNFα | Same as above | 33.0 | 36.0 |
| pH 6.6 | N/A | 20.2 | 18.9 |
| Hydrogen peroxide | 200 µM | 95.5 | 98.4 |

In Table 11, the concentrations of cytokines, growth factors and thrombin used were selected from literature values to have maximal stimulatory effect on cultured endothelial cells. These concentrations did not cause toxicity over the period of the test (24 h) as judged by morphological appearance, a lack of detachment, and a lack of uptake of trypan blue. The concentration of $H_2O_2$ employed was the maximal concentration that did not cause cytotoxicity under the chosen conditions.

The basal binding of $^{125}$I-annexin V was determined in the presence of growth medium alone. Maximal PS exposure was determined after induction of apoptosis by the combined treatment with actinomycin D and TNF α. Average of duplicates from three separate studies is presented. Standard error was less than 5%.

Untreated cells were largely devoid of externalized PS, as judged by annexin V or anti-PS (9D2) antibody binding (Table 11). The basal binding in the presence of growth medium alone was 0.44 and 0.68 pmoles of $^{125}$I-annexin V for ABAE and bEnd.3 cells, respectively. This corresponds to approximately 7.1% and 10.9% of the maximal binding for ABAE and bEnd.3 cells, respectively, which correlated well with the finding that approximately 10% of cells bound biotinylated annexin V under the same conditions.

VEGF, HGF, FGF, TGFβ$_1$, PDGF, IL-6, IL-8 and IL-10 did not increase binding of $^{125}$I-annexin V above the basal level for untreated cells. Inflammatory mediators (IL-1α, IL-1β, TNFα and interferon) caused a small but reproducible increase in PS and anionic phospholipid translocation that ranged from 5 to 8% of the maximal level for ABAE cells and from 3 to 14% for bEnd3 cells.

Hypoxia/reoxygenation, thrombin or acidic external conditions (pH 6.8-6.6) induced a moderately high externalization of PS and anionic phospholipid that ranged from 8 to 20% of the maximal level for ABAE cells and from 17 to 22% of the maximal level for bend.3 cells. The largest increase in PS and anionic phospholipid translocation was observed after treatment with 100 to 200 µM of hydrogen peroxide. This treatment caused nearly complete (95%) externalization of PS in both cell types as judged by $^{125}$I-annexin V binding (Table 11). More than 70% of ABAE and bEnd.3 cells bound biotinylated annexin V, as judged immunohistochemically.

Endothelial cells in which PS and anionic phospholipid translocation was generated by treatment with hypoxia/reoxygenation, thrombin, acidity, TNFα, IL-1 or $H_2O_2$ remained attached to the matrix during time period of the assay (24 h), retained cell-cell contact and retained their ability to exclude trypan blue dye. Normal PS and anionic phospholipid orientation was restored 24 to 48 h later in the majority of the cells after the inducing-factor was removed, or the culture conditions were returned to normal. These results indicate that mild oxidative stress, created by direct application of $H_2O_2$ or indirectly by hypoxia/reoxygenation, acidity, thrombin, or inflammatory cytokines, triggers a transient translocation of PS and anionic phospholipids on viable endothelial cells.

4. Combined Effects of Inflammatory Cytokines and Hypoxia/Reoxygenation

Figure 5:
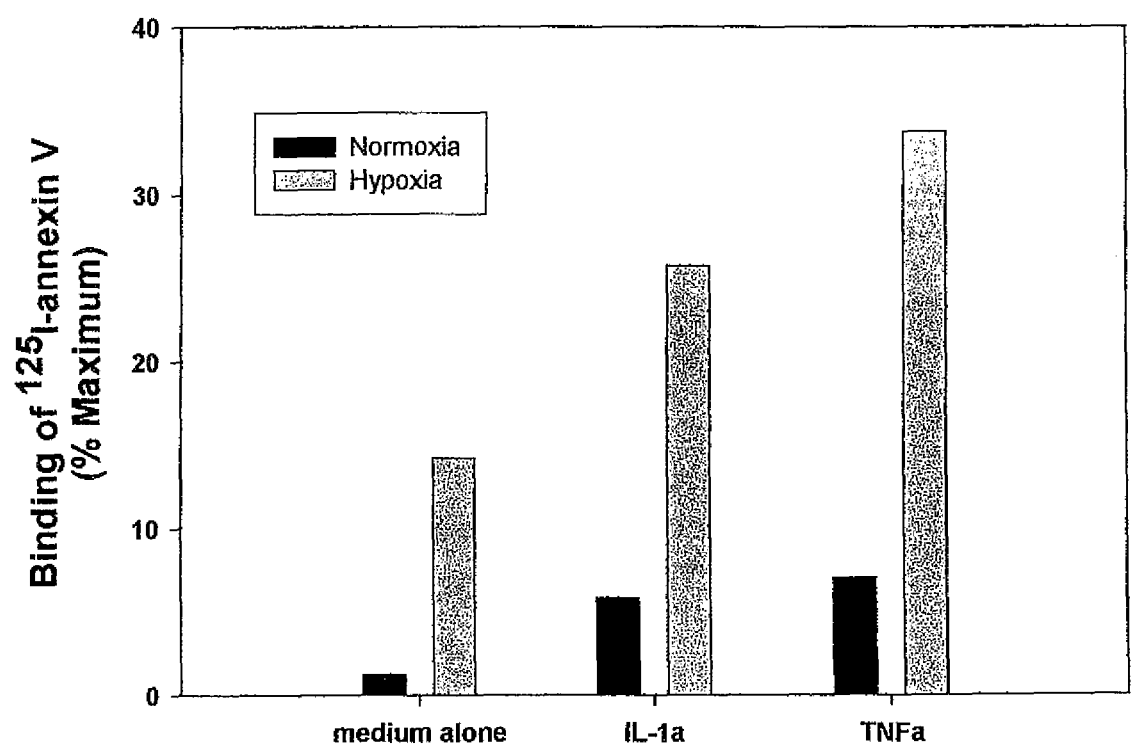
FIG. 5. Combined effects of hypoxia and inflammatory cytokines on PS exposure. bEnd.3 cells were treated for 24 h with IL-1α and TNFα under normoxic (white bars) and hypoxia (gray bars) conditions. The cell monolayers remained intact and viable under these conditions. PS externalization was determined by measuring binding of $^{125}$I-annexin V. The level of PS exposure was expressed as a percentage of that in cells treated with combination of actinomycin D and TNFα.

Enhanced PS and anionic phospholipid exposure was observed when ABAE and bEnd.3 cells were subjected to hypoxia/re-oxygenation in the presence of IL-1α or TNFα. In the absence of the cytokines, hypoxia/reoxygenation increased PS-exposure by ABAE cells to 15%-17.5% of the maximum level for cells treated with apoptotic concentrations of actinomycin D and TNFα. In the presence of sub-toxic concentrations of IL-1α or TNFα, hypoxia/reoxygenation increased anionic phospholipid-exposure to 26% and 33% respectively of the maximum (FIG. 5; Table 11). Comparison with the effect of cytokines in the absence of hypoxia/reoxygenation indicates that the combination of cytokines and hypoxia/reoxygenation had a greater than additive effects on PS-exposure. Similar effects were observed on bEnd.3 cells.

Therefore, in the tumor environment, the exposure of PS and anionic phospholipids induced by hypoxia/re-oxygenation may be amplified by inflammatory cytokines and possibly by such other stimuli as acidity and thrombin.

These in vitro studies shed light on the mechanism of PS exposure on tumor endothelial cells in vivo. They show that various factors induce PS exposure on endothelial cells without causing cytotoxicity, which mimics the situation in tumors in vivo. Hypoxia followed by reoxygenation, acidity, and thrombin most increased PS exposure on viable endothelial cells. Inflammatory cytokines (TNFα and IL-1α) also caused a weak but definite induction of PS exposure.

These conditions are likely to be the major inducing stimuli in tumors in vivo because: i) PS positive endothelium is prevalent in and around regions of necrosis where hypoxia, acidity, thrombosed blood vessels, and infiltrating host leukocytes are commonly observed; ii) the finding that hypoxia/reoxygenation amplifies the weak PS-exposing activity of TNFα and IL-1 on endothelial cells in vitro correlates with the situation in vivo in tumors where hypoxia and cytokine-secreting tumor and host cells co-exist; iii) hypoxia/reoxygenation and thrombin have been reported to generate reactive oxygen species (ROS) in endothelial cells through activation of NADPH oxidase-like membrane enzyme (Zulueta et al., 1995). ROS produced by malignant cells might contribute to endothelial cell injury (Shaughnessy et al. 1989). Hydrogen peroxide was the most powerful inducer of PS exposure on cultured endothelial cells found in the present study, providing indirect support for the involvement of ROS.

Externalized PS provides a negative phospholipid surface upon which coagulation factors concentrate and assemble. This may contribute to the procoagulant status on the tumor endothelium that has long been recognized. PS also provides an attachment site for circulating macrophages (McEvoy et al., 1986), T lymphocytes (Qu et al., 1996) and polymorphonuclear cells that assist in leukocyte infiltration into tumors. Adherence of activated macrophages, polymorphonuclear cells and platelets to PS on tumor endothelium may lead to further secretion of reactive oxygen species and further amplification of PS exposure.

EXAMPLE VIII

Anti-Tumor Effects of Annexin Conjugates

The surprising finding that aminophospholipids and anionic phospholipids are stable markers of tumor vasculature means that antibody-therapeutic agent constructs can be used in cancer treatment. In addition to using antibodies as targeting agents, annexins, and other specific binding proteins, can also be used to specifically deliver therapeutic agents to tumor vasculature. The following data shows the anti-tumor effects that result from the in vivo administration of annexin-TF constructs.

A. Methods

An annexin V-tTF conjugate was prepared and administered to nu/nu mice with solid tumors. The tumors were formed from human HT29 colorectal carcinoma cells that formed tumors of at least about 1.2 cm³. The annexin V-tTF coaguligand (10 µg) was administered intravenously and allowed to circulate for 24 hours. Saline-treated mice were separately maintained as control animals. After the one day treatment period, the mice were sacrificed and exsanguinated and the tumors and major organs were harvested for analysis.

B. Results

The annexin V-tTF conjugate was found to induce specific tumor blood vessel coagulation in HT29 tumor bearing mice. Approximately 55% of the tumor blood vessels in the annexin V-tTF conjugate treated animals were thrombosed following a single injection. In contrast, there was minimal evidence of thrombosis in the tumor vasculature of the control animals.

EXAMPLE IX

Anti-Tumor Effects of 3SB Anti-PS Antibodies

The present example shows the anti-tumor effects of anti-PS antibodies using syngeneic and xenogeneic tumor models. The 3SB antibody used in this study binds to PS (and PA), but is essentially devoid of reactivity with PE. This anti-PS antibody caused tumor vascular injury, accompanied by thrombosis, and tumor necrosis.

The effects of anti-PS antibodies were first examined in syngeneic and xenogeneic tumor models using the 3SB antibody. For the syngeneic model, $1 \times 10^7$ cells of murine colorectal carcinoma Colo 26 (obtained from Dr. Ian Hart, ICRF, London) were injected subcutaneously into the right flank of BALB/c mice. In the xenogeneic model, a human Hodgkin's lymphoma L540 xenograft was established by injecting $1 \times 10^7$ cells subcutaneously into the right flank of male CB17 SCID mice. Tumors were allowed to grow to a size of about 0.6-0.9 cm³ before treatment.

Tumor-bearing mice (4 animals per group) were injected i.p. with 20 µg of 3SB anti-PS antibody (IgM), control mouse IgM or saline. Treatment was repeated 3 times with a 48 hour interval. Animals were monitored daily for tumor measurements and body weight. Tumor volume was calculated as described in Example I. Mice were sacrificed when tumors had reached 2 cm³, or earlier if tumors showed signs of necrosis or ulceration.

Figure 6A:
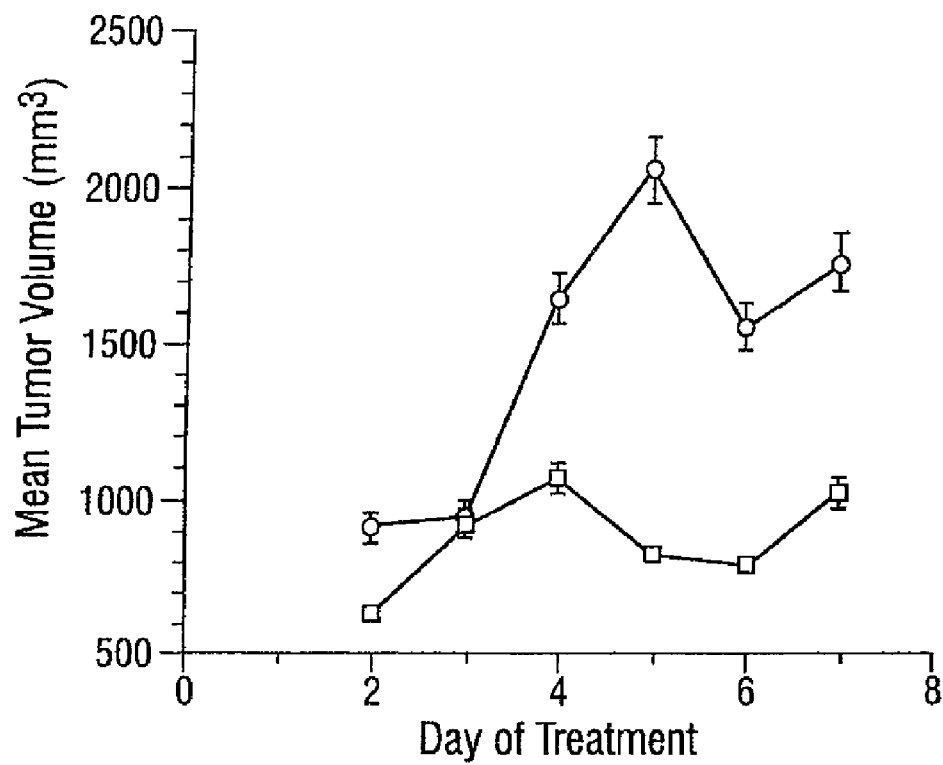
FIG. 6A and FIG. 6B. Anti-tumor effects of anti-PS antibody (3SB) in animals with syngeneic and xenogeneic tumors. $1\times10^7$ cells of murine colorectal carcinoma Colo 26 (FIG. 6A) or human Hodgkin's lymphoma L540 (FIG. 6B) were injected subcutaneously into the right flank of BALB/c mice (FIG. 6A) or male CB17 SCID mice (FIG. 6B), respectively. Tumors were allowed to grow to a size of about 0.6-0.9 cm³ and then the mice (4 animals per group) were injected i.p. with 20 µg of naked anti-PS antibody (open squares) or saline (open circles). Treatment was repeated 3 times with a 48 hour interval. Animals were monitored daily for tumor measurements and body weight. Mice were sacrificed when tumors had reached 2 cm³, or earlier if tumors showed signs of necrosis or ulceration. Control mouse IgM gave similar results to saline.
Figure 6B:
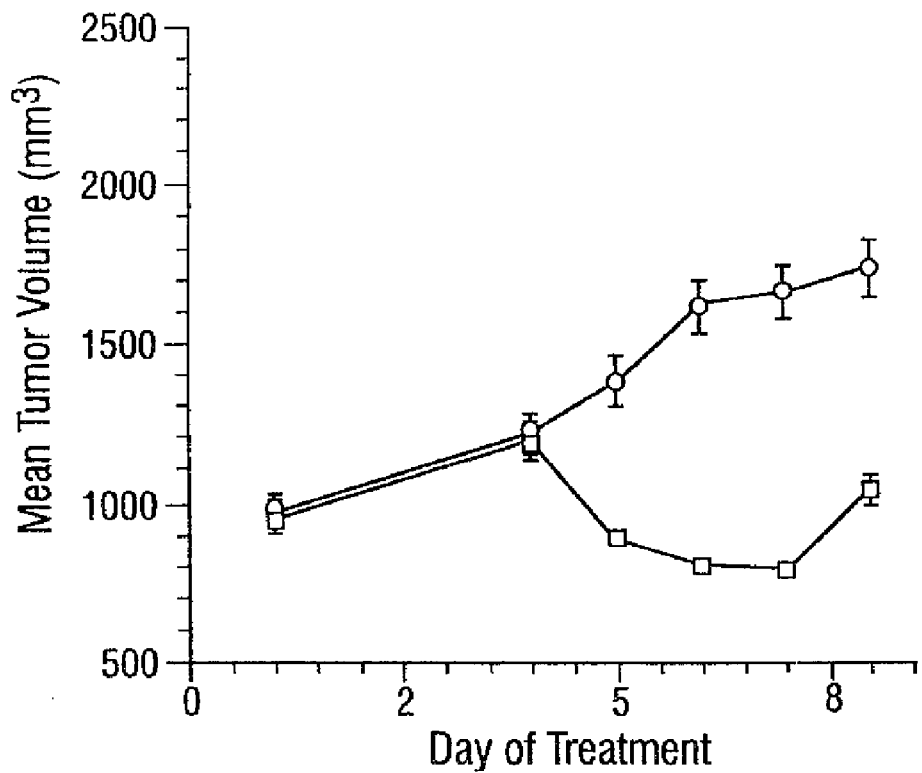

The growth of both syngeneic and xenogeneic tumors was effectively inhibited by treatment with 3SB anti-PS antibodies (FIG. 6A and FIG. 6B). Anti-PS antibodies caused tumor vascular injury, accompanied by thrombosis, and tumor necrosis. The presence of clots and disintegration of tumor mass surrounding blocked blood vessels was evident.

Quantitatively, the 3SB anti-PS antibody treatment inhibited tumor growth by up to 60% of control tumor volume in mice bearing large Colo 26 (FIG. 6A) and L540 (FIG. 6B) tumors. No retardation of tumor growth was found in mice treated with saline or control IgM. No toxicity was observed in mice treated with anti-PS antibodies, with normal organs preserving unaltered morphology, indistinguishable from untreated or saline-treated mice.

Tumor regression started 24 hours after the first treatment and tumors continue to decline in size for the next 6 days. This was observed in both syngeneic and immunocompromised +tumor models, indicating that the effect was mediated by immune status-independent mechanism(s). Moreover, the decline in tumor burden was associated with the increase of alertness and generally healthy appearance of the animals, compared to control mice bearing tumors larger than 1500 mm³. Tumor re-growth occurred 7-8 days after the first treatment.

The results obtained with anti-PS treatment of L540 tumors are further compelling for the following reasons. Notably, the tumor necrosis observed in L540 tumor treatment occurred despite the fact that the percentage of vessels that stained positive for PS in L540 tumors was less than in HT 29 and NCI-H358 tumors. This implies that even more rapid necrosis would likely result when treating other tumor types. Furthermore, L540 tumors are generally chosen as an experimental model because they provide clean histological sections and they are, in fact, known to be resistant to necrosis.

EXAMPLE X

Anti-Tumor Effects of Antibody (9D2) Against Anionic Phospholipids

This example demonstrates the effects of the 9D2 antibody, which binds to PS and other anionic phospholipids, in anti-tumor studies in vivo.

A high dose (>150 µg) of the rat antibody that binds to anionic phospholipids, 9D2, was injected into nude mice bearing H358 tumors. Immunolocalization studies shows that it strongly localized to tumor endothelium (4+), although some low level, non-specific binding of 9D2 by normal vessels was observed due to the high dose (as would be observed for a control IgM antibody of irrelevant specificity).

When 9D2 was injected i.p. into a SCID mouse with an L540 tumor for ascites production, the tumor became necrotic and collapsed. Upon injection of a control antibody (MK 2.7, rat IgG) into a SCID mouse with an L540 tumor, no similar effects were observed.

The effect of the 9D2 anti-PS antibody on the growth of L540 tumors in vivo was then determined more precisely. Treatment was started when tumors reached 200-250 µl (day 0). From day 0 to day 7, mice were injected i.p. with ~150 µg of IgM (200 µl supernatant) or 200 µl of 10% DMEM. From day 7 to day 22, mice were injected i.p. with ~300 µg of IgM (400 µl supernatant) or 400 µl of 10% DMEM. Day 22 was the last day of treatment and the mice were sacrificed.

As shown in Table 12, from days 10 to 22, tumor growth is generally inhibited by about 40% to 50%. At the end of the study, only 4 mice in the treated group have tumors larger than 2000 µl in volume, in contrast to 9/9 in the control group.

TABLE 12

Effects of Anti-PS Antibodies on L540 Tumors In Vivo

| Day after start of the treatment | Average Tumor Volume (µl) | | % Inhibition | Number of mice with tumor volume >2000 µl | |
|---|---|---|---|---|---|
| | Control | Treated | | Control | Treated |
| 0 | 341 | 320 | 6.2 | 0 | 0 |
| 1 | 464 | 325 | 10.8 | 0 | 0 |
| 3 | 412 | 415 | 0 | 0 | 0 |
| 7 | 687 | 455 | 33.8 | 0 | 0 |
| 10 | 904 | 544 | 39.9 | 1/9 | 0 |
| 13 | 945 | 545 | 42.4 | 1/9 | 0 |

TABLE 12-continued

Effects of Anti-PS Antibodies on L540 Tumors In Vivo

| Day after start of the treatment | Average Tumor Volume (µl) | | % Inhibition | Number of mice with tumor volume >2000 µl | |
|---|---|---|---|---|---|
| | Control | Treated | | Control | Treated |
| 15 | 1373 | 685 | 50.1 | 4/9 | 1/10 |
| 17 | 1426 | 842 | 41.0 | 4/9 | 4/10 |
| 20 | 1992 | 987 | 50.5 | 6/9 | 4/10 |
| 22 | 2560 | 1365 | 53.3 | 9/9 | 4/10 |

In another in vivo study, the effects of the rat anti-PS antibody on the growth of L540 tumors in CB17 SCID mice were followed for 45 days after tumor cell injections. These tumor-bearing mice were treated with 300 µg of anti-PS antibody daily, i.p. or with 300 µl of 10% DMEM daily, i.p., as a control. Various parameters of tumor treatment were markedly better in the treated group in comparison to those of the controls (Table 13).

TABLE 13

Effects of Anti-PS Antibodies on L540 Tumors In Vivo

| Other parameters | Control | Treated |
|---|---|---|
| % Regressed tumors[1] (60 days post treatment) | 0 | 40% |
| % Regressed tumors[1] (90 days post treatment) | 0 | 20% |
| Average volume of secondary tumors (µl)[2] | 537 ± 30 | 366 ± 56 |

[1]Tumors too small to measure in treated mice at indicated times (60 vs. 90 days) after treatment
[2]Metastases in lymph nodes In a further study, the 9D2 antibody was injected intraperitoneally at a dose of 100 µg 3 times per week to mice with L540 tumors. The tumor size was measured with calipers twice a week. The anti-tumor effects in comparison to the control group is shown in FIG. 7. The numbers in parenthesis indicate the number of mice with regressed tumors per total number of mice per group.

EXAMPLE XI

Anti-Tumor Effects of Anti-PS Antibody 3G4

The present example demonstrates additional anti-tumor effects using the anti-PS antibody 3G4 in syngeneic and xenogeneic tumor models. The 3G4 antibody used in this study is an IgG antibody that binds to PS and other anionic phospholipids (Example IV).

A. Protocols for Animal Tumor Studies

The effects of 3G4 was examined in syngeneic and xenogeneic tumor models. The general protocol for the animal tumor treatment studies is conducted as follows. Unless particular differences are specified, this is the protocol used throughout the studies of the present application.

The animals are obtained from Charles Rivers Laboratories. The mice are 4-5 weeks, female, C.B-17 SCID or Fox Chase SCID mice. Mice are housed in autoclaved caging, sterile food and water, with sterile handling. All procedures performed in laminar flow hoods. Mice are acclimated 1 week and then ear-tagged and a blood sample (approximately 75-100 µl) taken from the tail vein to check for leakiness by ELISA. Any mice that fail the leakiness ELISA test should not be used for test procedures. Mice are injected orthotopically with tumor cells into mammary fat pad (MFP) or subcutaneously into the right flank 2-3 days post ear-tagging and blood sample removal.

In the orthotopic model, $1 \times 10^7$ cells in 0.1 ml DMEM are typically injected into MFP of anesthetized mice. Mice are anesthetized with 0.075 ml of mouse cocktail injected IP. The mouse cocktail is 5 ml Ketamine (100 mg/ml); 2.5 ml Xylazine (20 mg/ml); 1 ml Acepromazine (10 mg/ml); 11 ml sterile water. Dosage is 0.1 ml per 20-30 grams body weight via the IP route for a duration of 30 minutes.

Once the mouse is anesthetized, as measured by no response to toe/foot pinch, the mouse is laid on its left side and wiped with 70% ethanol just behind the head and around the right forearm/back area. A 2-3 mm incision is made just behind the right forearm (lateral thorax), which reveals a whitish fat pad when the skin flap is raised. 0.1 ml of cells are injected into the fat pad using a 1 ml syringe and a 27-gauge needle, producing a bleb in the fat pad. The incision is closed using a 9 mm sterile wound clip. The mouse is returned to its cage and observed until it has wakened from anesthesia and is mobile. Post-operative health status is determined, and if any signs of distress are observed, the animal is given acetaminophen (0.24 mg/ml)+codeine (0.024 mg/ml) in the drinking water. The wound clip is removed after 1 week. This method is used so that the cells are accurately placed into the selected site and not into the subcutaneous region. Tumors will be approximately 200 µl in volume (L×W×W) in 14-15 days and the take rate is essentially 100%.

In the subcutaneous model, mice are typically injected with $1 \times 10^7$ cells in 0.2 ml. Mice are not anesthetized, but are restrained using a steady grip of mouse skin exposing the right flank. A 1 ml syringe with a 23 gauge needle is used to inject $1 \times 10^7$ cells in 200 µl, just under the skin of the mice and a bleb will be seen. It is not unusual to observe a small amount of fluid leak from the injection site. A twisting motion may be used when withdrawing the needle from the subcutaneous injection to reduce this leakage. Tumor volume is measured by L×W×H.

In the perfusion protocol, mice are injected IV with 1000 U of heparin in 0.2 ml saline. Mice are then be sedated by injecting the mouse IP with 0.1 ml mouse cocktail. Once the mouse is sedated enough, as measured by no reflex when toe/foot is pinched, the thoracic cavity is opened to expose the heart and lungs. A 30 gauge needle attached to tubing and perfusion pump is inserted into the left ventricle. The right ventricle is snipped so that blood can drip out. Saline is pumped through for 12 minutes at a speed of 1 ml per minute. At the end of the perfusion, the needle and tubing are removed. Tissues are removed for further studies, either immunohistochemistry or pathology.

B. Tumor Treatment Results

For the syngeneic model, Meth A mouse fibrosarcoma tumor cells were used. In one xenogeneic model, human MDA-MB-231 breast tumor cells were seeded into the mammary fat pad. In another xenogeneic model, a large human Hodgkin's lymphoma L540 xenograft was established by injecting cells and allowing the tumor to grow to a size of over 500 mm³ before treatment. Tumor-bearing mice (10 animals per group) were injected i.p. with 100 µg of 3G4 anti-PS antibody (IgG) as opposed to control. Treatment was repeated 3 times a week. Animals were monitored twice a week for tumor measurements.

The growth of both syngeneic and xenogeneic tumors was effectively inhibited by treatment with 3G4 anti-PS antibodies. Treatment for the first 20 to 30 days is shown in FIG. 8A, FIG. 8B and FIG. 8C. The antibodies caused tumor vascular injury, localized thrombosis and tumor necrosis.

The treatment of the syngeneic, Meth A tumor cells was particularly successful, and the treatment of the human MDA-MB-231 breast tumor cells growing in the mammary fat pad also produced tumor regressions (FIG. 8A and FIG. 8B). Even in mice bearing large L540 tumors, known to be resistant to necrosis, the 3G4 antibody treatment inhibited tumor growth in comparison to control. No retardation of tumor growth was found in control mice. No toxicity was observed in mice treated with anti-PS antibodies.

Tumors were also established using MD-MBA-435s cells and treated as described above. The growth of these tumors was also effectively inhibited by treatment with the 3G4 antibody. The treatment of large L540 tumors, MDA-MB-231 and MD-MBA-435s tumor cells for 60 days is shown in FIG. 8D, FIG. 8E and FIG. 8F. The antibodies caused tumor vascular injury, thrombosis and necrosis and retarded tumor growth, with no evidence of toxicity.

MD-MBA-435s luciferase cells were obtained from Dr. Angels Sierra Jimenez, Barcelona, Spain and were grown in 10% DMEM. Mice were injected with tumor cells as described as above, and at 2 weeks post injection, the tumors were measured and the volume recorded. Treatment of mice with tumors of similar average volumes (200 mm$^3$) was performed using the 3G4 antibody and the chimeric 3G4 antibody, produced as described in Example XIX, versus control. Treatment was initiated by IP injection (800 µg) at day 15 and continued with injections of 200 µg every two to three days until the final injection of 400 µg at day 35. Tumor volumes and mouse body weights were measured on injection days. Mice were sacrificed and perfused with saline for 12 minutes. The organs and tumor were removed, snap-frozen in liquid nitrogen and the tumor sectioned for immunohistochemical analysis.

This study showed that both the 3G4 antibody and the chimeric 3G4 antibody effectively retarded tumor growth as opposed to control (FIG. 8G).

EXAMPLE XII

Anti-Viral Effects of Anti-PS Antibodies Against CMV

Surprisingly switching fields from tumor vasculature to viral infections, the inventors next reasoned that antibodies to aminophospholipids and anionic phospholipids would also likely exert an anti-viral effect. The present example indeed shows this to be true, first using the 3G4 antibody in the treatment of cytomegalovirus (CMV) infection.

A. Methods
1. Treatment of CMV-Infected Cells In Vitro

Confluent monolayers of human diploid foreskin fibroblasts (HHF-R2) in 6-well plates were infected with human CMV AD169 expressing green fluorescent protein (GFP) at an MOI=0.01 as previously described (Bresnahan et al., 1996). Briefly, the cells were incubated with virus in a total volume of 1 ml per well at 37° C. for 90 minutes. During the infection, the plates were gently rocked every 30 minutes. Following the infection, the cell supernatant was removed and DMEM/10% FBS/pen-strep (2 ml per well) was added to each well.

Dilutions of 3G4 or the isotype matched control antibody GV39G (100 µg/ml and 50 µg/ml) were added to the wells. The infected cells were incubated at 37° C. for a total of 19 days. The medium and antibody in each well was replaced every 3 days. On day 19, the cells and supernatants from each well were harvested and frozen at −80° C. until the plaque assays were carried out.

2. Fluorescent Microscopy

The recombinant CMV expresses GFP under the control of the SV40 promoter. Hence, infected cells appear green under a fluorescent microscope. In these studies, the antibody treated CMV-infected cells were observed under a fluorescent microscope at days 2, 3 and 9.

3. Plaque Assays

The plaque assays were carried out using standard protocols. Briefly, the frozen cells cell suspensions were thawed quickly at 37° C. and centrifuged to remove debris at 1000 rpm for 1 minute. Different dilutions of the cell supernatants were added to sub-confluent monolayers of HHF-R2 cells in 6-well plates and the cells incubated at 37° C. for 90 minutes (the plates were gently rocked every 30 minutes). Following the infection, the cell supernatants were removed and replaced with 2 ml of DMEM/10% FBS. On day 4, the supernatant in each well was removed and the cells overlayed with 0.01% low melting point agarose/DMEM/10% FBS. The plates were incubated at 37° C. for a total of 14 days postinfection. On day 14, the infected monolayers were fixed with 10% buffered formalin and stained with methylene blue to visualize the plaques.

B. Results
1. 3G4 Inhibits Viral Spread of CMV

To investigate whether 3G4 has an inhibitory effect on CMV infection and replication, confluent human fibroblasts were pretreated with 3G4 before CMV was added at a low m.o.i. The CMV used in these studies expresses green fluorescent protein (GFP). Hence, infected cells appear green when observed under a fluorescence microscope.

On day 3 of treatment, with both 50 µg/ml and 100 µg/ml of antibody, there are single infected cells both in untreated wells and in wells treated with 3G4 or isotype-matched control antibody, GV39G. Thus, treating the fibroblasts with 3G4 does not appear to significantly inhibit the entry of the virus into the cells.

On day 9, however, there is a dramatic difference in the number of infected cells in 3G4-treated vs. control, GV39G-treated wells (FIG. 9A and FIG. 9B; compare top right panel to middle and bottom right panels). While the virus has spread to approximately 80% of the monolayer in the control wells, the virus is restricted to the original singly-infected cell in the 3G4-treated wells. Hence, 3G4 limits the spread of CMV from the original infected cell to the surrounding cells. This inhibition of viral spread is observed when cells are treated with 100 µg/ml (FIG. 9A) and 50 µg/ml (FIG. 9B).

2. Viral Inhibition is Antibody Concentration-Dependent

In order to determine what concentration of 3G4 is necessary for the anti-viral effect at a low m.o.i., infected cells were treated with different concentrations of 3G4 and the control antibody, GV39G. As shown in FIG. 10, the complete inhibition of cell-to-cell spread is observed with 3G4 at 100 µg/ml and 50 µg/ml. When the cells were treated with 25, 12.5 and 6.25 µg/ml of 3G4, there are increasing numbers of GFP positive CMV-infected cells. Although 3G4 does not totally prevent viral spread from the primary infected cells at these lower concentrations, it still has a meaningful anti-viral effect, since fewer GFP-positive CMV-infected cells are seen in the 3G4-treated well as compared to GV39G-treated, control wells (FIG. 10).

3. Quantification of Viral Load at a Low M.O.I.

The anti-viral effect of 3G4 was quantitated by carrying out plaque assays to determine the viral load following antibody-treatment. The controls included untreated cells, the GV39G antibody and an additional antibody control using the C44 antibody, a mouse $IgG_{2a}$ isotype antibody to colchicine.

Treatment of infected cells (m.o.i.=0.01 pfu/cell) with 100 µg/ml of 3G4 resulted in a dramatic 6 $\log_{10}$ decrease in viral titer as compared to control, GV39G-treated cells (FIG. 11A). This inhibition translates into an approximately 99.9999% inhibition of viral replication. At a concentration of 50 µg/ml, treatment with 3G4 results in a 3.5 $\log_{10}$ decrease in viral titer as compared to GV39G-treatment. Using 3G4 at 25 µg/ml and 12.5 µg/ml, the results are still dramatic, and even at 6.25 µg/ml an inhibitory effect is still observed (FIG. 11A).

4. Quantification of Viral Load at a High M.O.I.

3G4 treatment of fibroblasts infected at a high m.o.i. of 3 also results in a dramatic reduction in viral titer. At 100 µg/ml, treatment with 3G4 resulted in a 5 $\log_{10}$ decrease in viral titer as compared to control, GV39G-treated cells (FIG. 11B). At 50 µg/ml, 3G4 inhibited viral replication by 3 logs when compared to GV39G (FIG. 11B).

5. Inhibition of Replication at a Late Stage

To determine which stage of the CMV replicative cycle is blocked by 3G4, a timed addition study was performed. For this, 3G4 was added to fibroblasts infected at a high m.o.i. at different time points after the infection. The viral load (in both the cells and supernatant) was quantified using a standard plaque assay.

Addition of 3G4 up to 24 hours after infection resulted in a 5-6 $\log_{10}$ decrease in viral titer (FIG. 11C). However, when addition of 3G4 was delayed to 48 hours, the inhibitory effect of 3G4 was reduced to 2 $\log_{10}$ and when addition was delayed to 72 to 96 hours, the inhibitory effect was further reduced. This shows that 3G4 interferes with a late stage of CMV replication that occurs between 24-48 hours after infection. Thus, 3G4 does not significantly interfere with infection or with immediate early or early gene expression. It rather acts later in the viral replication cycle, e.g., on late gene expression, viral DNA synthesis, viral packaging or egress.

EXAMPLE XIII

Anti-Viral Effects of Anti-PS Antibodies Against RSV

In addition to the dramatic anti-viral effects against CMV shown in Example XII, the present example demonstrates the use of three different anti-PS antibodies in the inhibition of Respiratory Syncitial Virus (RSV) replication.

A. Methods

1. Treatment of RSV-Infected Cells In Vitro

A-549 cells were grown to 100% confluence in three Costar 12-well tissue culture plates. 200 µL of minimum essential Eagle medium was added to all wells. Anti-phospholipid antibody (Ab) was added (100 µg in 100 µL) to 9 wells of each plate and 30 min. later cells in 6 of those initial 9 wells were infected with an MOI of 1 with RSV long strain in a volume of 100 µL. The three remaining wells were left as non-infected, antibody-treated wells. The three other wells with no antibody were infected with RSV at the same MOI as described above.

Each plate was used to test the three different antibodies: 3G4, 3SB and 1B9 (Example IV). Cells were incubated in 5% $CO_2$ at 40° C. for 2 hours and then 600 µL of medium was added to complete 1 mL volume in each well. An A-549 cell plate was kept in the same conditions, as control. Supernatants were collected at 4, 24 and 72 hours after infection. At each time point, four wells from each plate were sampled: one well with only-Ab treated cells, two wells had Ab-treated/RSV-infected cells and one well had RSV-infected only cells. The samples were frozen at −80 until the plaque assay.

2. Plaque Assays

The plaque assays were carried out as previously described (Kisch et al., 1963; Graham et al., 1988). Briefly, the frozen cells cell suspensions were thawed quickly at 37° C. Three 10-fold dilutions were made from the undiluted cell supernatants: $10^{-1}$, $10^{-2}$, and $10^{-3}$. 100 µL of each dilution plus the undiluted sample were inoculated into 80% confluent Hep-2 cell line plates, all in triplicates. Plates were placed in the 5% $CO_2$, 40° C. incubator for 5 days. On the 5$^{th}$ day, the plates were developed and stained with hematoxylin and eosin to reveal the plaques in each well. The plaques were counted using a dissecting microscope to calculate the RSV viral load in pfu (plaque forming units)/mL.

B. Results

As seen in FIG. 12, treatment of RSV-infected cells with either 3SB or 1B9 resulted in a log decrease in viral replication. The anti-viral effect was even more pronounced when the infected cells were treated with 3G4. Treatment with 3G4 resulted in a 2 $\log_{10}$ decrease in viral titer (FIG. 12). The inhibition was lower than seen with CMV, most likely because the concentration of 3G4 was low (25-50 µg/ml).

EXAMPLE XIV

Single Chain Anti-PS Antibodies

Given the many uses of anti-PS antibodies described herein, including as anti-tumor agents alone, as targeting agents for delivering attached therapeutic agents to tumors, and as anti-viral agents, the present example describes techniques suitable for generating single chain (scFv) anti-PS antibodies, i.e., wherein the $V_H$ and $V_L$ domains are present in a single polypeptide chain, generally joined by a peptide linker.

A. Preparation of the Phage Antibody Library

The secondary stock of the bacterial library (about 1×10$^{10}$ clones) was inoculated into 100 ml 2×TY containing 100 µg/ml ampicillin and 1% glucose. It was grown with shaking at 37° C. until the OD at 600 nm was 0.5.

M13KO7 helper phage was added at 10$^{13}$ pfu and incubated without shaking in a 37° C. water bath for 30 min. The infected cells were centrifuged at 3,500 g for 10 min. The pellet was resuspended in 200 ml of 2×TY containing 100 µg/ml ampicillin and 75 µg/ml kanamycin and incubated with shaking at 30° C. overnight.

The culture was centrifuged at 10,800 g for 10 min. ⅕ volume PEG/NaCl was added to the supernatant, mixed well and left for 1 hr at 4° C. It was then centrifuged at 10,800 g for 30 min. The pellet was resuspended in 40 ml PBS and 8 ml PEG/NaCl was added. It was mixed and left for 20 min at 4° C. It was then centrifuged at 10,800 g for 10 min and the supernatant aspirated. The pellet was resuspended in 2 ml 10% human serum and centrifuged at 11,600 g for 10 min in a microcentrifuge to remove most of the remaining bacterial debris.

To pre-pan, the phage antibody library in 10% human serum was added to the PC coated dish and incubated for 60 min at room temperature.

B. Selection on Biotinylated Liposomes

20 µmol phosphatidylinositol and 20 µmol biotinylated phosphatidylserine were dissolved in 10 ml hexane. This solution was dried to a thin layer on the surface of a flask using a rotating evaporator. 2 ml PBS was added and bath sonicated 4° C. for 30 minutes.

100 µl phage scFv and 100 µl biotinylated liposomes were then mixed in the presence of 10% human serum and gently rotated for one hour at room temperature. Blocking was done with 100 µl streptavidin M-280 dynabeads by adding 600 µl 2.5% casein/0.5% BSA for 30 min at room temperature. The beads were separated from the blocking buffer with a MPC-E (Magnetic Particle Concentrator from Dynal) for 4-5 min.

The beads were resuspended in 100 µl PBS. 100 µl of blocked streptavidin Dynabeads was added to the phage bound to the biotinylated antigen and gently rotated for 15 min at room temperature. Separation was achieved with a MPC-E for 5 minutes and the supernatant poured off. It was washed five times with 1 ml PBS. For each wash, the beads were resuspended and brought down with a MPC-E.

Finally, the phage was eluted from the beads by resuspending in 300 µl 100 mM triethalamine for 30 mins. 150 µl 1 M Tris pH=7.4 was added for neutralization. The beads were separated again with the MPC-E.

150 µl of the phage supernatant was used to infect 10 ml TG1 bacteria in log phase. The 10 ml culture was shaken in the presence of 20 µg/ml ampicillin at 37° C. for one hour. Ampicillin was added to the final concentration of 50 µg/ml and shaken for another hour. $10^{13}$ pfu M13 helper phage was added to this culture, transferred to 100 ml 2TY medium containing 100 µg/ml ampicillin and shaken at 37° C. for one hour. Kanamycin was added to the final concentration of 100 µg/ml and shaken at 30° C. overnight.

The phage preparation procedure was repeated and the selection procedure repeated another 3 to 4 times.

C. Monoclonal Single Chain Antibody ELISA

Individual HB2151 colonies from the plates (after 4 rounds of selection) were inoculated into 500 µl 2×TY containing 100 µg/ml ampicillin and 1% glucose in 96-well plates and grown with shaking (300 rpm.) overnight at 37° C. 5 µl from this plate were transferred to a second 96-well plate containing 500 µl 2×TY containing 100 µg/ml ampicillin per well and grown shaking at 37° C. for 3 hr (OD600=0.9).

To each well was added 50 µl 2×TY containing 100 µg/ml ampicillin, 10 mM IPTG (final concentration is 1 mM), which was grown with shaking overnight at 30° C. It was centrifuged at 1,800 g for 10 min and 100 µl of the supernatant used in the following ELISA.

96 well plates (DYNEX IMMULON® 1B) were coated with PS dissolved in ethanol at a concentration of 10 µg/ml (P6641 10 mg/ml solvent was Chloroform:MeOH 95:5). 10 µg/ml PC was coated in the same way. These plates were evaporated at 4° C. in the cold room. 250 µl 2.5% casein was added to each well, and the plates were covered and blocked at 37° C. for 1 hour.

Wells were rinsed 3 times with PBS, 100 µl/well 10% human serum and 100 µl/well supernatant containing soluble scFv was added and incubated for 60 min at 37° C. The solution was discarded and washed 6 times with PBS. 100 µl 9E10 in 5% casein/0.5% BSA-PBS (1:5000 dilution) was added to each well, incubated at 37° C. for 1 hour and washed 6 times with PBS. 100 µl HRP-goat-anti-mouse antibody (1:10000 dilution) was added to each well, incubated at 37° C. for 1 hour and washed 5 times with PBS. 100 µl 0.05% OPD was added to each well and developed for 5 minutes. 100 µl 0.18 M $H_2SO_4$ was added to stop the reaction and read at O.D. 490.

Antigen-positive clones were streaked on 2×TYAG plates and grown overnight at 30° C. Positive single colonies were picked into 3 ml 2×TYAG media and grown 12 hours at 37° C. Plasmids were extracted and scFv gene inserts checked by enzyme digestion and PCR. The ones with the correct size inserts were sequenced.

The colonies with the correct size inserts were grown into 100 ml 2×TYAG media and shaken at 37° C. OD 600=0.5. These were transferred into 900 ml 2×TYA and grown until OD 600=0.9. 1 M IPTG was added to a final concentration of 1 mM and shaken at 30° C. overnight. The supernatant was checked using the same ELISA method as previously. The scFv protein was purified from the periplasmic fraction using $Ni^{++}$-agarose affinity chromatography.

D. Results

After 4 rounds of panning, the following clones gave promising ELISA signal on PS plates and have the correct size insert: 3E5, 3A2, G5, C8, E4 and 4D5. These have been subcloned, wherein E4 gave 5 positive subclones and 4D5 gave 5 positive subclones (Table 14).

TABLE 14

| ELISA on PS Plate | | | | | | | | | | | |
|---|---|---|---|---|---|---|---|---|---|---|---|
| 0.099 | 0.107 | 0.118 | 0.115 | 0.100 | 0.094 | 0.084 | 0.086 | 0.166 | 0.164 | 0.102 | 0.191 |
| 0.113 | 0.106 | 0.127 | 0.150 | 0.128 | 0.097 | 0.078 | 0.087 | 0.190 | 0.144 | 0.102 | 0.154 |
| 0.122 | 0.115 | 0.117 | 0.112 | 0.105 | 0.097 | 0.085 | 0.088 | 0.230 | 0.071 | 0.168 | 0.150 |
| 0.107 | 0.108 | 0.121 | 0.123 | 0.107 | 0.101 | 0.083 | 0.085 | 0.191 | 0.246 | 0.186 | 0.150 |
| 0.138 | 0.121 | 0.114 | 0.131 | 0.100 | 0.096 | 0.082 | 0.079 | 0.183 | 0.187 | 0.275 | 0.171 |
| 0.118 | 0.115 | 0.116 | 0.132 | 0.099 | 0.094 | 0.082 | 0.086 | 0.185 | 0.073 | 0.208 | 0.102 |
| 0.111 | 0.176 | 0.126 | 0.118 | 0.096 | 0.087 | 0.123 | 0.087 | 0.144 | 0.226 | 0.112 | 0.126 |
| 0.102 | 0.107 | 0.131 | 0.125 | 0.089 | 0.102 | 0.082 | 0.084 | 0.188 | 0.073 | 0.142 | 0.151 |
| 3E5 | | 3A2 | | G5 | | C8 | | E4 | | 4D5 | |

Once the positive clones were identified, they were sequenced. The ScFv nucleic acid and protein sequence of clone 3A2 is set forth in SEQ ID NO:5 and SEQ ID NO:6, respectively. The positive clones were grown up on a large scale and the scFv purified using Nickel agarose affinity chromatography. The purified scFv has been obtained using Phast-gel electrophoresis.

EXAMPLE XV

Synthesis of PE-Binding Peptide Derivatives

The present example concerns the design and synthesis of exemplary PE-binding peptide derivatives and conjugates for use in treating tumors and viral diseases. The structures for exemplary duramycin derivatives are set forth in the panels of FIG. 13A through FIG. 13O, which match the following description.

A. DLB 0.5 mg (0.251 mole) of duramycin dissolved in 0.387 ml 0.1M $NaHCO_3$ in water was added to 0.113 mg (0.25 µmole) of NHS-LC-Biotin (Sigma). The reaction mixture was incubated at room temperature for 1 hr and then at 4° C. overnight. The sample was loaded onto a silica column, washed with 0.1% trifluoroacetic acid (TFA), eluted with 0.1% TFA and 70% CH₃CN. The eluant was collected and concentrated by centrifugation. The total yield was 0.5 mg (FIG. 13A).

B. DIB 0.5 mg (0.25 μmole) of duramycin dissolved in 0.286 ml of 0.1M NaHCO₃ in water was added to 0.034 mg (0.25 μmole) of 2-iminothiolane hydrochloride (2-IT). The mixture was incubated at room temperature for 1 hr. 0.13 mg (0.261 mole) of iodoacetyl-LC-Biotin (Pierce) was added and the reaction incubated at room temperature for 1 hr and at 4° C. overnight. The sample was loaded onto a silica column, washed with 0.1% TFA, eluted with 0.1% TFA and 70% CH₃CN. The eluant was collected and concentrated by centrifugation. The total yield was 0.5 mg (FIG. 13B).

C. (DLB)₄NA 1.9 mg (0.94 μmole) duramycin was dissolved in 0.5 ml of 0.1M NaHCO₃ in water. To this, 0.4 mg (0.881 mole) NHS-LC-Biotin (Sigma) in 200 μl dimethylformamide (DMF) was added. The mixture was incubated at room temperature for 4 hr. 10 mg (0.17 μmole) neutravidin (NA) in 1 ml was added to the reaction mixture, which was incubated at room temperature for 2 hr and then at 4° C. overnight. The reaction mixture was then loaded onto a G-25 column (volume 50 ml) in PBS buffer. The fractions were collected and analyzed by SDS PAGE (phast gel). Protein-containing fractions (7-16) were pooled together, sterilized by filtration through a 0.22 μm filter and the concentration determined by measuring absorption at 280 nm. The total yield was 5.1 mg.

The sample was then fractionated by FPLC. Three peaks were collected that corresponded to the following: peak 1: [(DLB)₄NA]₃ (fractions 17-23); peak 2: [(DLB)₄]₂ (fractions 24 33) and peak 3: (DLB)₄NA (fractions 3548). All the samples were sterilized by filtration through a 0.22 μm filter. The final yields obtained were: 0.34 mg of [(DLB)₄NA]₃; 0.59 mg of [(DLB)₄]₂ and 1.41 mg of (DLB)₄NA (FIG. 13C).

D. (DLB)₄NA-F 0.61 mg of (DLB)₄NA in PBS buffer was added to 0.005 mg N-hydroxysuccinimidyl fluorescein (NHS-Fluorescein) (Sigma) in DMF. The mixture was incubated at room temperature for 1 hr. The reaction mixture was then fractionated on a PD10 column (10 ml). (DLB)₄NA-F was eluted in the protein-containing fractions (3 and 4), which were pooled together and sterilized by filtration through a 0.22 μm filter. The total yield was 0.5 mg (FIG. 13D).

E. (DIM)ₙ HIgG

Human IgG (HIgG) was first purified as follows: 1.3 ml HIgG (that included 100 mg/ml HIgG, 22.5 mg/ml glycine and 3 mg/ml albumin in borate buffer with 1 mM EDTA, pH 9) was applied to an FPLC (S200, 250 ml) column. The fractions were collected and analyzed by SDS PAGE on a phast gel. Fractions containing monomeric IgG (21-32) were pooled together and sterilized by filtration through a 0.22 μm filter. The total yield as determined by absorption at 280 nm was 111 mg.

Purified HIgG (55 mg in 13 ml of borate buffer, pH 9) was added to 1.003 mg in 0.5 ml of SMCC (Pierce) in DMF. The mixture was incubated at room temperature for 1 hr. At the same time, another reaction mixture containing 6 mg duramycin (3 μmole; dissolved in 0.5 ml 0.1M NaHCO₃) and 0.413 mg 2-IT (3 μmole; in 0.1M NaCO₃) was incubated at room temperature for 1 hr. After completion of the reactions, the two reaction mixtures were combined and incubated at room temperature for 2 hr and at 4° C. overnight. The reaction products were analyzed by SDS PAGE on a phast gel. The reaction products were loaded onto an FPLC column in borate buffer, pH 9. The FPLC fractions corresponding to trimer (5-14), dimer (15-24), and monomer (25-37) were pooled and sterilized by filtration through a 0.22 μm filter. The total yield of monomer was 54.6 mg. Five to seven duramycin groups were attached to each molecule of HigG (FIG. 13E).

F. (DIM)ₙ HIgG-F 1 mg (0.7 ml) of (DIM)ₙHIgG was added to 5 μl of NHS-Fluorescein in DMF. The reaction mixture was incubated at room temperature for 1 hr and desalted on a PD-10 column. Protein-containing fractions (2-3) were pooled and sterilized by filtration through a 0.22 μm filter. The total yield was 0.9 mg (FIG. 13F).

G. (DIM)ₙ HIgG-B and [(DIM)ₙHIgG]₂-B

To synthesize biotinylated derivatives of [(DIM)ₙHIgG]₂, 0.66 mg (1 ml) of [(DIM)ₙHIgG]₂ was added to 8 μl of 1 mg/ml of NHS-LC-Biotin (Pierce) in DMF. The mixture was incubated at room temperature for 1 hr. The reaction mixture was then desalted on a PD-10 column. Protein-containing fractions (3 and 4) were pooled and sterilized by filtration through a 0.22 μm filter. The final yield was 0.46 mg.

The biotinylation of the monomer (DIM)ₙHIgG was performed in the same manner. Briefly, 1.06 mg (0.75 ml) of (DIM)ₙHIgG were added to 12 μl of 1 mg/ml NHS-LC-Biotin in DMF. After incubation at room temperature for 1 hr, the reaction product was desalted on a PD-10 column. Protein-containing fractions (3 and 4) were pooled and sterilized by filtration through a 0.22 μm filter. The final yield was 0.62 mg (FIG. 13G).

H. (DIB)₄NA 2 mg (0.99 μmole) of duramycin were dissolved in 0.5 ml 0.1 M NaHCO₃ and added to 0.136 mg (0.99 μmole) of 2-IT. The reaction mixture was incubated at room temperature for 1 hr. Following this, 0.483 mg (0.951 mole) of iodoacetyl-LC-Biotin (Pierce) was added and the reaction mixture incubated at room temperature for 1 hr. 10 mg (0.17 μmole) of neutravidin in 1 ml of H₂O was added and incubated at 4° C. overnight. The reaction mixture was fractionated by FPLC. Three different peaks were collected and pooled: [(DIB)₄NA]₃ (fractions 17-23); [(DIB)₄NA]₂ (fractions 24-33); and (DIB)₄NA (fractions 35-48). All the samples were sterilized by filtration through a 0.22 μm filter. The total yields obtained were 0.87 mg of [(DIB)₄NA]₃; 1.25 mg of [(DIB)₄NA]₂; and 1.83 mg of (DIB)₄NA (FIG. 13H).

I. (DIB)₄NA-B 0.023 mg (0.3 μmole) of (DIB)₄NA was added to 0.9 μg of NHS-LC-Biotin (Pierce). The reaction was incubated at room temperature for 1 hr and then desalted on a PD-10 column. The total yield was 0.04 mg (FIG. 13I).

J. DS-1

5 mg (2.5 μmole) of duramycin dissolved in 0.5 ml of 0.1 M NaHCO₃ in water was added to 0.319 mg (2.6 μmole) of 1,3 propane sultone. The mixture was incubated at 4° C. overnight. The sample was loaded onto a silica column, washed with 0.1% TFA, eluted with 0.1% TFA and 70% CH₃CN. The eluant was collected and concentrated by centrifugation under reduced pressure. The total yield was 5 mg (FIG. 13J).

K. DS-2

1 mg (0.497 μmole) of duramycin dissolved in 0.3 ml of 0.1M NaHCO₃ in water was added to 0.072 mg (0.523 μmole) of 2-IT. The reaction mixture was incubated at room temperature for 1 hr. 0.125 mg (0.49 μmole) of SBF-Chloride (Pierce) was added. The reaction mixture was incubated at room temperature for 1 hr and 4° C. overnight. The peptide was purified on a silica column. The eluant was collected and concentrated by centrifugation under reduced pressure. The total yield was 1 mg (FIG. 13K).

L. DS-3

1 mg (0.497 μmole) of duramycin dissolved in 0.4 ml of 0.1M NaHCO₃ in water was added to 0.109 mg (0.592 μmole)

of 2-sulfobenzoic acid cyclic anhydride. The reaction was incubated at room temperature for 1 hr and 4° C. overnight. The peptide was purified on a silica column. The eluant was collected and concentrated by centrifugation under reduced pressure. The total yield was 1 mg (FIG. 13L).

M. DS-4

0.25 mg (0.124 µmole) of duramycin dissolved in 0.5 ml of 0.1M NaHCO$_3$ in water was added to 0.017 mg (0.124 µmole) of 2-IT. The reaction mixture was incubated at room temperature for 1 hr. The mixture was then added to 0.049 mg (0.124 µmole) Ellman's reagent. The mixture was incubated at room temperature for 2 hr and overnight at 4° C. 250 µl of 1 mg/ml of 4-Amino-5-hydroxy-2,7-naphthalene disulfonic acid mono-sodium salt hydrate was added to 100 µl of 1 mg/ml 2-IT. The reaction was incubated at room temperature for 1 hr. 50 µl of this reaction mixture was added to the previous reaction and incubated at room temperature for 1 hr. The peptide was purified on a silica column. The eluant was collected and concentrated by centrifugation under reduced pressure (FIG. 13M).

N. DS-5

5 mg (2.5 µmole) of duramycin dissolved in 0.5 ml of 0.1M NaHCO$_3$ in water was added to 0.356 mg (2.6 µmole) of 1,3 butane sultone. The mixture was incubated at 4° C. overnight. The sample was loaded onto a silica column, washed with 0.1% TFA, eluted with 0.1% TFA and 70% CH$_3$CN. The eluant was collected and concentrated by centrifugation under reduced pressure. The total yield was 5 mg (FIG. 13N).

O. DC-1

0.25 mg (0.124 µmole) of duramycin dissolved in 0.5 ml of 0.1M NaHCO$_3$ in water was added to 0.017 mg (0.124 µmole) of 2-IT. The reaction mixture was incubated at room temperature for 1 hr. The mixture was then added to 0.049 mg (0.124 µmole) Ellman's reagent. The mixture was incubated at room temperature for 2 hr and overnight at 4° C. The peptide was purified on a silica column. The eluant was collected and concentrated by centrifugation under reduced pressure (FIG. 13O).

EXAMPLE XVI

Duramycin Derivatives Specifically Bind PE

The present example shows that the duramycin derivatives synthesized in Example XV are specific for PE and can therefore be used as designed, by linking to cell-impermeant, targeting or anti-viral agents and use in the treatment of tumors and viral diseases.

To test the specificity of the duramycin derivatives, particularly the binding to PE in preference to other phospholipids, a series of competition ELISAs were performed. The ability of the duramycin derivatives to compete with either DIB or DLB for binding to PE was tested in the following method.

PE and PC were dissolved separately in ethanol. The final concentration was 5 µg/ml. 100 µl was added to each well of 96 well ELISA plates (DYNEX IMMULON® 1B). These plates were evaporated at 4° C. in a cold room. 250 µl 2.5% casein was added to each well, covered and blocked at 37° C. for 1 hour. The blocking buffer was discarded and 100 µl 2.5% casein added to each well. The duramycin compound was added as a serial dilution across the plate, such as (DIM)nHIgG, (DIB)4NA, (DLB)4NA, DS, duramycin and DIB.

The (DIM)nHIgG starting concentration was 1.4 mg/ml, the (DIB)4NA starting concentration was 800 µg/ml, and the (DLB)4NA starting concentration was 800 µg/ml. These were incubated at 37° C. for 1 hour and washed 5 times with PBS. 100 µl HRP-streptavidin (1:5000 dilution) was added to each well, incubated at 37° C. for 1 hour and washed 5 times with PBS. 100 µl 0.05% OPD was added to each well and developed for 5 minutes. 100 µl 0.18 M H2SO4 was added to stop the reaction and read at O.D. 490.

The resultant data was tabulated and then plotted graphically. As exemplified by the data in FIG. 14C and FIG. 14D, increasing concentrations of the duramycin derivatives decrease absorbance at 490 nm, showing that the duramycin derivatives compete with DIB and DLB for binding to phosphatidylethanolamine.

The phospholipid binding profiles of duramycin constructs were confirmed using further ELISAs. The respective test lipids PS, PE, PI, CL, PC, PG, SM, and cholesterol were dissolved separately in ethanol and used to coat ELISA plates. Duramycin compounds were added as serial dilutions across the plates. After incubation and washing steps, a secondary detection reagent was added to each well and reactivity determined using the colorimetric assay as described above.

Representative phospholipid binding profiles for the duramycin biotin derivatives, DIB and DLB are depicted in FIG. 14A. It is shown that DIB and DLB are specific for PE, with binding to each of PS, PI, CL, PC, PG and SM being negligible or undetectable. (DIM)$_n$HIgG-B and [(DIM)$_n$HIgG]$_2$-B had essentially the same binding profile as DLB. Although minimal binding to PS was observed at high concentrations of DIB (FIG. 14A), this is not meaningful in the context of this study, as binding to PS was undetectable at DIB concentrations that were saturating and half maximal for PE binding. Therefore, the duramycin constructs specifically bind to phosphatidylethanolamine.

It was also shown that serum has no significant effect on PE binding by duramycin derivatives. This is exemplified by binding of the duramycin biotin derivative, DLB to PE-coated ELISA plates in the presence and absence of serum (BSA), wherein the binding profiles show no significant differences (FIG. 14B).

EXAMPLE XVII

Anti-Viral Effects of PE-Binding Peptide Derivatives

In addition to the anti-viral effects mediated by anti-PS antibodies, as shown in Example XII and Example XIII, the present example demonstrates the anti-viral effects of peptide derivatives that specifically bind to the other common aminophospholipid, PE.

A. Methods

1. Treatment of CMV-Infected Cells In Vitro

Confluent monolayers of human diploid foreskin fibroblasts (HHF-R2) in 6-well plates were infected with human CMV AD169 expressing green fluorescent protein (GFP) at an MOI=0.01 as described in Example XII (Bresnahan et al., 1996). The cells were incubated with virus in a total volume of 1.5 ml per well at 37° C. for 90 minutes. During the infection, the plates were gently rocked every 30 minutes. Following the infection, the cell supernatant was removed and DMEM/10% FBS/pen-strep (2 ml per well) was added to each well.

Different dilutions of duramycin derivatives (DLB)$_4$NA, (DIM)$_n$HIgG, DS-1, DS-2, DS-3 and DC-1 were added to the wells before the addition of the virus, and following infection. The infected cells were incubated at 37° C. for a total of 14 days. The medium and duramycin derivative in each well were replaced every 3 days.

2. Fluorescent Microscopy

As in Example XII, the recombinant CMV expresses GFP under the control of the SV40 promoter. Hence, infected cells appear green under a fluorescent microscope. In these studies, the CMV-infected cells treated with the duramycin derivatives were observed under a fluorescent microscope at days 4 and 6.

B. Results

On day 4, there are single infected GFP-positive green cells in untreated wells and wells treated with (DLB)$_4$NA and (DIM)$_n$HIgG (FIG. 15, left panels). Thus, treatment of HHF-R2 cells with these duramycin derivatives does not appear to inhibit the entry of the virus into the cells. There is some preliminary evidence that the duramycin derivatives DS-1, DS-2 and DS-3 inhibit viral entry into the cells.

On day 6 after treatment with (DLB)$_4$NA and (DIM)$_n$-HIgG, there is a marked difference in the number of infected GFP-positive cells in untreated vs. the duramycin derivative treated wells (FIG. 15, middle panels). By day 6, the virus has spread from the single infected cell seen on day 4 surrounding cells in the untreated wells (FIG. 15, top, compare left panel to middle panel). However, on day 6 in the wells treated with (DLB)$_4$NA and (DIM)$_n$HIgG, the virus is limited to the original singly infected cell (FIG. 15, middle and bottom, compare left panels to middle panels).

Accordingly, (DLB)$_4$NA and (DIM)$_n$HIgG limit the spread of CMV from the original infected cell to the surrounding cells. This inhibition of viral spread is observed when cells were treated with different concentrations of (DIB)$_4$NA (100 µg/ml and 50 µg/ml) and (DIM)$_n$HIgG (200 µg/ml and 100 µg/ml).

EXAMPLE XVIII

Advantages of 3G4 Antibody

The 3G4 antibody developed by the inventors' unique protocol, as described in Example IV, has many advantages over the anti-PS antibodies in the literature, including the prominent anti-PS antibody, 3SB (Rote et al. (1993). The present example describes certain of those advantages.

A. Class and Specificity

3G4 is an IgG antibody, whereas 3SB is IgM. Antibodies of IgG class have numerous advantages over IgM, including higher affinity, lower clearance rate in vivo and simplicity of purification, modification and handling. A comparison of the PS binding of the IgM antibody, 3SB, with 3G4 and another IgG antibody is shown in FIG. 19A and FIG. 19B.

3G4 reacts strongly with the anionic phospholipids PS, PA, PI, PG and CL with approximately the same intensity, and binds to the aminophospholipid, PE less strongly. It has no reactivity with PC and SM and has the binding specificity profile: PS=PA=PI=PG>CL>>PE (Example IV; Table 4). 3G4 does not bind detectably to heparin, heparan sulfate or to double or single stranded DNA, nor to cellular proteins extracted from bEnd.3 cells on Western blots. The binding of 3G4 is unaffected by the presence of 5 mM EDTA, showing that Ca$^{2+}$ is not require for 3G4 binding to anionic phospholipids. 3G4 did not bind to ELISA plates that had been coated with phospholipids but then washed with 0.2% Tween 20 in saline, confirming that the binding was to the absorbed phospholipid.

The epitope recognized by 3G4 appears to lie within the phosphoglycerol core of the anionic phospholipids, which is the same in phospholipids from all mammalian species. The antibody thus reacts with both mouse and human phospholipids, which is important for pre-clinical and clinical development. 3G4 is more specific for anionic phospholipids than the natural ligand, annexin V. Unlike 3G4, annexin V also binds strongly to neutral phospholipids in physiological concentrations of Ca$^{2+}$.

The specificity of 3G4 for anionic phospholipids was confirmed by assays in which liposomes formed from different phospholipids were used to compete for 3G4 binding to immobilized PS. Liposomes were prepared from solutions of 5 mg of a single phospholipid in chloroform. The solutions were dried under nitrogen to form a thin layer in a round-bottomed glass flask. Ten ml of Tris buffer (0.1 M, pH 7.4) were then added and the flask was sonicated five times for 2 min. The 3G4 antibody (0.1 µg/ml) was added to either buffer or different phospholipid liposomes and pre-incubated for 30 minutes at room temperature. The mixture was added to PS-coated plates (after standard blocking), incubated for 1 hour, washed and the secondary antibody added. After 1 hour, the plates were washed and developed for 5 minutes using OPD.

As shown in Example IV, 3G4 binds to PS, PA, PI, PG and CL when immobilized and binds to immobilized PE to a lesser degree, but does not bind to immobilized PC. The ability of 3G4 to bind to immobilized PS in the presence or absence of the different liposomes is shown in FIG. 20. Results from these liposome competition studies show that binding of 3G4 to PS adsorbed to ELISA plates was blocked by liposomes prepared from PS, PA, PI, PG and CL, but that liposomes prepared from PE and PC did not result in a detectable reduction in 3G4 binding (FIG. 20). Also, SM liposomes were not inhibitory.

B. Inhibition of Cell Proliferation

3G4 binds to activated, dividing, injured, apoptotic and malignant cells that externalize PS and other anionic phospholipids. The 3G4 antibody inhibits the proliferation of endothelial cells in vitro, and shows a marked selective inhibition of dividing endothelial cells as opposed to quiescent cells.

The effect of the anti-PS antibodies 3G4, 9D2, 3B10, 1B9, 2G7, 7C5 and 3SB on the growth of bEnd.3 cells in vitro was determined. bEnd.3 cells (10,000/well) were seeded in 48 well plates and allowed to attach. 20% DMEM alone (control) or 20% DMEM containing the antibodies (20 µg to 40 µg total IgG per well) was added 4 hours after seeding. Each clone was tested on two separate plates in triplicates. Cells were detached 48 and 96 hours later, the cell count was determined in each well and the average cell number per treatment was calculated.

The 3G4 and 9D2 antibodies were particularly effective, followed by 3SB and 3B10, with 1B9, 2G7 and 7C5 having less inhibitory effects. Each of the antibodies show a selective inhibition of dividing (subconfluent) endothelial cells as opposed to quiescent (confluent) cells. In comparative studies, 3G4 showed the greatest inhibitory effect, followed by 9D2, each of which were more inhibitory than 3SB (FIG. 16).

C. Anti-Tumor Effects

3G4 binds to the surface of tumor vascular endothelial cells in vivo. When injected intravenously into mice bearing various tumors, 3G4 specifically and consistently localized to the tumor, but not to normal organs. Staining was observed on tumor vascular endothelium (FIG. 22), necrotic areas and individual malignant cells. There are multiple binding sites for 3G4 in tumors, which allows simultaneous targeting of both tumor endothelial and tumor cells.

3G4 suppresses angiogenesis and tumor growth in vivo and shows no detectable organ toxicity in tumor-bearing mice. In initial studies, 3G4 has shown impressive anti-tumor effects in syngeneic and xenogeneic tumor models, wherein the antibody causes tumor vascular injury, decrease in vascularity and tumor necrosis (Example XI). Regressions of established tumors have been observed in 30% to 50% of the animals treated.

Representative anti-angiogenic and vascular targeting effects of the 3G4 antibody are shown in FIG. 17A and FIG. 17B, respectively. Analyses of tumor sections from nude mice bearing MDA-MB-231 orthotopic tumors treated with 3G4 revealed anti-angiogenic effects in all treated tumors. FIG. 17A shows representative images of tumors from mice treated with 3G4 as opposed to control antibodies. The control tumor shows no signs of necrosis and is highly vascularized, as demonstrated by the pan-endothelial cell marker, CD31 detected on tumor blood vessels (FIG. 17A, left panel). In contrast, tumors from the mice treated with 3G4 have 80 to 90% necrosis and almost complete disappearance of CD31-positive structures, indicating that the treatment produced a substantial anti-angiogenic effect (FIG. 17A, right panel).

Another component of the anti-cancer activity of 3G4 is the induction of tumor vascular damage. This is illustrated in FIG. 17B, which provides representative images of H&E stained tumors derived from the same controlled study. The blood vessels in the control tumors are well perfused, morphologically intact and surrounded by viable dividing tumor cells (FIG. 17B, left panel). In contrast, the blood vessels in the 3G4-treated animals are frequently observed to have a disintegrating endothelial layer and are blocked by the detached endothelial cells and, likely, by host cells that are attracted to the denuded vessels (FIG. 17B, right panel). The representative vessel in the 3G4-treated tumor clearly shows loss of function, as indicated by the pre-necrotic layer of surrounding tumor cells (FIG. 17B, right panel).

In summary, the histological examination following the treatment of orthotopic MDA-MB-231 tumors using 3G4 shows: 1) disintegration of vascular endothelium in about 50% of vessels in the tumor; 2) attachment of leukocytes to tumor endothelium and infiltration of mononuclear cells into the tumor interstitium; 3) occlusion of tumor vessels by platelet aggregates and red cells; 4) a 70% reduction in microvascular density in tumors from 3G4 treated vs. untreated mice; and 5) central necrosis of the tumors, with survival of a peripheral rim of tumor cells, typical of a VTA. Thus, a primary anti-tumor action of the 3G4 antibody is exerted through effects on tumor vasculature. Other mechanisms, particularly antibody-dependent cellular cytotoxicity directed against the tumor cells themselves, likely contributes to the anti-tumor effect. This is important, and may permit killing of more tumor cells, including those in the peripheral rim.

In follow-up studies, the effect of 3G4 on tumor growth has been examined in other murine models, including syngeneic (mouse Meth A fibrosarcoma), subcutaneous xenografts (L540 human Hodgkin's lymphoma) and orthotopic tumors (human MDA-MB-231 breast cancer and human MDA-MB-435 breast cancer). Treatment of mice with 3G4 antibody resulted in 90%, 65% and 50% and 70% growth retardation of these tumors, respectively. Both small (0.1 cm diameter) and well-established (0.3 cm diameter, 200 mm$^3$) tumors were inhibited alike. Anti-PS treatment induced long-term complete remissions in 50% of Meth A-bearing mice and 30% of mice with MBA-MD-231 tumors. 3G4 has the highest inhibitory effect in immunocompetent mice. The orthotopic models of human breast tumors (MDA-MB-231 and MDA-MB-435), in which human breast tumors are grown in the mammary fat pads of mice, are important as these are practical and realistic models of human breast cancer growing within the breast of humans.

D. Safety Profile

The 3G4 antibody is different to anti-phospholipid antibodies described in the literature. Typically, anti-phospholipid antibodies are regarded as pathogenic antibodies that interfere with the coagulation cascade. They inhibit coagulation reactions in vitro and cause thrombosis in vivo. In contrast, 3G4, 9D2 and like antibodies are therapeutic antibodies without pathogenic effects.

1. Coagulation

An important aspect of the 3G4, 9D2 and like antibodies stems from the inventors' realization that desirable antibodies should preferably be selected using a screen to identify antibodies that bind to PS-coated plates as strongly in the presence of serum as in the absence of serum. This new development provides the ability to identify and exclude antibodies that recognize complexes of PS and serum proteins, as such complexes are believed to be the cause of, or an important factor in, anti-phospholipid syndrome and associated pathologies.

In studies of blood coagulation in vitro, a weak inhibition of Tissue Factor (TF)-induced coagulation was observed using high doses of 3G4 antibody. In other studies using lower doses, recalcified plasma from 3G4 treated mice coagulated at the same rate as did recalcified plasma from BBG3 treated mice in the presence of tissue factor. Also, the addition of 100 µg/ml of 3G4 to cells plus tissue factor in vitro did not affect the generation rate of coagulation Factor Xa in proplex (extrinsic coagulation pathway).

Despite the weak inhibition of TF-induced coagulation using high antibody levels in vitro, the 3G4 antibody has been tested in vivo and does not cause thrombotic complications in normal or tumor-bearing mice (e.g., see Example XI). The 3G4 antibody has also been tested in monkeys in vivo and no significant side effects have been observed.

2. Other Indicators of Low or No Toxicity

The first evidence that 3G4 has no or low toxicity in mice came from the finding that 3G4 grows as a hybridoma in mice without evidence of toxicity. Also, when 1 mg of purified 3G4 was injected intraperitoneally, no toxicity was observed.

Systematic in vivo studies have now been conducted in which groups of three 8 week old BALB/c mice were injected IP with 100 µg of purified 3G4 or with an isotype-matched control IgG$_3$ (BBG3) three times a week for 2 to 3 weeks. No physical signs of toxicity have been observed, and no histopathological signs of organ toxicity or morphological abnormalities have been detected in sections of major organs removed from 3G4-treated mice. The following parameters were specifically examined.

In terms of bodyweight, 3G4-treated mice gained weight at the same rate as BBG3 treated mice. No weight loss was observed in the earlier studies. There were no physical signs of toxicity, e.g. hair loss, loss of appetite, etc. There are no changes in blood cell counts, including red cells, platelets, white cells, absolute lymphocyte counts or absolute neutrophil counts. To analyze bone marrow cellularity, paraffin sections of bone marrow derived from 3G4 or BBG3-treated mice (six injections, 100 µg) were examined for total cellularity and cellular composition. Marrows in the treated animals were essentially completely cellular (as would be expected for a young mammal). Erythroid, granulocytic, lymphocytic progenitors and megakaryocytes were present in normal numbers.

In summary, no instance of toxicity has been observed in more than 200 mice treated with high doses of 3G4 (0.1 mg) three times a week for 2-3 weeks. Even when doses as high as 2 mg were given, no signs of toxicity were seen. Mice retain normal physical signs, bone marrow cellularity, white blood cell counts, histology and coagulation functions.

The 3G4 antibody has also been administered to monkeys in safety studies and no side effects have been observed.

Blood clearance kinetic studies have also been conducted in mice. 3G4 was radioiodinated using the Bolton Hunter reagent and was injected intravenously into mice (25 g). Samples of blood were removed via the tail vein at various later time points. The blood clearance rate of 3G4 was typical of a mouse IgG in the mouse. The half-life in the α-phase of clearance was 3 hours while that in the β-phase was 5 days. Volume of distribution was normal (100 ml/kg). These studies indicate that 3G4 does not interact with normal host tissues, leading to its accelerated clearance.

E. Anti-Viral Effects

The 3G4 antibody also exerts significant anti-viral effects. As shown in seen in Example XIII, the treatment of RSV-infected cells with 3G4 was superior to the effect observed using 3SB. These results therefore highlight another advantage of the 3G4 antibody over the prominent anti-PS antibody in the literature, 3SB (Rote et al. (1993).

The 3G4 antibody is also shown to be very effective in inhibiting CMV, both in vitro (Example XII) and in enhancing the survival of mice infected with mCMV in vivo (Example XXI). In addition, the 3G4 antibody is further shown to inhibit Pichinde virus infection, the infectious agent of Lassa fever (Example XXIV). The cell surface PS exposure herein shown to follow viral infection, and the ability of the 3G4 antibody to bind to cells infected with Vaccinia virus (Example XXIII), shows that the 3G4 antibody has enormous potential as a broad spectrum anti-viral agent.

EXAMPLE XIX

3G4 Antibody, CDR Sequences and Chimera

The 3G4 antibody thus possesses the combined properties of an anti-angiogenic, anti-tumor vascular and anti-viral agent. The inhibitory activities of 3G4 on cell division, angiogenesis, tumor growth and viral infectivity, taken together with lack of apparent toxicity, show broad therapeutic indications for this antibody, including in the treatment of angiogenic disorders, cancer, diabetes and viral infections.

Antibodies recognizing substantially the same epitope as the 3G4 antibody can be generated for use in one or more of the anti-angiogenic, anti-tumor vascular and anti-viral therapies, e.g., by immunization and confirmed by antibody competition studies. Antibodies that bind to essentially the same epitope as the 3G4 antibody can also be generated from a knowledge of the 3G4 antibody sequences provided herein. The present example provides the sequences of the complementarity determining regions (CDRs) of the 3G4 antibody and the use of the sequence information.

A. 3G4 Antibody Sequences

The original sequences of the antibody variable regions were obtained by RACE from the hybridoma that produces the 3G4 antibody and the sequences verified. The nucleic acid and amino acid sequences of the variable region of the heavy chain (Vh) of the 3G4 antibody CDR1-3 are represented by SEQ ID NO:1 and SEQ ID NO:2, respectively.

SEQ ID NO:1 and SEQ ID NO:2 include part of the mouse leader sequence and constant chain sequences, as shown in FIG. 18A. The leader sequence is represented by amino acids 1 through 19 of SEQ ID NO:2, and the mature protein begins as shown by the arrow in FIG. 18A. Sufficient complementarity determining region sequence information is included by the sequence of the mature protein up to the sequence portion concluding VSS, after which the amino acids are not essential for antigen binding. As such, the BstEII site in the nucleic acid sequence can be used as a convenient site to prepare a functional mouse variable region, e.g., for use in grafting onto a human constant region (FIG. 18A).

In practice, the 3G4-2BVH sequence has been grafted onto a human γ1 constant region at the BstEII site using a Lonza pEE vector. The resultant product contains the mouse leader sequence and its VH is joined to the human CH1 sequence in the manner shown in FIG. 18A, wherein ASTLGPSVF-PLAPSSKSTSG (SEQ ID NO:7) represents the first part of the human CH1 sequence.

The nucleic acid and amino acid sequences of the variable region of the light chain (Vκ) of the 3G4 antibody CDR1-3 are represented by SEQ ID NO:3 and SEQ ID NO:4, respectively. SEQ ID NO:3 and SEQ ID NO:4 again include part of the mouse leader sequence and constant chain sequences, as shown in FIG. 18B. The leader sequence is amino acids 1 through 22 of SEQ ID NO:4, and the mature protein begins as shown by the arrow in FIG. 18B. Sufficient complementarity determining region sequence information is included by the sequence of the mature protein up to the sequence portion concluding TVF, after which the amino acids are not essential for antigen binding. As such, the BbsI site in the nucleic acid sequence can be used as a convenient site to prepare a functional mouse variable region, e.g., for use in grafting onto a human constant region (FIG. 18B).

In practice, the 3G4-2BVL sequence has been grafted onto a human κ constant region at the BbsI site using a Lonza pEE vector. The resultant product contains the mouse leader sequence and its VL is joined within the human CL1 sequence in the manner shown in FIG. 18B, wherein IFPPSDEQLKS-GTAS (SEQ ID NO:8) represents the first part of the human κ constant region sequence.

B. Generation and Characterization of 3G4 Chimeric Antibody

The chimeric construct containing the murine complementarity determining regions and the human constant regions has been produced (ch3G4) and shown to behave essentially the same as the original murine antibody.

The murine 3G4 antibody was converted into a human-mouse chimeric antibody (Avanir (Xenerex) Biosciences San Diego, Calif.). The murine $V_H$ was cloned and grafted onto the human $γ_1$ constant region at the BstEII site of the Lonza 2BVH vector. The murine $V_K$ was cloned and grafted onto the human K constant region at the BbsI site of the Lonza 2BVL vector. The sequences were verified. The entire construct was expressed iii CHO cells and purified.

The resultant ch3G4 bound at least as did well as the murine 3G4 to phospholipid-coated ELISA plates. The in vitro binding profile of chimeric 3G4 to the panel of phospholipids is shown in FIG. 21, wherein binding to PS, PA, CL, PI and PG is shown to be similar. The binding was antigen-specific since no binding was observed with control antibodies of irrelevant specificity. In certain studies, an apparently greater binding of chimeric 3G4 vs. the 3G4 antibody was observed; this may be due to superior binding of the secondary antibody.

In vivo, ch3G4 localizes to tumor vascular endothelium and exerts anti-tumor effects. The anti-tumor effects of ch3G4 in MDA-MB-435 human breast cancer cells growing in mice is described in Example XI and shown in FIG. 8G. Treatment of mice with MDA-MB-435 tumors using the chimeric antibody effectively retarded tumor growth as opposed to control.

Localization of ch3G4 was examined in MDA-MB-435 human breast cancer cells growing in mice. Mice were injected intravenously with biotinylated ch3G4 or control IgG of irrelevant specificity. One hour later, the mice were exsanguinated, and their tumors were removed and frozen sections were cut. Biotinylated reagents were first incubated with streptavidin-Cy3 conjugate, washed in PBS, then incubated with MECA 32 antibody followed by FITC-tagged secondary antibody. Single images, taken with appropriate filters for Cy3 (red) and FITC (green) fluorescence respectively, were captured by digital camera and transferred to a computer. Converged images demonstrating yellow color (a product of merged green and red fluorescence) were superimposed with the aid of Metaview software.

In this double staining method, the biotinylated proteins and the vascular endothelium are labeled by red and green. Where the biotinylated proteins are bound to the endothelium, the converged image appears yellow. As shown in FIG. 22, biotinylated ch3G4 binds to the tumor vascular endothelium, because the staining patterns converges with that of MECA 32.

EXAMPLE XX

3G4 Antibody in Combination Therapy with Docetaxel

The present example concerns combination therapies for tumor treatment using the 3G4 antibody and the chemotherapeutic drug, docetaxel. These agents are designed to attack tumor vasculature endothelial cell and tumor cell compartments, leading to synergistic treatment with lower toxicity. The results showed that this combination therapy did indeed significantly enhanced treatment efficacy.

A. Fc Domain-Mediated Anti-Tumor Effects

The 3G4 antibody was tested for inhibitory effects on tumor cells in vitro. No direct inhibitory effect on tumor cells was observed. Therefore, it is likely that the anti-tumor effects of the 3G4 antibody include Fc domain-mediated augmentation of immune effector functions, such as antibody mediated phagocytosis, ADCC, CDC and stimulation of cytokine production, or these mechanisms combined.

The effects of 3G4 on the phagocytosis of PS-positive cells by macrophages have been evaluated. Fluorescent tumor cells were treated with $H_2O_2$ to induce PS exposure. Treated and untreated cells were then harvested and contacted with the 3G4 antibody or a control antibody (BBG). Mouse bone marrow macrophages were then added, and the ability of the macrophages to phagocytose the fluorescent tumor cells was analyzed using a fluorescent microscope.

It was determined that 3G4 could increase the phagocytosis of PS-positive cells by macrophages by more than three fold (FIG. 23). This finding supports the inventors' reasoning that the Fc domain of the 3G4 antibody contributes to the anti-tumor effects of the antibody. That is, the Fc domain activates host immune effector functions, which then exert anti-tumor effects. The 3G4 antibody should therefore enhance the lytic activity of NK cells, leading to more effective ADCC.

B. Docetaxel Induces PS Exposure on Endothelial Cells

The induction of PS exposure on endothelial cells by subclinical concentrations of docetaxel was examined in vitro by FACS analysis. Human umbilical vein endothelial cells (HUVEC) and human microvessel endothelial cells (HMVEC) were treated with 10 nM of docetaxel for 24 hrs and examined by FACS. Both treated HUVEC and HMVEC showed significant increase in 3G4 binding as compared to untreated cells (FIG. 24A and FIG. 24B, respectively). Docetaxel incubations for 48 and 72 hrs were also conducted.

C. Docetaxel Induces PS Exposure on Tumor Cells

The in vitro induction of PS exposure by subclinical concentrations of docetaxel was also examined by FACS analysis using a panel of tumor cell lines. Mouse lewis lung carcinoma 3LL, mouse colon carcinoma Colo26 and human breast cancer MDA-MB-435 cells were treated with 10 nM of docetaxel for 24 hrs and examined by FACS. All tumor cell lines tested showed significant increase in 3G4 binding as compared with untreated cells (FIG. 25A, FIG. 25B and FIG. 25C, respectively). Docetaxel incubations for 48 and 72 hrs were also conducted. Mouse melanoma B16 and mouse fibrosarcoma Meth A tumor cell lines were further examined and also showed significant increase in 3G4 binding as compared with untreated cells.

Human breast cancer MDA-MB-231 cells were treated with 10 nM of docetaxel for 24 hrs and incubated with either the chimeric 3G4 antibody (ch3G4) or control, human IgG and analyzed by FACS. These results show that the significant increase in antibody binding is antigen-specific and that the chimeric antibody behaves like the parent 3G4 antibody (FIG. 26).

D. Synergistic Tumor Treatment with 3G4 and Docetaxel

The inventors have thus shown that the treatment of endothelial cells and tumor cells with docetaxel at subclinical concentration significantly increases 3G4 binding. They have also shown that the 3G4 antibody facilitates macrophage-mediated phagocytosis of tumor cells on which PS is exposed at the surface. The increased 3G4 binding mediated by docetaxel should therefore augment the phagocytosis of tumor cells and other anti-tumor effects mediated by the Fc domain of the 3G4 antibody, such as increasing the lytic activity of NK cells, leading to more effective ADCC. Studies of others have also shown that treatment of breast cancer patients with docetaxel leads to an increase in serum IFN-$\gamma$, IL-2, IL-6 and GM-CSF cytokine levels and enhancement of NK and LAK cell activity (Tsavaris et al., 2002).

The anti-tumor effect of the combined therapy of 3G4 with docetaxel was therefore examined in an orthotopic model in SCID mice bearing human MDA-MB-435 breast carcinoma. Mice bearing orthotopic MDA-MB-435 human breast tumor were treated i.p. with 3G4 alone (100 µg/dose), docetaxel alone (10 mg/kg), or 3G4 in combination with docetaxel (100 µg/dose and 10 mg/kg, respectively), for three weeks, with administration 3 times a week. Treatment started 6 days after tumor cell implantation.

These studies showed that the combined therapy of 3G4 plus docetaxel resulted in growth inhibition of 90%. Growth inhibition of 3G4 plus docetaxel was significantly superior to 3G4 alone ($p<0.005$) and docetaxel alone ($p<0.01$).

E. 3G4-Targeting of Apoptotic Tumor Cells to Fc$\gamma$R on Dendritic Cells

Tumors from mice treated with 3G4 plus docetaxel also contained unusual amount of lymphocytes, as compared to control tumors. Although this phenomenon could represent typical chemoattraction of immune cells by disintegrating tumor cells, it could also reflect activation of the immune system by 3G4 mediated through Fc binding to Fc$\gamma$R on immune effector cells.

To characterize the effects of 3G4 and docetaxel administration on the intratumoral immune cell infiltrate, the types of cells present in these infiltrates can be identified by immunostaining of frozen sections and/or paraffin sections of tumor tissues using antibodies directed against specific markers of macrophages, neutrophils, granulocytes, NK cells and activated lymphocytes (Pharmingen, San Diego, Calif.). The extent, phenotype, and activation status of this infiltrate can be graded. Cytokine production by infiltrating immune cells, including IL-2 and INF, can also be analyzed via immunohistochemical techniques. Serum cytokine levels can be evaluated by ELISA and intracellular staining can be used to identify the specific cellular compartments responsible for cytokine production. The effects of infiltrating immune cells on tumor cell proliferation and apoptosis can thus be systematically evaluated.

In light of the foregoing data, the inventors further contemplate methods enhancing the potency of immunotherapy of breast cancer by 3G4-mediated targeting of apoptotic tumor cells to the Fc gamma receptor (Fc($\gamma$)R) on dendritic cells. Efficient antigen presentation, which induces effective cellular and humoral immune responses, is important for the development of tumor vaccines and immunotherapies. Dendritic cells (DC) are the most potent antigen-presenting cells (APC) that prime cytotoxic T lymphocytes against tumor-associated antigens. Improvement of tumor antigen presentation by dendritic cells (DCs) should lead to develop more potent tumor vaccines.

Antigenic presentation by Fc($\gamma$)R receptor-mediated internalization of DCs can be enhanced up to 1,000-fold compared with fluid phase antigen pinocytosis. Apoptotic tumor cells (ATC) are an excellent source of antigens for dendritic cell loading because multiple tumor specific antigens (both known and unknown) can be efficiently presented to naïve T cells, making the occurrence of immune escape variants less likely due to the lock of certain epitopes. In animal studies, DCs pulsed with ATCs have been shown to produce potent anti-tumor immunity in vitro and in vivo. However, recent data has demonstrated that ATCs alone were somewhat inefficient for activating anti-tumor immunity, possibly because of their insufficient uptake and inability to induce DC maturation.

Recent studies have also demonstrated that ATC-immune complex, formed by binding of anti-tumor antibody to apoptotic tumor cells, can be targeted to Fc($\gamma$)R on DC. Compared with ATCs alone, ATC-immune complexes were more efficiently internalized by DC, more efficient in inducing DC activation and maturation, and more importantly, ATC-immune complexes can significantly enhance both MHC I and II-restricted antigen presentation, therefore induce potent anti-tumor T helper and CTL immunity.

The inventors therefore envision using the anti-PS antibodies of the present invention to enhance both hormonal and cellular anti-tumor immunity, and boost the efficacy of ATC based DC tumor vaccines. As PS is a universal and the most abundant specific marker of apoptotic tumor cells, the panel of antibodies of the invention, particularly 3G4, can bind to PS on ATCs. The inventors have already demonstrated that 3G4 can enhance DC uptake of apoptotic tumor cells by 300% through Fc($\gamma$)R mediated internalization of 3G4-ATC complexes. By enhancing the uptake of ATC by DC mediated through Fc($\gamma$)R, it is therefore reasoned that 3G4 and like antibodies can greatly enhance both MHC I and II restricted antigen presentation, induce both potent hormonal and cellular anti-tumor immunity, and boost the efficacy of ATC based DC tumor vaccines. This can be demonstrated by establishing the efficacy of DC loaded with 3G4-ATC immune complexes in the induction of T h1, CTL and antibody response in vivo, and by determining the potency of anti-tumor immunity induced by immunization of DC loaded with 3G4-ATC immune complexes in vivo.

EXAMPLE XXI

Anti-PS Antibodies Treat CMV Infections In Vivo

Following the anti-viral effects against CMV in vitro shown in Example XII, the present example demonstrates the enhanced survival of mice infected with the murine version of the CMV virus, mCMV.

Balb/C mice (6 week old, five mice per group) were infected i.p. with $5\times10^{15}$ pfu of mCMV RVG102. The mice were treated i.p. on day 1 with the 3G4 antibody (1 mg/mouse), or the human-mouse chimeric antibody, ch3G4 described above (1 mg/mouse). Untreated mice served as the control. The mice were treated every four days thereafter with 0.5 mg/mouse of antibody or chimeric antibody until day 26. The mice were monitored for survival past 90 days post infection.

Treatment with both the parent and chimeric forms of the 3G4 antibody resulted in increased survival of the mCMV-infected mice. Mice treated with 3G4 or ch3G4 had 100% and 80% survival, respectively, as compared to untreated mice, wherein only 25% of the mice survived the infection (FIG. 27).

EXAMPLE XXII

PE-Binding Peptide Derivative Treats CMV Infection In Vivo

In addition to the in vitro anti-viral effects against CMV shown in Example XVII, this example demonstrates that the duramycin-biotin derivative, DLB increased survival of mice infected with mCMV.

Balb/C mice (6 week old, five mice per group) were infected i.p. with $5\times10^5$ pfu of mCMV RVG102. The mice were treated i.p. on day 1 and every four days with 20 µg/mouse of the duramycin derivative, DLB. Untreated mice served as the control. The mice were monitored for survival past 90 days post infection.

Treatment with the duramycin-biotin derivative, DLB enhanced survival of the mCMV-infected mice. Mice treated with DLB had 100% survival, as compared to untreated mice, wherein only 25% of the mice survived the infection (FIG. 28).

EXAMPLE XXIII

Anti-PS Antibodies Bind to Virally Infected Cells

The present example shows that viral infection induces PS exposure at the cell surface and that anti-PS antibodies bind to virally infected cells. Cells infected with Vaccinia virus become PS-positive, as shown by increased binding of the chimeric 3G4 antibody to the cell surface demonstrated in FACS analyses.

U937 cells were infected with trypsinized Vaccinia virus at a high m.o.i of 2. Briefly, Vaccinia virus was treated with an equal volume of 0.25 mg/ml trypsin for 30 minutes at 37° C. The virus was added to U937 cells in a total volume of 0.5 ml. After 1.5 hr, fresh medium was added to the cells and the cells were incubated in a T25 flask at 37° C. for 2 days. Uninfected cells served as the controls.

Infected and uninfected U937 cells were stained with a primary antibody, either with the chimeric 3G4 antibody (ch3G4) or with human IgG (HIgG) as a control. The cells were washed, blocked with normal mouse serum and then stained with the primary antibody for 45 minutes on ice. After three washes, the cells were stained with a 1:400 dilution of goat anti-human FITC-conjugated secondary antibody and were analyzed on a FACScan.

Results from the FACS analyses show that there is a significant shift with ch3G4 on U-937 cells infected with Vaccinia virus (FIG. 29B, right (green) peak), as compared to that obtained on uninfected U937 cells (FIG. 29A, right (green) peak). This study therefore shows that infection of cells with Vaccinia virus leads to PS exposure on the cell surface and that the chimeric version of the anti-PS antibody, 3G4 is capable of binding to these virally infected cells.

EXAMPLE XXIV

Anti-Viral Effects of Anti-PS Antibodies Against Pichinde Virus

In addition to the anti-viral effects against CMV and RSV, the present example further shows that anti-PS antibodies inhibit Pichinde virus infection in vitro. Pichinde virus is New World arenavirus, which is non-pathogenic in man, and is used in an animal model for Lassa fever.

Confluent monolayers of Vero cells were treated with the 3G4 antibody or an isotype-matched control antibody, GV39G, after infection with Pichinde virus at a low m.o.i. of 0.01 pfu/cell. Briefly, the cells were incubated with virus in a total volume of 1 ml per well at 37° C. for 90 minutes. During the infection, the plates were gently rocked every 30 minutes. Following the infection, the cell supernatant was removed and DMEM/10% FBS/pen-strep was added to each well (2 ml per well). On day 2, the cells were harvested with trypsin and allowed to adhere to Biocoat chamber slides. They were fixed and stained with polyclonal rabbit anti-PIC serum followed by a biotin-conjugated goat anti-rabbit secondary (secondary antibody alone produced no staining, as shown in FIG. 30C). The number of infected cells per field of 100 cells was counted.

In cells treated with 3G4, the virus is restricted to single cells that stain a dark red, numbering about one in about a hundred cells (FIG. 30A). These are probably the cells that were originally infected by the virus, as was seen with CMV (Example XII). However, in cells treated with the control, GV39G antibody, the virus has spread and infected all the cells (FIG. 30B).

This pattern of inhibition of viral replication is similar to that observed when 3G4 was used to treat CMV-infected human fibroblasts. Thus, the anti-PS antibody, 3G4 effectively prevents the spread of Pichinde virus from cell to cell, as quantified in FIG. 30D.

EXAMPLE XXV

Tumor Treatment Using PE-Binding Peptide Derivative

Further to the anti-viral effects of duramycin derivatives, both in vitro and in vivo, the present example demonstrates the localization of duramycin derivatives to tumor vasculature and associated anti-tumor effects.

A. Tumor Treatment with Duramycin-HuIgG Conjugate

Human IgG (HIgG) was first purified as described in Example XV. Purified HIgG was linked to duramycin using the SIAB linker, and the resultant (D-SIAB)$_n$HIgG conjugate purified.

Mouse fibrosarcoma cell-line MethA was grown, harvested at log phase and resuspended in DPBS. Approximately $10^6$ MethA tumor cells were injected subcutaneously in the middle dorsum of 6-8 week old BALB/c male mice. 5 days after implantation, the mice were randomly separated into two groups (n=15). From day 10, one group received 150 µg Duramycin-HuIgG conjugate by intraperitoneal injection for consecutive 2 weeks. The other group received the same amount of HuIgG as a control. Tumor volumes were measured twice a week and were calculated using the formula ½ab$^2$, (where "a" is the long axis and "b" the short axis of the tumor). Mice were sacrificed when the tumors reached a size of approximately 1400 mm$^3$.

The duramycin-HIgG conjugate inhibited MethA tumor growth in BALB/c mice at the dose of 150 µg/day, as compared to the human IgG control (FIG. 31).

B. Duramycin-HuIgG Conjugate Localizes to Tumor Vasculature

Using the same MethA mouse tumor model as above, when the tumor size reach 500 mm$^3$, 100 µg (D-SIAB)$_n$HIgG in 100 µl PBS was injected through the tail vein. The same amount of human IgG was injected as a control. After 4 hours, mice was euthanized and perfused with normal saline for 5 minutes and 1% paraformaldehyde for 10 minutes. The tumor and other major organs were dissected and frozen in liquid nitrogen. After embedding in OCT, tissue was cryosected in 10 µm section and placed on silanized slides. After fixing in cold acetone for 10 minutes, slides were stained with peroxidase labeled goat anti human IgG to detect the biodistribution of duramycin-HuIgG. Meca32 and peroxidase labeled goat anti-rat IgG were used to detect blood vasculature of tissue.

This study showed that the duramycin-HIgG conjugate localized to the tumor vasculature in the treated animals.

EXAMPLE XXVI

Biodistribution and Properties of Duramycin Conjugates

The present example demonstrates the lack of toxicity of cell-impermeant duramycin derivatives in vitro, the biodistribution of duramycin derivatives administered in vivo and the ability of duramycin-antibody conjugates to increase the phagocytosis of apoptotic cells by macrophages.

A. Duramycin-Biotin Conjugates are not Cytotoxic

The duramycin derivatives and conjugates of the invention are designed to minimize the non-specific toxic effects of the parent duramycin molecule. In many examples, this is achieved by linking duramycin to a cell impermeant group (Example XV).

The biotinylated duramycin construct DLB was prepared as described in Example XV. The unmodified duramycin compound and DLB were tested for cytotoxic effects on HUVEC using an MTT assay. Whilst the unmodified duramycin showed dose-dependent toxicity, DLB was non-toxic, matching the untreated control (FIG. 32).

B. Localization of Duramycin-Biotin Conjugate to Macrophages in Lung

The human breast cancer cell line MDA-MB-435 was grown, harvested at log phase, and resuspended in DPBS. Approximately $10^7$ cells were injected into the mammary fat pad of 6-8 week old female ethylic nude mice. 100 µg duramycin-biotin in 100 µl PBS was injected through the tail vein. After 4 hours, mice was euthanized and perfused with normal saline for 5 minutes and 1% paraformaldehyde for 10 minutes. Major organs, including heart, lung, liver, kidney, brain, intestine, testes and spleen were dissected and frozen in liquid nitrogen. After embedding in OCT, tissue was cryosected in 10 µm sections and placed on silanized slides. After fixing in cold acetone for 10 minutes, slides were stained with Cy3 labeled streptavidin to detect the biodistribution of the duramycin-biotin construct. Meca32 and FITC labeled goat anti rat IgG were used to detect blood vasculature of tissue.

The intravenous injection of the duramycin-biotin conjugate into nude mice bearing MDA-MB-435 tumors resulted in the deposition of drug in the tumor cells, renal tubules and in the macrophages in the lung. There was minimal deposition in liver and no detectable distribution in brain, intestine, testes. The localization to macrophages in the lung can be exploited in the anti-viral embodiments of the invention.

C. Duramycin-Antibody Conjugate Enhances Phagocytosis of Apoptotic Cells

The ability of a duramycin-antibody conjugate (duramycin-C44, DuC44) to increase the phagocytosis of apoptotic cells was next investigated.

Macrophages were isolated and cultured from mouse bone marrow. The medium used for the isolation, culture, and stimulation of BM macrophages was DMEM containing 2 mM glutamine, 0.37% (w/v) $NaHCO_3$, 10% (v/v) heat-inactivated FCS, and 0.5 ng/ml mouse GM-CSF. Bone marrow cells were flushed aseptically from the dissected femurs with jet of complete medium directed through a 25-gauge needle. The cells were then adjusted to a density of approximately $3 \times 10^5$ cells/ml of complete medium, and were distributed in 0.5 ml aliquots into 8 well chamber slides.

Cells were incubated for 1 hour at 37° C. in 5% $CO_2$, in a humidified chamber to allow macrophages to adhere and spread. Nonadherent cells were removed by adding 5 ml of warmed PBS to each well, resuspending nonadherent cells by moderately tapping the plate, and flicking the slides to discard the nonadherent cells. This washing was performed a total of three times. The cells were maintained at 37° C. under a 7.5% (v/v) $CO_2$ atmosphere for 5 days. The complete medium was changed every other day until the cells were used.

The following method was used to label HL-60 target cells with a fluorescent cell tracer. A 10 mM CFDA SE stock solution was prepared immediately prior to use by dissolving the contents of one vial dye in 90 µL of the DMSO and diluting in PBS to 10 µM. Centrifugation was used to obtain a HL-60 cell pellet and the supernatant aspirated. The cells were resuspend in CFDA/PBS and incubated at 37° C. for 15 minutes. The samples was centrifuged and the supernatant aspirated. The cells were resuspend in media and incubated for another 30 minutes. The cell viability and fluorescence were confirmed to be over 95%.

In this phagocytosis assay, labeled HL-60 cells were exposed to UV 254 nm for 5 minutes and incubated at 37° C. for one hour to induce apoptosis. $10^4$ apoptotic HL-60 cells were incubated with macrophages for one hour. Duramycin-C44 conjugate was included at the concentration of 10 µg/ml. The same concentration of mouse antibody BBG3 was used as a negative control, and the 3G4 antibody was also included for comparison. Hoechst 33342 was added in media in the last 45 minutes at the concentration of 10 µg/ml.

Slides were washed with PBS 3 times, and fixed in 4% paraformaldehyde for 15 minutes. The slides were stained with rat anti-mouse CD11 antibody (CD11 is a macrophage marker), diluted in 0.2% gelatin for one hour, washed and stained with Texas red labeled goat anti-rat secondary antibody.

The cells were analyzed under the fluorescence microscope. Macrophages are identified as red cells, due to the CD11 marker. Macrophages that have phagocytosed apoptotic cells are identified as green cells, due to the fluorescent tracer in the target cells. Red and green cells are counted and the phagocytosis is quantified as the percent phagocytes positive for uptake.

This study shows that the duramycin-antibody conjugate, DuC44 enhanced phagocytosis of apoptotic HL-60 cells by macrophages (FIG. 33). Thus, the duramycin portion is binding to the surface of the apoptotic cells, permitting the protruding antibody portion of the conjugate to be recognized by the macrophages. The duramycin-antibody conjugate thus functioned similarly to the 3G4 antibody. As expected, an $(Fab)_2$ fragment of the 3G4 antibody, lacking the Fc region, did not induce phagocytosis above control levels.

As the earlier study showed duramycin-biotin conjugates to localize to macrophages in the lung following administration in vivo, the stimulation of macrophage-mediated phagocytosis of apoptotic cells shown in the present study has important implications for the therapeutic uses of the present invention, such as in treating pulmonary viral infections.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abrams and Oldham, In: Monoclonal Antibody Therapy of Human Cancer, Foon and Morgan (Eds.), Martinus Nijhoff Publishing, Boston, pp. 103-120, 1985.

Adler, Ng, Rote, "Monoclonal antiphosphatidylserine antibody inhibits intercellular fusion of the choriocarcinoma line, JAR," Biol. Reprod., 53(4):905-910, 1995.

Alving, Banerji, Fogler and Alving, "Lupus anticoagulant activities of murine monoclonal antibodies to liposomal phosphatidylinositol phosphate", Clin. Exp. Immunol., 69:403-408, 1987.

Andree, Reutelingsperger, Hauptmann, Hemker, Hermens, Willems, "Binding of vascular anticoagulant α (VACα) to planar phospholipid bilayers," J. Biol. Chem., 265:4923-4928, 1990.

Antibodies: A Laboratory Manual, Cold Spring Harbor Laboratory, 1988.

Aoki, Uenaka, Aoki, Umeda and Inoue, "A Novel Peptide Probe for Studying the Transbilayer Movement of Phosphatidylethanolamine," J. Biochem., 116:291-297, 1994.

Asano, Yukita, Matsumoto, Kondo, Suzuki, "Inhibition of tumor growth and metastasis by an immunoneutralizing monoclonal antibody to human vascular endothelial growth factor/vascular permeability factor," Cancer Res., 55:5296-5301, 1995.

Baca et al., "Antibody humanization using monovalent phage display," J. Biol. Chem., 272(16):10678-84, 1997.

Barbas, Kang, Lerner, Benkovic, "Assembly of combinatorial antibody libraries on phage surfaces: the gene III site," Proc. Natl. Acad. Sci., USA, 88(18):7978-7982, 1991.

Barbas et al., Proc. Natl. Acad. Sci., USA, 88:4457-4461, 1992.

Barras, Bain, Hoekstra and Lerner, "Semisynthetic Combinatorial Antibody Libraries: A Chemical Solution to the Diversity Problem," Proc. Natl. Acad. Sci. USA, 89:4457-4461, 1992.

Berman, Mellis, Pollock, Smith, Suh, Heinke, Kowal, Surti, Chess, Cantor, et al., "Content and organization of the human Ig VH locus: definition of three new VH families and linkage to the Ig CH locus," *EMBO J.*, 7(3):727-738, 1988.

Bevers, Rosing, Zwaal, "Development of procoagulant binding sites on the platelet surface," *Adv. Exp. Med. Biol.*, 192:359-371, 1985.

Bevilacqua, "Endothelial-leukocyte adhesion molecules," *Ann. Rev. Immunol.*, 11:767-804, 1993.

Bitbol, Fellmann, Zachowski, Devaux, "Ion regulation of phosphatidylserine and phosphatidylethanolamine outside-inside translocation in human erythrocytes," *Biochim. Biophys. Acta*, 904(2):268-282, 1987.

Blackwood and Ernst, "Characterization of Ca2(+)-dependent phospholipid binding, vesicle aggregation and membrane fusion by annexins," *Biochem. J.*, 266(1): 195-200, 1990.

Blankenberg, Katsikis, Tait, Davis, Naumovski, Ohtsuki, Kopiwoda, Abrams, Darkes, Robbins, Maecker, Strauss, "In vivo detection and imaging of phosphatidylserine expression during programmed cell death," *Proc. Natl. Acad. Sci., USA*, 95(11):6349-6354, 1998.

Bocci, "Efficient labeling of serum proteins with $^{131}$I using chloramine T," *Int. J. Appl. Radiat. Isot.*, 15:449-456, 1964.

Bombeli, Karsan, Tait, Harlan, "Apoptotic vascular endothelial cells become procoagulant," *Blood*, 89(7):2429-2442, 1997.

Borgstrom et al., "Complete inhibition of angiogenesis and growth of microtumors by anti-vascular endothelial growth factor neutralizing antibody: novel concepts of angiostatic therapy from intravital videomicroscopy," *Cancer Res.*, 56(17):4032-1439, 1996.

Borgstrom et al., "Neutralizing anti-vascular endothelial growth factor antibody completely inhibits angiogenesis and growth of human prostate carcinoma micro tumors in vivo," *Prostate*, 35(1):1-10, 1998.

Bornstein, "Thrombospondins: structure and regulation of expression," *FASEB J*, 6(14):3290-3299, 1992.

Borrebaeck and Moller, "In vitro immunization. Effect of growth and differentiation factors on antigen-specific B cell activation and production of monoclonal antibodies to autologous antigens and weak immunogens," *J. Immunol.*, 136(10):3710-3715, 1986.

Boustead, Brown, Walker, "Isolation, characterization and localization of annexin V from chicken liver," *Biochem. J.*, 291:601-608, 1993.

Boyle, Pohlman, Cornejo, Verrier, "Endothelial cell injury in cardiovascular surgery: ischemia-reperfusion," *Ann. Thor. Surg.*, 62(6): 1868-1875, 1996.

Bradford, "A rapid and sensitive method for the quantitation of microgram quantities of protein utilizing the principle of protein-dye binding," *Anal. Biochem.*, 72:248-254, 1976.

Branch, Rote, Dostal, Scott, "Association of lupus anticoagulant with antibody against phosphatidylserine," *Clin. Immun. Immunopathol.*, 42:63-75, 1987.

Brem, "Angiogenesis antagonists: current clinical trials," *Angiogenesis*, 2:9-20, 1998.

Bresnahan, Boldogh, Thompson, and Albrecht, "Human Cytomegalovirus inhibits cellular DNA synthesis and arrests productively infected cells in late G1", *Virology*, 224:150-160, 1996.

Bruijn and Dinklo, "Distinct patterns of expression of intercellular adhesion molecule-1, vascular cell adhesion molecule-1, and endothelial-leukocyte adhesion molecule-1 in renal disease," *Lab. Invest.*, 69:329-335, 1993.

Burke et al., "Cloning of large segments of exogenous DNA into yeast by means of artificial chromosome vectors", *Science*, 236, 806-812, 1987.

Burrows, Watanabe, Thorpe, "A murine model for antibody-directed targeting of vascular endothelial cells in solid tumors," *Cancer Res.*, 52:5954-5962, 1992.

Burrows and Thorpe, "Eradication of large solid tumors in mice with an immunotoxin directed against tumor vasculature," *Proc. Natl. Acad. Sci. USA*, 90:8996-9000, 1993.

Calderon and DeVries, "Lipid composition and phospholipid asymmetry of membranes from a schwann cell line," *J. Neuro. Res.*, 49:372-380, 1997.

Callahan et al., *J. Immunol.*, 170:4840-4845, 2003

Campbell, In: *Monoclonal Antibody Technology, Laboratory Techniques in Biochemistry and Molecular Biology*, Vol. 13, Burden and Von Knippenberg (Eds.), Elseview, Amsterdam, pp. 75-83, 1984.

Carnemolla et al., "A tumor-associated fibronectin isoform generated by alternative splicing of messenger RNA precursors," *J. Cell Biol.*, 108:1139-1148, 1989.

Cheng, Huang, Nagane, Ji, Wang, Shih, Arap, Huang, Cavenee, "Suppression of glioblastoma angiogenicity and tumorigenicity by inhibition of endogenous expression of vascular endothelial growth factor," *Proc. Natl. Acad. Sci. USA*, 93:8502-8507, 1996.

Choung, Kobayashi, Inoue, Takemoto, Ishitsuka and Inoue, "Hemolytic Activity of a Cyclic Peptide Ro09-0198 Isolated from *Streptoverticillium*," *Biochim. Biophys. Acta.*, 940:171-179, 1988a.

Choung, Kobayashi, Takemoto, Ishitsuka and Inoue, "Interaction of a Cyclic Peptide, Ro09-0198, with Phosphatidylethanolamine in Liposomal Membranes," *Biochem. Biophys. Acta*, 940:180-187, 1988b.

Christiansen, Sims, Hamilton, "Complement C5b-9 increases plasminogen binding and activation on human endothelial cells," *Arterioscler. Thromb. Vasc. Biol.*, 17(1): 164-171, 1997.

Clapp et al., "The 16-kilodalton N-terminal fragment of human prolactin is a potent inhibitor of angiogenesis," *Endocrinology*, 133(3): 1292-1299, 1993.

Comfurius, Senden, Tilly, et al., "Loss of membrane phospholipid asymmetry in platelets and red cells may be associated with calcium-induced shedding of plasma membrane and inhibition of aminophospholipid translocase," *Biochim. Biophys. Acta.*, 1026(2):153-160, 1990.

Coughlin et al., "Interleukin-12 and interleukin-18 synergistically induce murine tumor regression which involves inhibition of angiogenesis," *J. Clin. Invest.*, 101(6):1441-1452, 1998.

Dachary-Prigent, Toti, Satta, Pasquet, Uzan, Freyssinet, "Physiopathological significance of catalytic phospholipids in the generation of thrombin," *Seminars In Thrombosis and Hemostasis*, 22:157-164, 1996.

D'Amato et al., "Thalidomide is an inhibitor of angiogenesis," *Proc. Natl. Acad. Sci. USA*, 91(9):4082-4085, 1994.

D'Angelo et al., "Activation of mitogen-activated protein kinases by vascular endothelial growth factor and basic fibroblast growth factor in capillary endothelial cells is inhibited by the antiangiogenic factor 16-kDa N-terminal fragment of prolactin," *Proc. Natl. Acad. Sci. USA*, 92(14): 6374-6378, 1995.

Daum, "Lipids of mitochondria," *Biochim. Biophys. Acta*, 822(1):1-42, 1985.

Davis and Yancopoulos, "The angiopoietins: Yin and Yang in angiogenesis", *Curr. Top. Microbiol. Immunol.*, 237:173-85, 1999.

Demo, Masuda, Rossi, et al., "Quantitative measurement of mast cell degranulation using a novel flow cytomeric annexin-V binding assay," *Cytometry*, 36(4):340-348, 1999.

Denekamp, "Vascular attack as a therapeutic strategy for cancer," *Cancer Metastasis Rev.*, 9:267-282, 1990.

Devaux, "Protein involvement in transmembrane lipid asymmetry," *Annu. Rev. Biophys. Biomol. Struct.*, 21:417-439, 1992.

DeVore et al., "Phase I Study of the Antineovascularization Drug CM101," *Clin. Cancer Res.*, 3(3):365-372, 1997.

Diehl, Pfreundschuh, Fonatsch, Stein, Falk, Burrichter, Schaadt, "Phenotypic genotypic analysis of Hodgkin's disease derived cell lines: histopathological and clinical implications," *Cancer Surveys*, 4:399-416, 1985.

Dillon, Mancini, Rosen, et al., "Annexin V binds to viable B cells and colocalizes with a marker of lipid rafts upon B cell receptor activation," *J. Immunol.*, 164(3):1322-1332, 2000.

Donati and Falanga, "Pathogenic mechanisms of thrombosis in malignancy," *Acta Haematol.*, 106(1-2):18-24, 2001.

Drouvalakis and Buchanan, "Phospholipid specificity of autoimmune and drug induced lupus anticoagulants; association of phosphatidylethanolamine reactivity with thrombosis in autoimmune disease," *J. Rheumatol.*, 25(2): 290-295, 1998.

Droz, Patey, Paraf, Chretien, Gogusev, "Composition of extracellular matrix and distribution of cell adhesion molecules in renal cell tumors," *Lab. Invest.*, 71:710-718, 1994.

Dvorak, Nagy, Dvorak, "Structure of Solid Tumors and Their Vasculature: Implications for Therapy with Monoclonal Antibodies," *Cancer Cells*, 3(3):77-85, 1991.

Edgington, Mackman, Brand, Ruf, "The Structural Biology of Expression and Function of Tissue Factor," *Thromb. Haemost.*, 66(1):67-79, 1991.

Emoto, Kobayashi, Yamaji, Aizawa, Yahara, Inoue and Umeda, "Redistribution of Phosphatidylethanolamine at the Cleavage Furrow of Dividing Cells During Cytokinesis," *Proc. Natl. Acad. Sci.*, 93:12867-12872, 1996.

Emoto, Toyama-Sorimachi, Karasuyama, Inoue and Umeda, "Exposure of Phosphatidylethanolamine on the Surface of Apoptotic Cells," *Exp. Cell Res.*, 232:430-434, 1997.

Ferrara, Clapp, Weiner, "The 16K fragment of prolactin specifically inhibits basal or fibroblast growth factor stimulated growth of capillary endothelial cells," *Endocrinology*, 129(2):896-900, 1991.

Ferrara, "The role of vascular endothelial growth factor in pathological angiogenesis," *Breast Cancer Res. Treat.*, 36:127-137, 1995.

Folkman et al., "Angiogenesis inhibition and tumor regression caused by heparin or a heparin fragment in the presence of cortisone," *Science*, 221:719-725, 1983.

Fotsis et al., "The endogenous oestrogen metabolite 2-methoxyoestradiol inhibits angiogenesis and suppresses tumour growth," *Nature*, 368(6468):237-239, 1994.

Frater-Schroder et al., "Tumor necrosis factor type alpha, a potent inhibitor of endothelial cell growth in vitro, is angiogenic in vivo," *Proc. Natl. Acad. Sci. USA*, 84(15):5277-5281, 1987.

Frazier, "Thrombospondins," *Curr. Opin. Cell Biol.*, 3(5): 792-799, 1991.

Fridrikksson, Shipkiva, Sheets, Holowka, Baird and McLafferty, "Quantitative analysis of phospholipids in functionally important membrane domains from RBL-2H3 mast cells using tandem high-resolution mass spectrometry, Biochemistry, 38: 8056-8063, 1999.

Fries, Williams, Atkins, Newman, Lipscomb, Collins, "Expression of VCAM-1 and E-selectin in an in vivo model of endothelial activation," *Am. J. Pathol.*, 143:725-737, 1993.

Gaffet, Bettache, Bienvenüe, "Transverse redistribution of phospholipids during human platelet activation: evidence for a vectorial outflux specific to aminophospholipids," *Biochem.*, 34:6762-6769, 1995.

Gagliardi, Hadd, Collins, "Inhibition of angiogenesis by suramin," *Cancer Res.*, 52(18):5073-5075, 1992.

Gagliardi and Collins, "Inhibition of angiogenesis by antiestrogens," *Cancer Res.*, 53(3):533-535, 1993.

Gagliardi et al., "Antiangiogenic and antiproliferative activity of suramin analogues," *Cancer Chemother. Pharmacol.*, 41(2):117-124, 1998.

Galli, Comfurius, Maassen Hemker, de Baets, van Breda-Vriesman, Barbui, Zwaal, Bevers, "Anticardiolipin antibodies (ACA) directed not to cardiolipin but to a plasma protein cofactor," *Lancet*, 335(8705):1544-1547, 1990.

Galli, Barbui, Zwaal, Comfurius, Bevers, "Antiphospholipid antibodies: involvement of protein cofactors," *Haematologica*, 78(1):1-4, 1993.

Gavrieli, Sherman, Ben-Sasson, "Identification of programmed cell death in situ via specific labeling of nuclear DNA fragmentation," *J. Cell Biol.*, 119(3):493-501, 1992.

Gefter et al., "A simple method for polyethylene glycol-promoted hybridization of mouse myeloma cells," *Somatic Cell Genet.*, 3:231-236, 1977.

Giovarelli et al., "Tumor rejection and immune memory elicited by locally released LEC chemokine are associated with an impressive recruitment of APCs, lymphocytes, and granulocytes", *J. Immunol.*, 164, 3200-3206, 2000.

Goding, In: *Monoclonal Antibodies: Principles and Practice*, 2nd Edition, Academic Press, Orlando, Fla., pp. 60-61, 65-66, 71-74, 1986.

Good et al., "A tumor suppressor-dependent inhibitor of angiogenesis is immunologically and functionally indistinguishable from a fragment of thrombospondin," *Proc. Natl. Acad. Sci. USA*, 87(17):6624-6628, 1990.

Graham, et al., "Primary respiratory syncytial virus infection in mice," *J. Med. Virol.*, 26(2):153-62, 1988.

Grant et al., "Fibronectin fragments modulate human retinal capillary cell proliferation and migration," *Diabetes*, 47(8):1335-1340, 1998.

Hammill, Uhr, Scheuermann, "Annexin V staining due to loss of membrane asymmetry can be reversible and precede commitment to apoptotic death," *Exp. Cell Res.*, 251(1): 16-21, 1999.

Haran et al., "Tamoxifen enhances cell death in implanted MCF7 breast cancer by inhibiting endothelium growth," *Cancer Res.*, 54(21):5511-5514, 1994.

Harris, Zhang, Moghaddam, Fox, Scott, Pattison, Gatter, Stratford, Bicknell, "Breast cancer angiogenesis—new approaches to therapy via antiangiogenesis, hypoxic activated drugs, and vascular targeting," *Breast Cancer Res. Treat.*, 38(1):97-108, 1996.

Hasegawa, Suzuki, Ishii, Takakuwa, Tanaka, "Establishment of two distinct anti-cardiolipin antibody-producing cell lines from the same individual by Epstein-Barr virus transformation," *Throm. Res.*, 74(1):77-84, 1994.

Hasselaar and Sage, "SPARC antagonizes the effect of basic fibroblast growth factor on the migration of bovine aortic endothelial cells," *J. Cell Biochem.*, 49(3):272-283, 1992.

Hayashi, Nagashima, Terui, Kawamura, Matsumoto and Itazaki, "The Structure of PA48009; The Revised Structure of Duramycin," *J. Antibiotics*, XLIII(11): 1421-1430, 1990.

Hellerqvist et al., "Antitumor effects of GBS toxin: a polysaccharide exotoxin from group B beta-hemolytic streptococcus," *J. Cancer Res. Clin. Oncol.*, 120(1-2):63-70, 1993.

Herrmann and Devaux, "Alteration of the aminophospholipid translocase activity during in vivo and artificial aging of human erythrocytes," *Biochim. Biophys. Acta*, 1027(1): 41-46, 1990.

Hinkovska-Galcheva, Petkova, Koumanov, "Changes in the phospholipid composition and phospholipid asymmetry of ram sperm plasma membranes after cryopreservation," *Cryobiology*, 26(1):70-75, 1989.

Hiscox and Jiang, "Interleukin-12, an emerging anti-tumour cytokine," *In Vivo*, 11(2):125-132, 1997.

Holash et al., "Vessel Cooption, Regression, and Growth in Tumors Mediated by Angiopoietins and VEGF", *Science*, 284:1994-1998, 1999.

Hori et al., "Differential effects of angiostatic steroids and dexamethasone on angiogenesis and cytokine levels in rat sponge implants," *Br. J. Pharmacol.*, 118(7):1584-1591, 1996.

Hotchkiss, Ashton, Mahmood, Russell, Sparano, Schwartz, "Inhibition of endothelial cell function in vitro and angiogenesis in vivo by docetaxel (Taxotere): association with impaired repositioning of the microtubule organizing center", *Mol. Cancer Ther.*, 1 (13):1191-200, 2002.

Hristova and Needham, In: *Stealth Liposomes*, Lasic D. and Martin, F., Eds. CRC Press, Boca Raton, pp. 35-49, 1993.

Huang, Molema, King, Watkins, Edgington, Thorpe, "Tumor infarction in mice by antibody-directed targeting of tissue factor to tumor vasculature," *Science*, 275:547-550, 1997.

Huse, Sastry, Iverson, Kang, Alting-Mees, Burton, Benkovic, Lerner, *Science*, 246(4935):1275-1281, 1989.

Igarashi, Umeda, Tokita, Soo Nam, Inoue, "Effective induction of anti-phospholipid and anticoagulant antibodies in normal mouse," *Thrombosis Res.*, 61:135-148, 1991.

Ingber et al., "Angioinhibins: Synthetic analogues of fumagillin which inhibit angiogenesis and suppress tumor growth," *Nature*, 48:555-557, 1990.

Iwamoto et al., "Inhibition of angiogenesis, tumour growth and experimental metastasis of human fibrosarcoma cells HT1080 by a multimeric form of the laminin sequence Tyr-Ile-Gly-Ser-Arg (YIGSR)," *Br. J. Cancer*, 73(5):589-595, 1996.

Jackson et al., "Stimulation and inhibition of angiogenesis by placental proliferin and proliferin-related protein," *Science*, 266(5190):1581-1584, 1994.

Jendraschak and Sage, "Regulation of angiogenesis by SPARC and angiostatin: implications for tumor cell biology," *Semin. Cancer Biol.*, 7(3):139-146, 1996.

Jirholt, Ohlin, Borrebaeck, Soderlind, "Exploiting Sequence Space: Shuffling In Vivo Formed Complementarity Determining Regions Into a Master Framework," *Gene*, 215: 471-476, 1998.

Jones, Dear, Foote, Neuberger, Winter, *Nature*, 321(6069): 522-525, 1986.

Julien, Tournier, Tocanne, "Differences in the transbilayer and lateral motions of fluorescent analogs of phosphatidylcholine and phosphatidylethanolamine in the apical plasma membrane of bovine aortic endothelial cells," *Exp. Cell. Res.*, 208(2):387-389, 1993.

Julien, Tournier, Tocanne, "Basic fibroblast growth factor modulates the aminophospholipid translocase activity present in the plasma membrane of bovine aortic endothelial cells," *Eur. J. Biochem.*, 230:287-297, 1995.

Julien, Millot, Tocanne, Tournier, "12-O-Tetradecanoylphorbol-13-Acetate inhibits aminophospholipid translocase activity and modifies the lateral motions of fluorescent phospholipid analogs in the plasma membrane of bovine aortic endothelial cells," *Experimental Cell Res.*, 234:125-131, 1997.

Kabat et al., "Sequences of Proteins of Immunological Interest" 5th Ed. Public Health Service, National Institutes of Health, Bethesda, Md., 1991, pp 647-669 in particular.

Kang, Barbas, Janda, Benkovic, Lerner, *Proc. Natl. Acad. Sci., U.S.A*, 88(10):4363-4366, 1991.

Katsuragawa, Kanzaki, Inoue, Hirano, Mori, Rote, "Monoclonal antibody against phosphatidylserine inhibits in vitro human trophoblastic hormone production and invasion," *Biology of Reproduction*, 56:50-58, 1997.

Kellermann, Lottspeich, Henschen, Muller-Esterl, "Completion of the primary structure of human high-molecular-mass kininogen. The amino acid sequence of the entire heavy chain and evidence for its evolution by gene triplication," *Eur. J. Biochem.*, 154(2):471-478, 1986.

Kendall and Thomas, "Inhibition of vascular endothelial cell growth factor activity by an endogenously encoded soluble receptor," *Proc. Natl. Acad. Sci. USA*, 90:10705-10709, 1993.

Kenyon, Browne, D'Amato, "Effects of thalidomide and related metabolites in a mouse corneal model of neovascularization," *Exp. Eye Res.*, 64(6):971-978, 1997.

Keyt et al., "Identification of vascular endothelial growth factor determinants for binding KDR and FLT-1 receptors. Generation of receptor-selective VEGF variants by site-directed mutagenesis," *J. Biol. Chem.*, 271(10):5638-46, 1996.

Kim, Li, Houck, Winer, Ferrara, "The vascular endothelial growth factor proteins: identification of biologically relevant regions by neutralizing monoclonal antibodies," *Growth Factors*, 7:53-64, 1992.

Kim et al., "Inhibition of vascular endothelial growth factor-induced angiogenesis suppresses tumour growth in vivo," *Nature*, 362:341-844, 1993.

Kim, Kwak, Ahn, So, Liu, Koh, Koh, "Molecular cloning and characterization of a novel angiopoietin family protein, angiopoietin-3", *FEBS Lett.*, 443(3):353-6, 1999.

Kim et al., "Immunohistological analysis of immune cell infiltration of a human colon tumor xenograft after treatment with Stealth liposome-encapsulated tumor necrosis factor-alpha and radiation", *Int. J. Oncol.*, 21(5):973-9, 2002.

Kisch, and Johnson, "A plaque assay for respiratory syncytial virus," *Proc. Soc. Exp. Biol. Med.*, 112:583-9, 1963.

Kitamura, Kitagawa, Fukushima, Takagaki, Miyata. Nakanishi, "Structural organization of the human kininogen gene and a model for its evolution," *J. Biol. Chem.*, 260(14): 8610-8617, 1985.

Kleinman et al., "The laminins: a family of basement membrane glycoproteins important in cell differentiation and tumor metastases," *Vitam. Horm.*, 47:161-186, 1993.

Kohler and Milstein, "Continuous cultures of fused cells secreting antibody of predefined specificity," *Nature*, 256: 495-497, 1975.

Kohler and Milstein, "Derivation of specific antibody-producing tissue culture and tumor lines by cell fusion," *Eur. J. Immunol.*, 6:511-519, 1976.

Kondo, Asano, Suzuki, "Significance of vascular endothelial growth factor/vascular permeability factor for solid tumor growth, and its inhibition by the antibody," *Biochem. Biophys. Res. Commun.*, 194:1234-1241, 1993.

Konieczny, Bobrzecka, Laidler, Rybarska, "The combination of IgM subunits and proteolytic IgG fragment by controlled formation of interchain disulphides," *Haematologia*, 14(1):95-99, 1981.

Krajewska, Wang, Krajewski, et al., "Immunohistochemical analysis of in vivo patterns of expression of CPP32 (Caspase-3), a cell death protease," *Cancer Res.*, 57(8): 1605-1613, 1997.

Kuzu, Bicknell, Fletcher, Gatter, "Expression of adhesion molecules on the endothelium of normal tissue vessels and vascular tumors," *Lab. Invest.*, 69(3):322-328, 1993.

Kyte and Doolittle, "A simple method for displaying the hydropathic character of a protein," *J. Mol. Biol.*, 157(1): 105-132, 1982.

Lane, Iruela-Arispe, Sage, "Regulation of gene expression by SPARC during angiogenesis in vitro. Changes in fibronectin, thrombospondin-1, and plasminogen activator inhibitor-1," *J. Biol. Chem.*, 267(23):16736-16745, 1992.

Lee et al., "Inhibition of urokinase activity by the antiangiogenic factor 16K prolactin: activation of plasminogen activator inhibitor 1 expression," *Endocrinology*, 139(9): 3696-3703, 1998.

Leppink, Bishop, Sedmak, Henry, Ferguson, Streeter, Butcher, Orosz, "Inducible expression of an endothelial cell antigen on murine myocardial vasculature in association with interstitial cellular infiltration," *Transplantation*, 48(5):874-877, 1989.

Levy, Gharavi, Sammaritano, Habina, Lockshin, "Fatty acid chain is a critical epitope for antiphospholipid antibody," *J. Clin. Immunol.*, 10(3): 141-145, 1990.

Lichtenbeld, Van Dam-Mieras, Hillen, "Tumour angiogenesis: pathophysiology and clinical significance," *Neth. J. Med.*, 49(1):42-51, 1996.

Lin, Buxton, Acheson, Radziejewski, Maisonpierre, Yancopoulos, Channon, Hale, Dewhirst, George, Peters, "Anti-angiogenic gene therapy targeting the endothelium-specific receptor tyrosine kinase Tie2", *Proc. Natl. Acad. Sci., USA*, 95(15):8829-34, 1998.

Lin, Sankar, Shan, Dewhirst, Polyerini, Quinn, Peters, "Inhibition of tumor growth by targeting tumor endothelium using a soluble vascular endothelial growth factor receptor," *Cell Growth Differ.*, 9:49-58, 1998b.

Linder and Borden, "Effects of tamoxifen and interferon-beta or the combination on tumor-induced angiogenesis," *Int. J. Cancer*, 71 (3):456-461, 1997.

Lingen, Polverini, Bouck, "Inhibition of squamous cell carcinoma angiogenesis by direct interaction of retinoic acid with endothelial cells," *Lab. Invest.*, 74(2):476-483, 1996.

Lingen, Polverini, Bouck, "Retinoic acid and interferon alpha act synergistically as antiangiogenic and antitumor agents against human head and neck squamous cell carcinoma," *Cancer Res.*, 58(23):5551-5558, 1998.

Liu, Moy, Kim, Xia, Rajasekaran, Navarro, Knudsen, Bander, "Monoclonal antibodies to the extracellular domain of prostate-specific membrane antigen also react with tumor vascular endothelium", *Cancer Res.*, 57:3629-3634, 1997.

Lucas, Garcia, Donati, Hribar, Mandriota, Giroud, Buurman, Fransen, Suter, Nunez, Pepper, Grau, "Both TNF receptors are required for direct TNF-mediated cytotoxicity in microvascular endothelial cells," *Eur. J. Immunol.*, 28(11): 3577-3586, 1998.

Luo, Toyoda, Shibuya, "Differential inhibition of fluid accumulation and tumor growth in two mouse ascites tumors by an antivascular endothelial growth factor/permeability factor neutralizing antibody," *Cancer Res.*, 58(12):2594-2600, 1998a.

Luo et al., "Significant expression of vascular endothelial growth factor/vascular permeability factor in mouse ascites tumors," *Cancer Res.*, 58(12):2652-2660, 1998b.

Lupu, Moldovan, Ryan, Stern, Simionescu, "Intrinsic procoagulant surface induced by hypercholestrolaemia on rabbit aortic endothelium," *Blood Coagul. Fibrinolysis*, 4(5):743-752, 1993.

Majewski et al., "Vitamin D3 is a potent inhibitor of tumor cell-induced angiogenesis," *J. Investig. Dermatol. Symp. Proc.*, 1(1):97-101, 1996.

Maneta-Peyret, Bessoule, Geffard, Cassagne, "Demonstration of high specificity antibodies against phosphatidylserine," *J. Immun. Meth.*, 108:123-127, 1988.

Maneta-Peyret, Freyburger, Bessoule, Cassagne, "Specific immunocytochemical visualization of phosphatidylserine," *J. Immun. Methods*, 122:155-159, 1989.

Manetti et al., "Synthesis and binding mode of heterocyclic analogues of suramin inhibiting the human basic fibroblast growth factor," *Bioorg. Med. Chem.*, 6(7):947-958, 1998.

Massey et al., *Nature*, 328:457-458, 1987.

McEvoy, Williamson, Schlegel, "Membrane phospholipid asymmetry as a determinant of erythrocyte recognition by macrophages," *Proc. Natl. Acad. Sci. USA*, 83(10):3311-3315, 1986.

McNeil, Simpson, Chesterman, Krilis, "Anti-phospholipid antibodies are directed against a complex antigen that includes a lipid-binding inhibitor of coagulation: beta 2-glycoprotein I (apolipoprotein H)," *Proc. Natl. Acad. Sci. USA*, 87(11):4120-4124, 1990.

Menon, Rahman, Ravirajan, Kandiah, Longhurst, McNally, Willaims, Latchman, Isenberg, "The production, binding characteristics and sequence analysis of four human IgG monoclonal antiphospholipid antibodies", *J. Autoimmunity*, 10:43-57, 1997.

Mesiano, Ferrara, Jaffe, "Role of vascular endothelial growth factor in ovarian cancer: inhibition of ascites formation by immunoneutralization," *Am. J. Pathol.*, 153(4):1249-1256, 1998.

Millauer, Longhi, Plate, Shawver, Risau, Ullrich, Strawn, "Dominant-negative inhibition of Flk-1 suppresses the growth of many tumor types in vivo," *Cancer Res.*, 56:1615-1620, 1996.

Mills, Brooker, Camerini-Otero, "Sequences of human immunoglobulin switch regions: implications for recombination and transcription," *Nucl. Acids Res.*, 18:7305-7316, 1990.

Moore et al., "Tumor angiogenesis is regulated by CXC chemokines," *J. Lab. Clin. Med.*, 132(2):97-103, 1998.

Morrison, Johnson, Herzenberg, Oi, "Chimeric human antibody molecules: mouse antigen-binding domains with human constant region domains," *Proc. Natl. Acad. Sci. USA*, 81(21):6851-6855, 1984.

Morrison, Wims, Kobrin, Oi, "Production of novel immunoglobulin molecules by gene transfection," *Mt. Sinai J. Med.*, 53(3):175, 1986.

Muller, et al., "VEGF and the Fab fragment of a humanized neutralizing antibody: crystal structure of the complex at 2.4 A resolution and mutational analysis of the interface," *Structure*, 6(9):1153-67, 1998.

Muyldermans, Cambillau and Wyne, "Recognition of Antigens by Single-Domain Antibody Fragments: The Superfluous Luxury of Paired Domains," *TRENDS*, 26(4):230-235, 2001.

Munro, "Endothelial-leukocyte adhesive interactions in inflammatory diseases," *European. Heart Journal*, 14:72-77, 1993.

Nagler, Feferman, Shoshan, "Reduction in basic fibroblast growth factor mediated angiogenesis in vivo by linomide," *Connect Tissue Res.*, 37(1-2):61-68, 1998.

Nakamura et al., Enzyme Immunoassays: Heterogeneous and Homogeneous Systems, Chapter 27.

Nakamura and Racker, "Inhibitory Effect of Duramycin or Partial Reactions Catalyzed by (Na$^+$, K$^+$)-Adenosinetriphosphatase from Dog Kidney," *Biochemistry*, 23(2):385-389, 1984.

Nilsson, Kosmehl, Zardi, Neri, "Targeted delivery of tissue factor to the ED-B domain of fibronectin, a marker of angiogenesis, mediates the infarction of solid tumors in mice," *Cancer Res.*, 61(2):711-716, 2001.

Nuttall, Irving and Hudson, "Immunoglobulin V$_H$ Domains and beyond: Design and Selection of Single-Domain Binding and Targeting Reagents," *Current Pharma. Biotech.*, 1(3):253-262, 2000.

Ohizumi, Tsunoda, Taniguchi, Saito, Esaki, Makimoto, Wakai, Tsutsumi, Nakagawa, Utoguchi, Kaiho, Ohsugi, Mayumi, "Antibody-based therapy targeting tumor vascular endothelial cells suppresses solid tumor growth in rats," *Biochem. Biophys. Res. Comm.*, 236:493-496, 1997.

Oikawa et al., "A highly potent antiangiogenic activity of retinoids," *Cancer Lett.*, 48(2): 157-162, 1989.

O'Reilly et al., "Angiostatin: a novel angiogenesis inhibitor that mediates the suppression of metastases by a Lewis lung carcinoma," *Cell*, 79:315-328, 1994.

O'Reilly et al., "Endostatin: an endogenous inhibitor of angiogenesis and tumor growth," *Cell*, 88(2):277-285, 1997.

Orr, Wang, Lafrenie, Scherbarth, Nance, "Interactions between cancer cells and the endothelium in metastasis," *J. Pathology*, 190:310-329, 2000.

Parmley and Smith, "Antibody-selectable filamentous fd phage vectors: affinity purification of target genes," *Gene*, 73(2):305-318, 1988.

Patey, Vazeux, Canioni, Potter, Gallatin, Brousse, "Intercellular adhesion molecule-3 on endothelial cells: Expression in tumors but not in inflammatory responses," *Am. J. Pathol.*, 148:465-472, 1996.

Pepper et al., "Leukemia inhibitory factor (LIF) inhibits angiogenesis in vitro," *J. Cell Sci.*, 108(Pt 1):73-83, 1995.

Presta, Chen, O'Connor, Chisholm, Meng, Krummen, Winkler, Ferrara, "Humanization of an anti-vascular endothelial growth factor monoclonal antibody for the therapy of solid tumors and other disorders," *Cancer Res.*, 57:4593-4599, 1997.

Price, "Metastasis from human breast cancer cell lines," *Breast Cancer Research Treatment.*, 39:93-102, 1996.

Qamar, Gharavi, Levy, Lockshin, "Lysophosphatidylethanolamine is the antigen to which apparent antibody to phosphatidylethanolamine binds," *J. Clin. Immunol.*, 10(4):200-203, 1990.

Qu, Conroy, Walker, Wooding, Lucy, "Phosphatidylserine-mediated adhesion of T-cells to endothelial cells," *J. Biochem.*, 317(Pt 2):343-346, 1996.

Quinn et al., CM101, a polysaccharide antitumor agent, does not inhibit wound healing in murine models," *J. Cancer Res. Clin. Oncol.*, 121(4):253-256, 1995.

Ran, Gao, Duffy, Watkins, Rote, Thorpe, "Infarction of solid Hodgkin's tumors in mice by antibody-directed targeting of tissue factor to tumor vasculature," *Cancer Res.*, 58(20): 4646-4653, 1998.

Ran, Downes, Thorpe, "Increased exposure of anionic phospholipids on the surface of activated endothelial cells and tumor blood vessels," *Proceedings of AACR*, No. 2615 (Abstract):527, 2002.

Rao, Tait, Hoang, "Binding of annexin V to a human ovarian carcinoma cell line (OC-2008). Contrasting effects on cell surface factor VIIa/tissue factor activity and prothrombinase activity," *Thromb. Res.*, 67(5):517-531, 1992.

Rauch, Tannenbaum, Tannenbaum, Ramelson, Cullis, Tilcock, Hope, Janoff, "Human hybridoma lupus anticoagulants distinguish between lamellar and hexagonal phase lipid systems," *J. Biol. Chem.*, 261(21):9672-9677, 1986.

Rauch and Janoff, "Phospholipid in the hexagonal II phase is immunogenic: evidence for immunorecognition of nonbilayer lipid phases in vivo," *Proc. Natl. Acad. Sci., USA*, 87(11):4112-4114, 1990.

Ravirajan, Harmer, McNally, Hohmann, Mackworth-Young, Isenberg, "Phospholipid binding specificities and idiotype expression of hybridoma derived monoclonal autoantibodies from splenic cells of patients with systemic lupus erythematosus", *Ann. Rheumatic Diseases*, 54:471-476, 1995.

RayChaudhury and D'Amore, "Endothelial cell regulation by transforming growth factor-beta," *J. Cell Biochem.*, 47(3):224-229, 1991.

Richer and Lo, "Introduction of human DNA into mouse eggs by injection of dissected human chromosome fragments", *Science* 245, 175-177, 1989.

Riechmann, Clark, Waldmann, Winter, "Reshaping human antibodies for therapy," *Nature*, 332(6162):323-327, 1988.

Riechmann and Muyldermans, "Single Domain Antibodies: Comparison of Camel VH and Camelised Human VH Domains," *J. Immunol. Methods.*, 231:25-38, 1999.

Rimassa et al., "Unexpected low efficacy of stealth liposomal doxorubicin (Caelyx) and vinorelbine in the treatment of metastatic breast cancer", *Breast Cancer Research and Treatment*, 77 (2):185-8, 2003.

Rosenthal et al., "A phase I study of SPI-077 (Stealth liposomal cisplatin) concurrent with radiation therapy for locally advanced head and neck cancer", *Investigational New Drugs*, 20(3)343-9, 2002.

Rote, Ng, Dostal-Johnson, Nicholson, Siekman, "Immunologic detection of phosphatidylserine externalization during thrombin-induced platelet activation," *Clin. Immunol. Immunopathol.*, 66:193-200, 1993.

Rote, Chang, Katsuragawa, Ng, Lyden, Mori, "Expression of phosphatidylserine-dependent antigens on the surface of differentiating BeWo human choriocarcinoma cells," *Am. J. Reprod. Immun.*, 33:114-121, 1995.

Rote, "Antiphospholipid antibodies and recurrent pregnancy loss," *Am. J. Reprod. Immun.*, 35:394-401, 1996.

Ruf, Rehemtulla, Edgington, "Phospholipid-independent and -dependent interactions required for tissue factor receptor and cofactor function," *Biol. Chem.*, 266:2158-2166, 1991.

Ruf and Edgington, "Structural biology of tissue factor, the initiator of thrombogenesis in vivo," *FASEB J.*, 8:385-390, 1994.

Sakamoto et al., "Heparin plus cortisone acetate inhibit tumor growth by blocking endothelial cell proliferation," *Canc. J.*, 1:55-58, 1986.

Saleh, Stacker, Wilks, "Inhibition of growth of C6 glioma cells in vivo by expression of antisense vascular endothelial growth factor sequence," *Cancer Res.*, 56:393-401, 1996.

Sambrook, Fritsch, Maniatis, *Molecular Cloning: A Laboratory Manual*, 2nd Ed., Cold Spring Harbor Press, Cold Spring Harbor, N.Y., 1989.

Sang, "Complex role of matrix metalloproteinases in angiogenesis," *Cell Res.*, 8(3):171-177, 1998.

Sanlioglu, Williams, Samavati, Butler, Wang, McCray, Ritchie, Hunninghake, Zandi, and Engelhardt, *J. Biol. Chem.*, 32:30188, 2001.

Schlaepfer, Mehlman, Burgess, Haigler, "Structural and functional characterization of endonexin II, a calcium- and phospholipid-binding protein," *Proc. Natl. Acad. Sci. USA,* 84(17):6078-6082, 1987.

Schorer, Rick, Swaim, Moldow, "Structural features of endotoxin required for stimulation of endothelial cell tissue factor production; exposure of preformed tissue factor after oxidant-mediated endothelial cell injury," *J. Lab. Clin. Med.,* 106:38-42, 1985.

Seigneuret and Devaux, "ATP-dependent asymmetric distribution of spin-labeled phospholipids in the erythrocyte membrane: relation to shape changes," *Proc. Natl. Acad. Sci. USA,* 81(12):3751-3755, 1984.

Sessions and Horwitz, "Myoblast aminophospholipid asymmetry differs from that of fibroblasts," *FEBS Lett.,* 134(1): 75-78, 1981.

Shaughnessy, Buchanan, Turple, Richardson, Orr, "Walker carcinosarcoma cells damage endothelial cells by the generation of reactive oxygen speciesm" *A. J. Path.,* 134(4): 787-796, 1989.

Sheibani and Frazier, "Thrombospondin 1 expression in transformed endothelial cells restores a normal phenotype and suppresses their tumorigenesis," *Proc. Natl. Acad. Sci. USA,* 92(15):6788-6792, 1995.

Sheu et al., "Inhibition of angiogenesis in vitro and in vivo: comparison of the relative activities of triflavin, an Arg-Gly-Asp-containing peptide and anti-alpha(v)beta3 integrin monoclonal antibody," *Biochim. Biophys. Acta,* 1336 (3):445-454, 1997.

Shotwell, Stodola, Michael, Lindenfelser, Dworschack and Pridham, "Antibiotics Against Plant Disease. III. Duramycin, a New Antibiotic from *Streptomyces Cinnamomeus* Forma*Azacoluta, N. Utiliza. Res. Dev. Div.,* 80:3912-3915, 1958.

Sideras, Mizuta, Kanamori, Suzuki, Okamoto, Kuze, Ohno, Doi, Fukuhara, Hassan, et al., "Production of sterile transcripts of C gamma genes in an IgM-producing human neoplastic B cell line that switches to IgG-producing cells," *Intl. Immunol.,* 1(6):631-642, 1989.

Siemeister, Martiny-Baron, Marme, "The pivotal role of VEGF in tumor angiogenesis: molecular facts and therapeutic opportunities," *Cancer Metastasis Rev.,* 17(2):241-248., 1998.

Singh et al., "Stealth monensin liposomes as a potentiator of adriamycin in cancer treatment", *Journal of Controlled Release,* 59(1):43-53, 1999.

Sioussat, Dvorak, Brock, Senger, "Inhibition of vascular permeability factor (vascular endothelial growth factor) with antipeptide antibodies," *Arch. Biochem. Biophys.,* 301:15-20, 1993.

Sipos et al., "Inhibition of tumor angiogenesis," *Ann. NY Acad. Sci.,* 732:263-272, 1994.

Sluiter, Pietersma, Lamers, Koster, "Leukocyte adhesion molecules on the vascular endothelium: their role in the pathogenesis of cardiovascular disease and the mechanisms underlying their expression," *J. Cardiol. Pharmacol.,* 22:S37-S44, 1993.

Smirnov, Triplett, Comp, Esmon, Esmon, "On the role of phosphatidylethanolamine in the inhibition of activated protein C activity by antiphospholipid antibodies," *J. Clin. Invest.,* 95(1):309-316, 1995.

Soares, Shaughnessy, MacLarkey, Orr, "Quantification and morphologic demonstration of reactive oxygen species produced by Walker 256 tumor cells in vitro and during metastasis in vivo," *Laboratory Invest.,* 71 (4):480-489, 1994.

Soderlind, Ohlin and Carlsson, "Complementarity-Determining Region (CDR) Implantation: A Theme of Recombination," *Immunotech.,* 4:279-285, 1999.

Soderlind, Strandberg, Jirholt, Kobayashi, Alexeiva, Aberg, Nilsson, Jansson, Ohlin, Wingren, Danielsson, Carisson and Borrebaeck, "Recombining Germline-Derived CDR Sequences for Creating Diverse Single-Framework Antibody Libraries," *Nature Biotech.,* 18:852-856, 2000.

Soff et al., "Expression of plasminogen activator inhibitor type 1 by human prostate carcinoma cells inhibits primary tumor growth, tumor-associated angiogenesis, and metastasis to lung and liver in an athymic mouse model," *J. Clin. Invest.,* 96(6):2593-2600, 1995.

Staal-van den Brekel, Thunnissen, Buurman, Wouters, "Expression of E-selectin, intercellular adhesion molecule (ICAM)-1 and vascular cell adhesion molecule (VCAM)-1 in non-small-cell lung carcinoma," *Virchows Arch.,* 428: 21-27, 1996.

Staub, Harris, Khamashta, Savidge, Chahade, Hughes, "Antibody to phosphatidylethanolamine in a patient with lupus anticoagulant and thrombosis," *Ann. Rheum. Dis.,* 48(2): 166-169, 1989.

Stella et al., "Prodrugs: A chemical approach to targeted drug delivery", *Directed Drug Delivery*, Borchardt et al., Eds. Human Press, 1985, pp 247-267.

Stone, Ruf, Miles, Edgington, Wright, "Recombinant soluble human tissue factor secreted by *Saccharomyces cerevisiae* and refolded from *E. coli* inclusion bodies: glycosylation of mutants, activity, and physical characterization," *Biochem. J.,* 310(2):605-614, 1995.

Sugi and McIntyre, "Autoantibodies to phosphatidylethanolamine (PE) recognize a kininogen-PE complex," *Blood,* 86(8):3083-3089, 1995.

Sugi and McIntyre, "Phosphatidylethanolamine induces specific conformational changes in the kininogens recognizable by antiphosphatidylethanolamine antibodies," *Thromb. Haemost.,* 76(3):354-360, 1996a.

Sugi and McIntyre, "Autoantibodies to kininogen-phosphatidylethanolamine complexes augment thrombin-induced platelet aggregation," *Thromb. Res.,* 84(2):97-109, 1996b.

Sugimura, Donato, Kakar, Scully, "Annexin V as a probe of the contribution of anionic phospholipids to the procoagulant activity of tumor cell surfaces," *Blood Coagul. Fibrinolysis,* 5(3):365-373, 1994.

Symon et al., "Selective delivery of doxorubicin to patients with breast carcinoma metastases by stealth liposomes", *Cancer,* 86(1):72-8, 1999.

Tada et al., "Inhibition of tubular morphogenesis in human microvascular endothelial cells by co-culture with chondrocytes and involvement of transforming growth factor beta: a model for avascularity in human cartilage," *Biochim. Biophys. Acta,* 1201(2):135-142, 1994.

Tait and Smith, "Phosphatidylserine receptors: role of CD36 in binding of anionic phospholipid vesicles to monocytic cells," *J. Biol. Chem.,* 274(5):3048-3054, 1999.

Takano et al., "Suramin, an anticancer and angiosuppressive agent, inhibits endothelial cell binding of basic fibroblast growth factor, migration, proliferation, and induction of urokinase-type plasminogen activator," *Cancer Res.,* 54(10):2654-2660, 1994.

Tanaka et al., "Viral vector-mediated transduction of a modified platelet factor 4 cDNA inhibits angiogenesis and tumor growth," *Nat. Med.,* 3(4):437-442, 1997.

Test and Mitsuyoshi, "Activation of the alternative pathway of complement by calcium-loaded erythrocytes resulting from loss of membrane phospholipid asymmetry," *J. Lab. Clin. Med.,* 130(2):169-182, 1997.

Thornhill, Kyan-Aung, Haskard, "IL-4 increases human endothelial cell adhesiveness for T cells but not for neutrophils," *J. Immunol.*, 144:3060-3065, 1990.

Thorpe et al., "Heparin-Steroid Conjugates: New Angiogenesis Inhibitors with Antitumor Activity in Mice," *Cancer Res.*, 53:3000-3007, 1993.

Thorpe and Ran, "Tumor infarction by targeting tissue factor to tumor vasculature", *Cancer J. Sci. Am.*, 6(Suppl 3):S237-S244, 2000.

Tolsma et al., "Peptides derived from two separate domains of the matrix protein thrombospondin-1 have anti-angiogenic activity," *J. Cell Biol.*, 122(2):497-511, 1993.

Tryggvason, "The laminin family," *Curr. Opin. Cell Biol.*, 5(5):877-882, 1993.

Tsavaris, Kosmas, Vadiaka, Kanelopoulos, Boulamatsis, "Immune changes in patients with advanced breast cancer undergoing chemotherapy with taxanes", *Brit. J. Cancer*, 87(1):21-7, 2002.

Umeda, Igarashi, Nam, Inoue, "Effective production of monoclonal antibodies against phosphatidylserine: Stereospecific recognition of phosphatidylserine by monoclonal antibody," *J. Immun.*, 143(7):2273-2279, 1989.

Umeda and Emoto, "Membrane Phospholipid Dynamics During Cytokinesis: Regulation of Actin Filament Assembly by Redistribution of Membrane Surface Phospholipid", *Chem. Phys. Lipids*, 101:81-91, 1999.

Utsugi, Schroit, Connor, Bucana, Fidler, "Elevated expression of phosphatidylserine in the outer membrane leaflet of human tumor cells and recognition by activated human blood monocytes," *Cancer Res.*, 51(11):3062-3066, 1991.

Valenzuela, Griffiths, Rojas, Aldrich, Jones, Zhou, McClain, Copeland, Gilbert, Jenkins, Huang, Papadopoulos, Maisonpierre, Davis, Yancopoulos, "Angiopoietins 3 and 4: diverging gene counterparts in mice and humans", *Proc. Natl. Acad. Sci., USA*, 96(5):1904-9, 1999.

van Dijk, Wamaar, van Eendenburg, Thienpont, Braakman, Boot, Fleuren, Bolhuis, "Induction of tumor-cell lysis by bi-specific monoclonal antibodies recognizing renal-cell carcinoma and CD3 antigen," *Int. J. Cancer*, 43:344-349, 1989.

Vitetta et al., "Phase I immunotoxin trial in patients with B-cell lymphoma," *Cancer Res.*, 15:4052-4058, 1991.

Vlachoyiannopoulos, Beigbeder, Duelanes, Youinou, Hunt, Krilis, Moutsopoulos, "Antibodies to phosphatidylethanolamine in antiphospholipid syndrome and systemic lupus erythematosus: their correlation with anticardiolipin antibodies and beta 2 glycoprotein-I plasma levels," *Autoimmunity*, 16(4):245-249, 1993.

Vogt, Ng, Rote, "A model for the antiphospholipid antibody syndrome: Monoclonal antiphosphatidylserine antibody induces intrauterine growth restriction in mice," *Am. J. Obstet. Gynecol.*, 174:700-707, 1996.

Vogt, Ng, Rote, "Antiphosphatidylserine antibody removes Annexin V and facilitates the binding prothrombin at the surface of a choriocarcinoma model of trophoblast differentiation," *Am. J. Obstet. Gynecol.*, 177:964-972, 1997.

Volpert, Lawler, Bouck, "A human fibrosarcoma inhibits systemic angiogenesis and the growth of experimental metastases via thrombospondin-1," *Proc. Natl. Acad. Sci. USA*, 95(11):6343-6348, 1998.

Vukanovic et al., "Antiangiogenic effects of the quinoline-3-carboxamide linomide," *Cancer Res.*, 53(8):1833-1837, 1993.

Wakamatsu, Choung, Kobayashi, Inoue, Higashijima and Miyazawa, "Complex Formation of Peptide Antibiotic Ro09-0198 with Lysophosphatidylethanolamine: $^1$H NMR Analysis in Dimethyl Sulfoxide Solution," *Biochemistry*, 29(1): 113-118, 1986.

Waltenberger et al., "Suramin is a potent inhibitor of vascular endothelial growth factor. A contribution to the molecular basis of its antiangiogenic action," *J. Mol. Cell Cardiol.*, 28(7): 1523-1529, 1996.

Wamil et al., "Soluble E-selectin in cancer patients as a marker of the therapeutic efficacy of CM101, a tumor-inhibiting anti-neovascularization agent, evaluated in phase I clinical trail," *J. Cancer Res. Clin. Oncol.*, 123(3): 173-179, 1997.

Wang and Joseph, "Mechanisms of hydrogen peroxide-induced calcium dysregulation in PC 12 cells," *Free Rad. Biol. Med.*, 28(8): 1222-1231, 2000.

Wells, "Starving cancer into submission", *Chem. Biol.*, 5(4): R87-88, 1998.

Wiesmann, et al., "Crystal structure at 1.7 A resolution of VEGF in complex with domain 2 of the Flt-1 receptor," *Cell*, 91(5):695-704, 1997.

Weiss, Young, LoBuglio, Slivka and Nimeh, "Role of Hydrogen Peroxide in Neutrophil-Mediated Destruction of Cultured Endothelial Cells," *J. Clin. Invest.*, 68:714-721, 1981.

Williamson and Schlegel, "Back and forth: the regulation and function of transbilayer phospholipid movement in eukaryotic cells," *Molec. Mem. Biol.*, 111:199-216, 1994.

Willman et al., "Prodrugs in cancer therapy", *Biochem. Soc. Trans.*, 14:375-382, 1988.

Winter and Milstein, "Man-made antibodies," *Nature*, 349: 293-299, 1991.

Wolff et al., "Dexamethasone inhibits glioma-induced formation of capillary like structures in vitro and angiogenesis in vivo," *Klin. Padiatr.*, 209(4):275-277, 1997.

Woodle, Engbers, Zalipsky, *Bioconjugate Chem.*, 5:493-496, 1994.

Yamada, Moldow, Sacks, Craddock, Boogaens and Jacob, "Deleterious Effects of Endotoxin on Cultured Endothelial Cells: An in vitro Model of Vascular injury," *Inflammation*, 5:115-116, 1981.

Yamamura et al., "Effect of Matrigel and laminin peptide YIGSR on tumor growth and metastasis," *Semin. Cancer Biol.*, 4(4):259-265, 1993.

Yoon et al., "Inhibitory effect of Korean mistletoe (*Viscum album coloratum*) extract on tumour angiogenesis and metastasis of haematogenous and non-haematogenous tumour cells in mice," *Cancer Lett.*, 97(1):83-91, 1995.

Yoshida et al., "Suppression of hepatoma growth and angiogenesis by a fumagillin derivative TNP470: possible involvement of nitric oxide synthase," *Cancer Res.*, 58(16):3751-3756, 1998.

Zapata et al., *Protein Eng.*, 8(10):1057-1062, 1995.

Zhao, Zhou, Wiedmer, Sims, "Level of expression of phospholipid scramblase regulates induced movement of phosphatidylserine to the cell surface," *J. Biol. Chem.*, 273: 6603-6606, 1998.

Zhou, Zhao, Stout, Luhm, Wiedmer, Sims, "Molecular cloning of human plasma membrane phospholipid scramblase. A protein mediating transbilayer movement of plasma membrane phospholipids," *J. Biol. Chem.*, 272(29): 18240-18244, 1997.

Ziche et al., "Linomide blocks angiogenesis by breast carcinoma vascular endothelial growth factor transfectants," *Br. J. Cancer*, 77(7):1123-1129, 1998.

Zulueta, Yu, Hertig, Thannickal, Hassoun, "Release of hydrogen peroxide in response to hypoxia-reoxygenation: role of an NAD(P)H oxidase-like enzyme in endothelial cell plasma membrane," *Am. J. Respir. Cell Mol. Biol.*, 12(1): 41-49, 1995.

Zwaal, Bevers, Comfurius, Rosing, Tilly, Verhallen, "Loss of membrane phospholipid asymmetry during activation of blood platelets and sickled red cells; mechanisms and physiological significance," *Mol. Cell. Biochem.*, 91:23-31, 1989.

Zwaal and Schroit, "Pathophysiologic implications of membrane phospholipid asymmetry in blood cells," *Blood*, 89(4):1121-1132, 1997.

---

What is claimed is:

1. A composition comprising a liposome or nanoparticle operatively associated with a targeting agent and at least a first anti-viral agent; wherein said targeting agent is a duramycin peptide that binds to phosphatidylethanolamine.

2. The composition of claim 1, wherein said composition is a pharmaceutically acceptable composition.

3. A composition comprising a liposome or nanoparticle operatively associated with a duramycin peptide and at least a first anti-viral agent; wherein said duramycin peptide binds to phosphatidylethanolamine at the cell surface of virally infected cells and delivers said anti-viral agent to said virally infected cells.

4. The composition of claim 3, wherein said composition comprises said liposome.

5. The composition of claim 4, wherein said liposome is a stealthed liposome.

6. The composition of claim 3, wherein said composition comprises said nanoparticle.

7. The composition of claim 3, wherein said liposome or nanoparticle comprises an outer membrane and a central core and wherein said outer membrane is coated with said duramycin peptide.

8. The composition of claim 3, wherein said liposome or nanoparticle comprises an outer membrane and a central core and wherein said at least a first anti-viral agent is maintained within said central core.

9. The composition of claim 3, wherein said liposome or nanoparticle comprises an outer membrane and a central core; wherein said outer membrane is coated with said duramycin peptide and wherein said at least a first anti-viral agent is maintained within said central core.

10. The composition of claim 3, wherein said duramycin peptide is operatively attached to albumin.

11. The composition of claim 3, wherein said at least a first anti-viral agent is a nucleoside, a nucleoside reverse transcriptase inhibitor, a non-nucleoside reverse transcriptase inhibitor or a protease inhibitor.

12. The composition of claim 3, wherein said at least a first anti-viral agent is ribavirin.

13. The composition of claim 3, wherein said composition is a pharmaceutically acceptable composition formulated for administration as an aerosol.

* * * * *

SEQUENCE LISTING

<160> NUMBER OF SEQ ID NOS: 9

<210> SEQ ID NO 1
<211> LENGTH: 519
<212> TYPE: DNA
<213> ORGANISM: Mus musculus

<400> SEQUENCE: 1

```
atgggatgga cctggatctt tattttaatc ctgtcagtaa ctacaggtgt ccactctgag      60
gtccagctgc agcagtctgg acctgagctg gagaagcctg gcgcttcagt gaagctatcc     120
tgcaaggctt ctggttactc attcactggc tacaacatga actgggtgaa acagagccat     180
ggaaagagcc ttgaatggat tggacatatt gatccttact atggtgatac ttcctacaac     240
cagaagttca ggggcaaggc cacattgact gtagacaaat cctccagcac agcctacatg     300
cagctcaaga gcctgacatc tgaggactct gcagtctatt actgtgtaaa gggggggttac    360 tacgggcact ggtacttcga tgtctggggc gcagggacca cggtcaccgt ctcctcagct     420
acaacaacag ccccatctgt ctatcccttg gtcccgggcg gatcccccgg gctgcaggaa     480
ttcgatatca agcttatcga taccgtcgac ctcgagggg                            519
```

<210> SEQ ID NO 2
<211> LENGTH: 152
<212> TYPE: PRT
<213> ORGANISM: Mus musculus

<400> SEQUENCE: 2

```
Met Gly Trp Thr Trp Ile Phe Ile Leu Ile Leu Ser Val Thr Thr Gly
1               5                   10                  15

Val His Ser Glu Val Gln Leu Gln Gln Ser Gly Pro Glu Leu Glu Lys
            20                  25                  30

Pro Gly Ala Ser Val Lys Leu Ser Cys Lys Ala Ser Gly Tyr Ser Phe
        35                  40                  45

Thr Gly Tyr Asn Met Asn Trp Val Lys Gln Ser His Gly Lys Ser Leu
    50                  55                  60

Glu Trp Ile Gly His Ile Asp Pro Tyr Tyr Gly Asp Thr Ser Tyr Asn
65                  70                  75                  80

Gln Lys Phe Arg Gly Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Val Lys Gly Gly Tyr Tyr Gly His Trp Tyr Phe Asp Val
        115                 120                 125

Trp Gly Ala Gly Thr Thr Val Thr Val Ser Ser Ala Thr Thr Thr Ala
    130                 135                 140

Pro Ser Val Tyr Pro Leu Val Pro
145                 150
```

<210> SEQ ID NO 3
<211> LENGTH: 435

```
<212> TYPE: DNA
<213> ORGANISM: Mus musculus

<400> SEQUENCE: 3
atggacatga gggctcctgc acagattttg ggcttcttgt tgctcttgtt tccaggtacc      60
agatgtgaca tccagatgac ccagtctcca tcctccttat ctgcctctct gggagaaaga     120
gtcagtctca cttgtcgggc aagtcaggac attggtagta gcttaaactg gcttcagcag     180
ggaccagatg gaactattaa acgcctgatc tacgccacat ccagtttaga ttctggtgtc     240
cccaaaaggt tcagtggcag taggtctggg tcagattatt ctctcaccat cagcagcctt     300
gagtctgaag attttgtaga ctattactgt ctacaatatg ttagttctcc tcccacgttc     360
ggtgctggga ccaagctgga gctgaaacgg gctgatgctg caccaactgt cttcatcttc     420
gggcggatcc cccgg                                                      435

<210> SEQ ID NO 4
<211> LENGTH: 144
<212> TYPE: PRT
<213> ORGANISM: Mus musculus

<400> SEQUENCE: 4

Met Asp Met Arg Ala Pro Ala Gln Ile Leu Gly Phe Leu Leu Leu Leu
1               5                   10                  15

Phe Pro Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Asp Ile Gly Ser Ser Leu Asn Trp Leu Gln Gln Gly Pro Asp Gly
    50                  55                  60

Thr Ile Lys Arg Leu Ile Tyr Ala Thr Ser Ser Leu Asp Ser Gly Val
65                  70                  75                  80

Pro Lys Arg Phe Ser Gly Ser Arg Ser Gly Ser Asp Tyr Ser Leu Thr
                85                  90                  95

Ile Ser Ser Leu Glu Ser Glu Asp Phe Val Asp Tyr Tyr Cys Leu Gln
            100                 105                 110

Tyr Val Ser Ser Pro Pro Thr Phe Gly Ala Gly Thr Lys Leu Glu Leu
        115                 120                 125

Lys Arg Ala Asp Ala Ala Pro Thr Val Phe Ile Phe Gly Arg Ile Pro
    130                 135                 140

<210> SEQ ID NO 5
<211> LENGTH: 783
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 5
gcccagccgg ccatggccga ggtgcagctg gtggagtctg ggggaggcgt ggtccagcct      60
gggaggtccc tgagactctc ctgtgcagcc tctggattca ccttcagtag ctatggcatg     120
cactgggtcc gccaggctcc aggcaagggg ctggagtggg tggcagttat atcatatgat     180
ggaagtaata atactatgc agactccgtg aagggccgat tcaccatctc cagagacaat      240
tccaagaaca cgctgtatct gcaaatgaac agcctgagag ctgaggacac ggccgtgtat     300
tactgtgcaa gattgcatgc tcagacttgg ggccaaggta ccctggtcac cgtctcgagt     360
ggtggaggcg gttcaggcgg aggtggctct ggcggtagtg cacttcagtc tgtgctgacg     420
```

```
cagccgcctt cagtgtctgc ggccccagga cagaaggtca ccatctcctg ctctggaagc      480
agctccgaca tggggaatta tgcggtatcc tggtaccagc agctcccagg aacagccccc      540
aaactcctca tctatgaaaa taataagcga ccctcaggga ttcctgaccg attctctggc      600
tccaagtctg gcacctcagc caccctgggc atcactggcc tctggcctga ggacgaggcc      660
gattattact gcttagcatg ggataccagc ccgcggaatg tattcggcgg agggaccaag      720
ctgaccgtcc taggtgcggc cgcacatcat catcaccatc acggggccgc agaacaaaaa      780
ctc                                                                    783
```

```
<210> SEQ ID NO 6
<211> LENGTH: 261
<212> TYPE: PRT
<213> ORGANISM: ARTIFICIAL SEQUENCE
<220> FEATURE:
<223> OTHER INFORMATION: POLYPEPTIDE

<400> SEQUENCE: 6
```

Ala Gln Pro Ala Met Ala Glu Val Gln Leu Val Glu Ser Gly Gly Gly
1               5                   10                  15

Val Val Gln Pro Gly Arg Ser Leu Arg Leu Ser Cys Ala Ala Ser Gly
            20                  25                  30

Phe Thr Phe Ser Ser Tyr Gly Met His Trp Val Arg Gln Ala Pro Gly
        35                  40                  45

Lys Gly Leu Glu Trp Val Ala Val Ile Ser Tyr Asp Gly Ser Asn Lys
    50                  55                  60

Tyr Tyr Ala Asp Ser Val Lys Gly Arg Phe Thr Ile Ser Arg Asp Asn
65                  70                  75                  80

Ser Lys Asn Thr Leu Tyr Leu Gln Met Asn Ser Leu Arg Ala Glu Asp
                85                  90                  95

Thr Ala Val Tyr Tyr Cys Ala Arg Leu His Ala Gln Thr Trp Gly Gln
            100                 105                 110

Gly Thr Leu Val Thr Val Ser Ser Gly Gly Gly Ser Gly Gly Gly
        115                 120                 125

Gly Ser Gly Gly Ser Ala Leu Gln Ser Val Leu Thr Gln Pro Pro Ser
    130                 135                 140

Val Ser Ala Ala Pro Gly Gln Lys Val Thr Ile Ser Cys Ser Gly Ser
145                 150                 155                 160

Ser Ser Asp Met Gly Asn Tyr Ala Val Ser Trp Tyr Gln Gln Leu Pro
                165                 170                 175

Gly Thr Ala Pro Lys Leu Leu Ile Tyr Glu Asn Asn Lys Arg Pro Ser
            180                 185                 190

Gly Ile Pro Asp Arg Phe Ser Gly Ser Lys Ser Gly Thr Ser Ala Thr
        195                 200                 205

Leu Gly Ile Thr Gly Leu Trp Pro Glu Asp Glu Ala Asp Tyr Tyr Cys
    210                 215                 220

Leu Ala Trp Asp Thr Ser Pro Arg Asn Val Phe Gly Gly Gly Thr Lys
225                 230                 235                 240

Leu Thr Val Leu Gly Ala Ala Ala His His His His His Gly Ala
                245                 250                 255

Ala Glu Gln Lys Leu
            260

```
<210> SEQ ID NO 7
<211> LENGTH: 20
<212> TYPE: PRT
<213> ORGANISM: Homo sapiens
```

```
<400> SEQUENCE: 7

Ala Ser Thr Lys Gly Pro Ser Val Phe Pro Leu Ala Pro Ser Ser Lys
1               5                   10                  15

Ser Thr Ser Gly
            20

<210> SEQ ID NO 8
<211> LENGTH: 15
<212> TYPE: PRT
<213> ORGANISM: Homo sapiens

<400> SEQUENCE: 8

Ile Phe Pro Pro Ser Asp Glu Gln Leu Lys Ser Gly Thr Ala Ser
1               5                   10                  15

<210> SEQ ID NO 9
<211> LENGTH: 19
<212> TYPE: PRT
<213> ORGANISM: Streptomyces cinnamoneus
<220> FEATURE:
<221> NAME/KEY: MISC_FEATURE
<222> LOCATION: (11)..(18)
<223> OTHER INFORMATION: Xaa = Abu

<400> SEQUENCE: 9

Ala Lys Gln Ala Ala Ala Phe Gly Pro Phe Xaa Phe Val Ala Asp Gly
1               5                   10                  15

Asn Xaa Lys
```